(12) United States Patent
Caenepeel et al.

(10) Patent No.: US 10,881,648 B2
(45) Date of Patent: Jan. 5, 2021

(54) COMBINATION THERAPY INCLUDING AN MDM2 INHIBITOR AND ONE OR MORE ADDITIONAL PHARMACEUTICALLY ACTIVE AGENTS FOR THE TREATMENT OF CANCERS

(71) Applicant: AMGEN INC., Thousand Oaks, CA (US)

(72) Inventors: Sean Caenepeel, Thousand Oaks, CA (US); Jude Canon, Marina Del Ray, CA (US); Paul Hughes, Santa Monica, CA (US); Jonathan D. Oliner, Garrett Park, MD (US); Richard J. Rickles, Arlington, MA (US); Anne Y. Saiki, Moorpark, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/229,150

(22) Filed: Dec. 21, 2018

(65) Prior Publication Data

US 2019/0290630 A1    Sep. 26, 2019

Related U.S. Application Data

(63) Continuation of application No. 15/035,438, filed as application No. PCT/US2014/065034 on Nov. 11, 2014, now abandoned.

(60) Provisional application No. 61/902,717, filed on Nov. 11, 2013.

(51) Int. Cl.

| *A61K 31/451* | (2006.01) |
|---|---|
| *A61K 31/166* | (2006.01) |
| *A61K 31/365* | (2006.01) |
| *A61K 31/4045* | (2006.01) |
| *A61K 31/437* | (2006.01) |
| *A61K 31/44* | (2006.01) |
| *A61K 31/496* | (2006.01) |
| *A61K 31/5025* | (2006.01) |
| *A61K 31/506* | (2006.01) |
| *A61K 31/519* | (2006.01) |
| *A61K 31/635* | (2006.01) |
| *A61K 31/704* | (2006.01) |
| *A61K 31/706* | (2006.01) |
| *A61K 31/7068* | (2006.01) |
| *A61P 35/02* | (2006.01) |
| *A61P 35/00* | (2006.01) |

(52) U.S. Cl.
CPC .......... *A61K 31/451* (2013.01); *A61K 31/166* (2013.01); *A61K 31/365* (2013.01); *A61K 31/4045* (2013.01); *A61K 31/437* (2013.01); *A61K 31/44* (2013.01); *A61K 31/496* (2013.01); *A61K 31/506* (2013.01); *A61K 31/5025* (2013.01); *A61K 31/519* (2013.01); *A61K 31/635* (2013.01); *A61K 31/704* (2013.01); *A61K 31/706* (2013.01); *A61K 31/7068* (2013.01); *A61P 35/00* (2018.01); *A61P 35/02* (2018.01)

(58) Field of Classification Search
CPC combination set(s) only.
See application file for complete search history.

(56) References Cited

U.S. PATENT DOCUMENTS

| 2011/0319378 | A1 | 12/2011 | Bartberger et al. |
|---|---|---|---|
| 2012/0077683 | A1 | 3/2012 | Son et al. |
| 2012/0196823 | A1 | 8/2012 | Tutino et al. |
| 2013/0245039 | A1 | 9/2013 | Higgins et al. |
| 2014/0364455 | A1* | 12/2014 | Bio .................... C07D 491/048 514/327 |

FOREIGN PATENT DOCUMENTS

| CL | 2008001047 | 1/2009 |
|---|---|---|
| CL | 201203415 | 8/2013 |
| CN | 103180296 A | 6/2011 |
| WO | 2011153509 A1 | 12/2011 |
| WO | 2013049250 A1 | 4/2013 |
| WO | 2013/139724 | 9/2013 |
| WO | 2013/144923 | 10/2013 |
| WO | 2014130470 A1 | 8/2014 |
| WO | 2014134201 A1 | 9/2014 |
| WO | 2014151863 A1 | 9/2014 |
| WO | 2014200937 A1 | 12/2014 |
| WO | 2015011234 | 1/2015 |

OTHER PUBLICATIONS

Song et al., Clincial outcome of treatment with a combined regimen of decitabine and aclacinomycin/cytarabine for patients with refractory acute myeloid leukemia, 2012, Ann Hematol, 91, pp. 1879-1886 (Year: 2012).*
Long et al., Multiple distinct molecular mechanisms influence sensitivity and resistance to MDM2 inhibitors in adult acute myelogenous leukemia, 2010, Blood, vol. 116, No. 1, pp. 71-80 (Year: 2010).*
Examination Report dated Feb. 25, 2020 for Australian Patent Application No. 2014346354, 5 pages.
Expert Report on Patent Application dated Feb. 25, 2020 for Chile Patent Application No. 201601131, 11 pages.
Expert Report on Patent Application dated Jan. 10, 2019 for Chile Patent Application No. 201901046, 9 pages.
First Office Action for Chinese Patent Application No. 201480072891, 13 pages.

(Continued)

*Primary Examiner* — Kortney L. Klinkel
*Assistant Examiner* — Tori Strong
(74) *Attorney, Agent, or Firm* — Morgan, Lewis & Bockius LLP

(57) ABSTRACT

The present invention provides combination therapy that includes an MDM2 inhibitor and one or more additional pharmaceutically active agents, particularly for the treatment of cancers. The invention also relates to pharmaceutical compositions that contain an MDM2 inhibitor and one or more additional pharmaceutically active agents for the treatment of cancers.

20 Claims, 165 Drawing Sheets

(56) References Cited

OTHER PUBLICATIONS

Third Office Action for Chinese Patent Application No. 201480072891, 5 pages.
Official Action 2 for Eurasian Patent Application No. 201690980, 2 pages.
Official Action 3 for Eurasian Patent Application No. 201690980, 2 pages.
Communication dated Sep. 25, 2018 for European Patent Application No. 14805743.3, 8 pages.
Communication dated Sep. 27, 2019 for European Patent Application No. 14805743.3, 6 pages.
Notice of the Result of the Second Substantive Examination dated Feb. 10, 2020 for Indonesia Patent Application No. P00201603843, 2 pages.
Notice of the Result of the First Substantive Examination dated Feb. 10, 2020 for Indonesia Patent Application No. P00201603843, 2 pages.
Office Action dated Apr. 1, 2020 for Israel Patent Application No. 245568, 3 pages.
Reasons for Refusal dated Aug. 23, 2018 for Japanese Patent Application No. 2016-553270, 3 pages.
Reasons for Refusal dated Mar. 26, 2020 for Japanese Patent Application No. 2019-078325, 8 pages.
Written Opinion dated Feb. 27, 2019 for Japanese Patent Application No. 2016-553270, 2 pages.
Giroux, S;. Overcoming acquired resistance to kinase inhibition: The cases of EGFR, ALK and BRAF; Cancer Res, 2008, 68(12),p. 4853-4861.
Substantive Examination Adverse Report dated Mar. 13, 2020 for Malaysian Patent Application No. PI2016000850, 10 pages.
2nd Substantive Examination Office Action dated Sep. 26, 2019 for Mexican Patent Application No. MX/a/2016/006025, 4 pages.
Substantive Examination Office Action dated Mar. 25, 2019 for Mexican Patent Application No. MX/a/2016/006025, 4 pages.
Office Action dated Sep. 12, 2018 for Israel Patent Application No. 245568, 3 pages.
Second Office Action for Chinese Patent Application No. 201480072891, 9 pages.
Expert Report on Patent Application dated May 7, 2018 for Chile Patent Application No. 201601131, 9 pages.
Official Action for Ukraine Application No. a 2016 06309, 12 pages.
International Preliminary Report on Patentability dated May 17, 2016 for International Patent Application No.PCT/US2014/065034, 18 pages.
Official Action 1 for Eurasian Patent Application No. 201690980, 2 pages.
Zeraati et al; Ascorbic Acid Interaction with Analgesic Effect of Morphine and Tramadol in Mice; Anesth Pain Med; Aug. 2014; 4(3); 5 pages.
Bose, "Mel-I as a therapeutic target in acute myelogenous leukemia (AML)," Leukemia Research Reports, 2(1)12-14 (2013).
Falchook, "Activity of the oral MEK Inhibitor Trametinib in Patients With Advanced Melanoma: A Phase I Dose-Escalation Trial," Lancet Oncology, 13:782-789 (2012).
Feng, "Stabilization of Mdm2 via Decreased Ubiquitination Is Mediated by Protein Kinase B/ Akt-Dependent Phosphorylation," The Journal of Biological Chemistry, 279(34):35510-355 I 7 (2004).
Flaherty, "Combined BRAF and MEK Inhibition in Melanoma with BRAF V600 Mutations," The New En~IandJournal of Medicine, 367(18):1694-1703 (2012).
Giles, "MK-0457, a Novel Aurora Kinase and BCR-ABL Inhibitor, Is Active Against BCR-ABL T315I Mutant Chronic Cyelogenous Leukemia (CML)," Blood, 108(11):163 (2006).
Gozgit, "Potent Activity of Ponatinib (AP24534) in Models ofFLT3-Driven Acute Myeloid Leukemia and Other Hematologic Malignancies," Molecular CancerTherapeutics, 10(6): 1028-1035 (2011).

Greger, "Combinations ofBRAF, MEK, and PI3K/mTOR Inhibitors Overcome Acquired Resistance to the BRAF Inhibitor GSK2118436 Dabrafenib, Mediated by NRAS or MEKMutations," Molecular Cancer Therapeutics, 11(4):909-920 (2012).
International Preliminary Report on Patentability and Written Opinion for International Patent Application No. PCT/US2014/065034, dated May 17, 2016.
International Search Report for International Patent Application No. PCT/US2014/065034, dated Jun. 29, 2015, pp. 1-12.
Ji, "p53 Rescue through HDM2 Antagonism Suppresses Melanoma Growth and Potentiates MEK Inhibition," Journal of Investigative Dermatolozv, 132(2):356-364 (2012).
Ji, "Vemurafenib Synergizes with Nutlin-3 to Deplete Survivin and Suppresses Melanoma Viability and Tumor Growth," Clinical Cancer Research, 19(16):4383-4391 (2013).
Kao, "Rapamycin increases the p53/MDM2 protein ratio and P53-dependent apoptosis by translational inhibition of mdm2 in cancer cells," Cancer Letters, 286(2):250-259 (2009).
Khan, "Determination of the class and isoform selectivity of small-molecule histone deacetylase inhibitors," Biochem. J., 409:581-589 (2008).
Khoury, "Bosutinib is active in chronic phase chronic myeloid leukemia after imatinib and dasatinib and/or nilotinib therapy failure," Blood, I 19(15):3403-3412 (2012).
Kojima, "Mitogen-Activated Protein Kinase Kinase Inhibition Enhances Nuclear S Proapoptotic Function of p53 in Acute Myelogenous Leukemia Cells," Cancer Research, 67(7):3210-3219 (2007).
Kojima, "Concomitant Inhibition ofMDM2 and Bcl-2 Protein Function Synergistically Induce Mitochondrial Apoptosis in AML," Cell Cycle, 5(23):2778-2786 (2006).
Kojima, "Mdm2 inhibitor Nutlin-3a induces p53-mediated apoptosis by transcription-dependent and transcription-independent mechanisms and may overcome Atmmediated resistance to fludarabine in chronic lymphocytic leukemia," Blood, 108:993-1000 (2006).
Liu, "Potent Inhibition of Thyroid Cancer Cells by the MEK Inhibitor PD0325901 and Its Potentiation by Suppression of the PI3K and NF-KB Pathways," Thyroid, 18(8): 1-12 (2008).
Long, "Multiple distinct molecular mechanisms influence sensitivity and resistance to MDM2 inhibitors in adult acute myelogenous leukemia," Blood, 116(1):71-80 (2010).
Lu, "Activation of p53 by roscovitine-mediated suppression ofMDM2 expression," OncoKene, 20:3206-3216 (2001).
Martinelli, "Anti tumor activity of pimasertib, a selective MEK 1/2 inhibitor, in combination with PI3K/mTOR inhibitors or with multi-targeted kinase inhibitors in pimasertib-resistant human lung and colorectal cancer cells," International Journal of Cancer, 133:2089-2101 (2013).
Palani, "Histone deacetylase inhibitors enhance the anticancer activity of nutlin-3 and induce p53 hyperacetylation and downregulation ofMDM2 and MDM4 gene expression," Invest. New DruKs, 30(1):25-36 (2012).
Wang, "Clinical experience of MEK inhibitors in cancer therapy," Biochimica et Biophysica Acta, 1773: 1248-1255 (2007).
Zauli, "Dasatinib Plus Nutlin-3 Shows Synergistic Antileukemic Activity in Both p53wild-type and p53mutated B Chronic Lymphocytic Leukemias by Inhibiting the Akt Pathway,"Clinical Cancer Research, 17(4):762-770 (2011).
Zhang, "Blockade of Mitogen-Activated Protein Kinase/Extracellular Signal-Regulated Kinase Kinase and Murine Double Minute Synergistically Induces Apoptosis in Acute Myeloid Leukemia via BH3-Only Proteins Puma and Bim," Cancer Research, 70(6)2424-2434 (2010).
Zhou, "Structural Mechanism of the Pan-BCR-ABL Inhibitor Ponatinib (AP24534): Lessons for Overcoming Kinase Inhibitor Resistance," Chem. Biol. Drug Des., 77:1-11 (2010).
Borthakur, Phase 1/11 Trial of the MEK Y, Inhibitor Trametinib (GSK1120212) in Relapsed/Refractory Myeloid malignancies: evidence of activity in patients with RAS mutation-positive disease, 2010, Blood, vol. 120, Abstract 677.

* cited by examiner

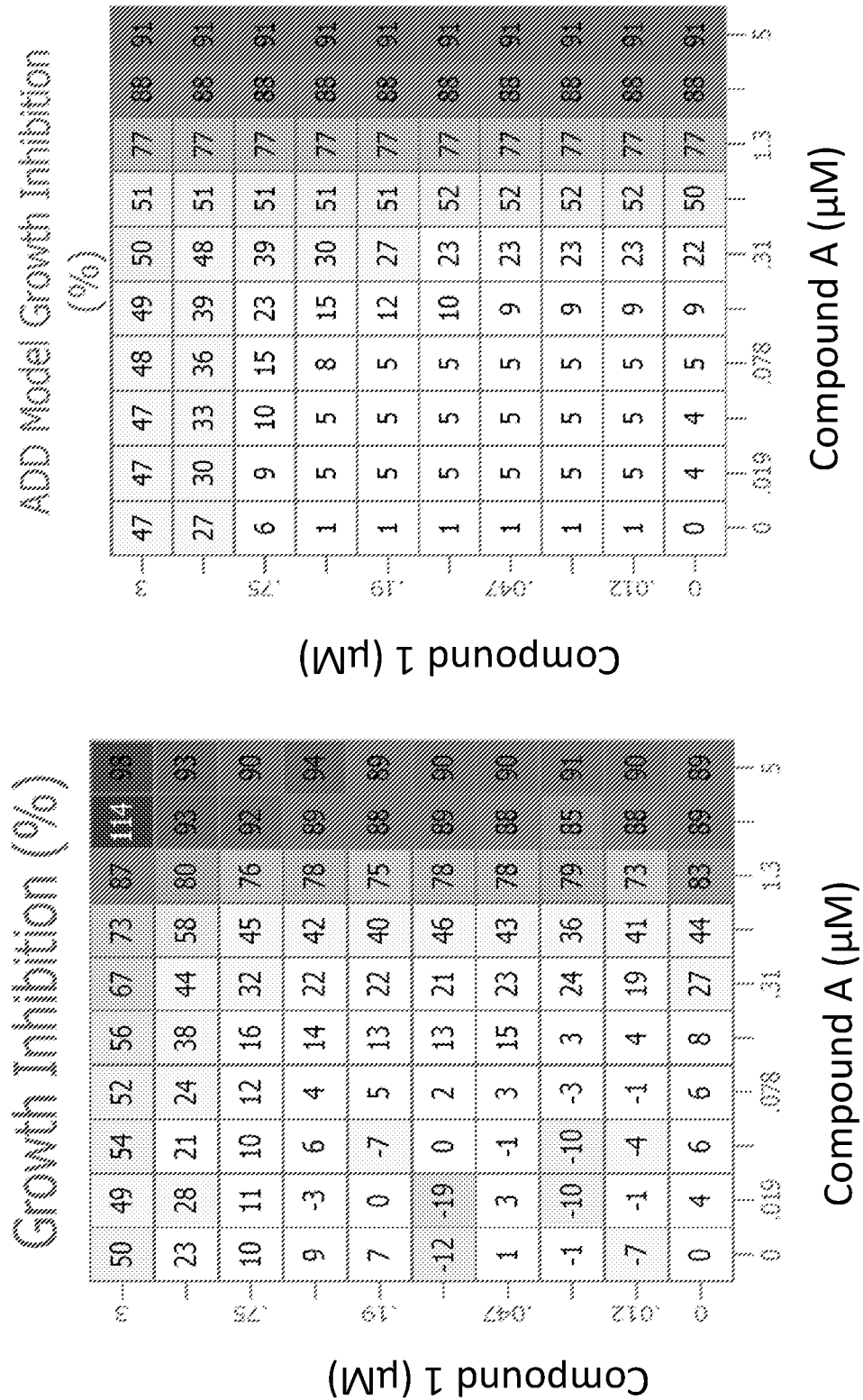
Figure 1-Example 1; A204 cells

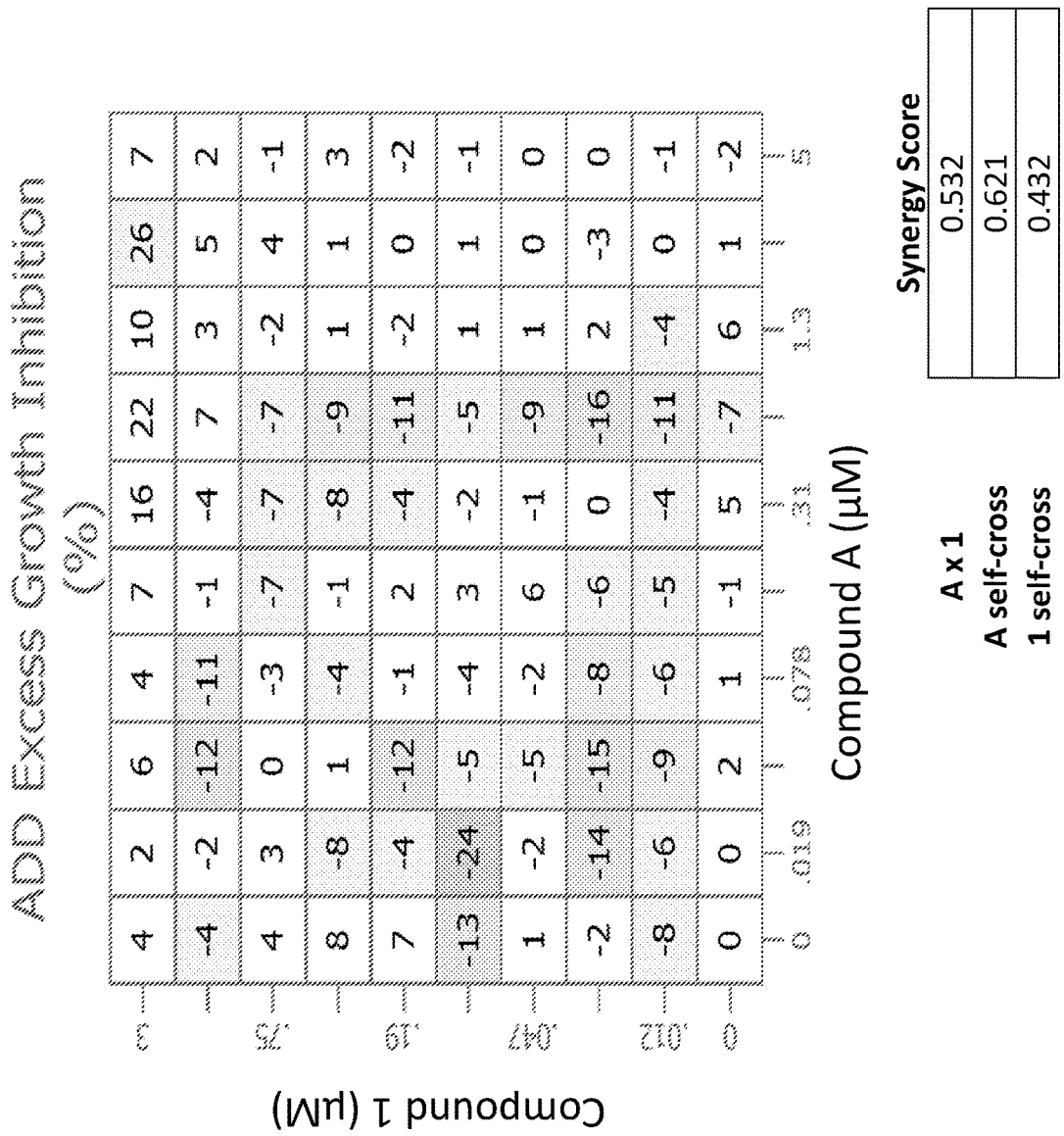

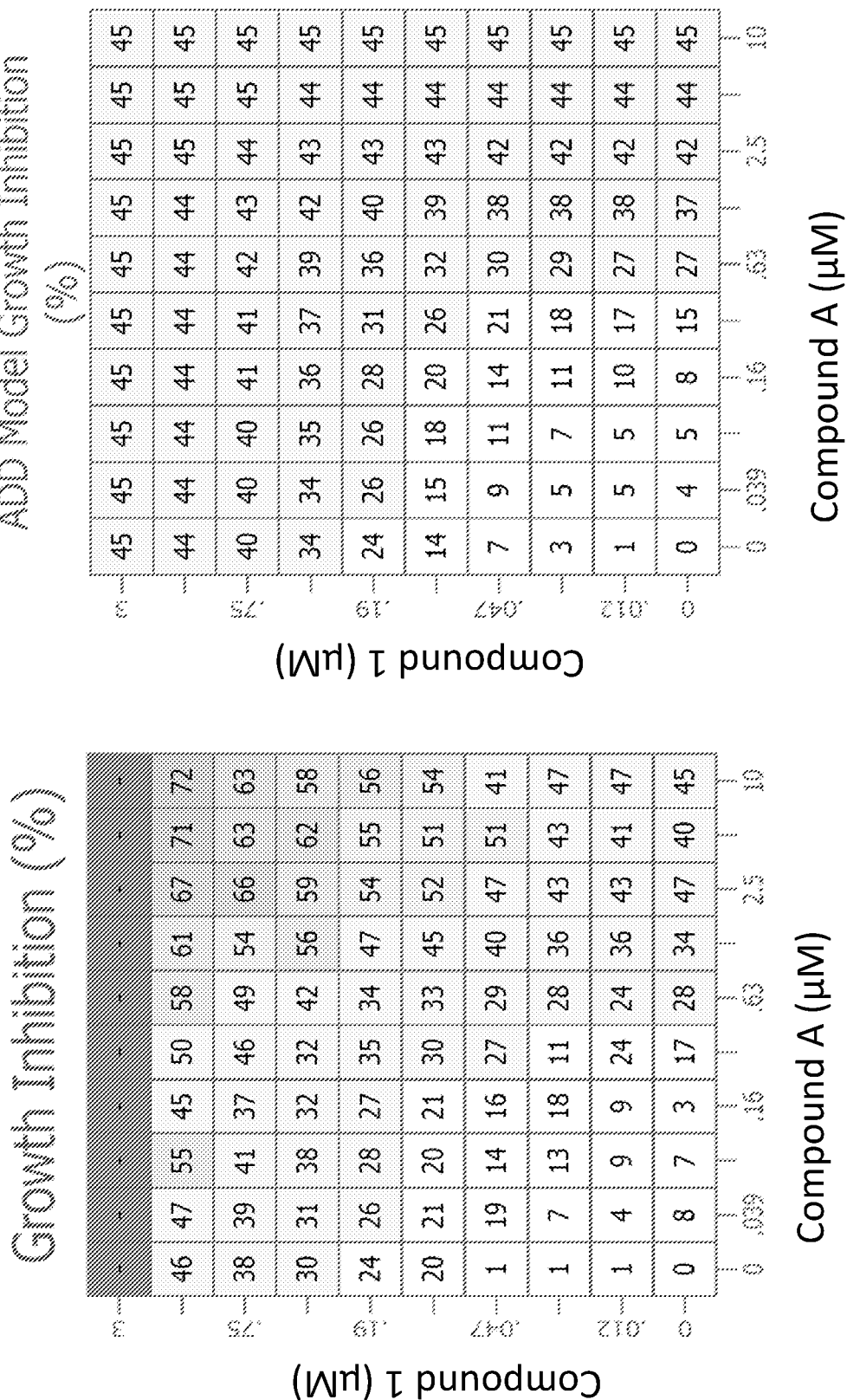
Figure 2-Example 2; A375sq2

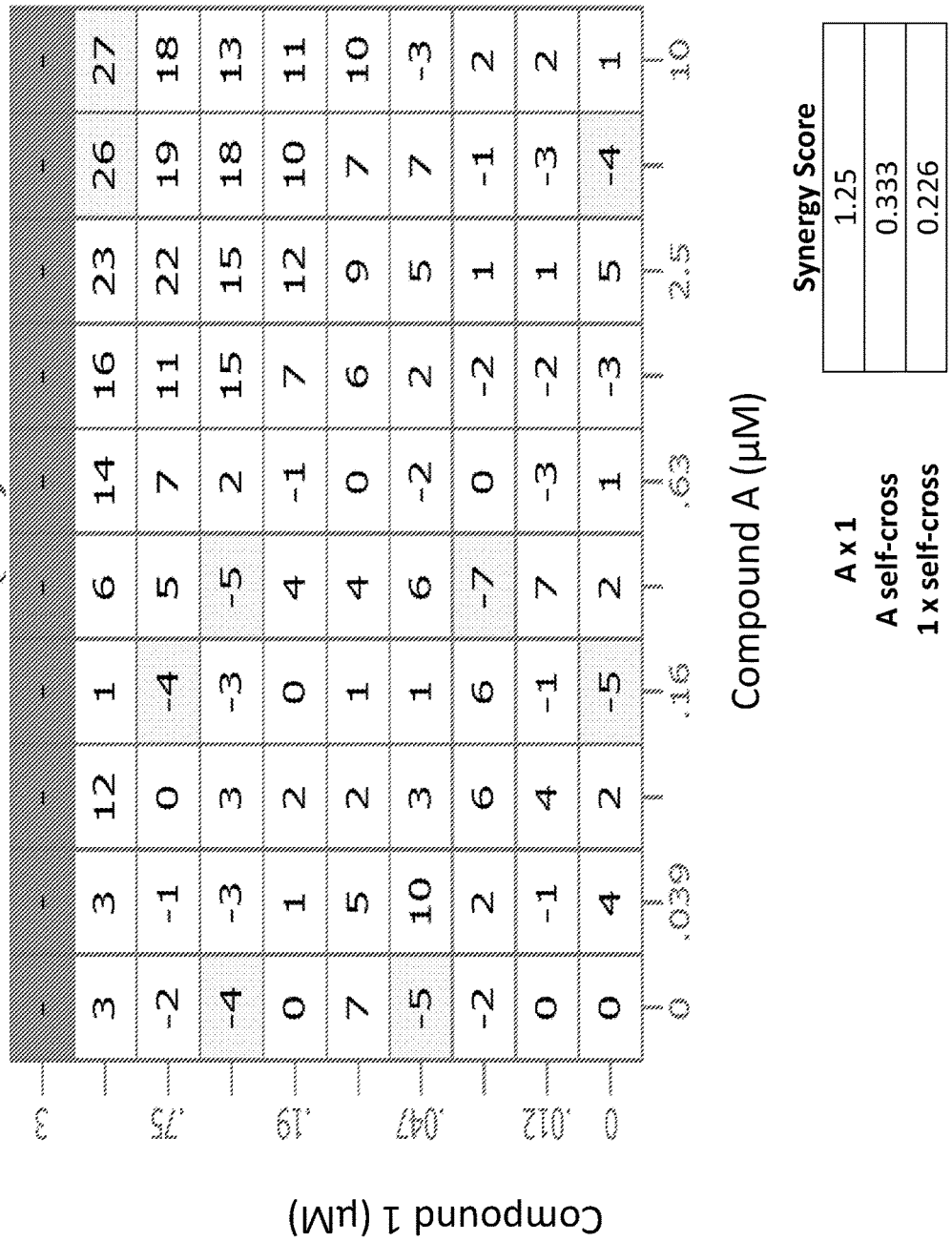
Figure 2a-Example 2; A375sq2 cells

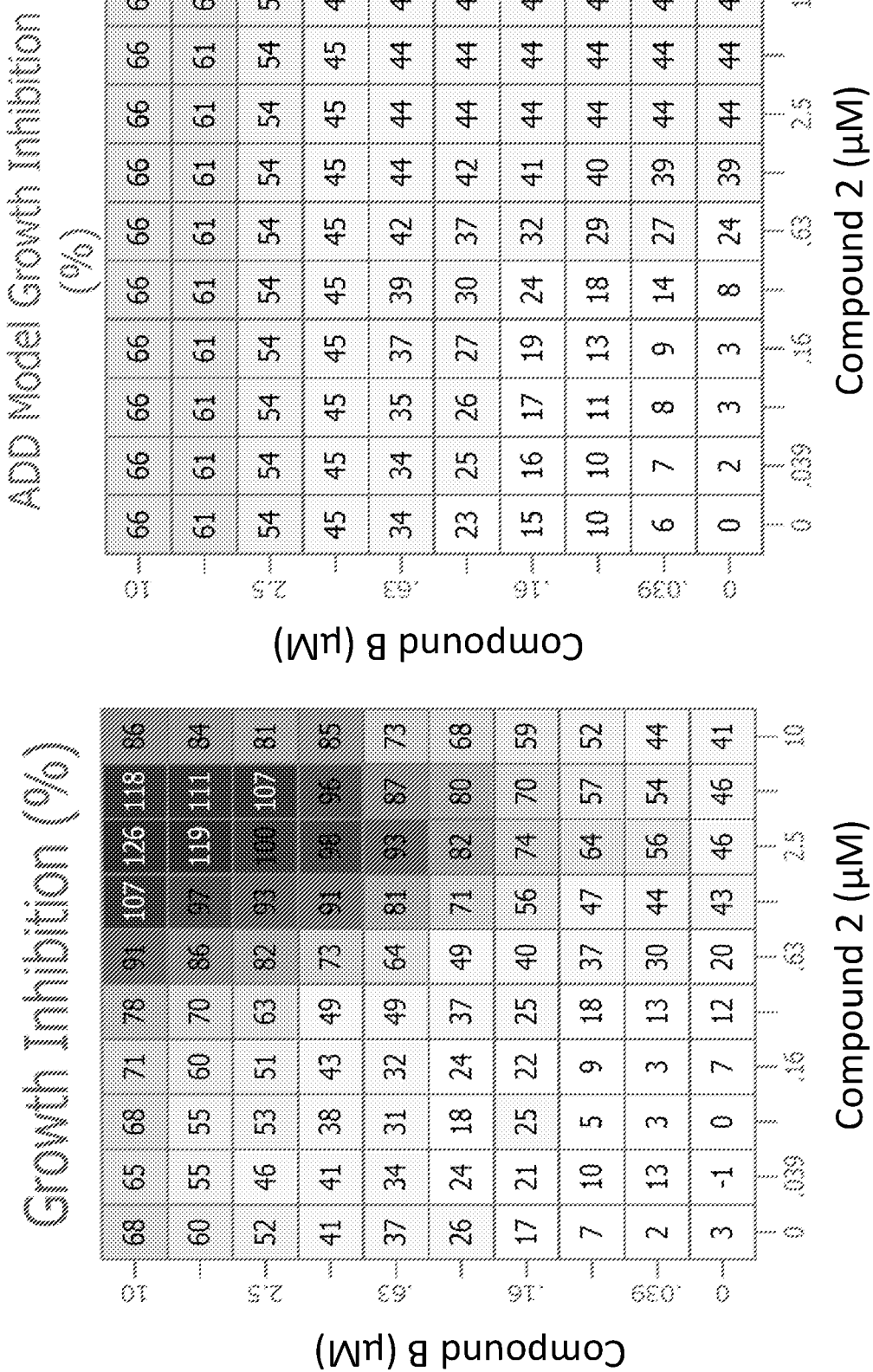
Figure 3-Example 3; A-427 cells

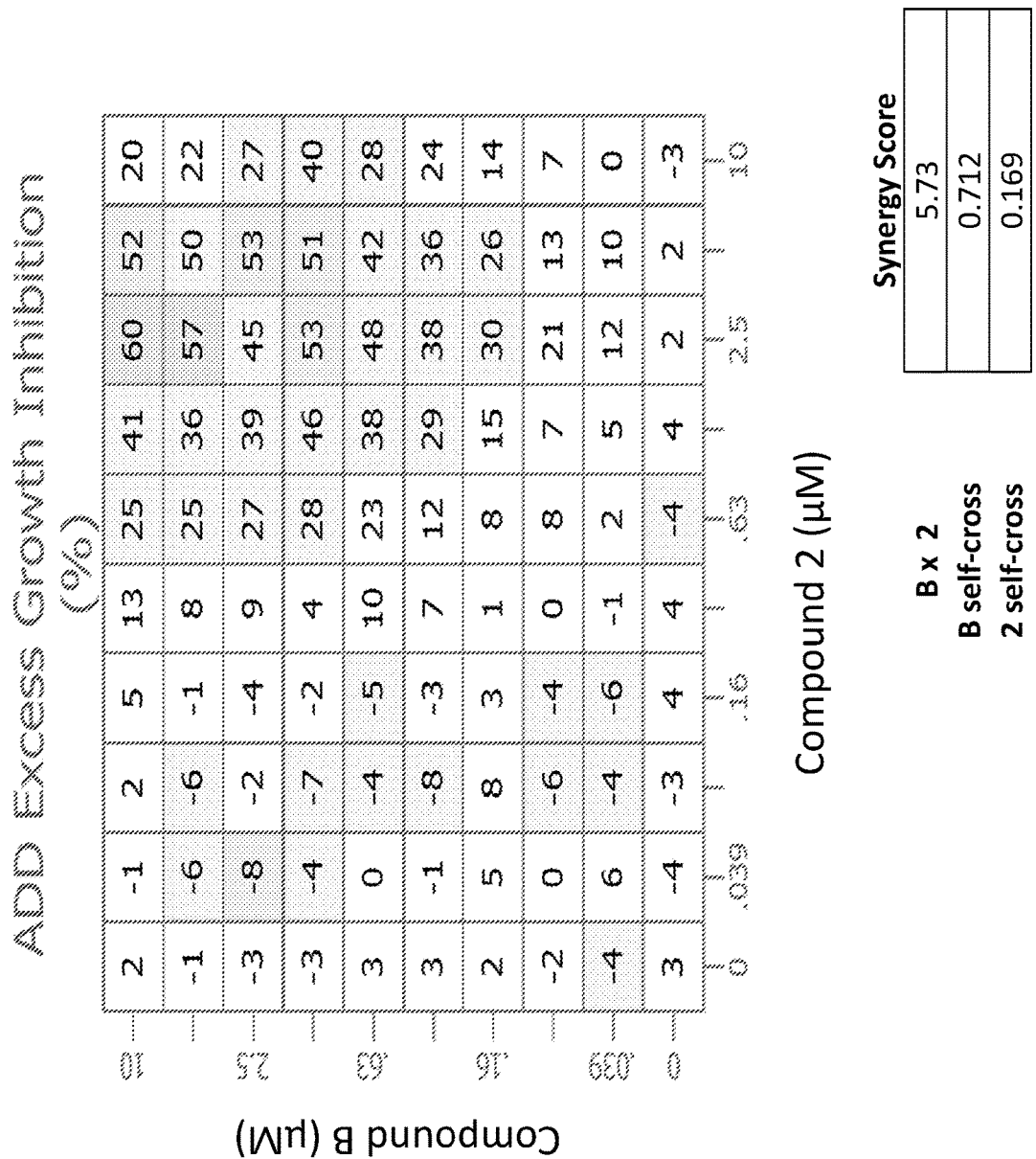

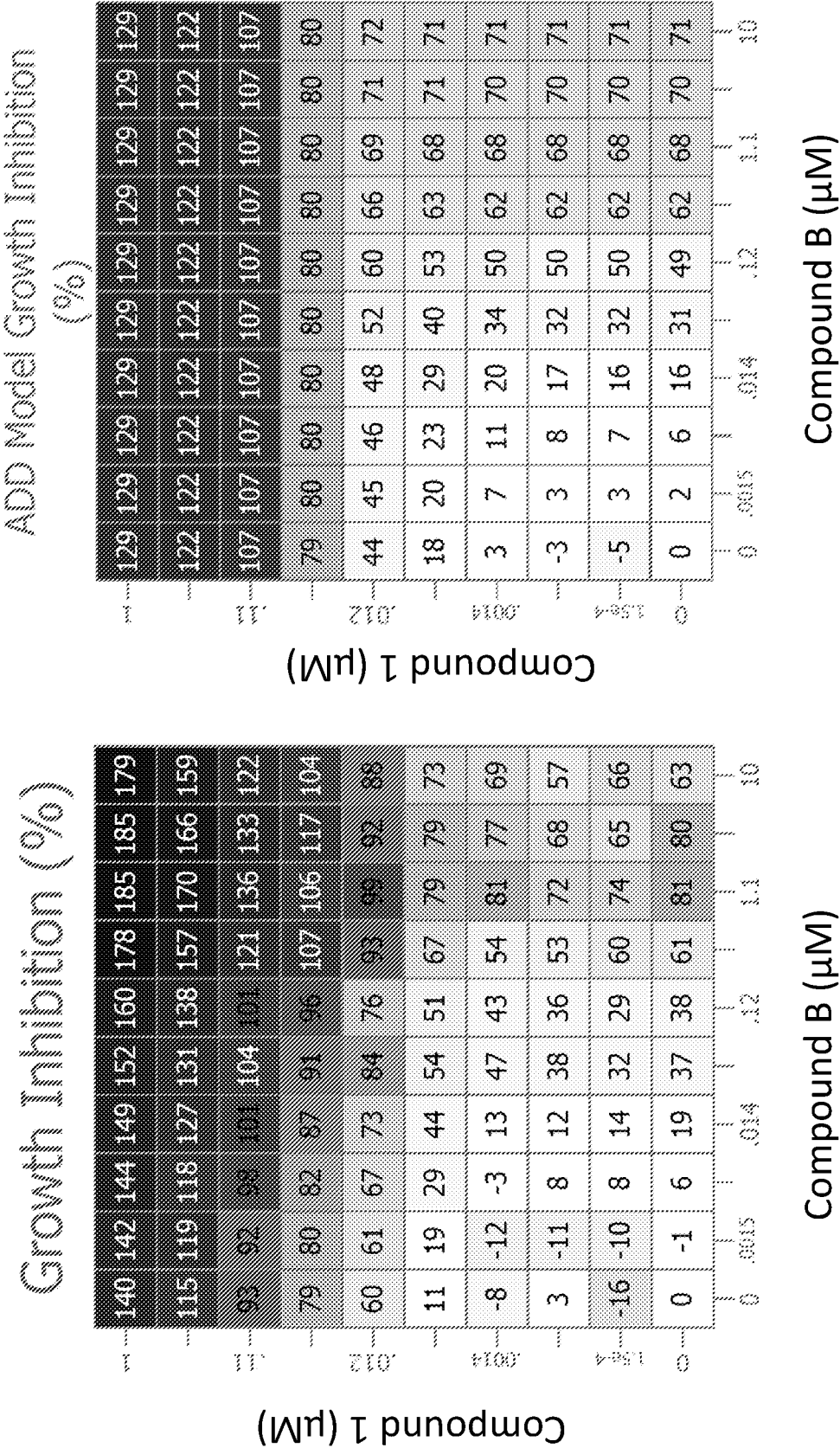
Figure 4-Example 4; C32 cells

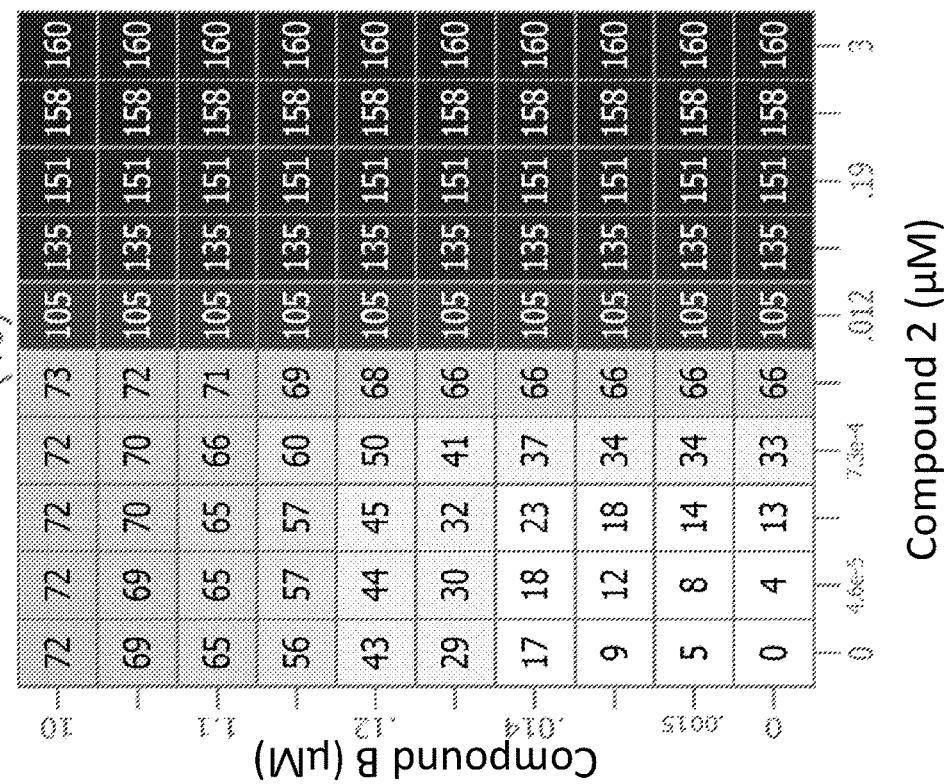
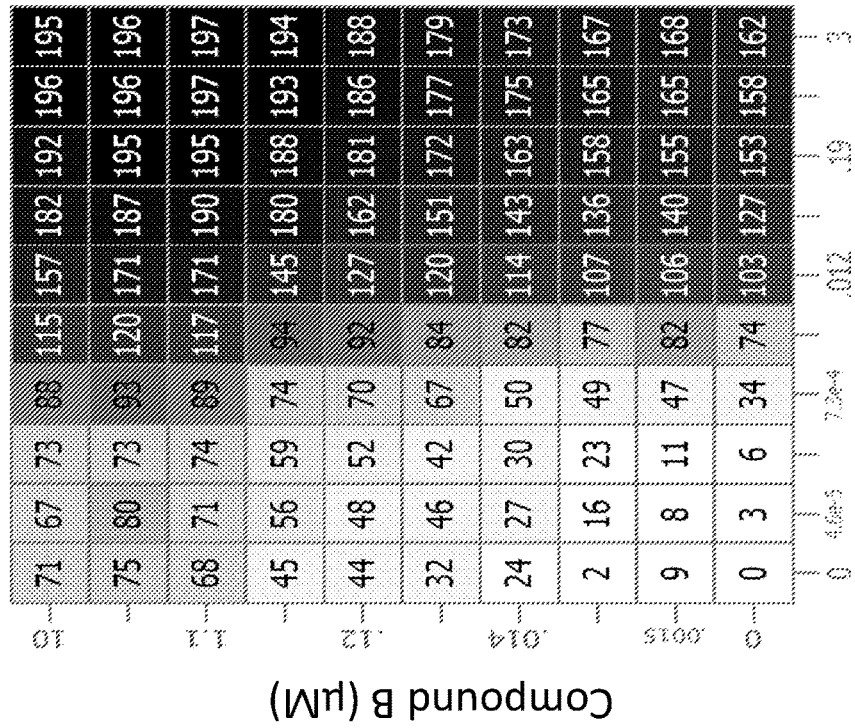
Figure 5-Example 5; C32 cells

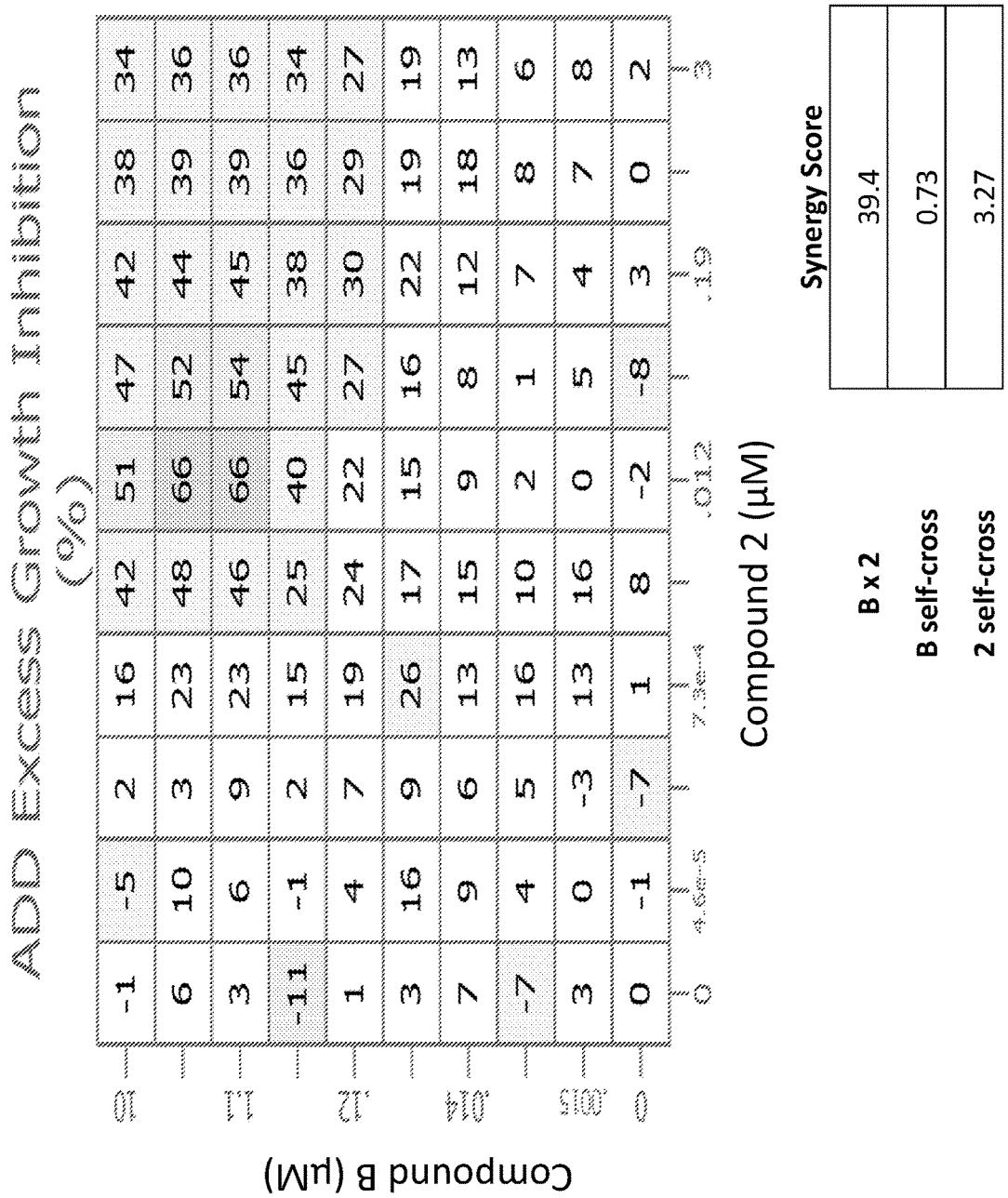
Figure 5a-Example 5; C32 cells

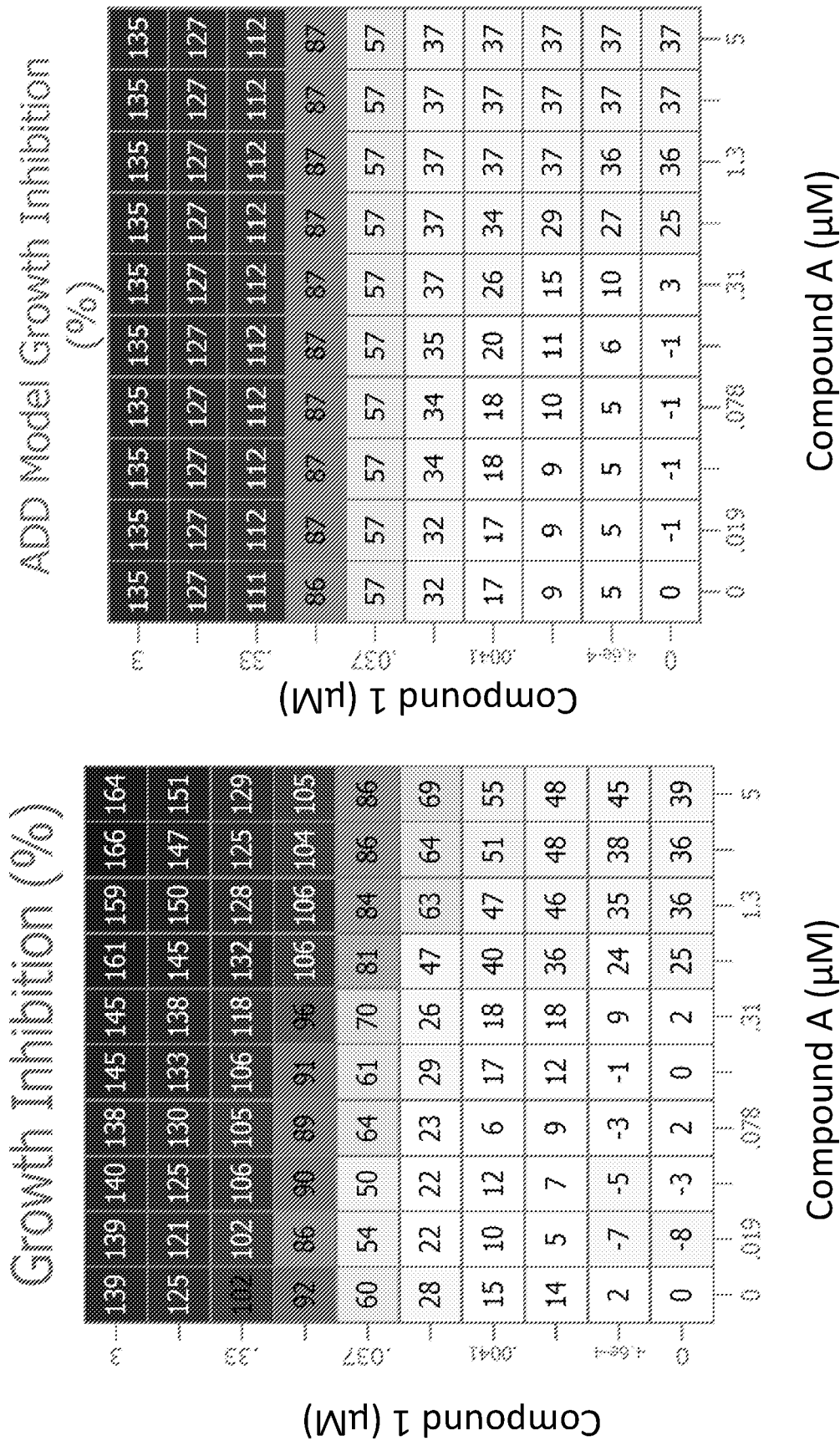

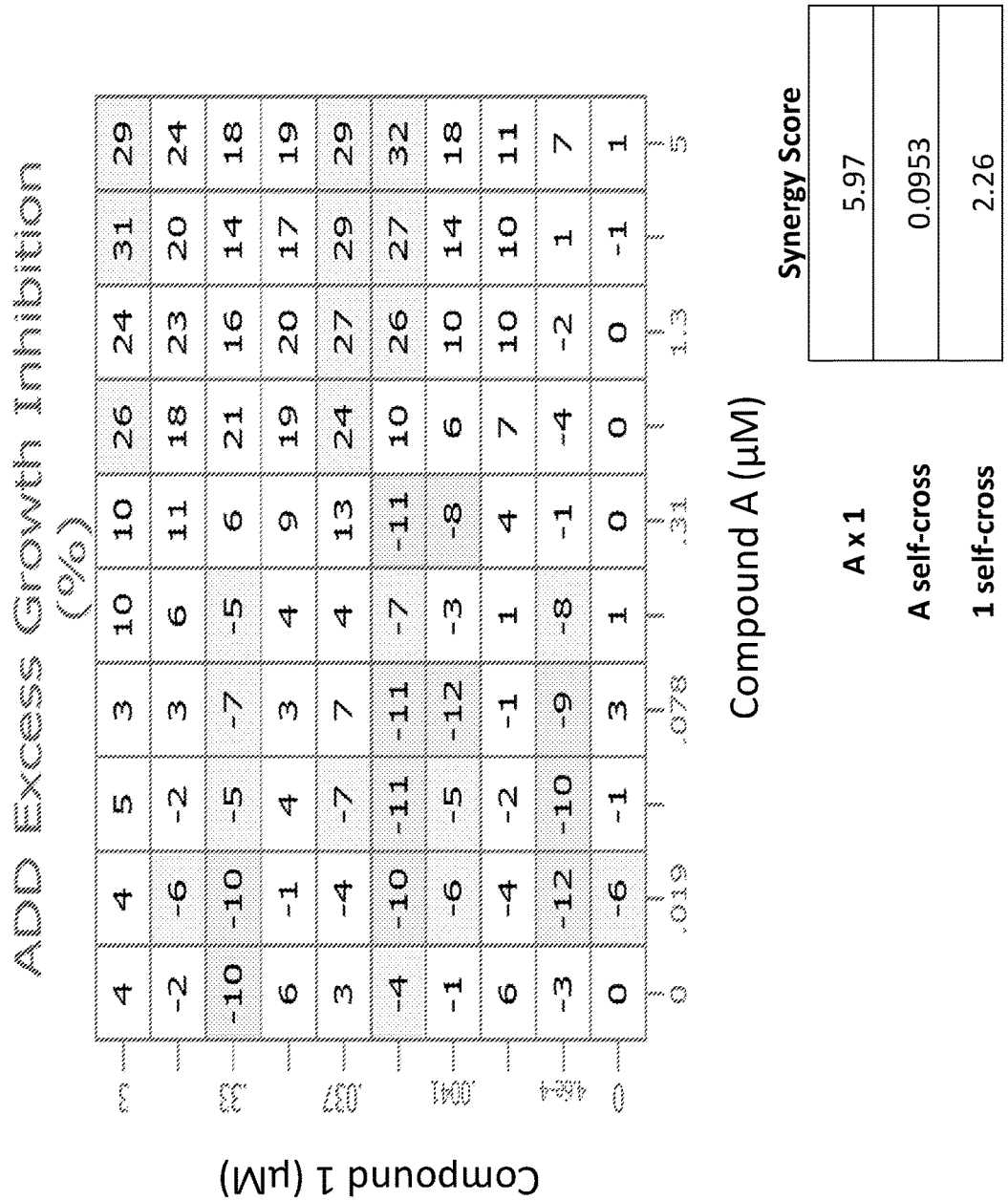

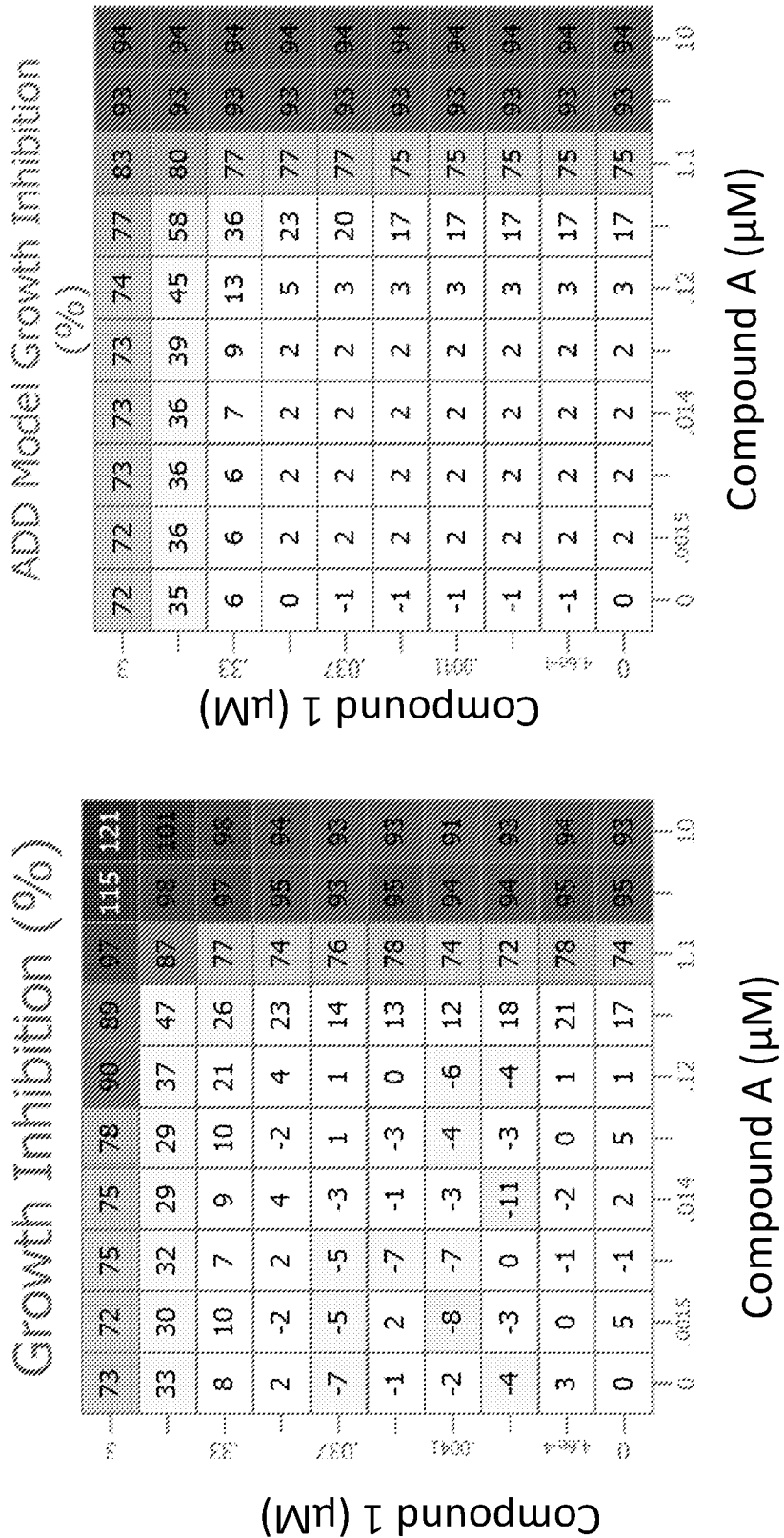
Figure 7-Example 7; LS 174T cells

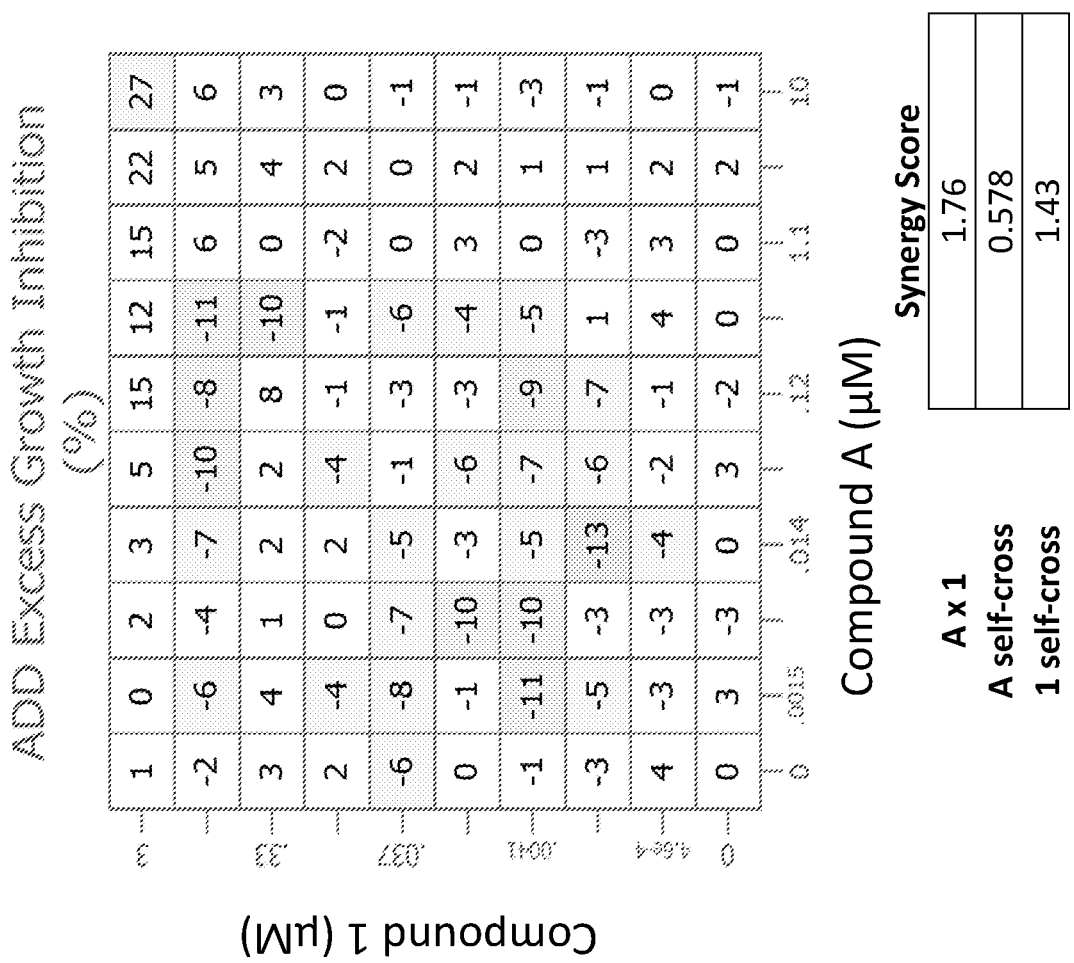
Figure 7a-Example 7; LS 174T cells

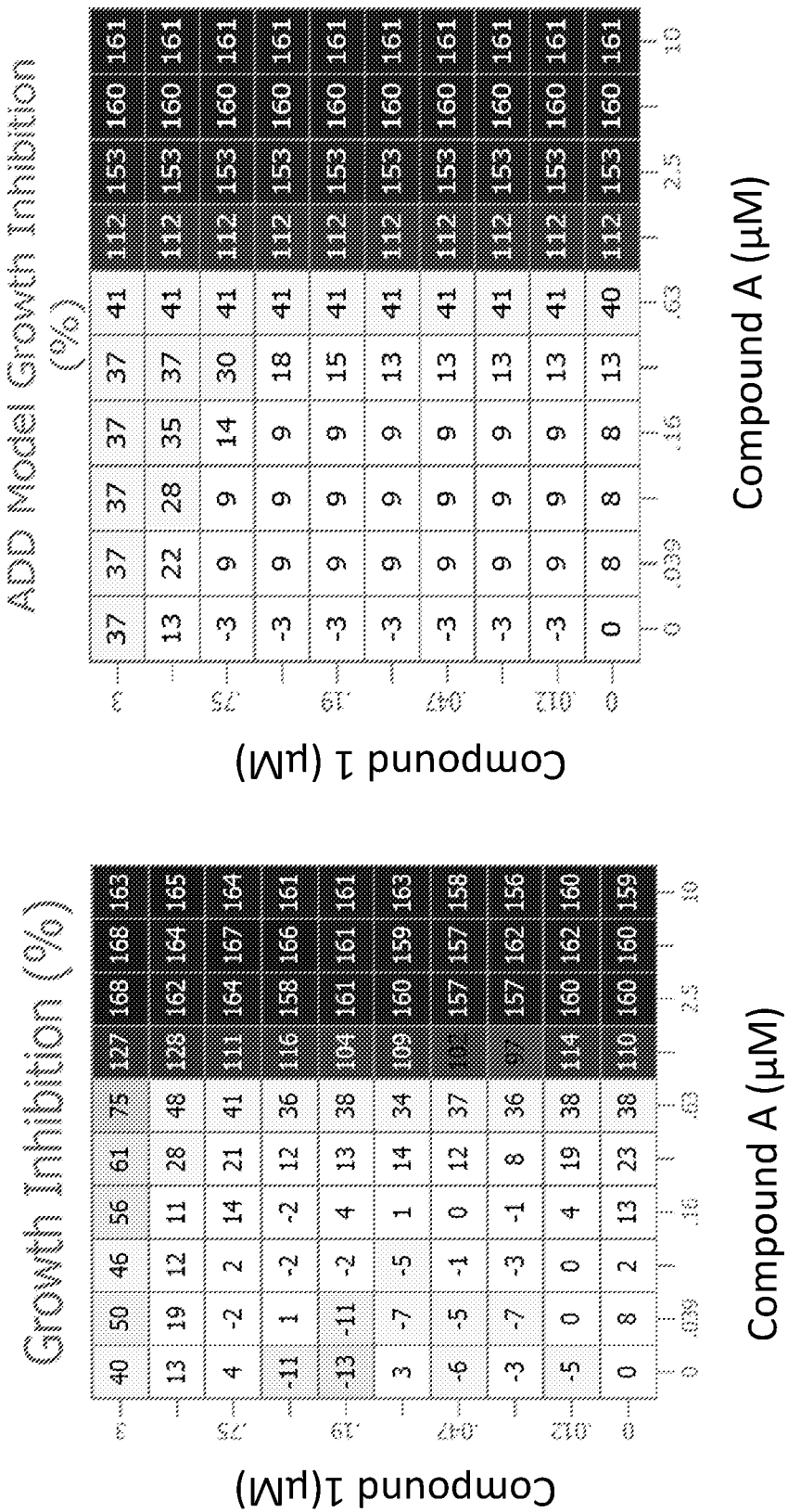
Figure 8-Example 8; MCF7 cells

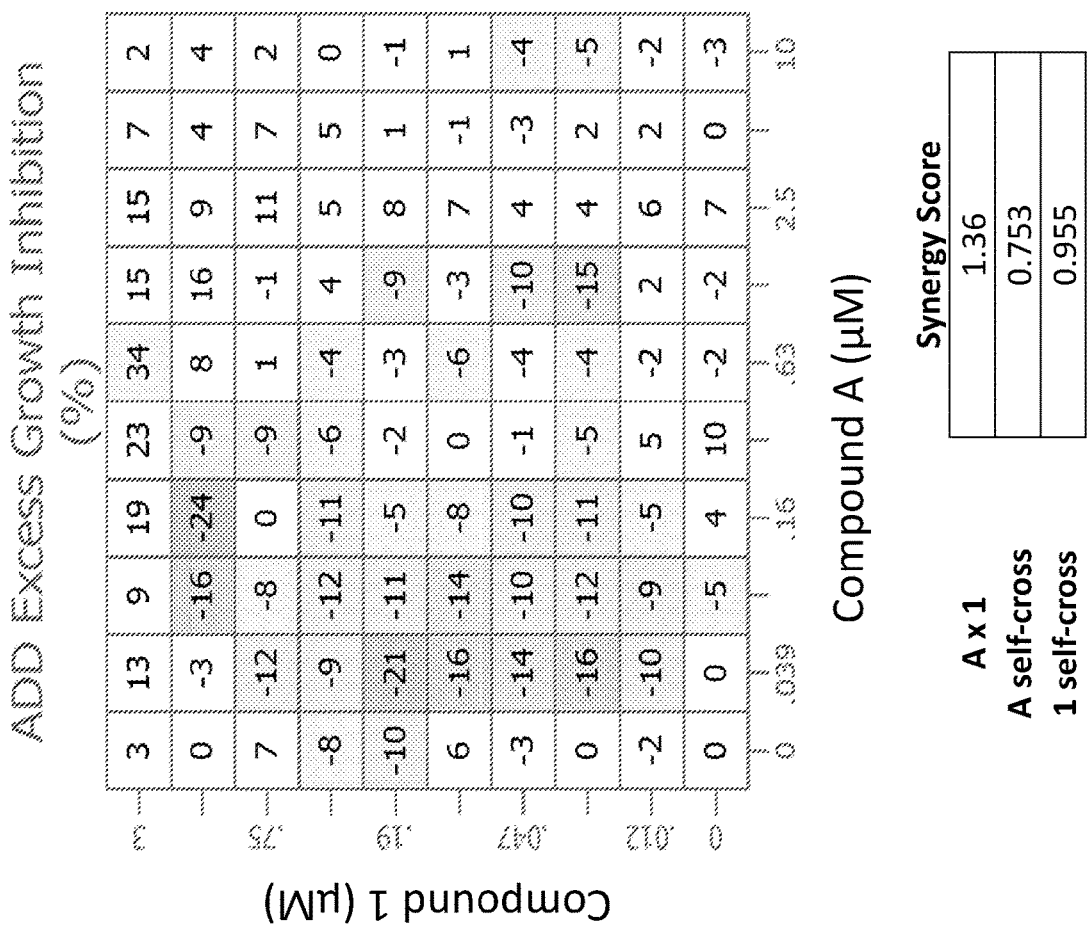
Figure 8a-Example 8, MCF7 cells

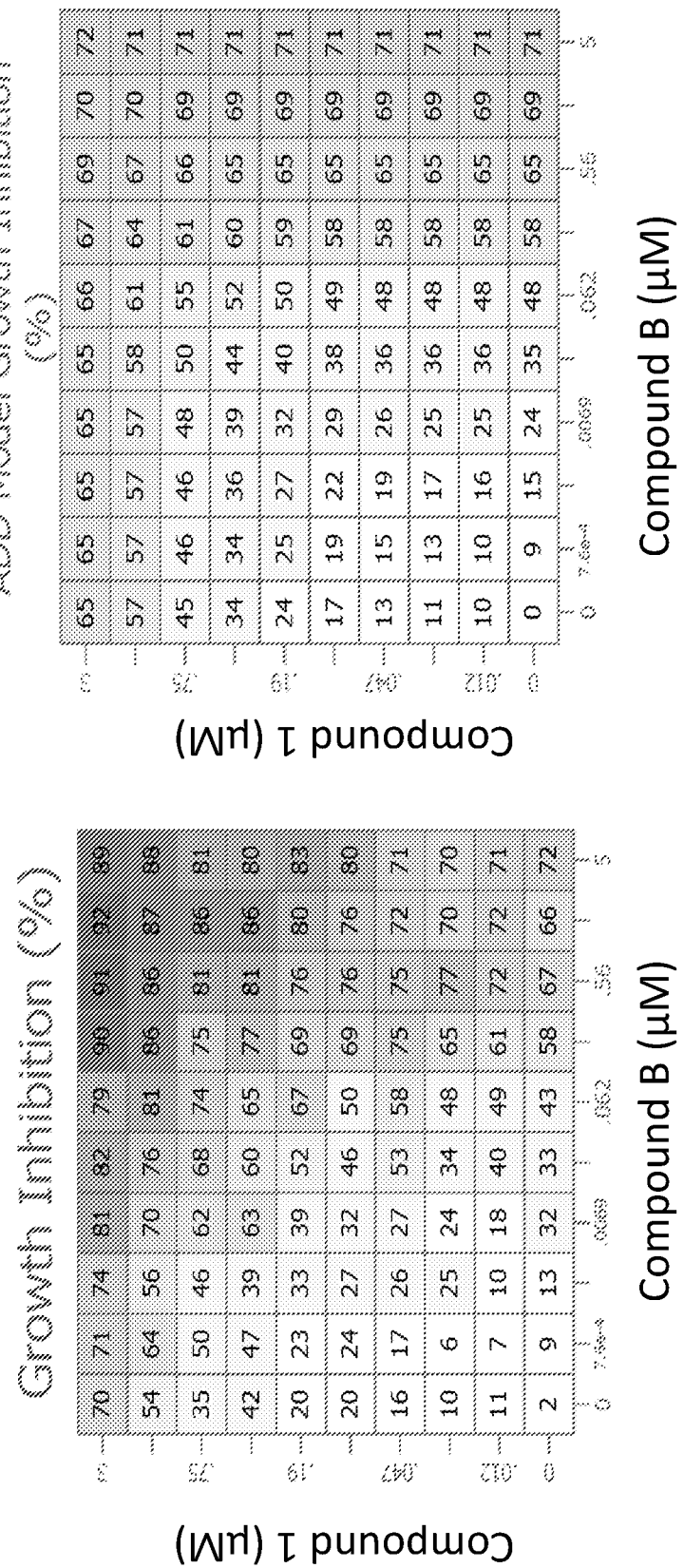
Figure 9-Example 9; NCI-H1666 cells

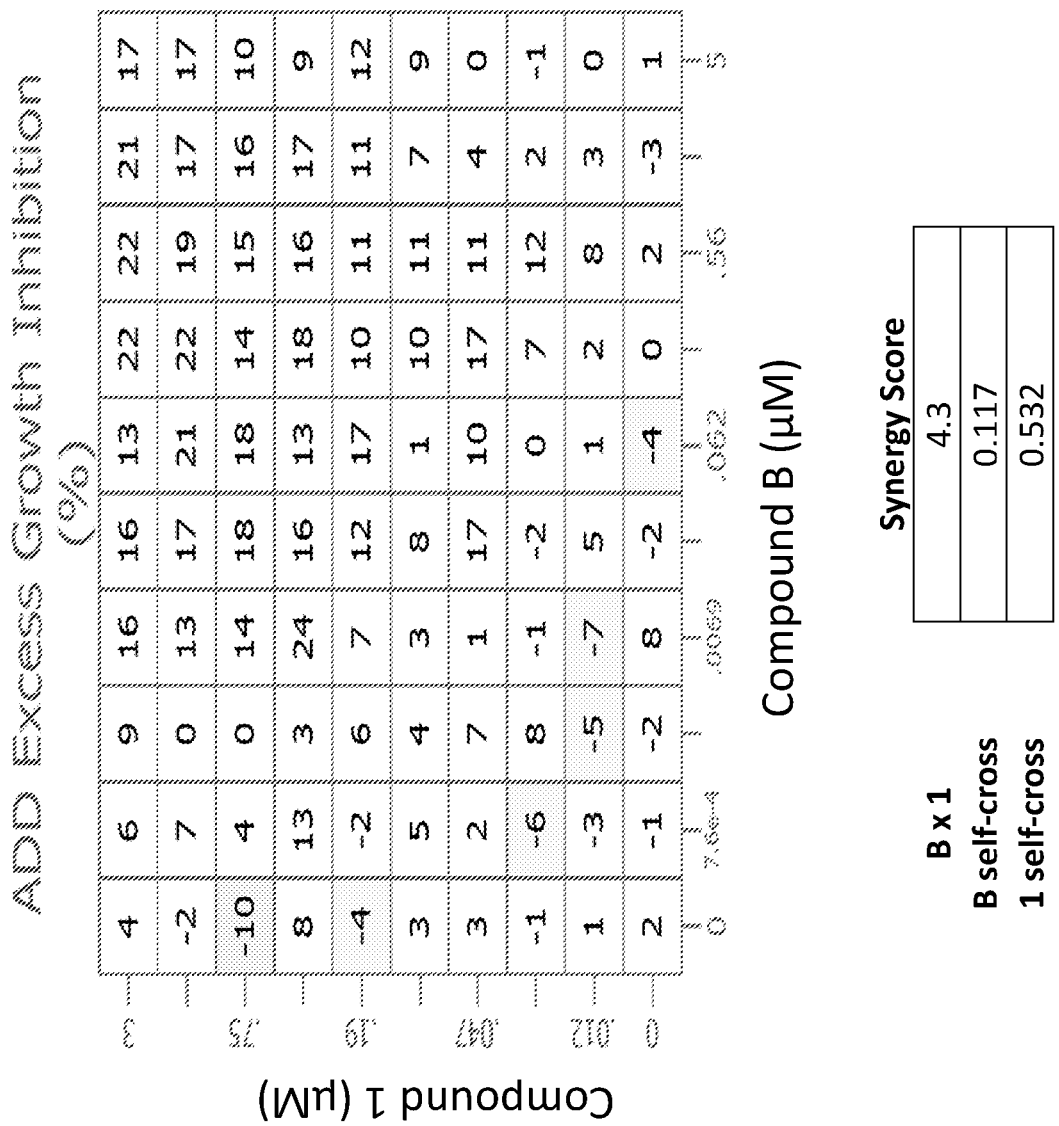
Figure 9a-Example 9; NCI-H1666 cells

Figure 10-Example 10; NCI-H1666 cells
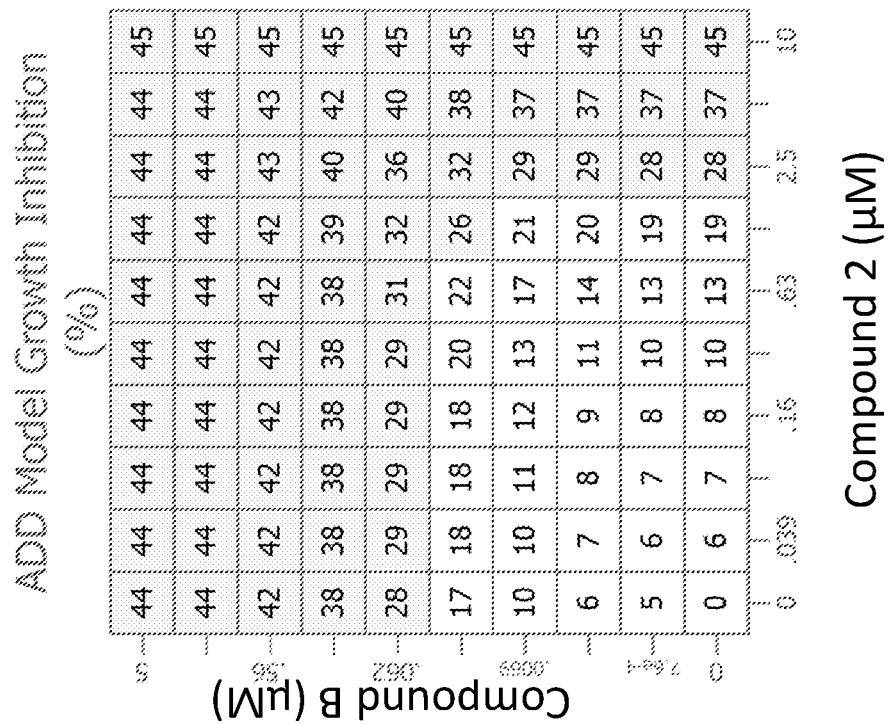
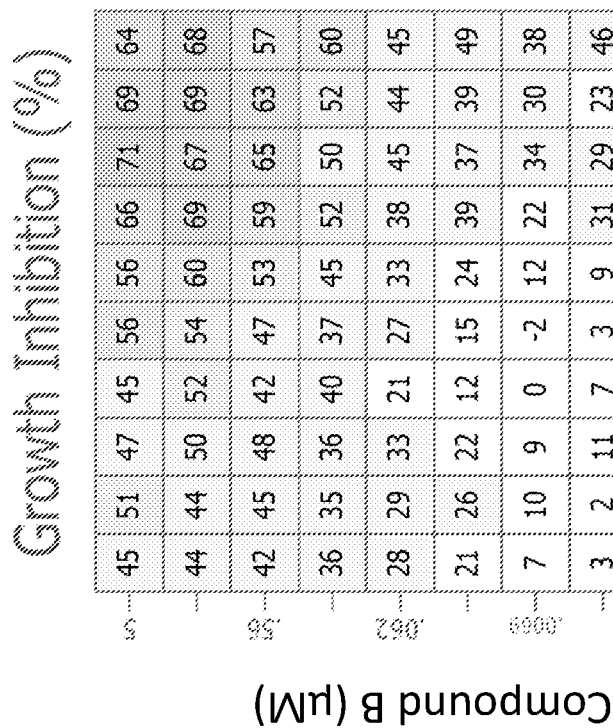

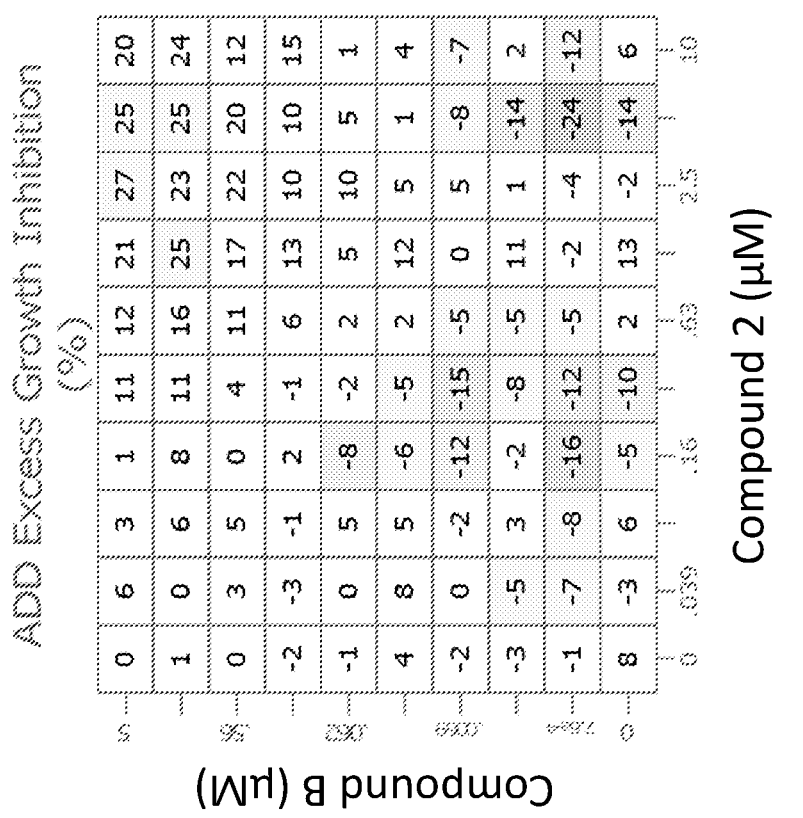
Figure 10a-Example 10; NCI-H1666 cells

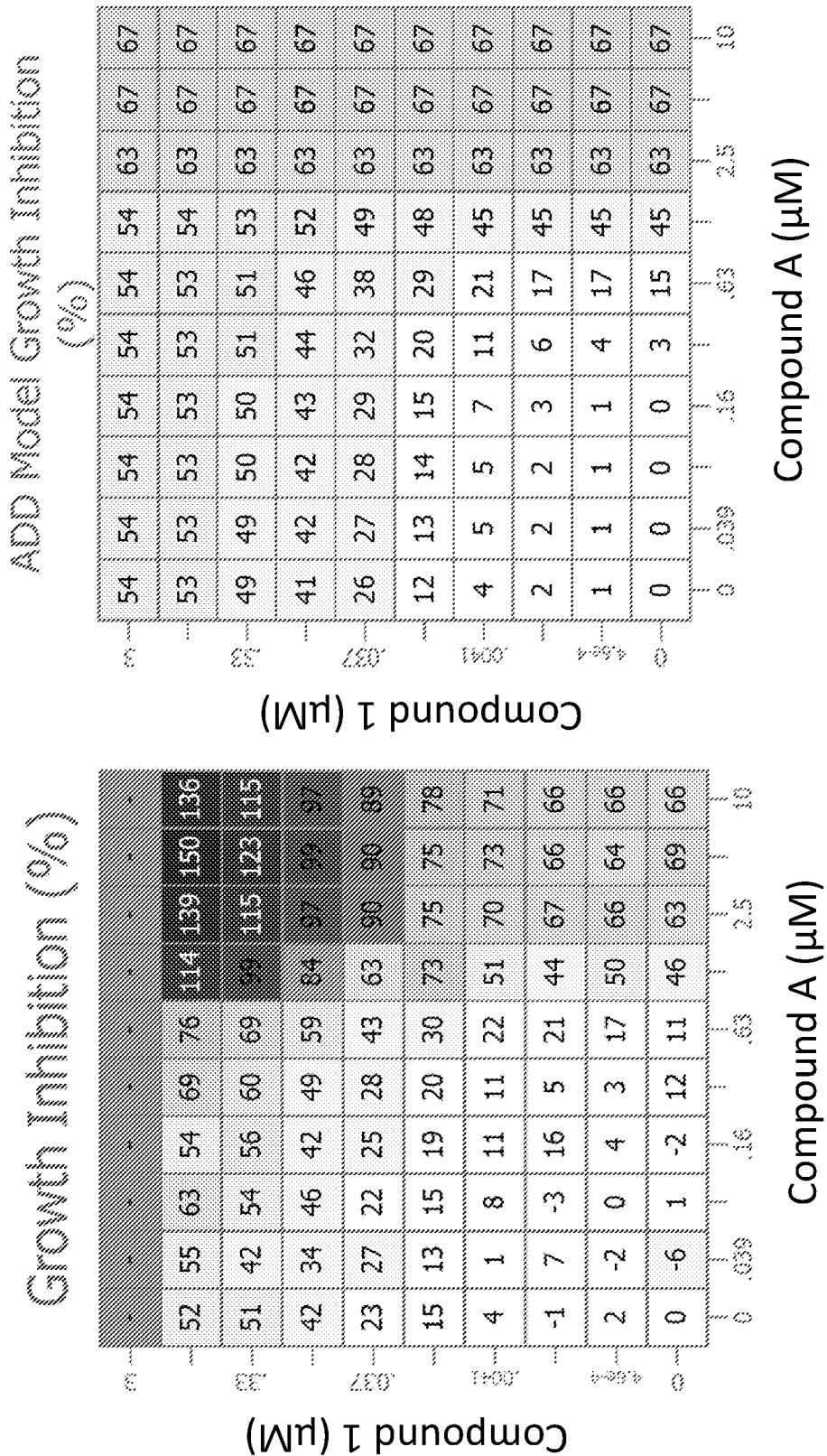
Figure 11-Example 11; RKO cells

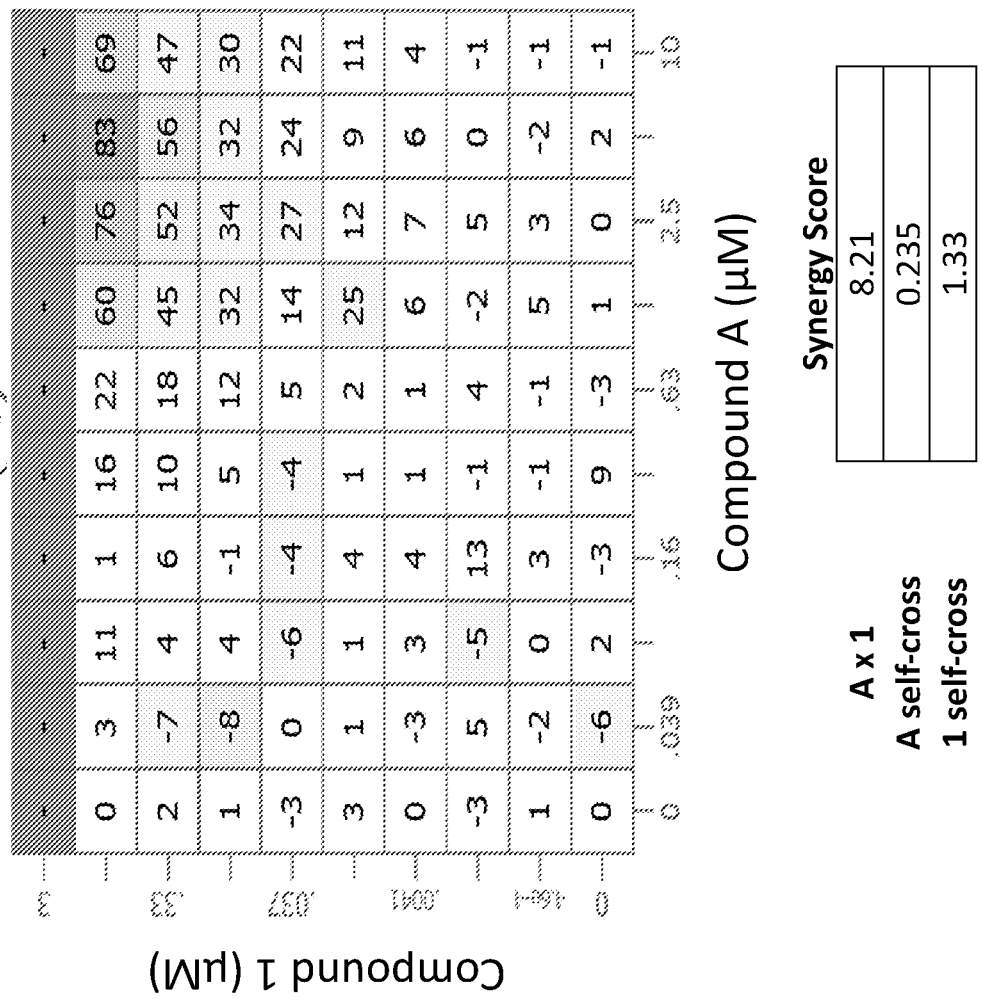
Figure 11a-Example 11; RKO cells

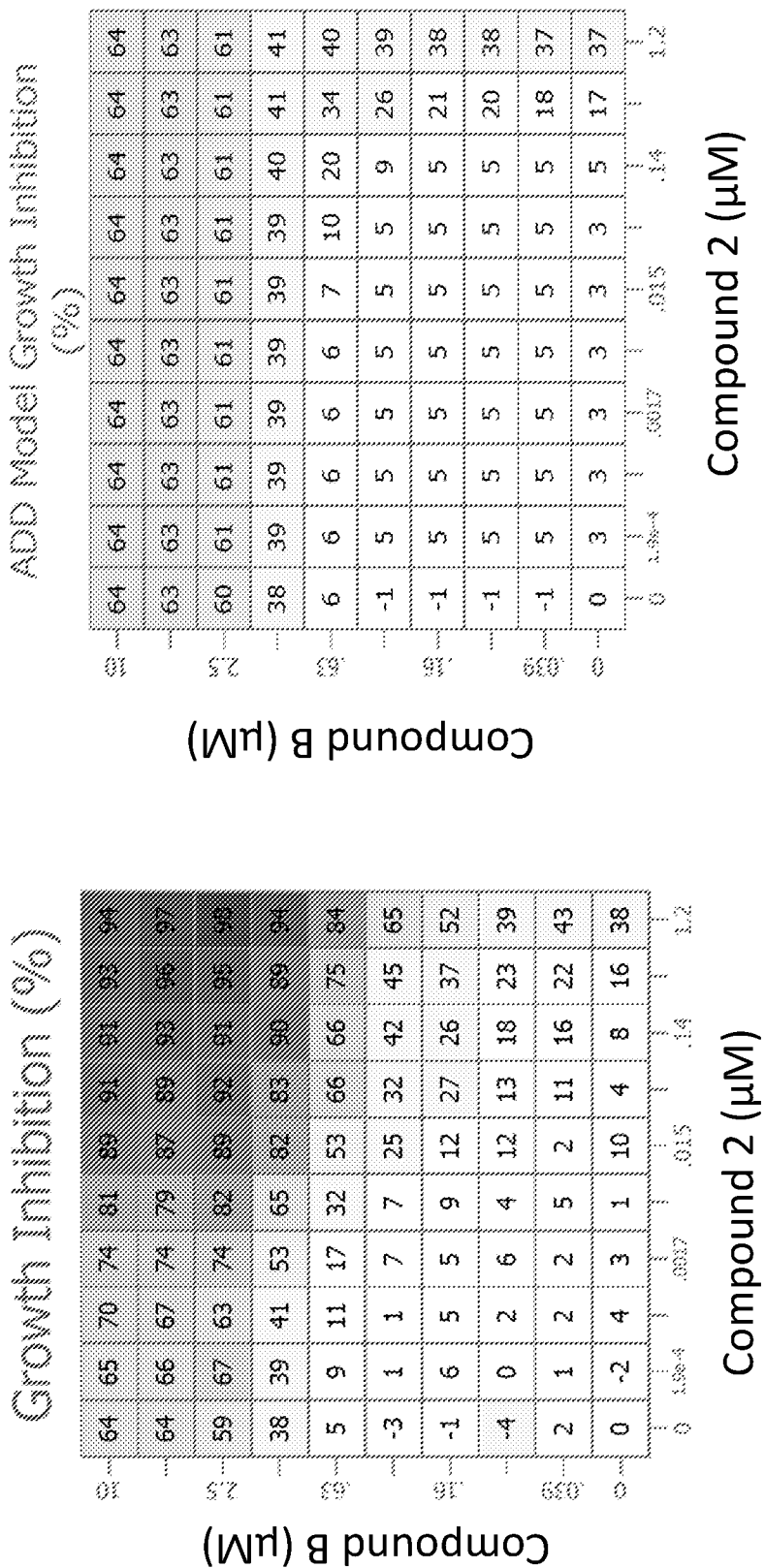
Figure 12-Example 12; RKO cells

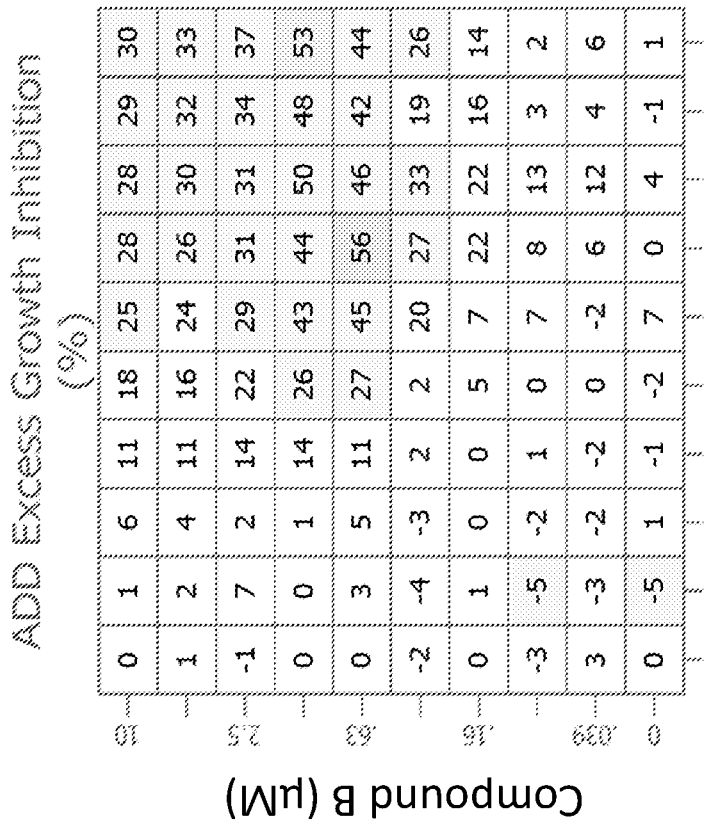

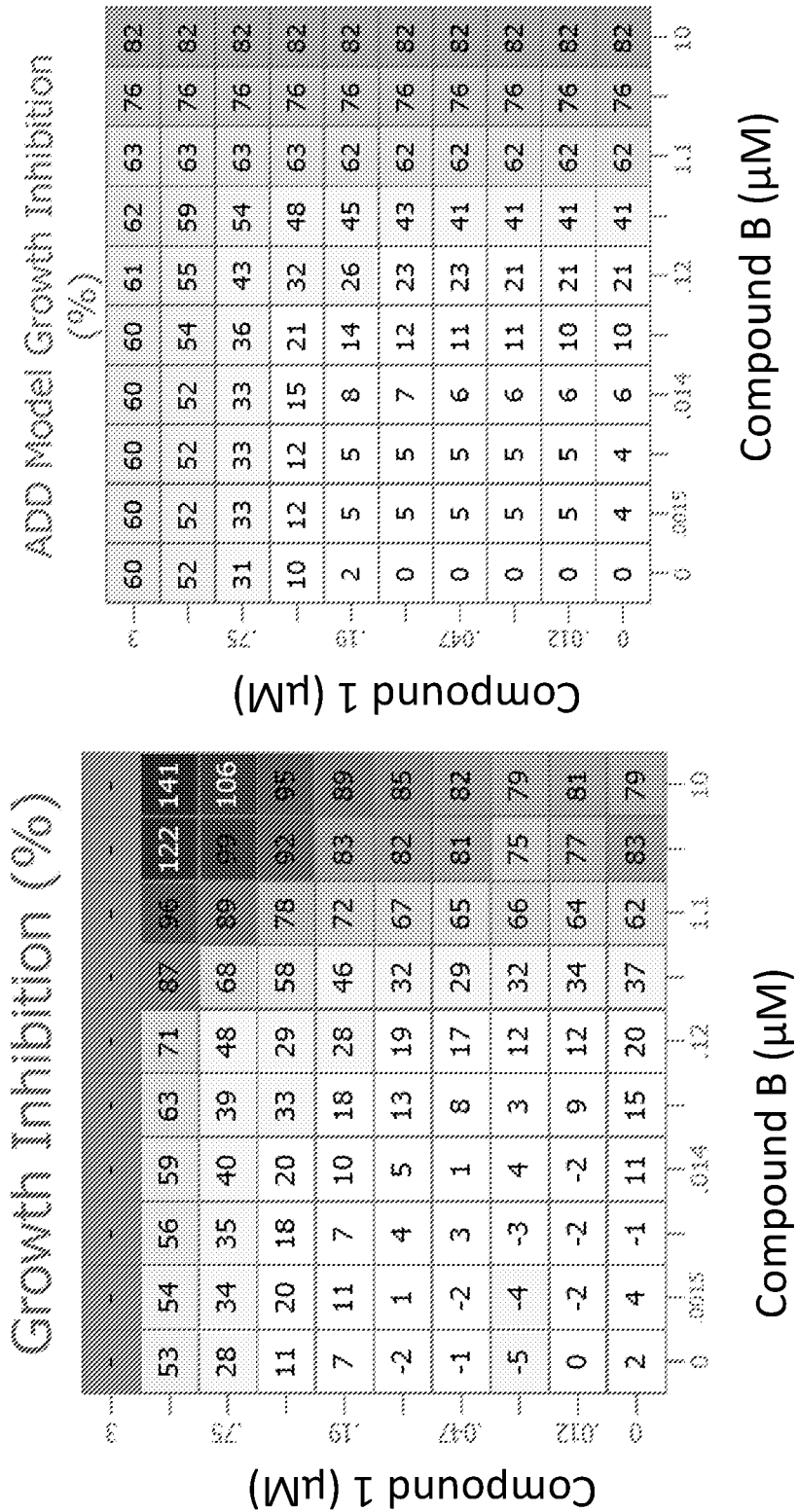
Figure 13-Example 13; RT4 cells

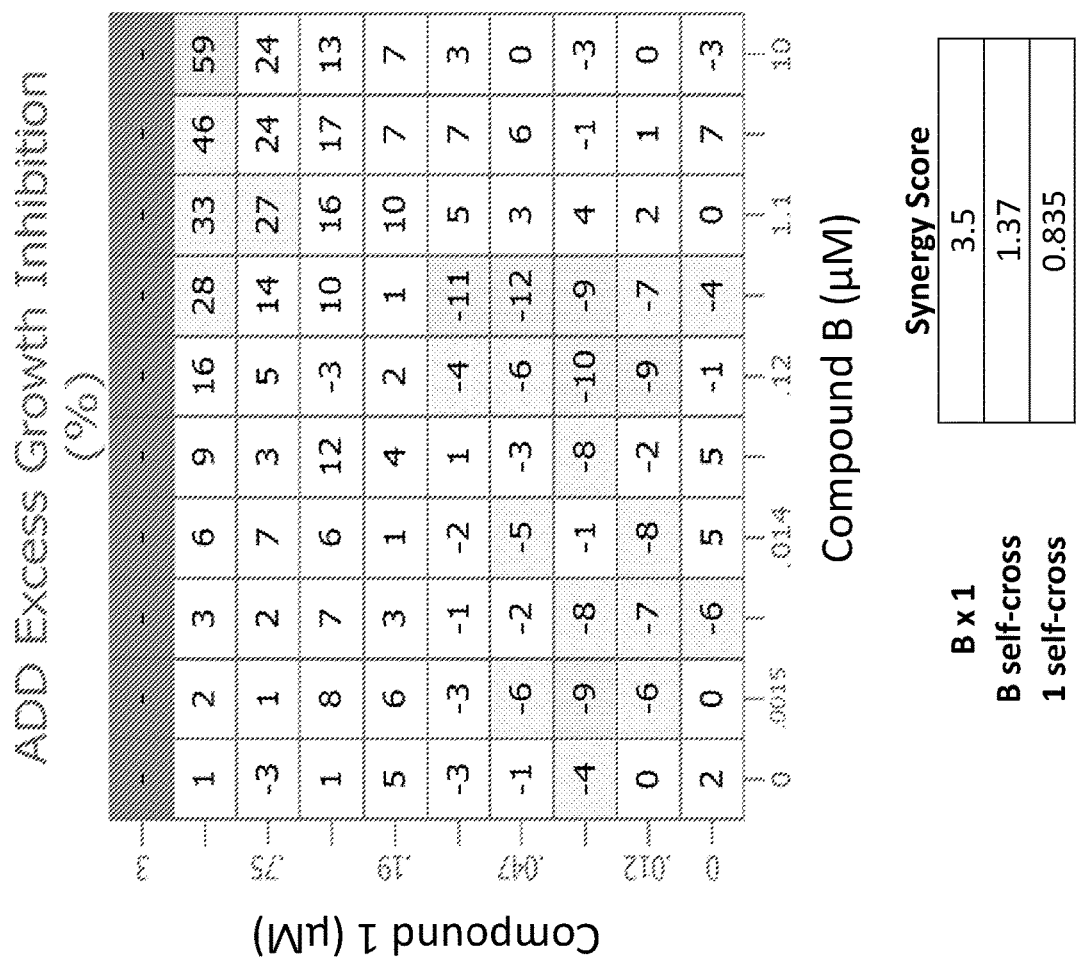
Figure 13a-Example 13; RT4 cells

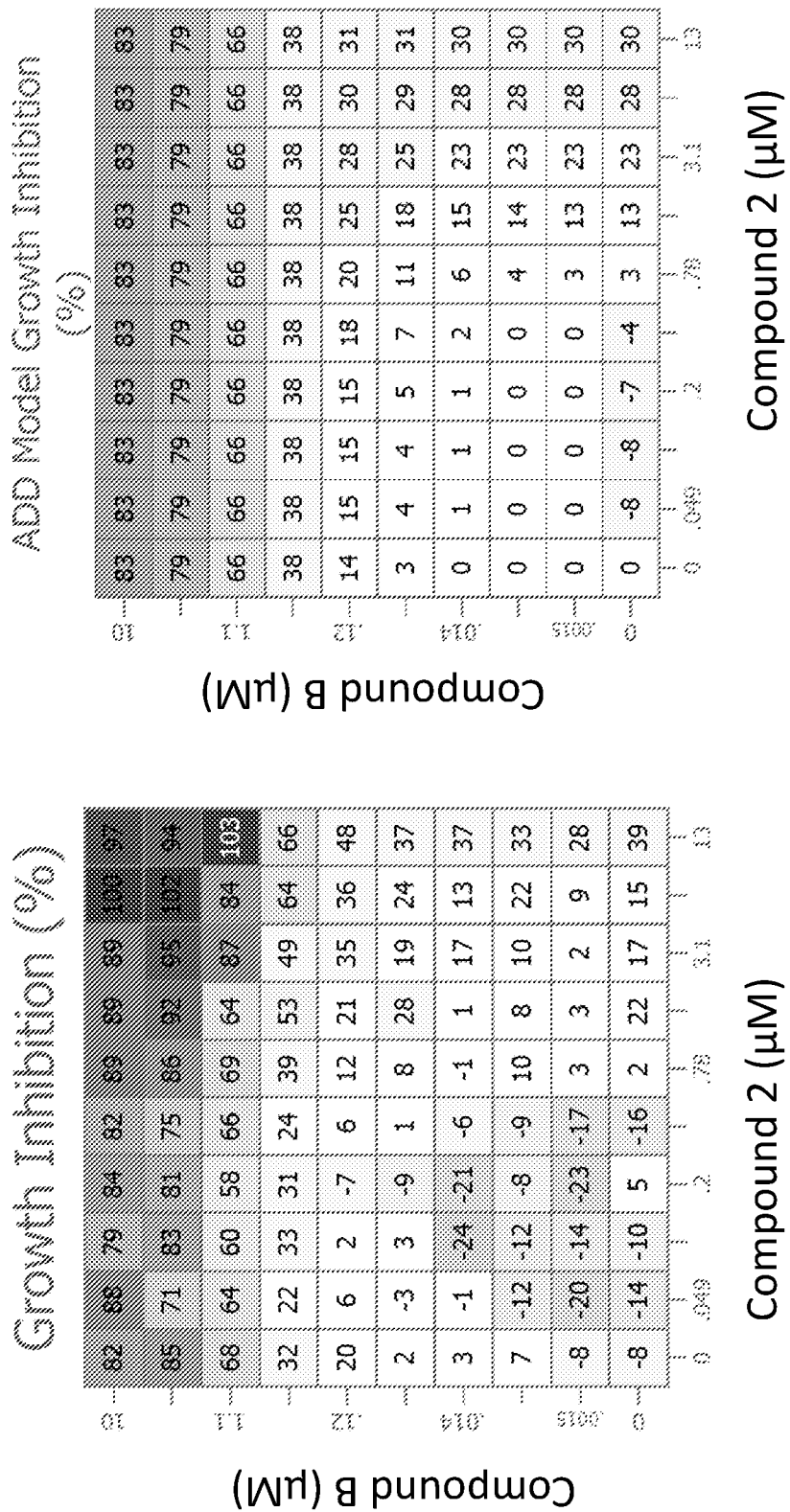
Figure 14-Example 14; RT4 cells

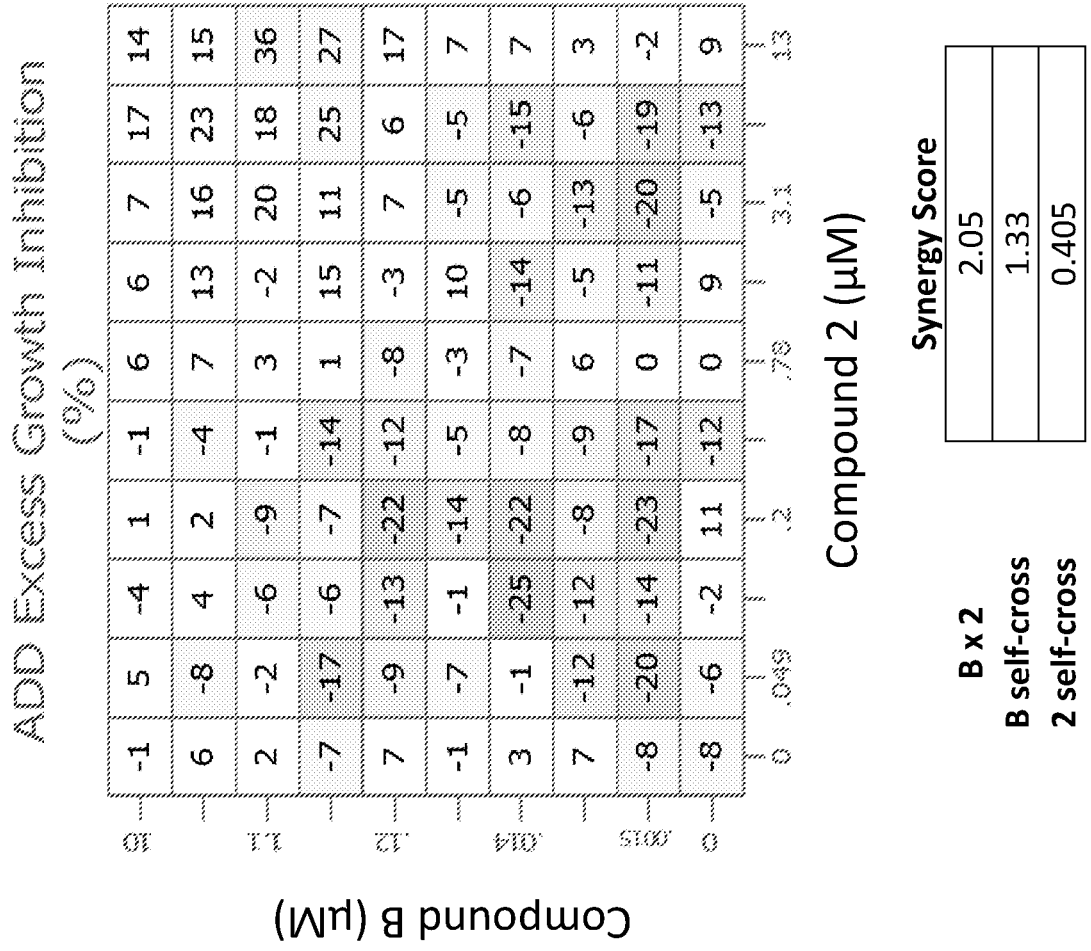
Figure 14a-Example 14; RT4 cells

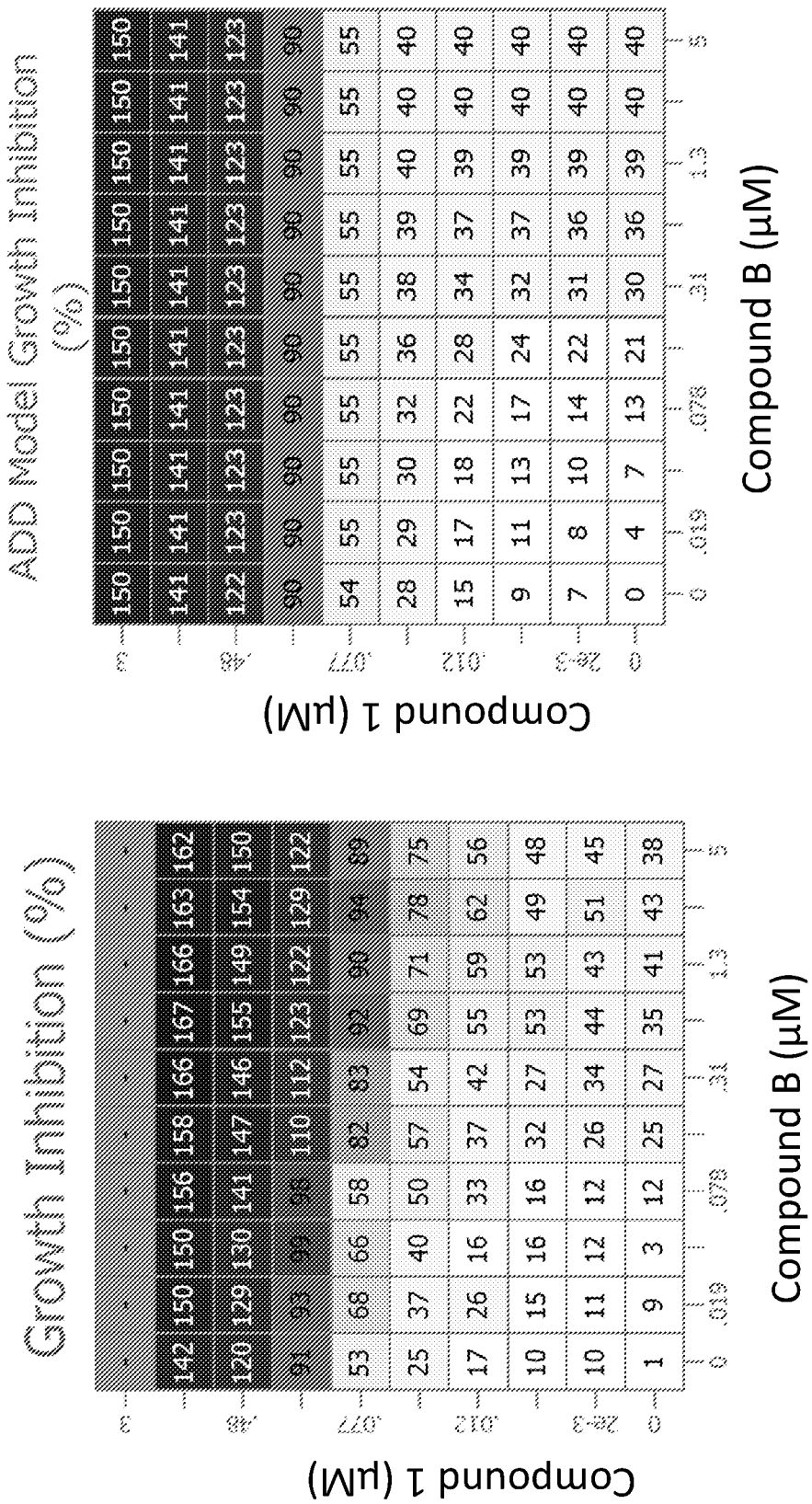
Figure 15-Example 15; SH-4 cells

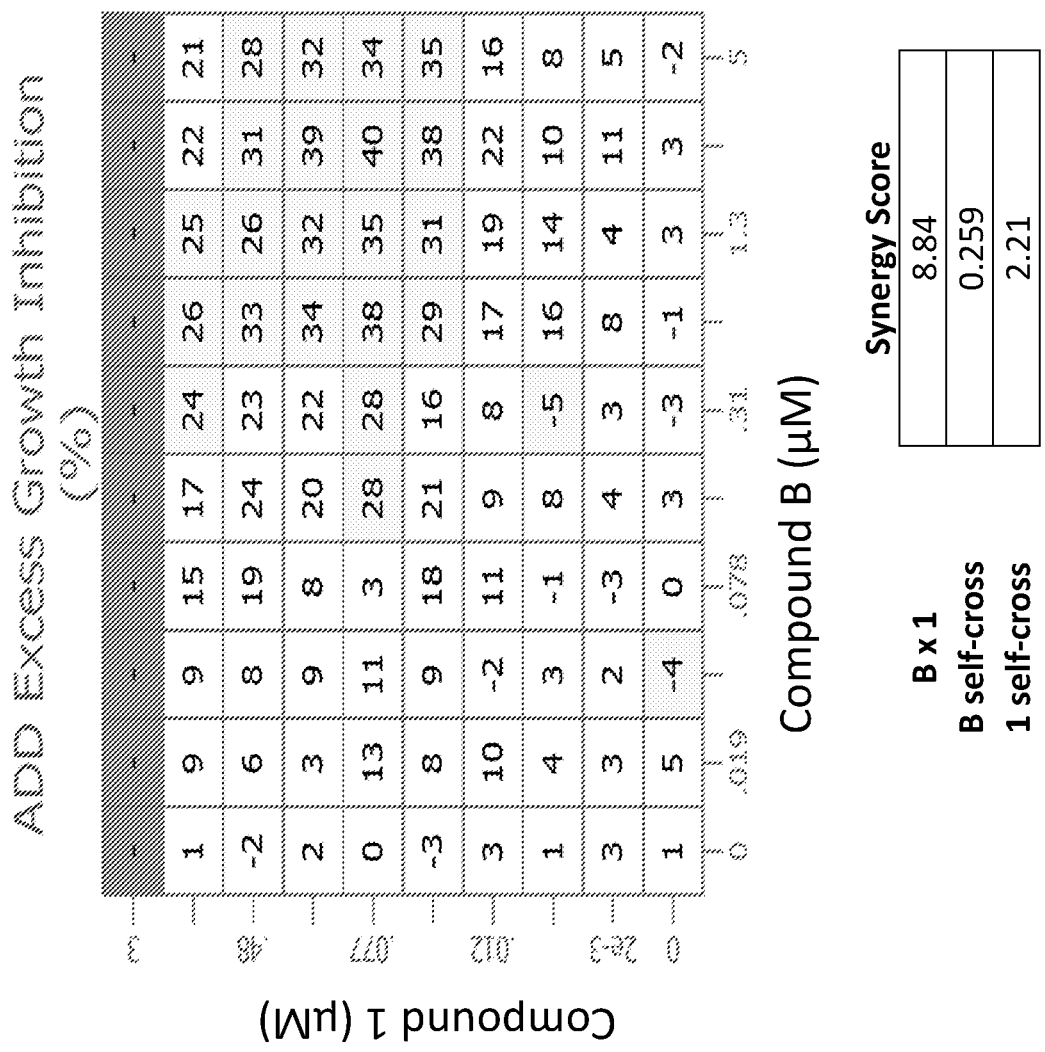
Figure 15a-Example 15; SH-4 cells

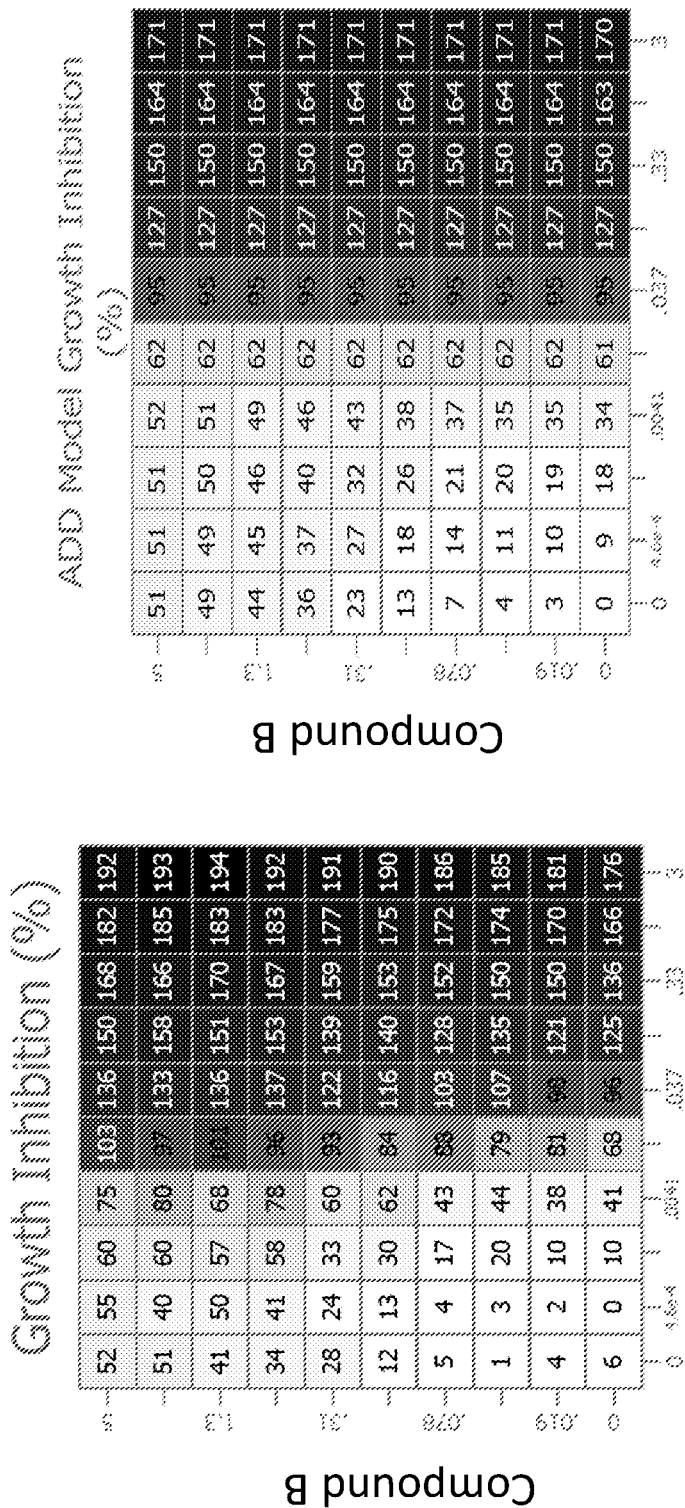
Figure 16-Example 16; SH-4 cells

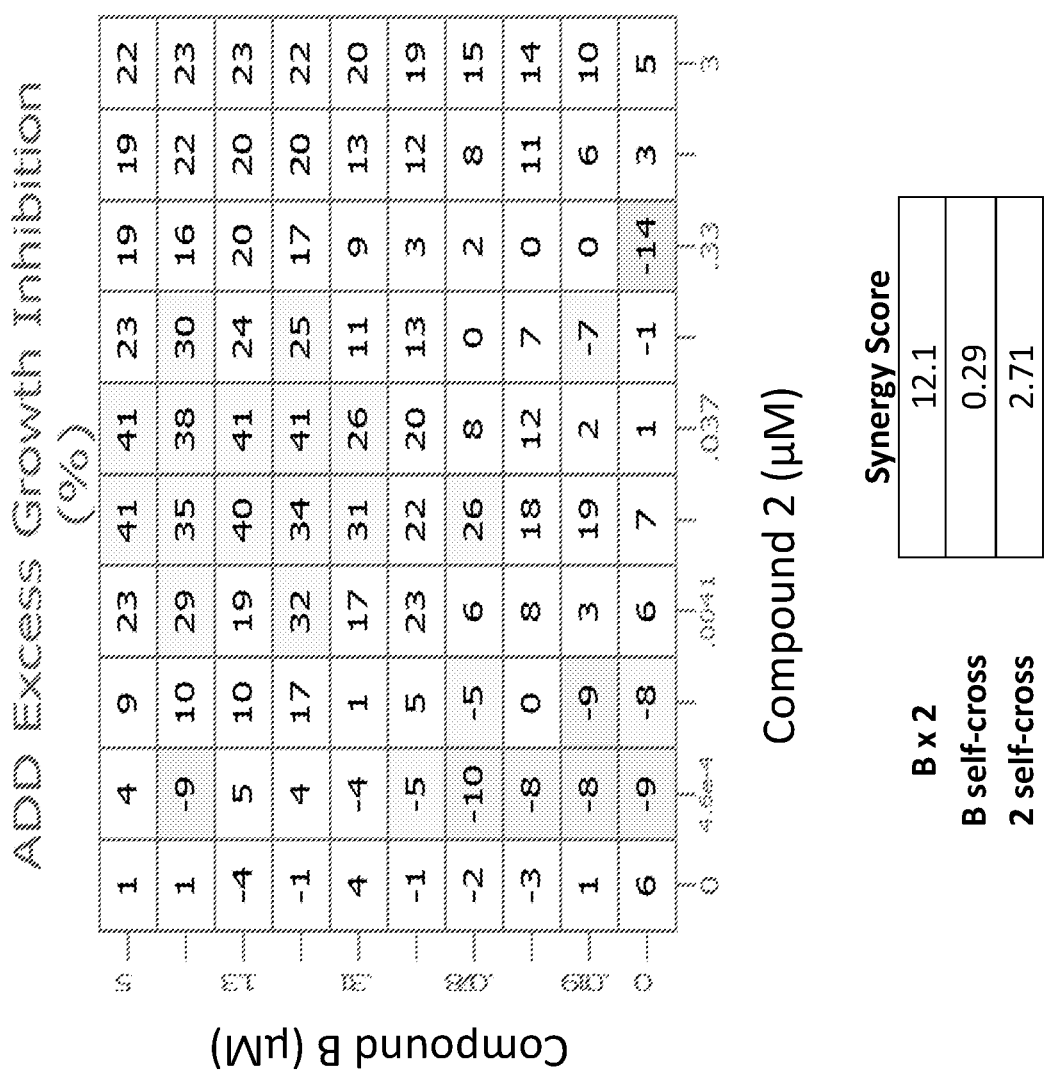
Figure 16a-Example 16; SH-4 cells

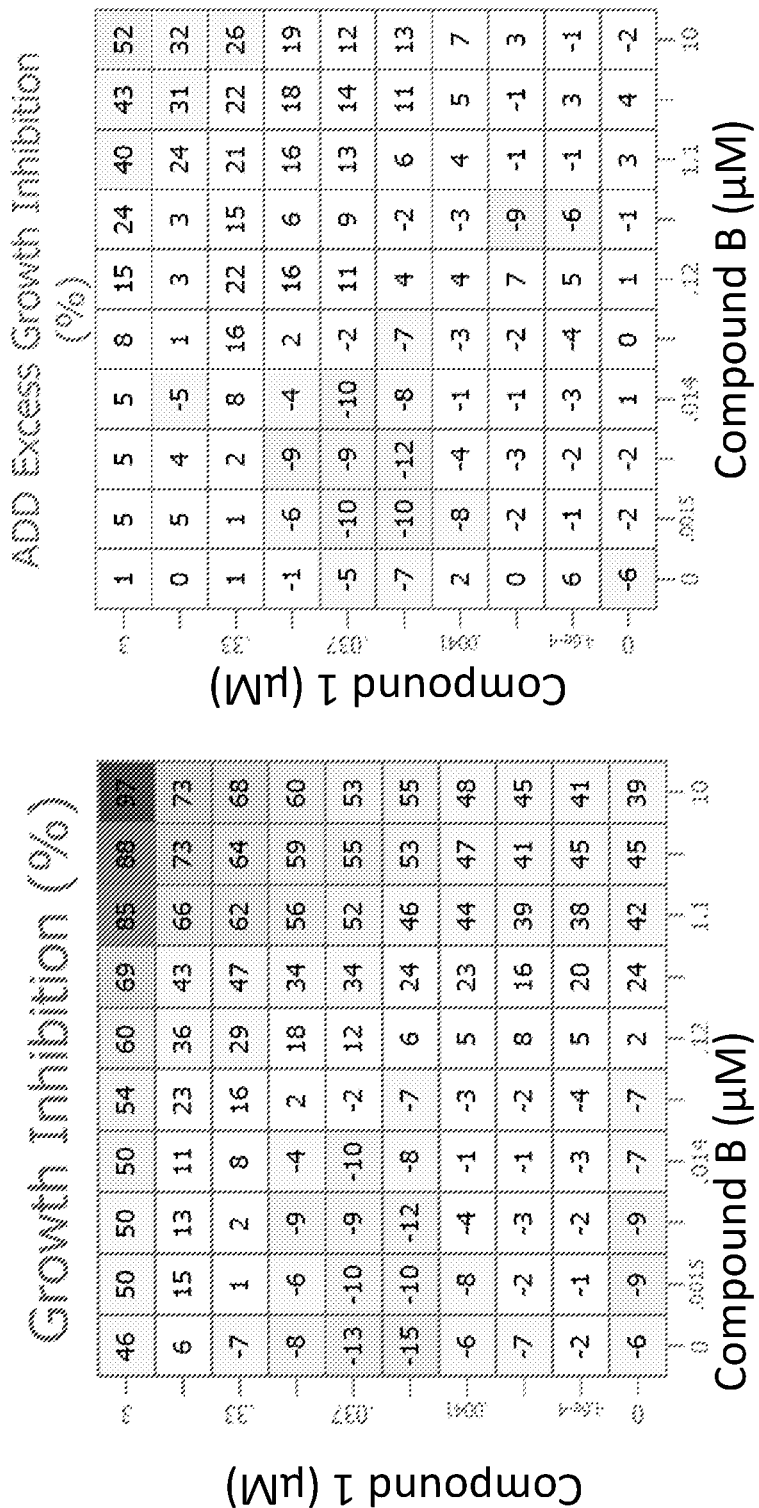
Figure 17-Example 17; SK-HEP-1

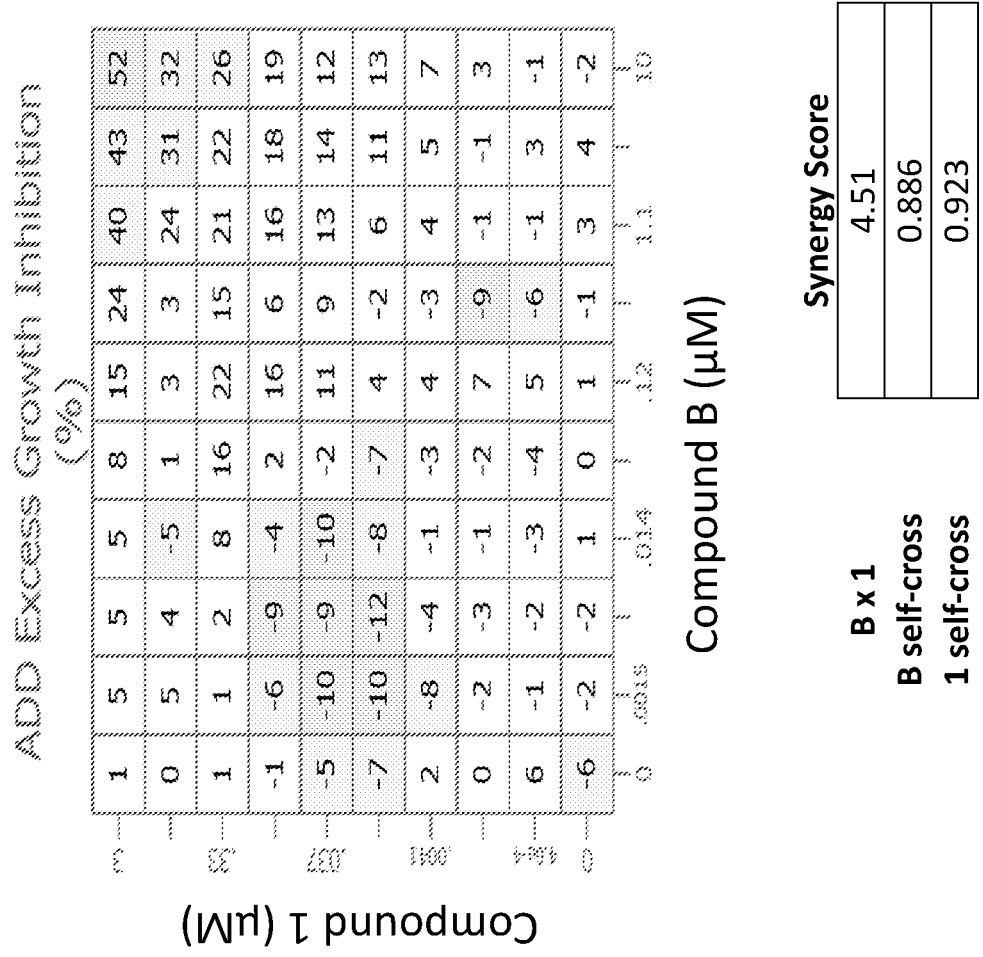
Figure 17a-Example 17; SK-HEP-1

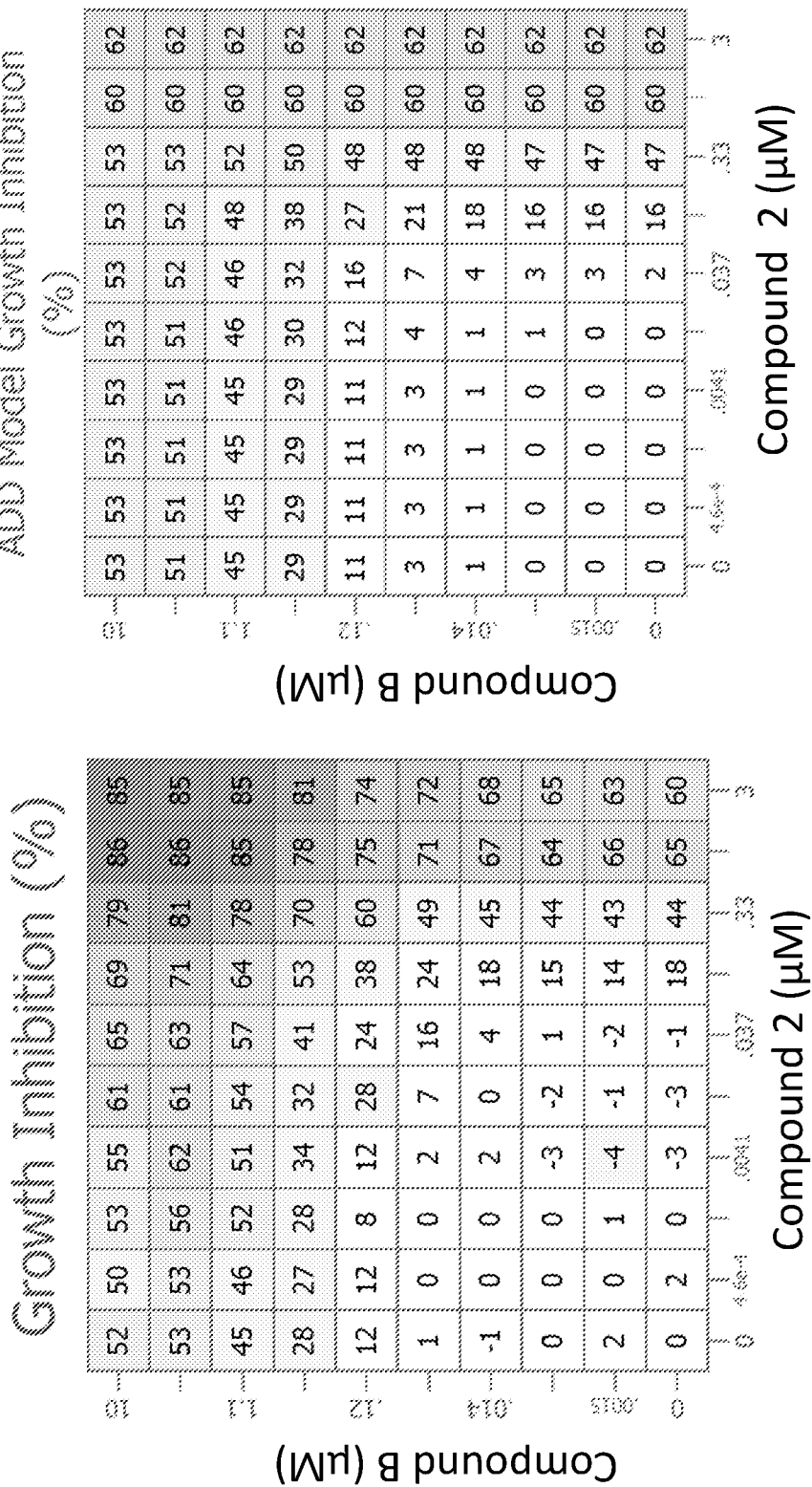
Figure 18-Example 18; SK-HEP-1 cells

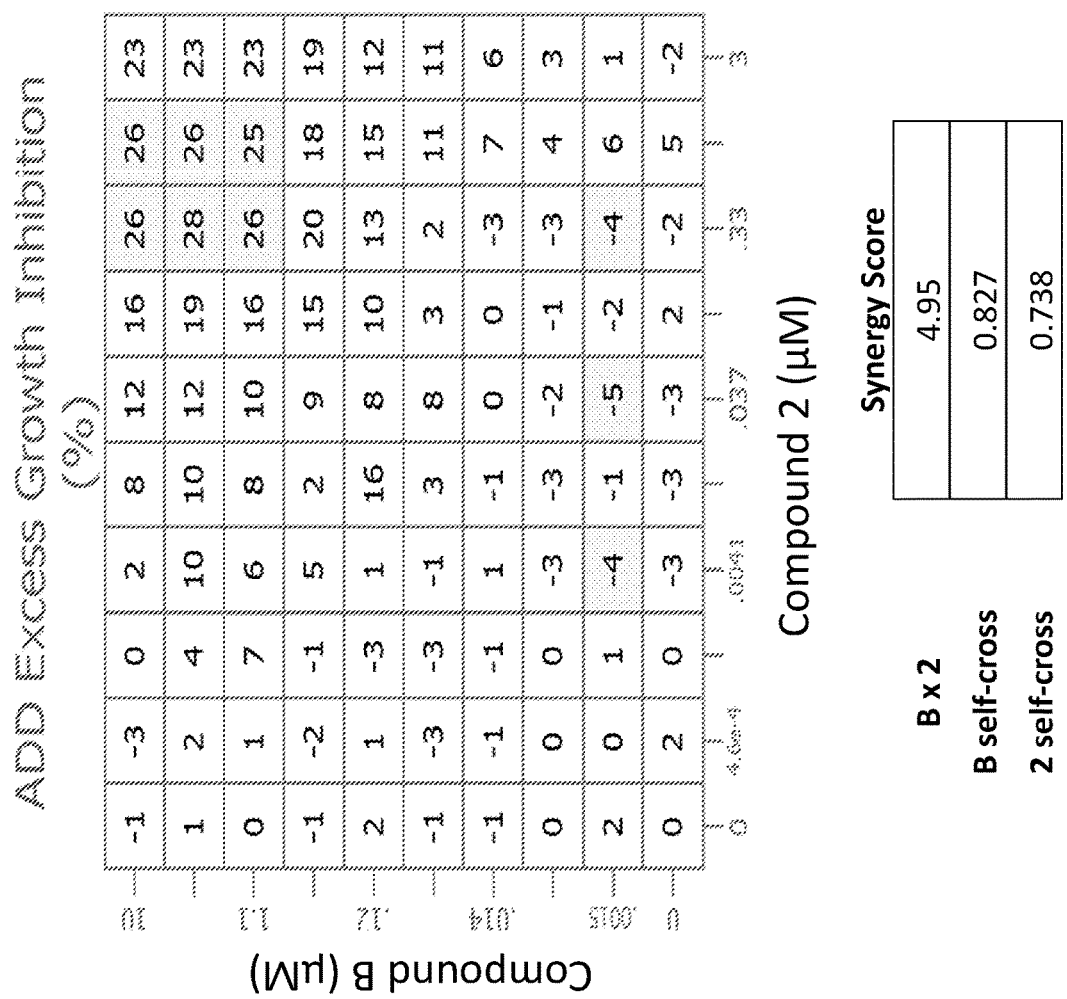
Figure 18a-Example 18; SK-HEP-1 cells

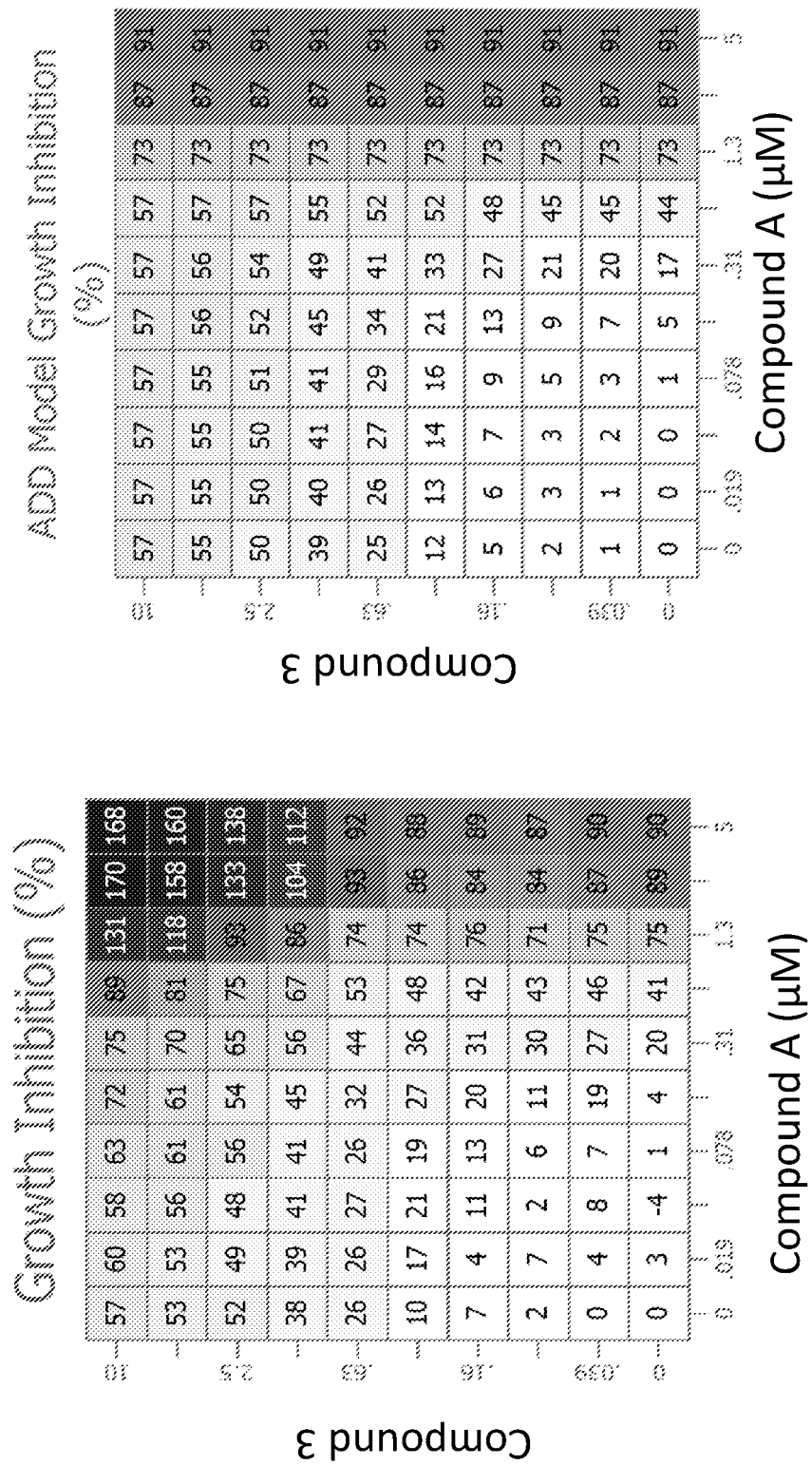
Figure 19-Example 19; A204 cells

Figure 19a-Example 19; A204 cells
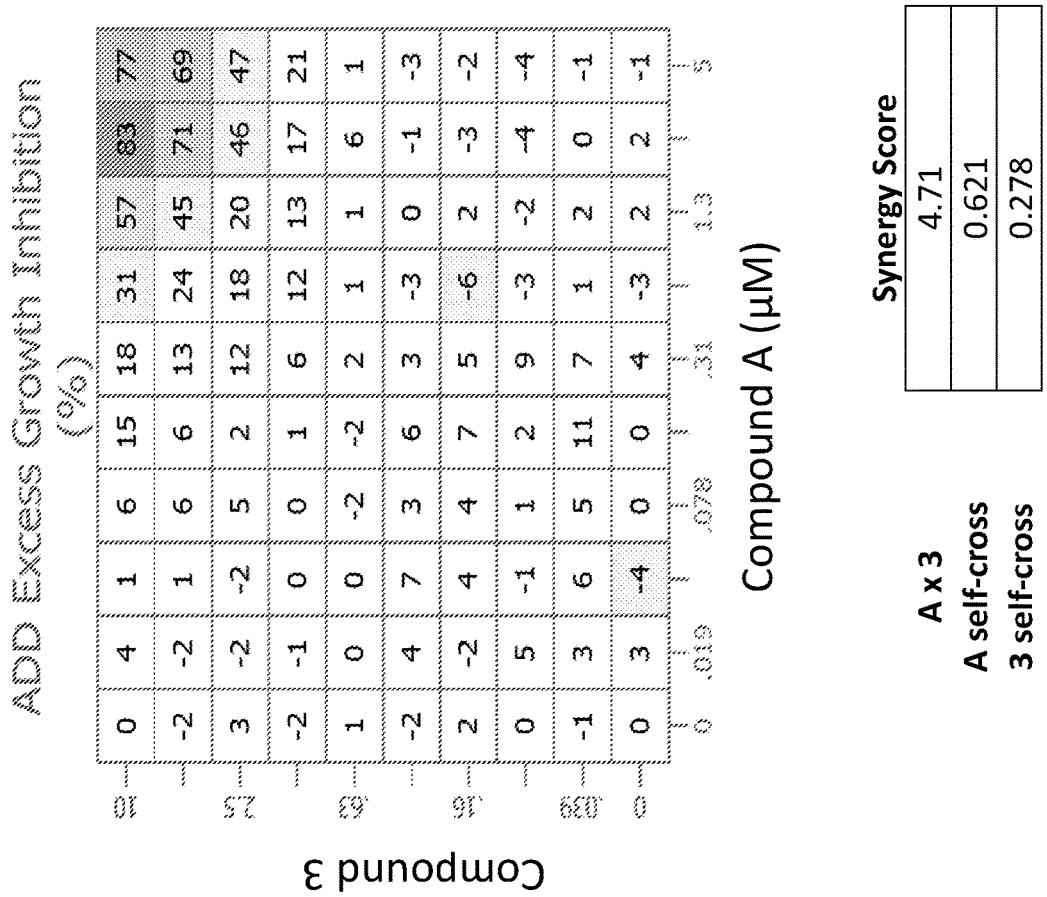

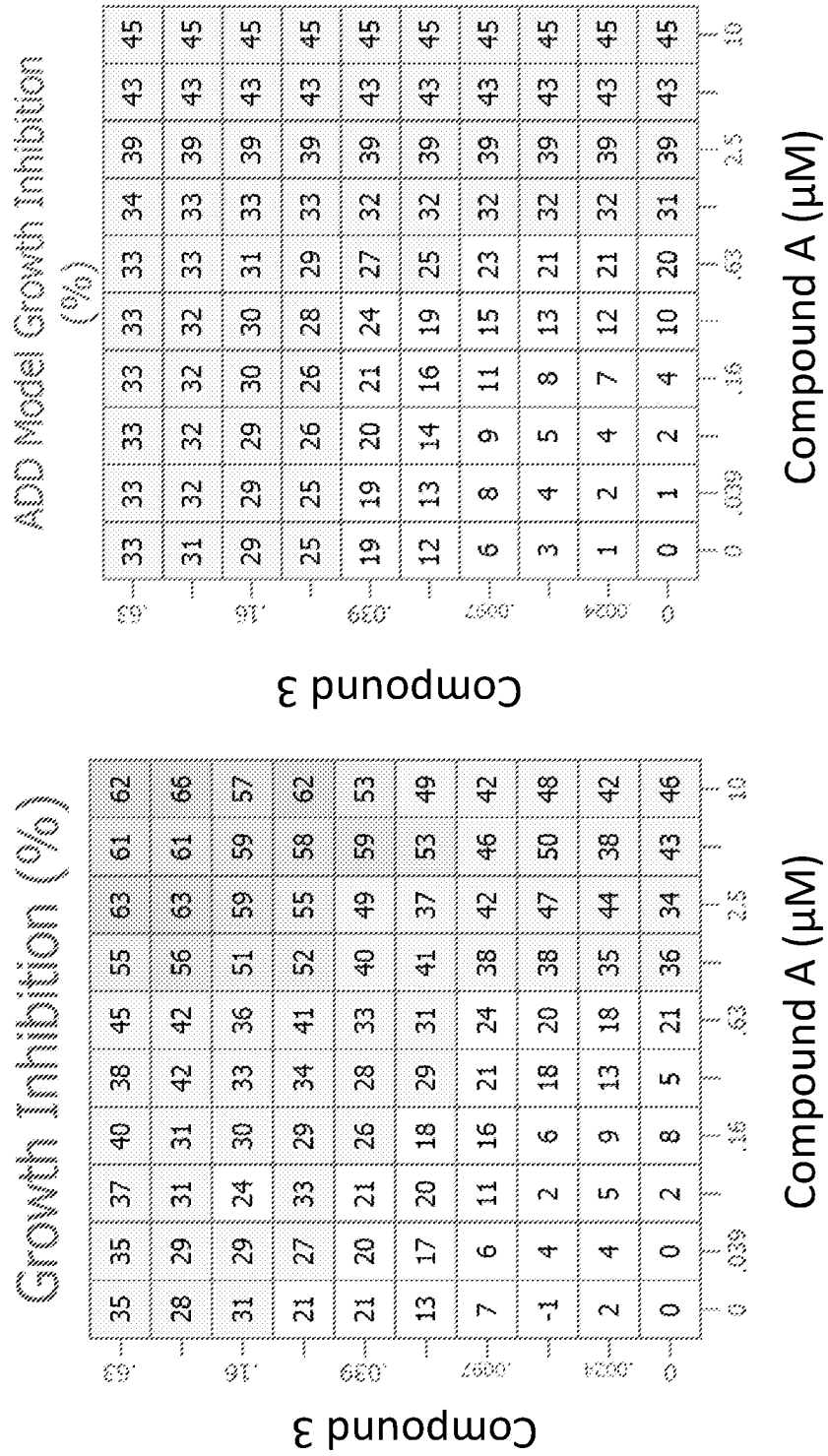
Figure 20-Example 20; A375sq2 cells

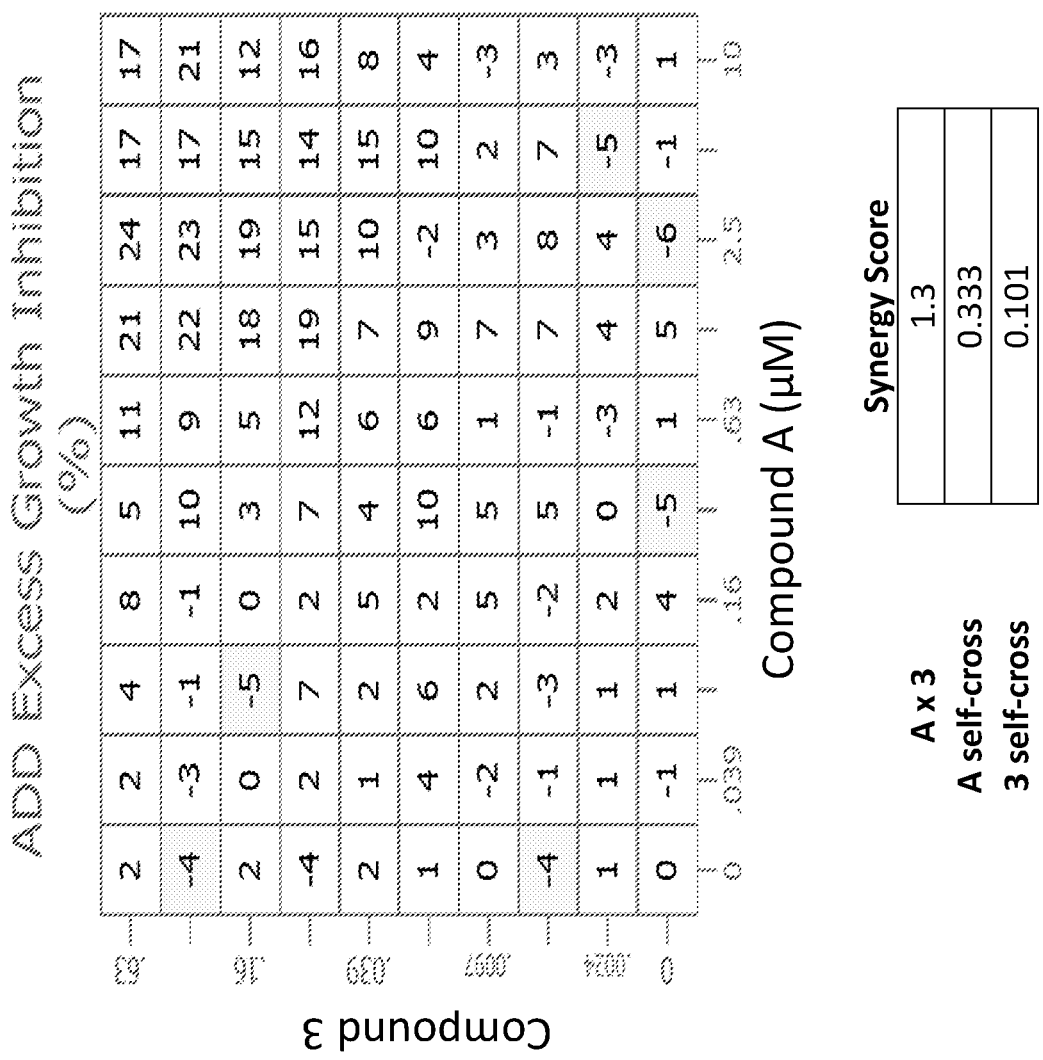
Figure 20a-Example 20; A375sq2 cells

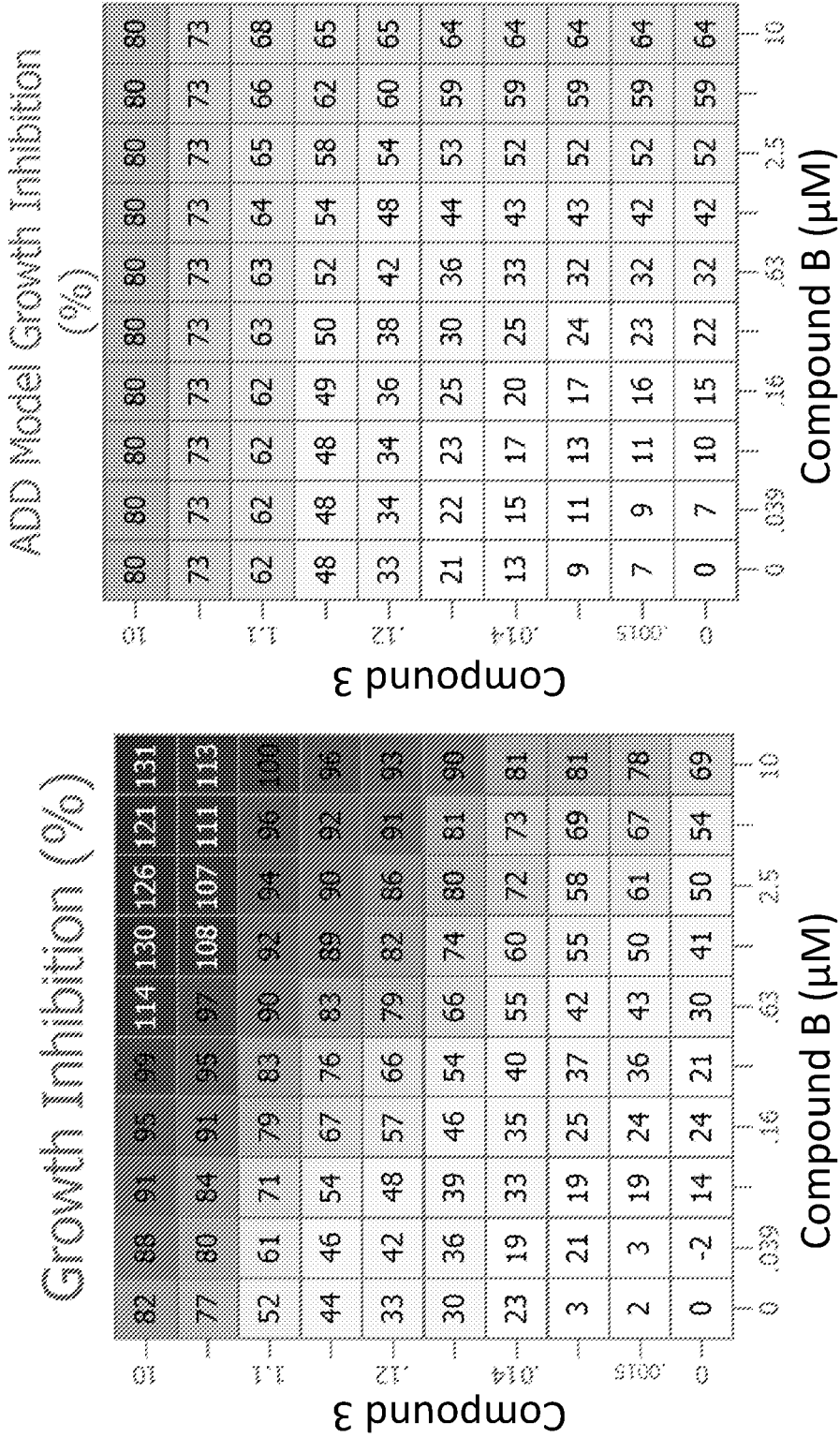
Figure 21-Example 21; A-427 cells

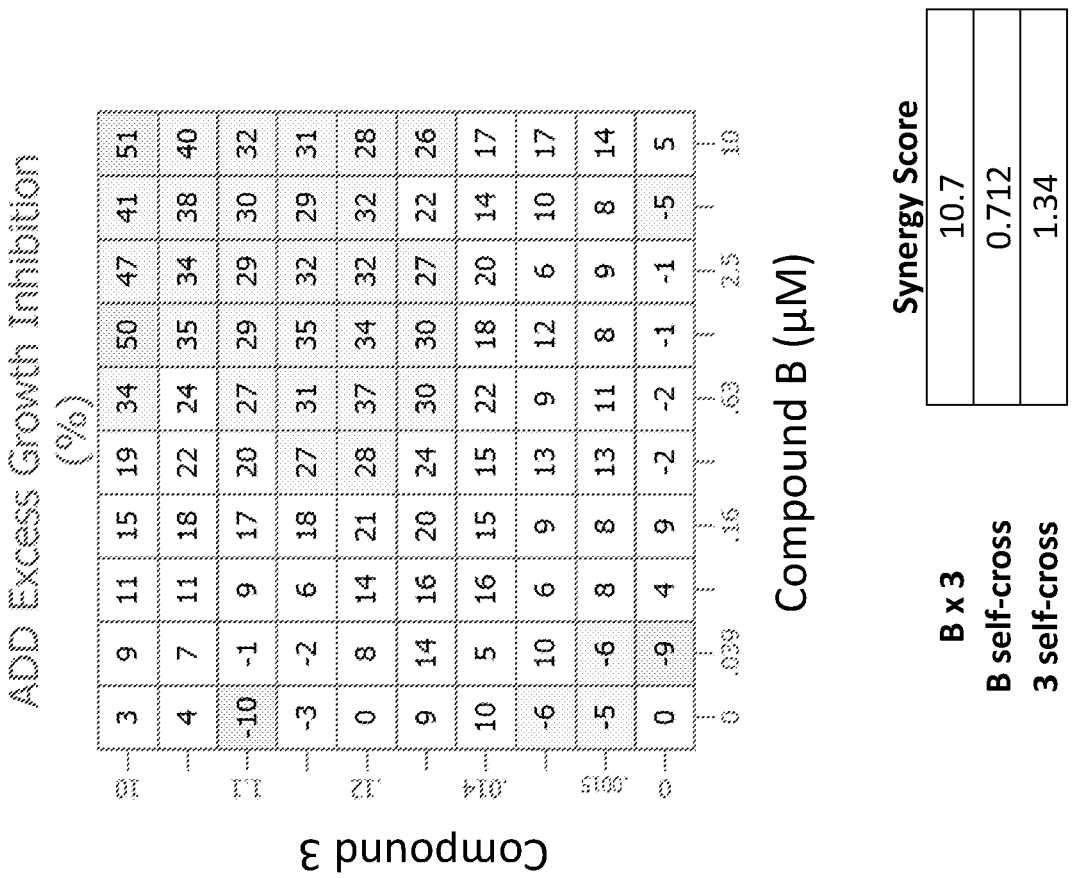
Figure 21a-Example 21; A-427 cells

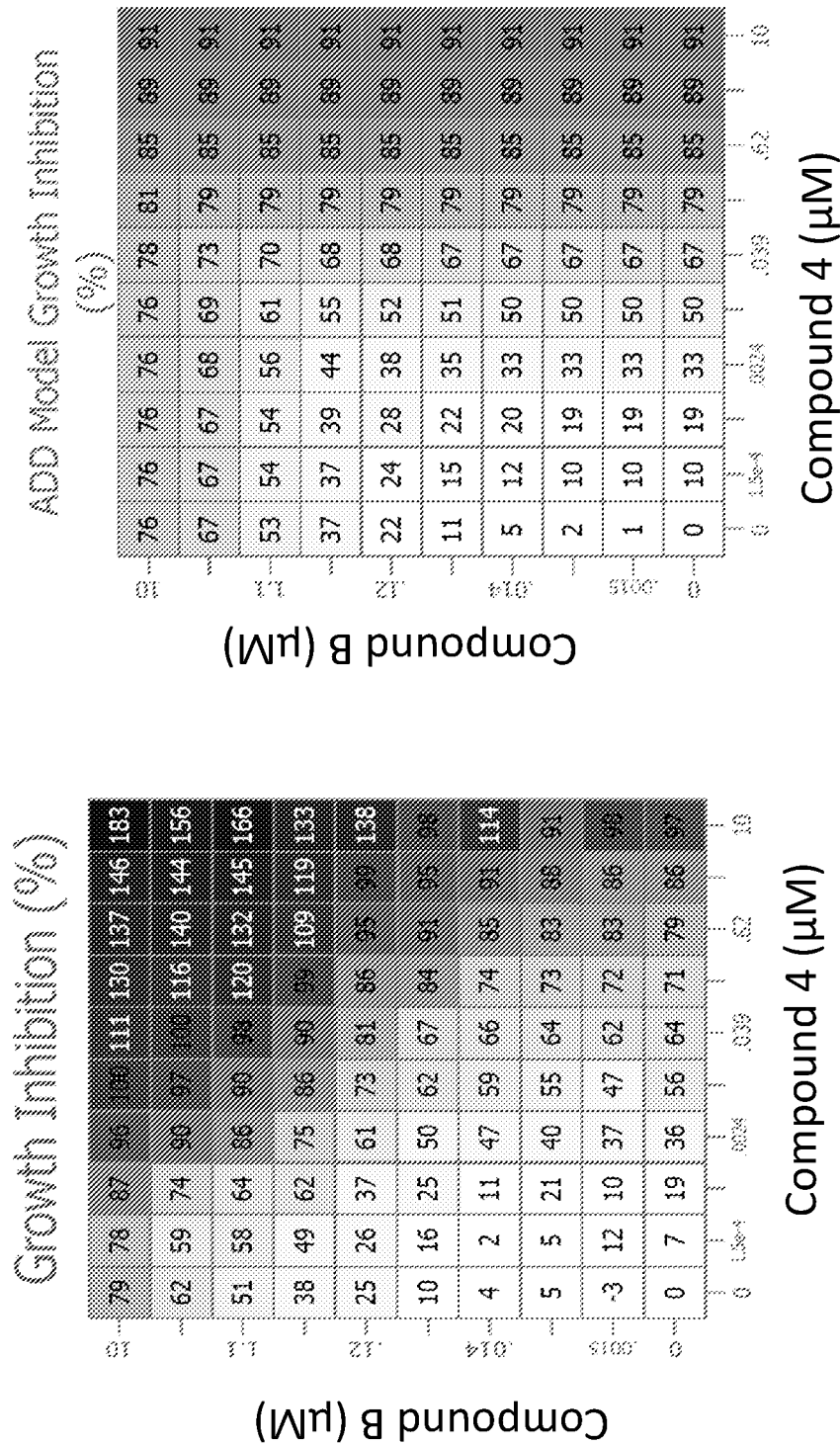
Figure 22-Example 22; A-427 cells

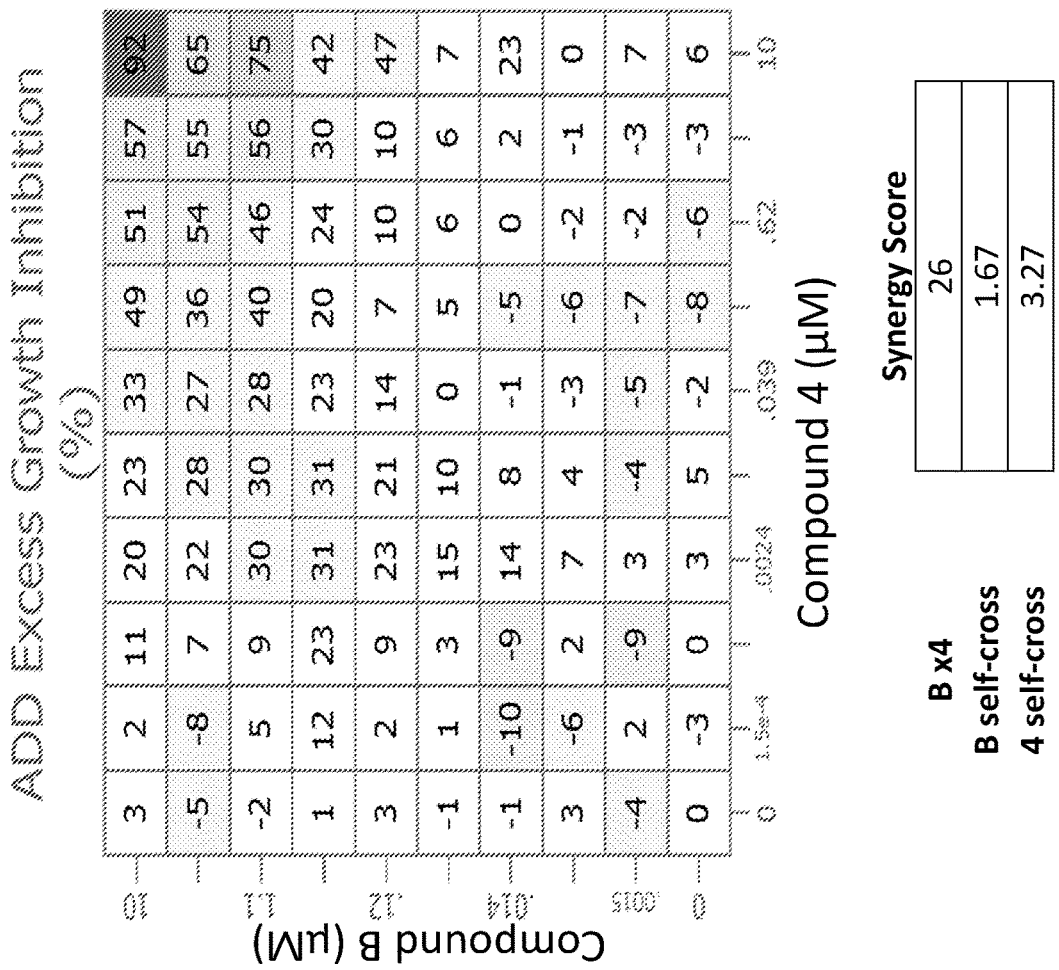
Figure 22a-Example 22; A-427 cells

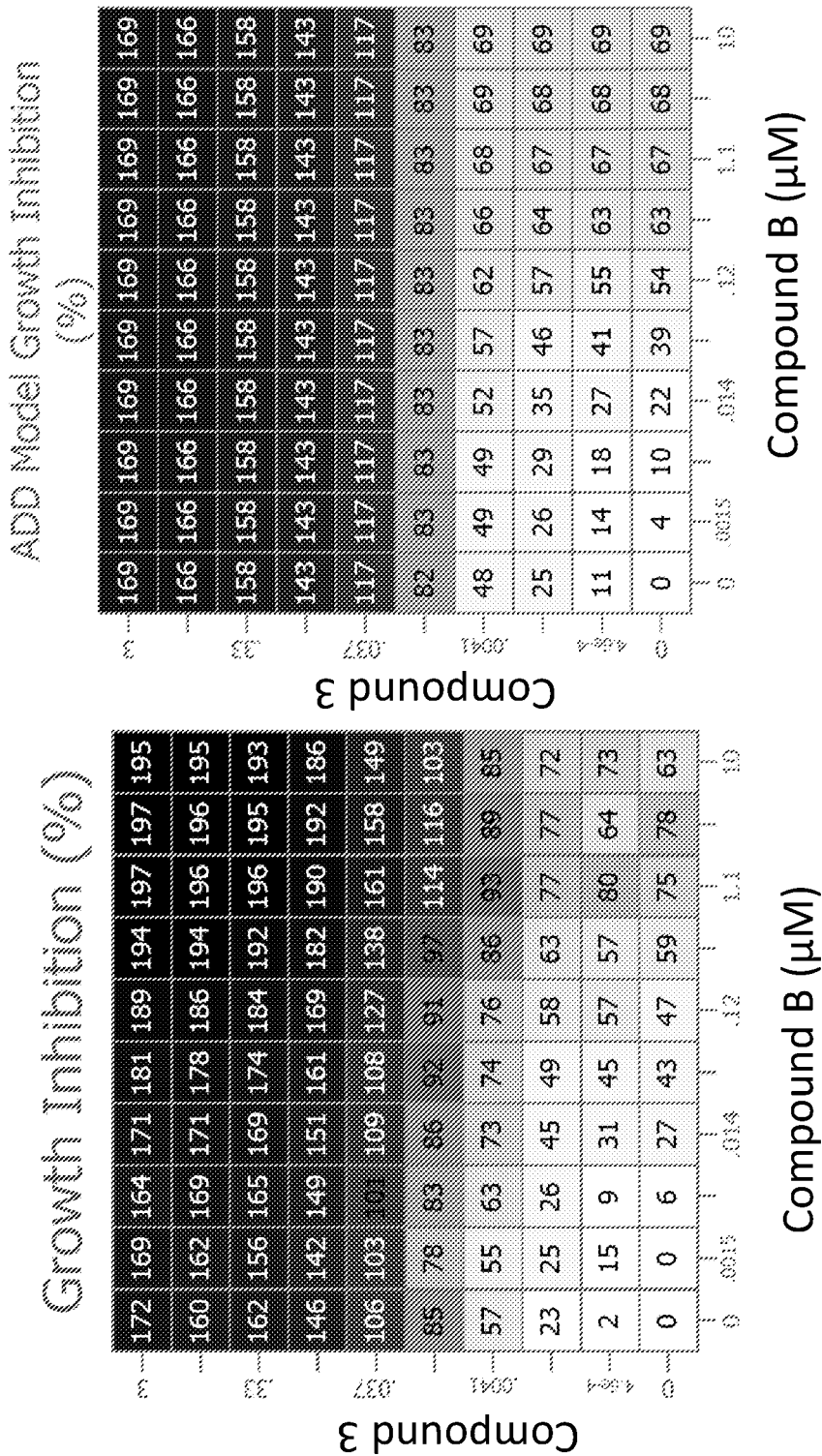
Figure 23-Example 23; C32 cells

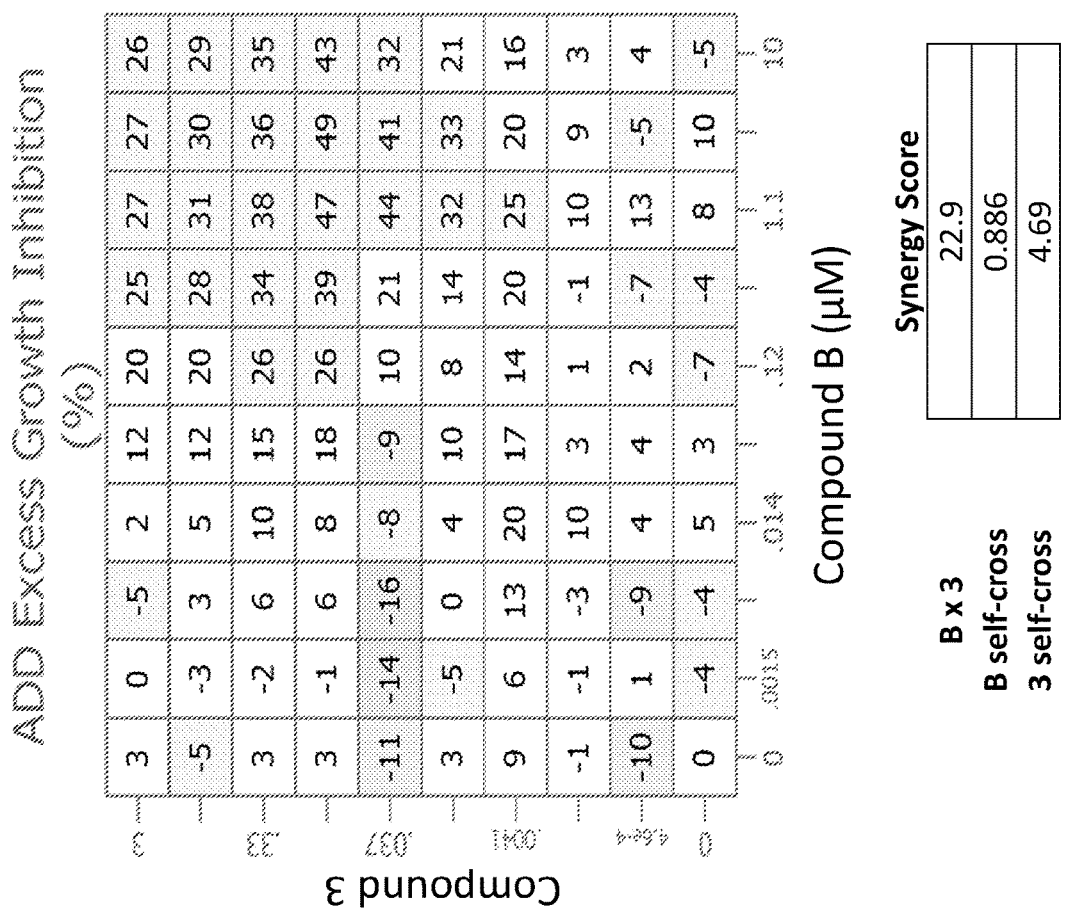
Figure 23a-Example 23; C32 cells

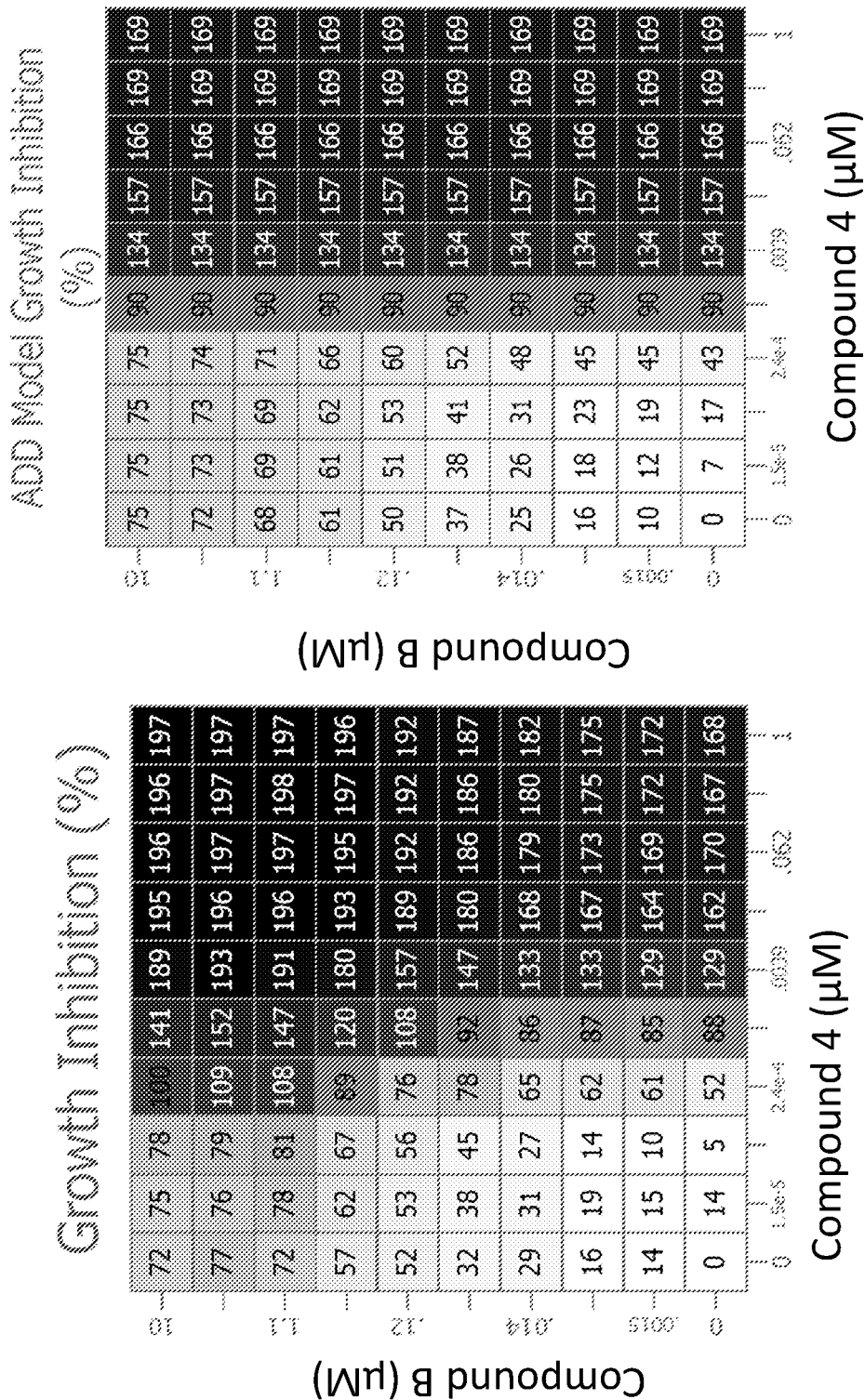
Figure 24-Example 24; C32 cells

Figure 24a-Exaxmple 24; c32 cells
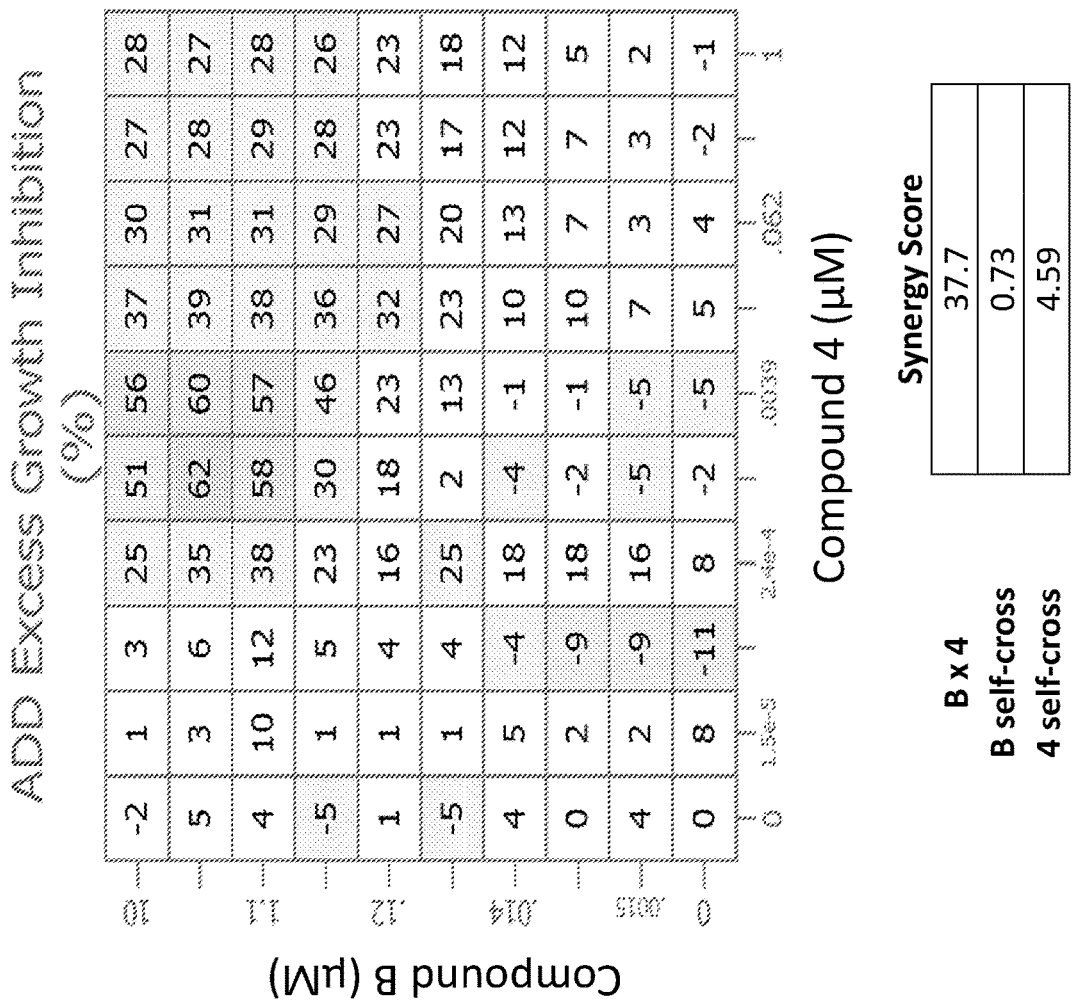

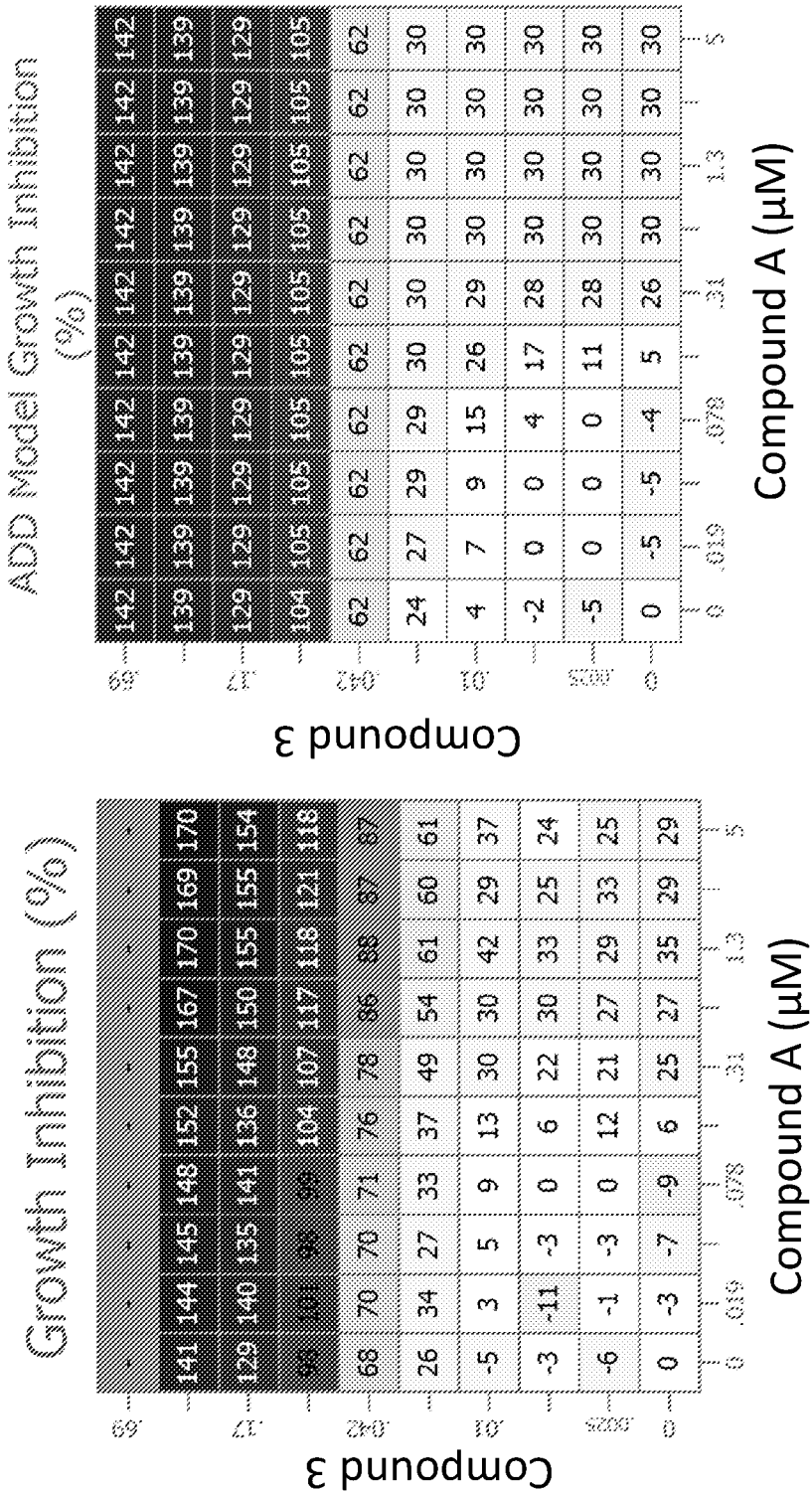
Figure 25-Example 25; G-361 cells

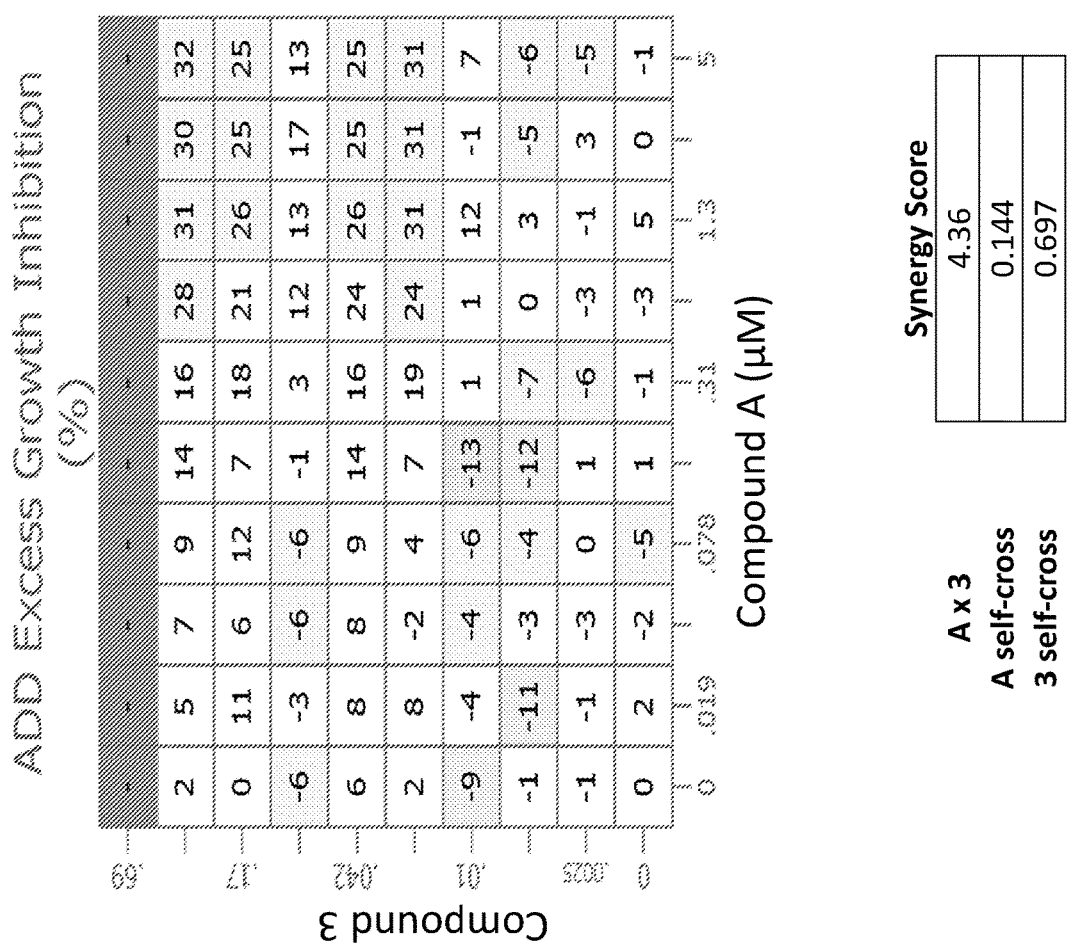
Figure 25a-Example 25; G-361 cells

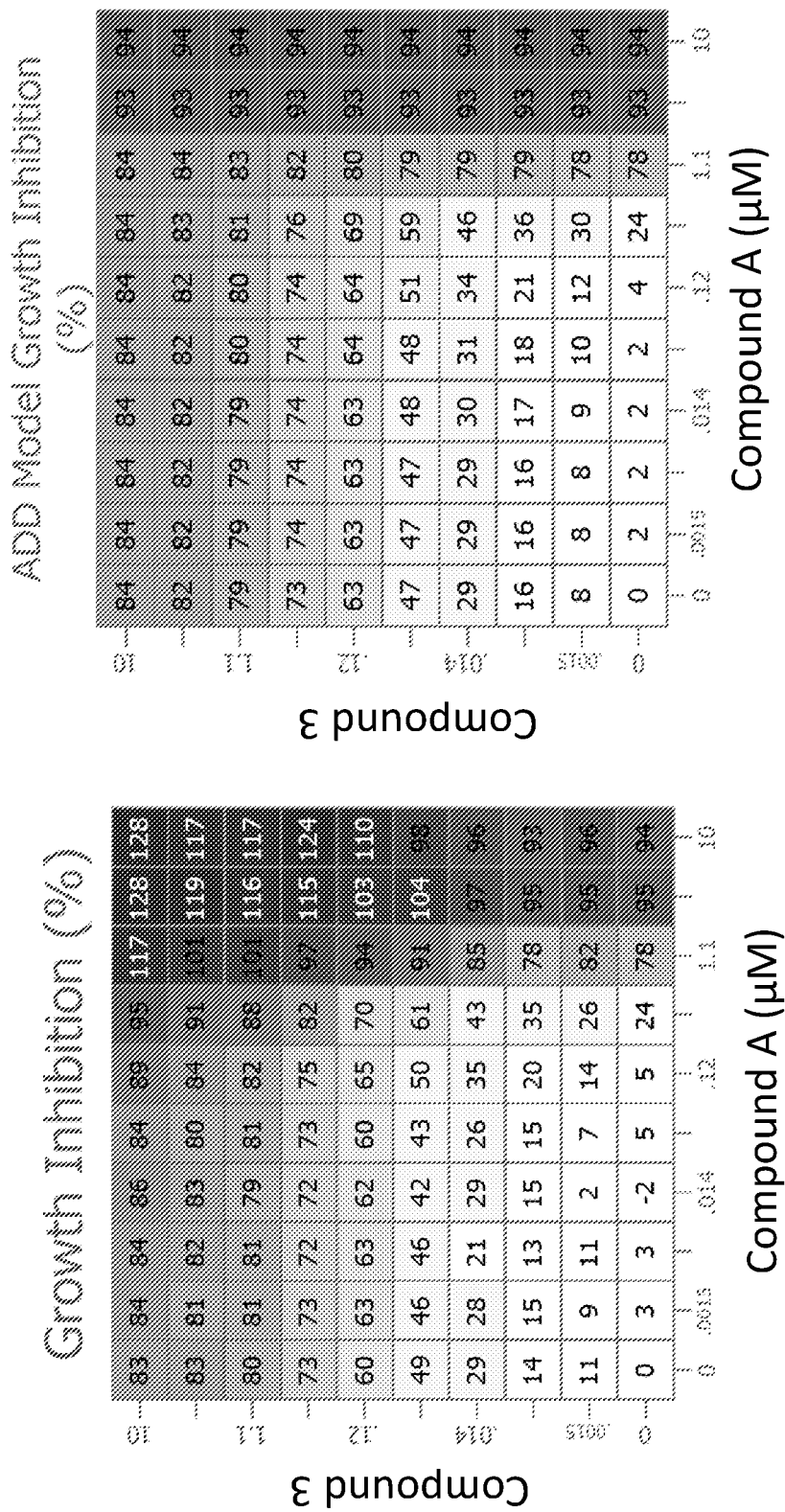
Figure 26-Example 26; LS 174T cells

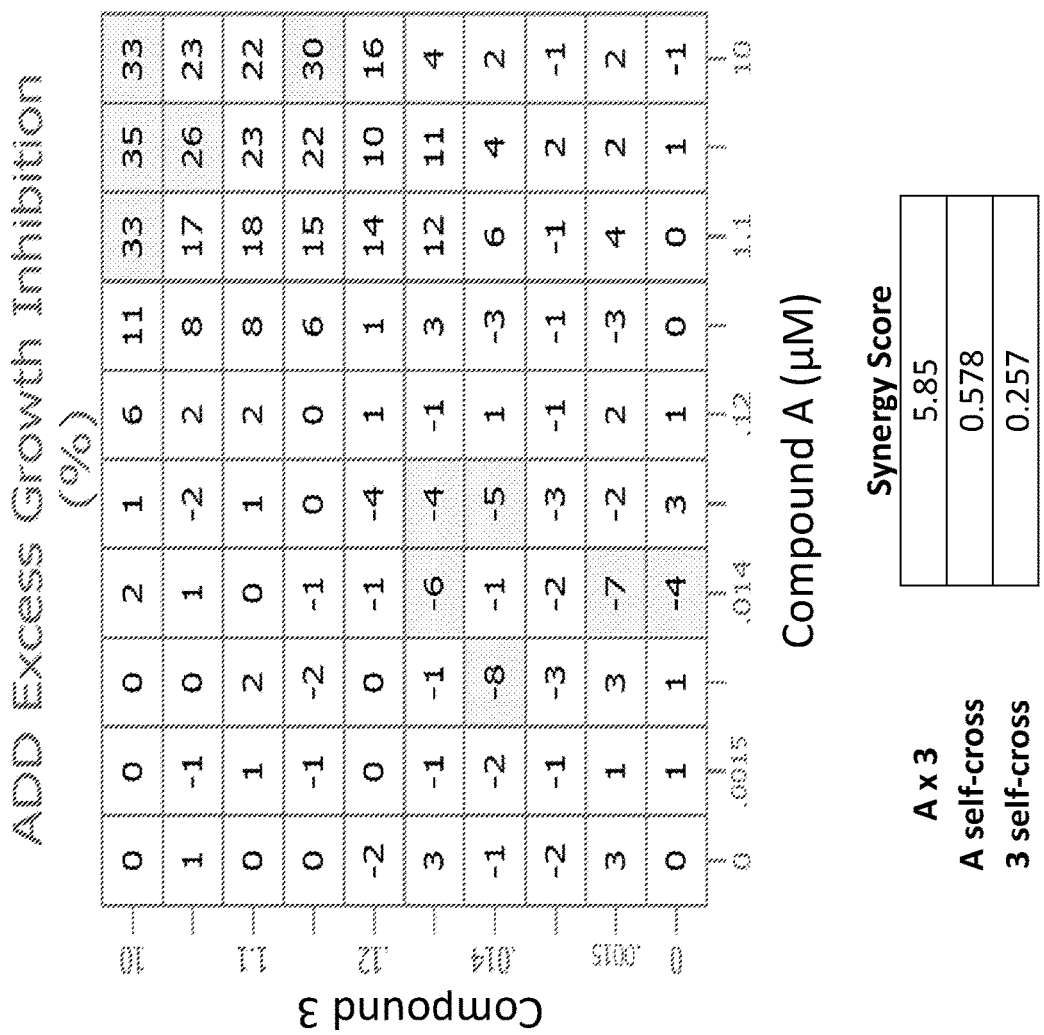
Figure 26a-Example 26; LS 174T cells

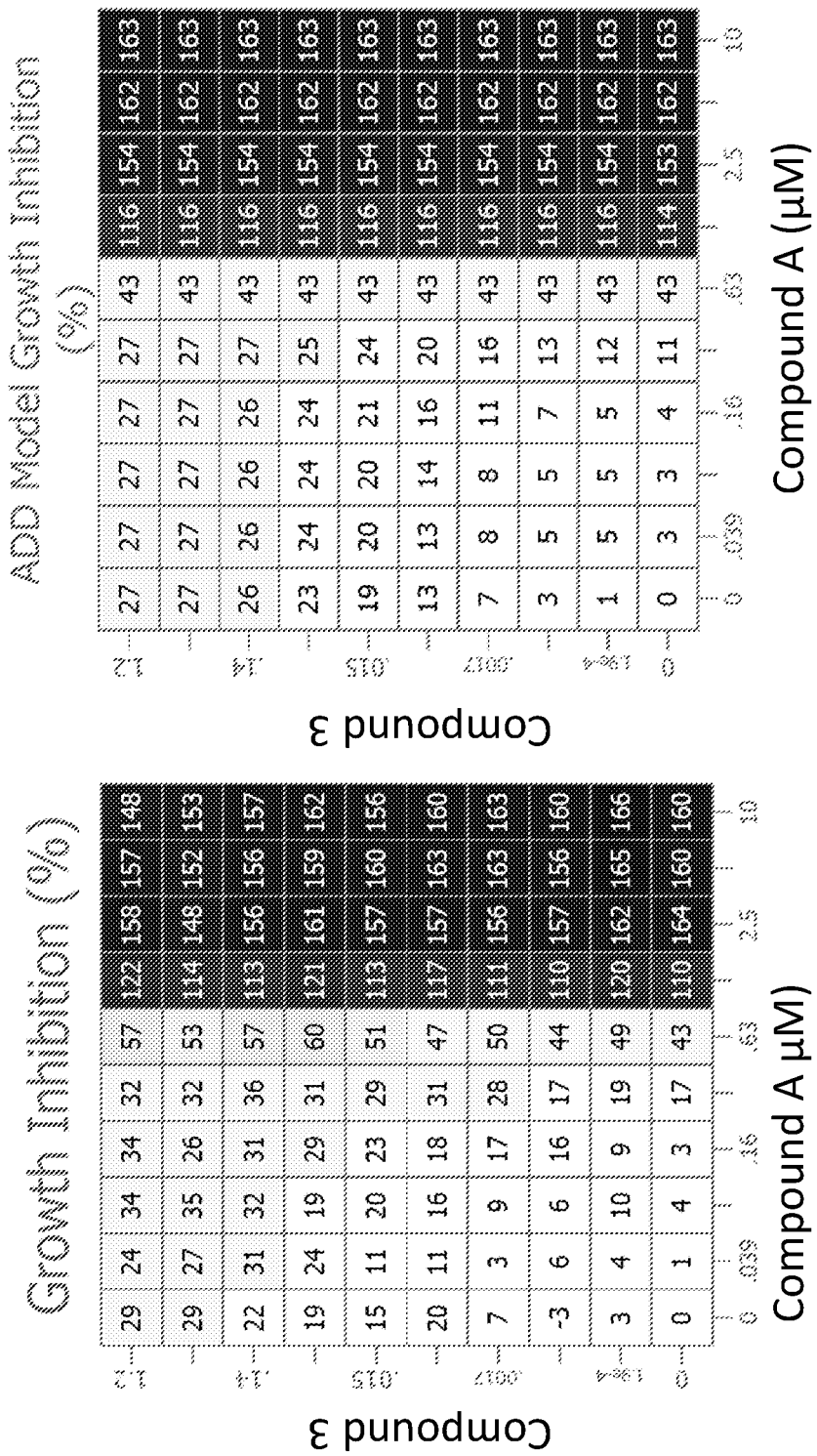
Figure 27-Example 27; MCF7 cells

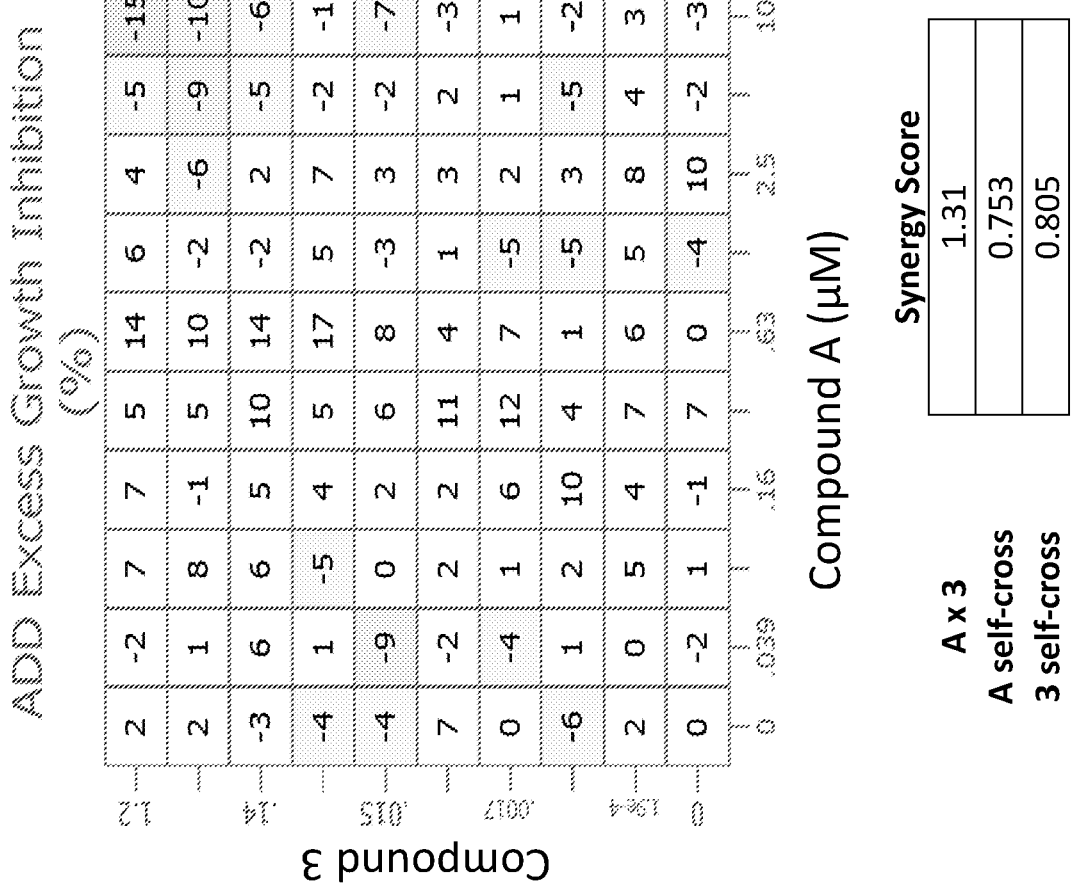
Figure 27a-Example 27; MCF7 cells

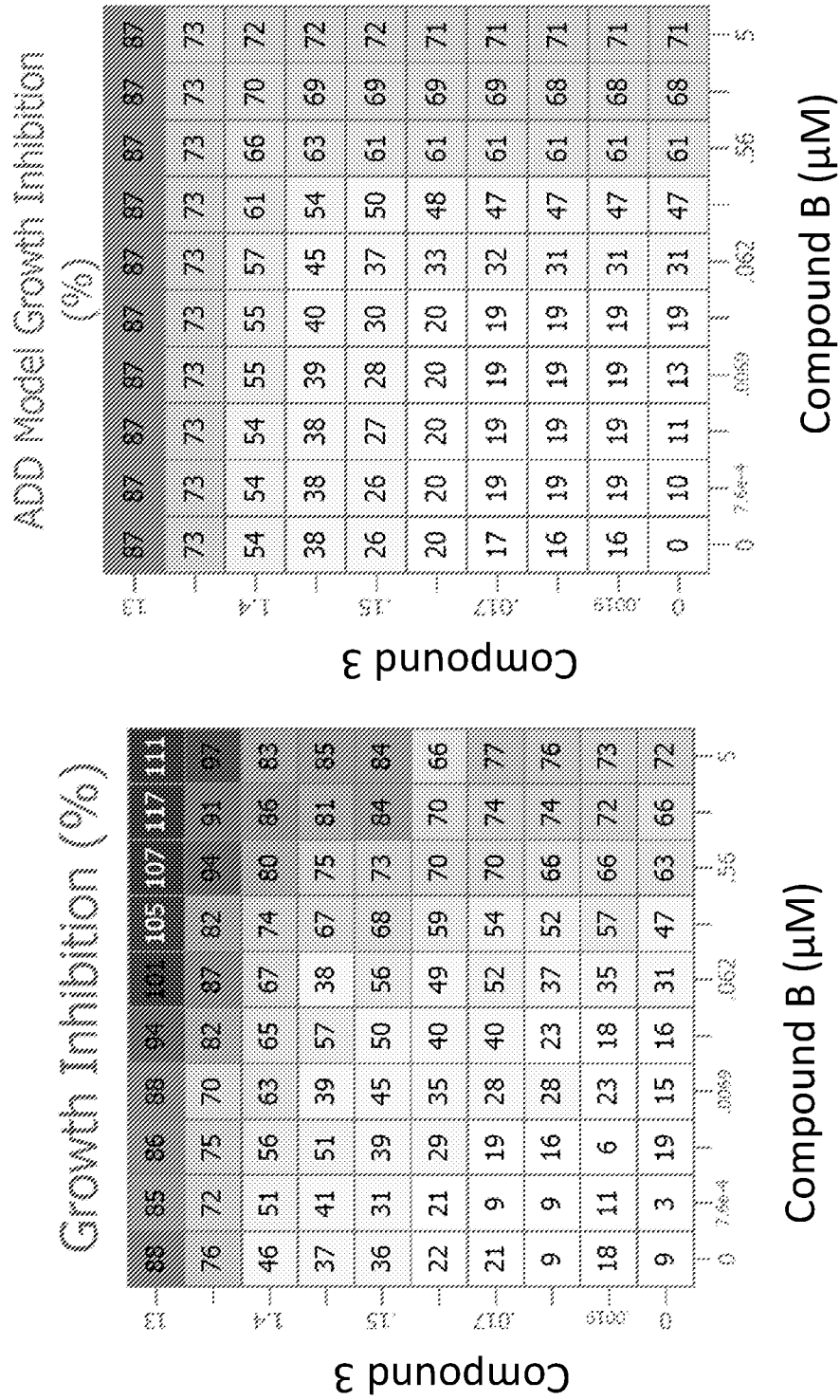
Figure 28-Example 28; NCI-H1666 cells

Figure 28a-Example 28; NCI-H1666 cells
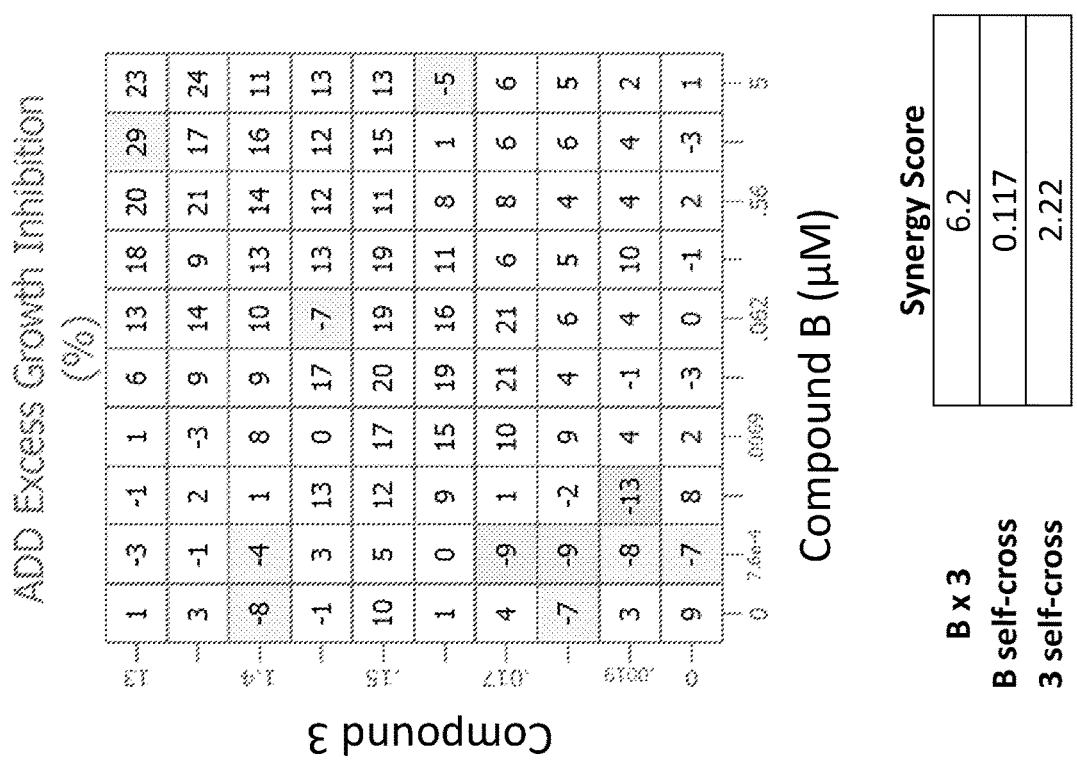

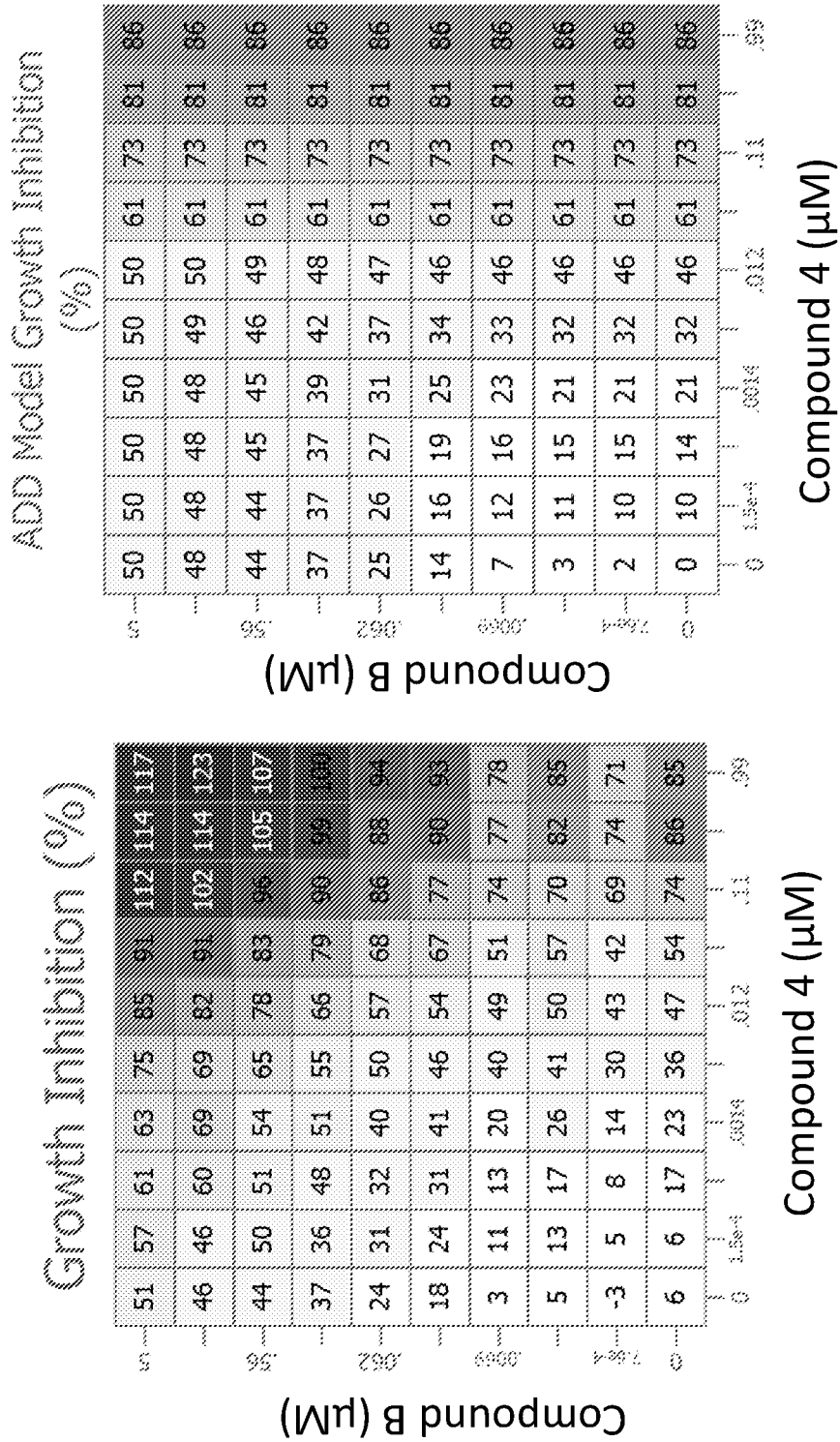
Figure 29-Example 29; NCI-H1666 cells

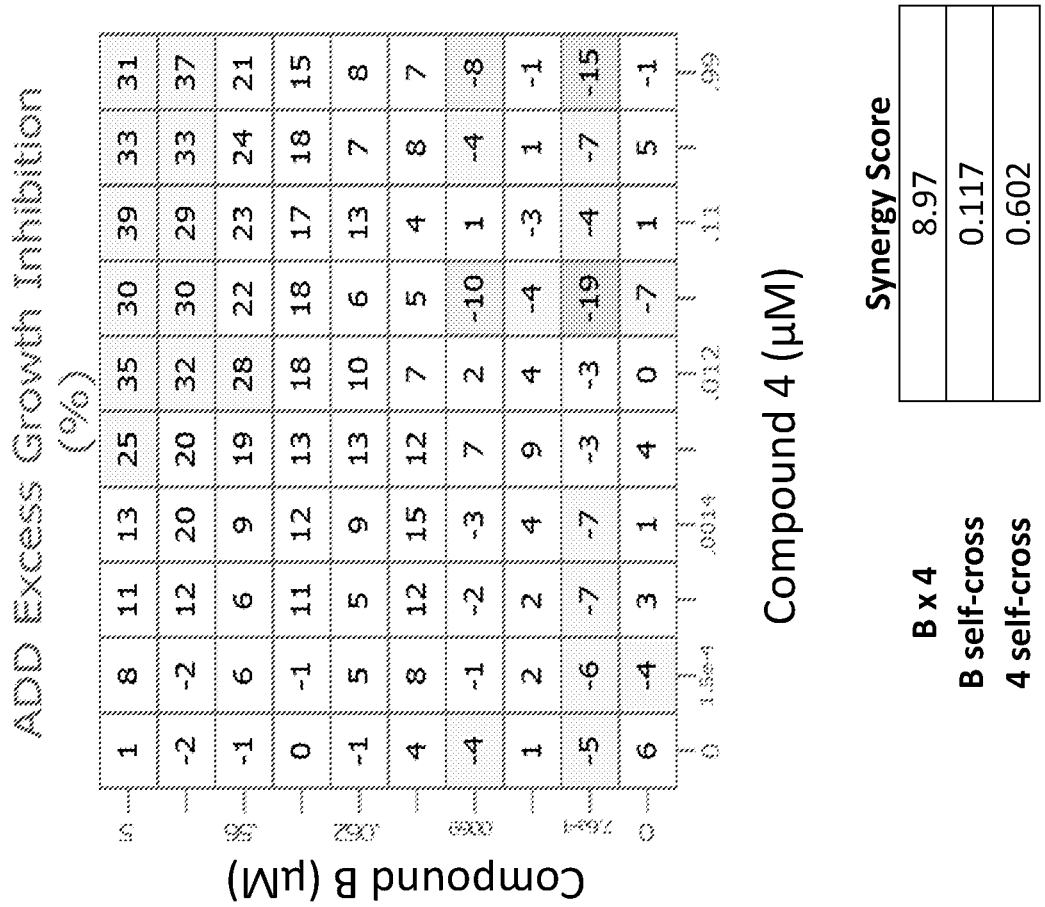
Figure 29a-Example 29; NCI-H1666 cells

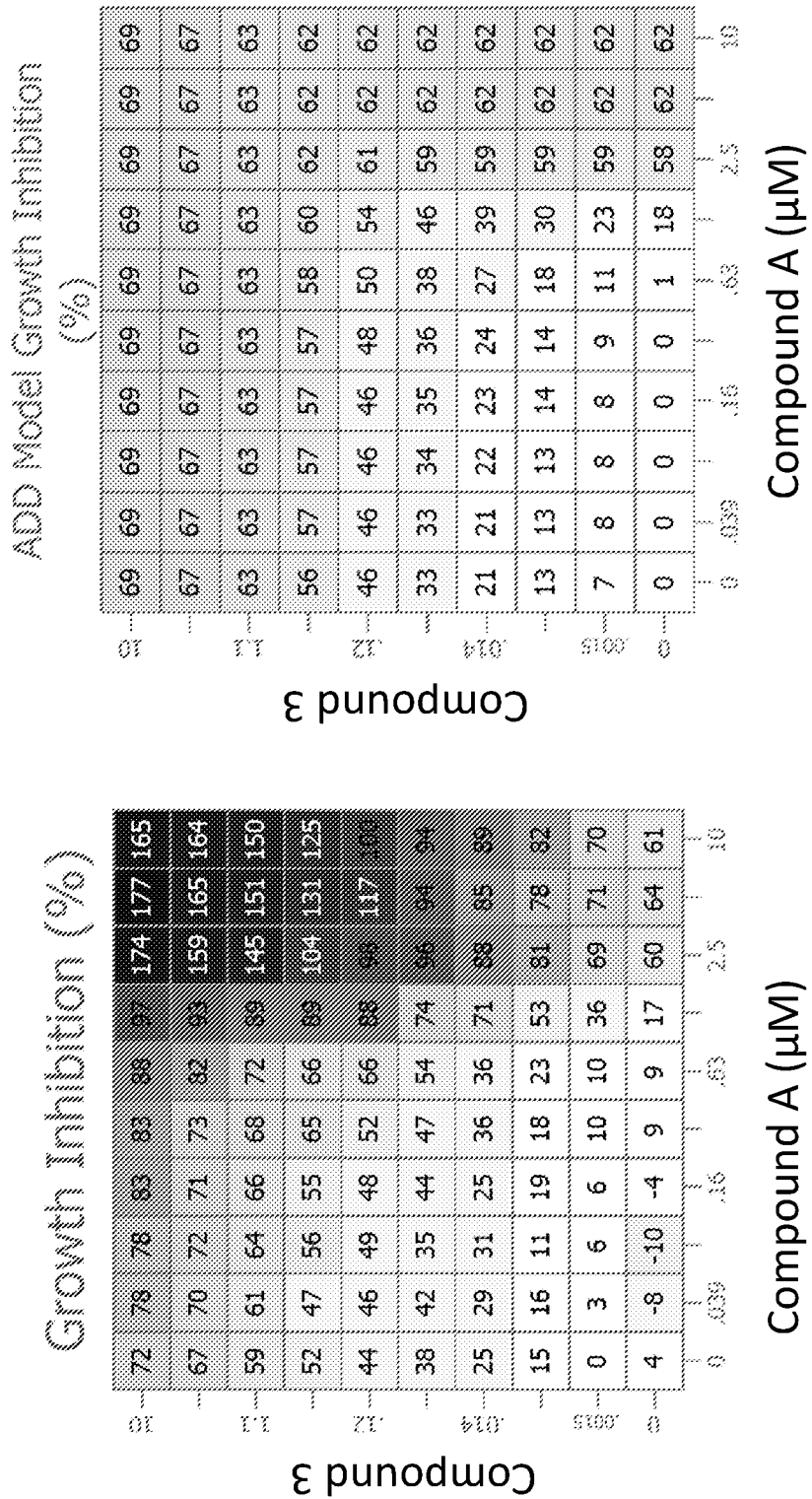
Figure 30-Example 30; RKO cells

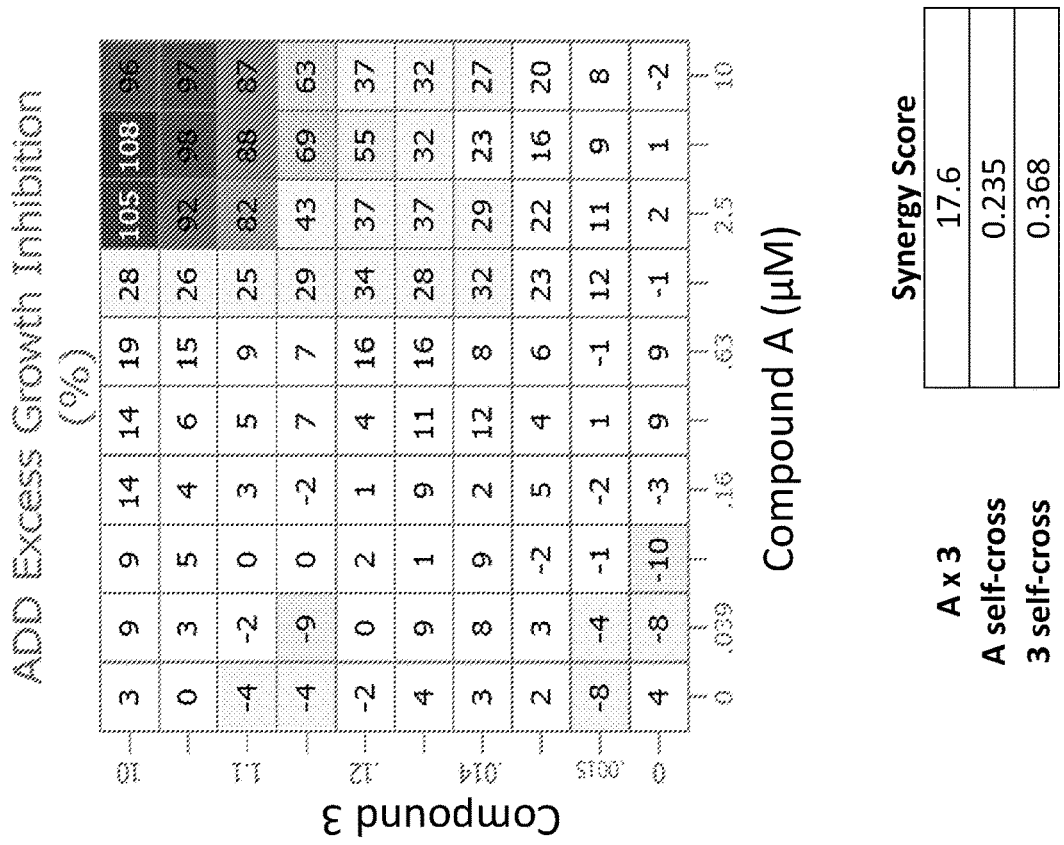
Figure 30a-Example 30; RKO cells

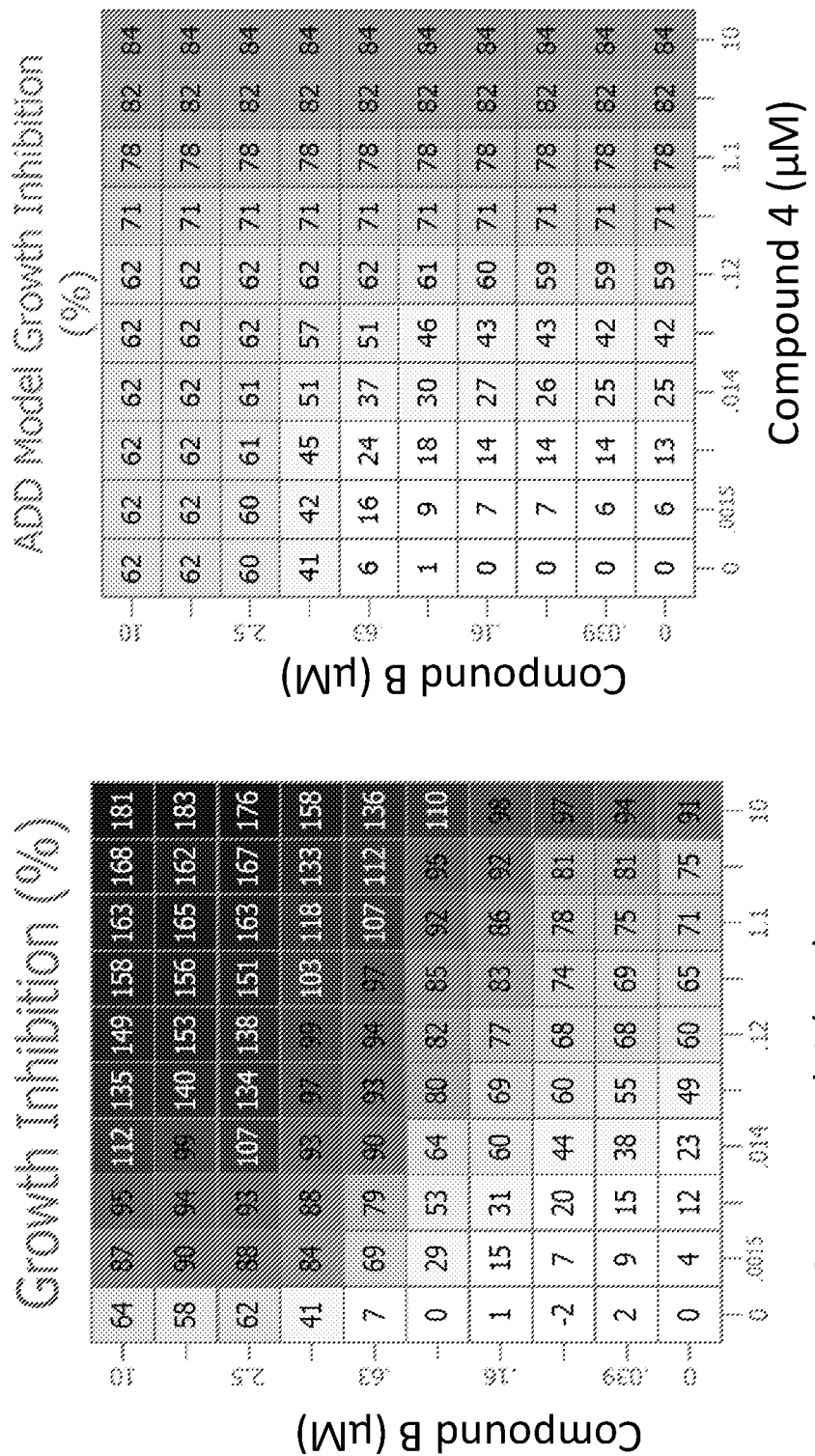
Figure 31-Example 31; RKO cells

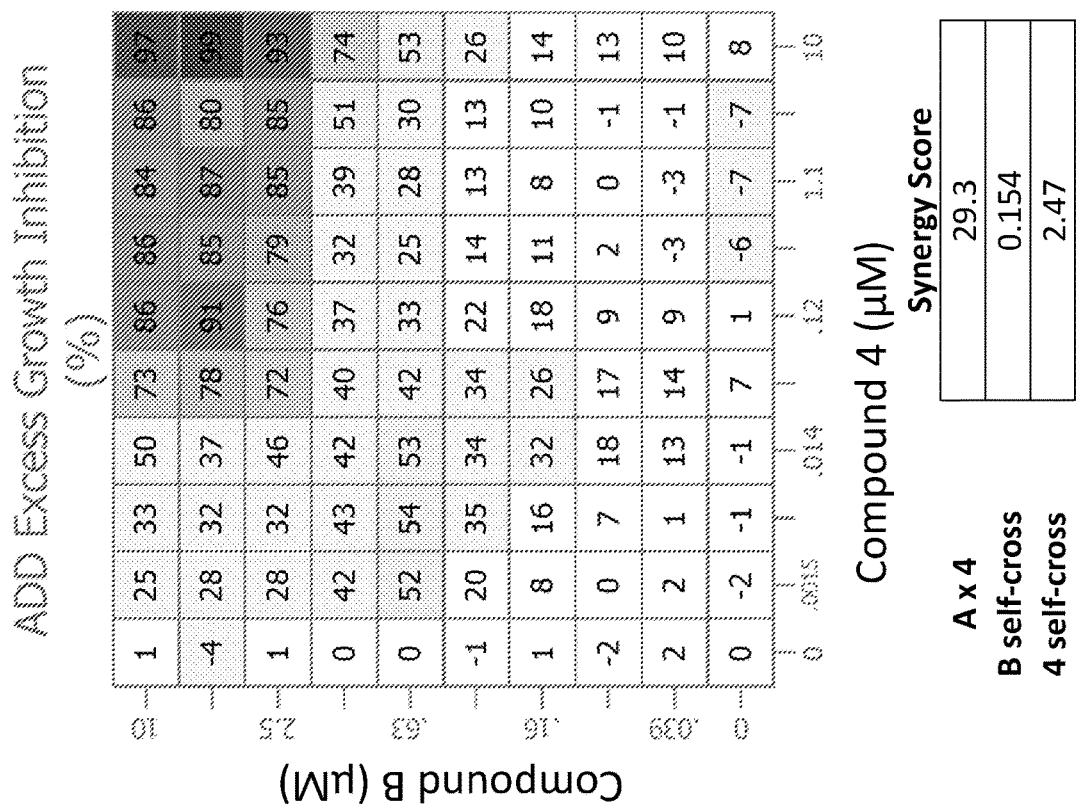
Figure 31a-Example 31; RKO cells

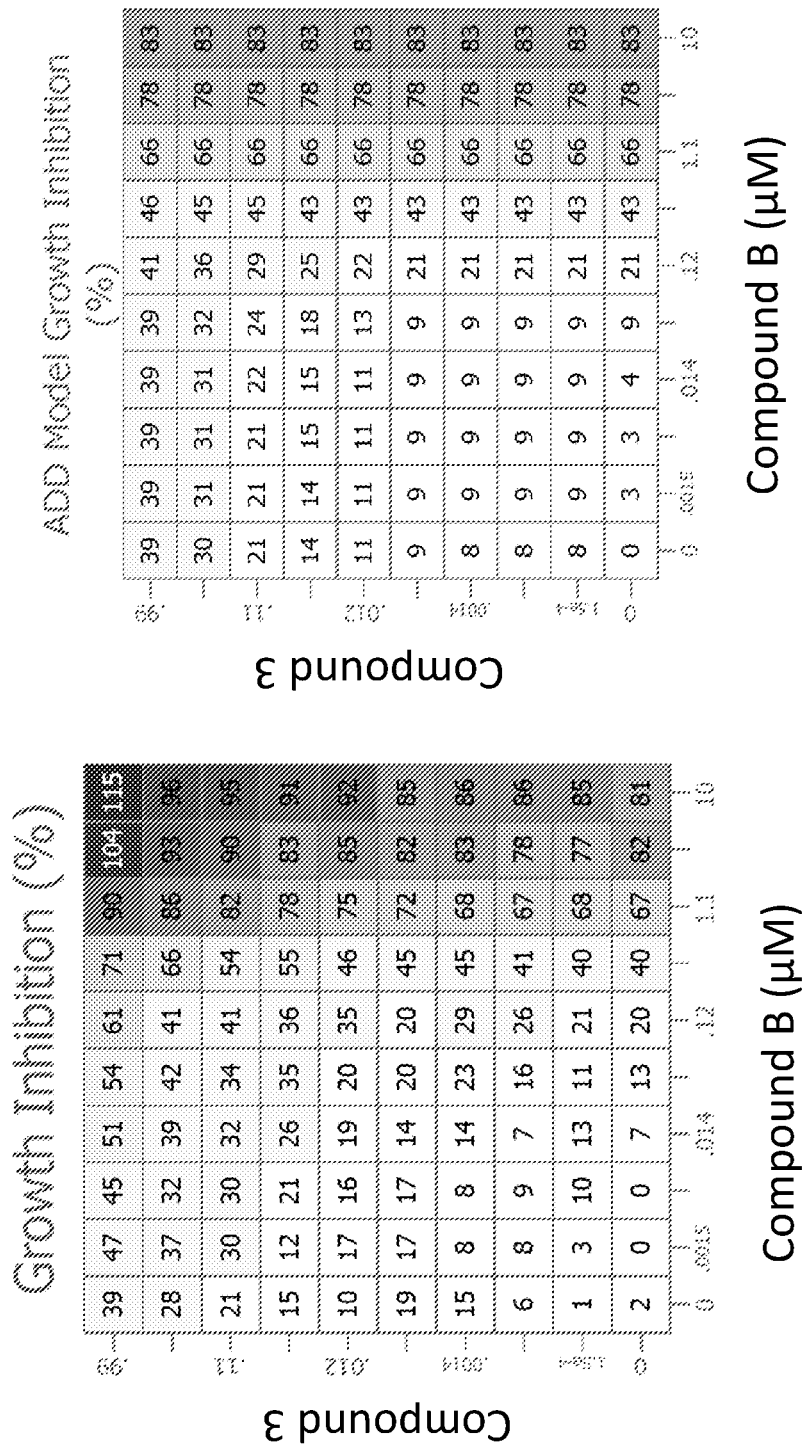
Figure 32-Example 32; RT4 cells

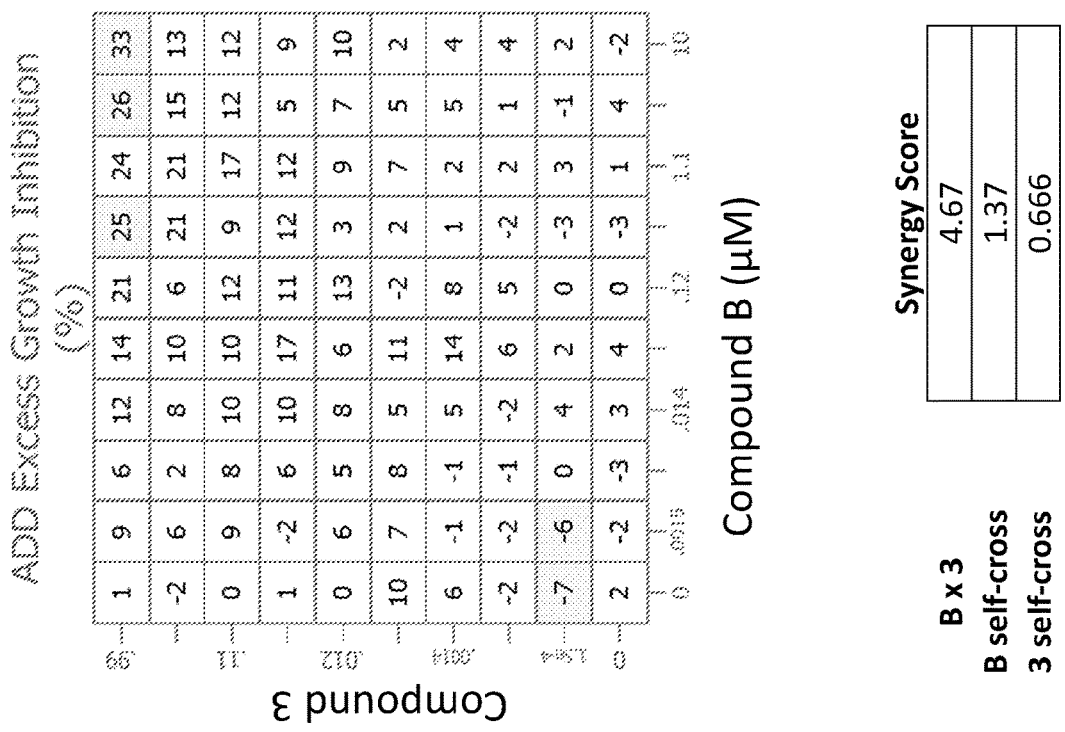
Figure 32a-Example 32; RT4 cells

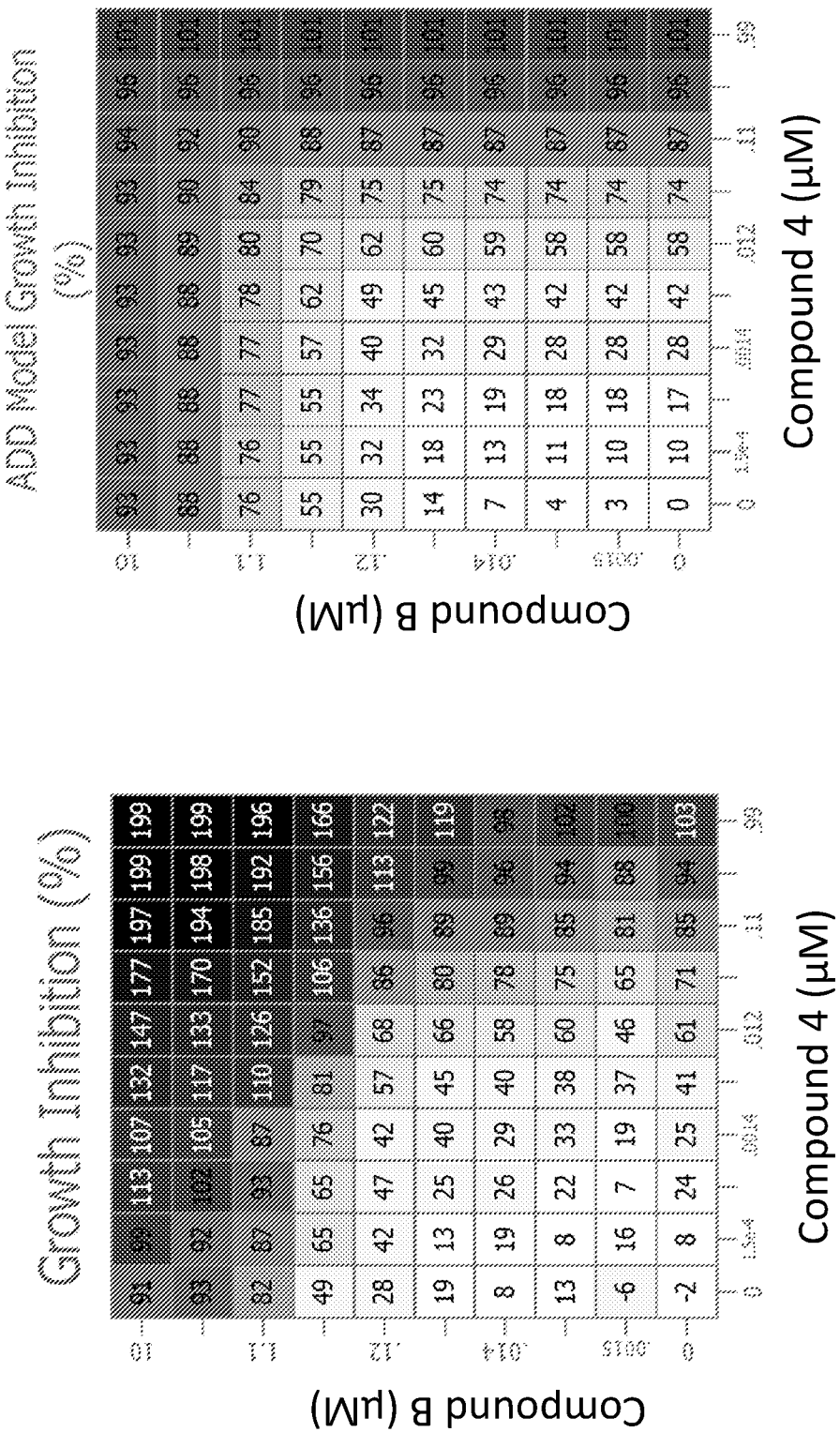
Figure 33-Example 33; RT4 cells

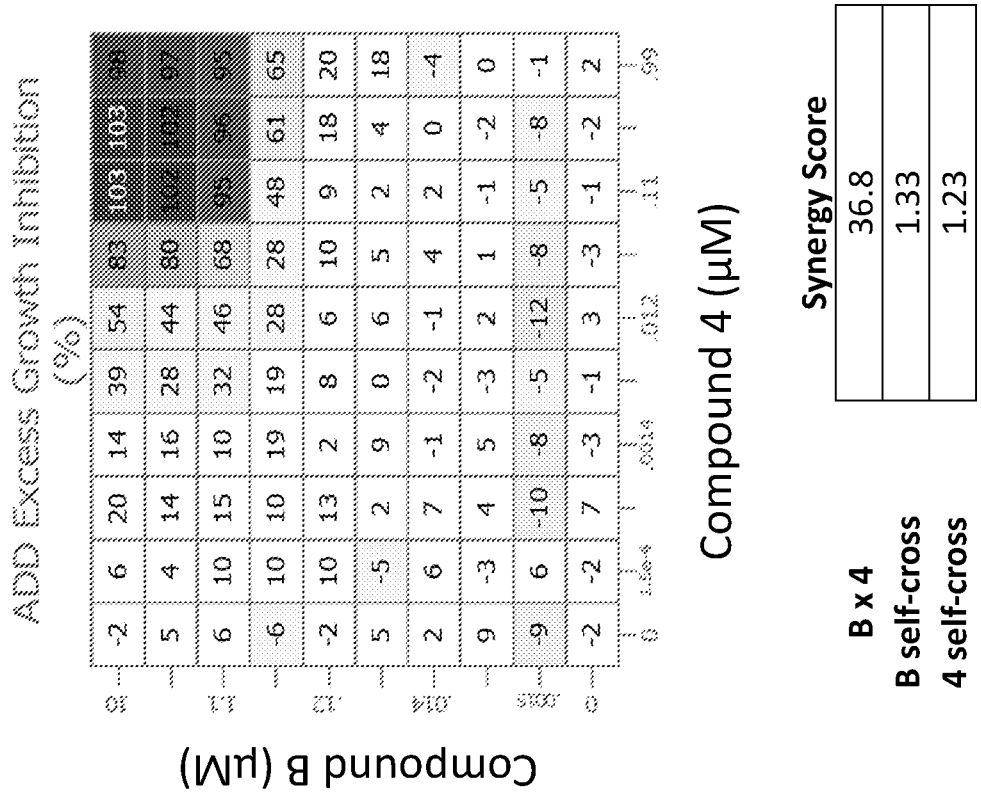
Figure 33a-Figure 33; RT4 cells

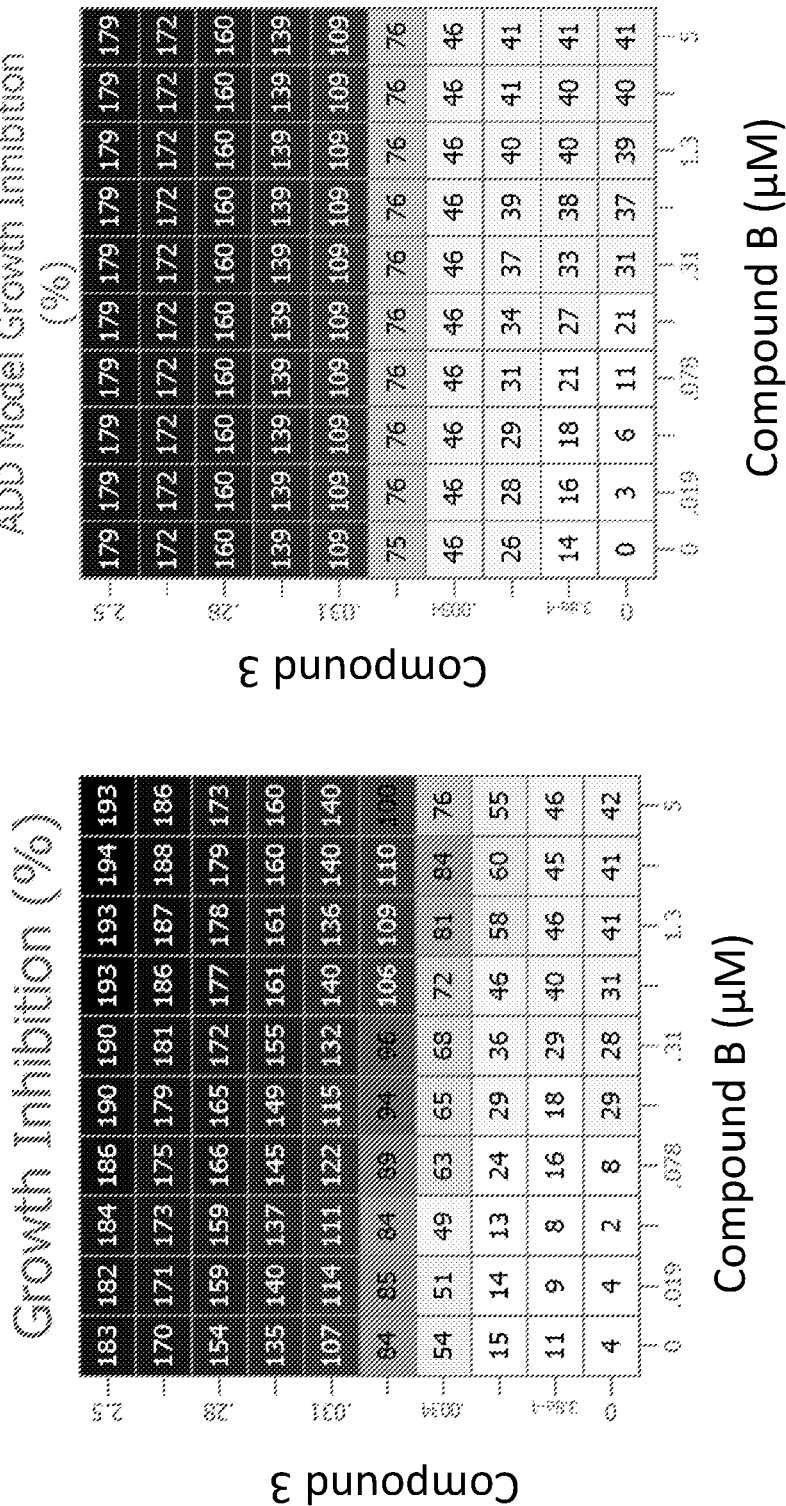
Figure 34-Example 34; SH-4 cells

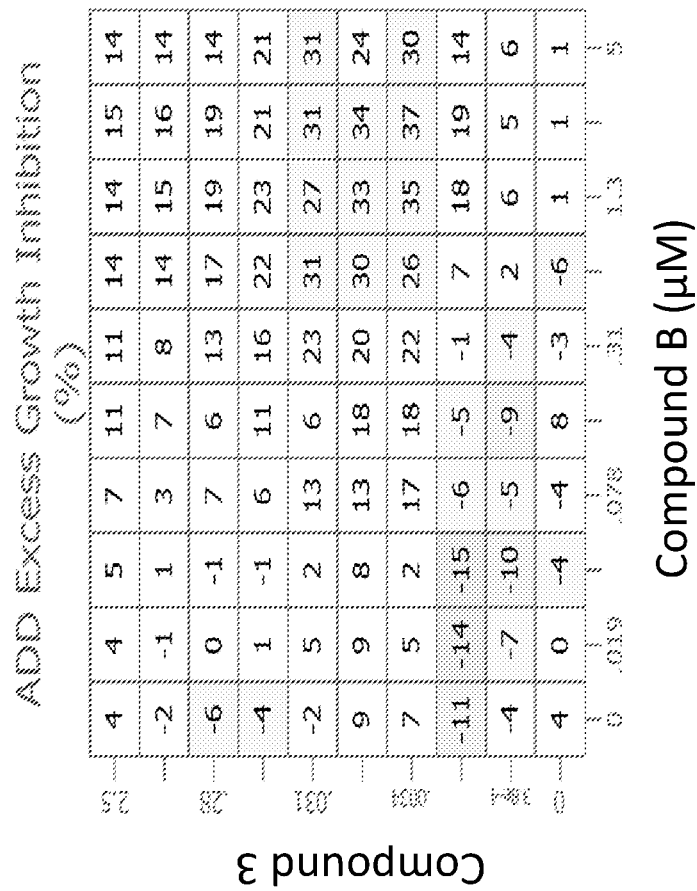
Figure 34a-Example 34; SH-4 cells

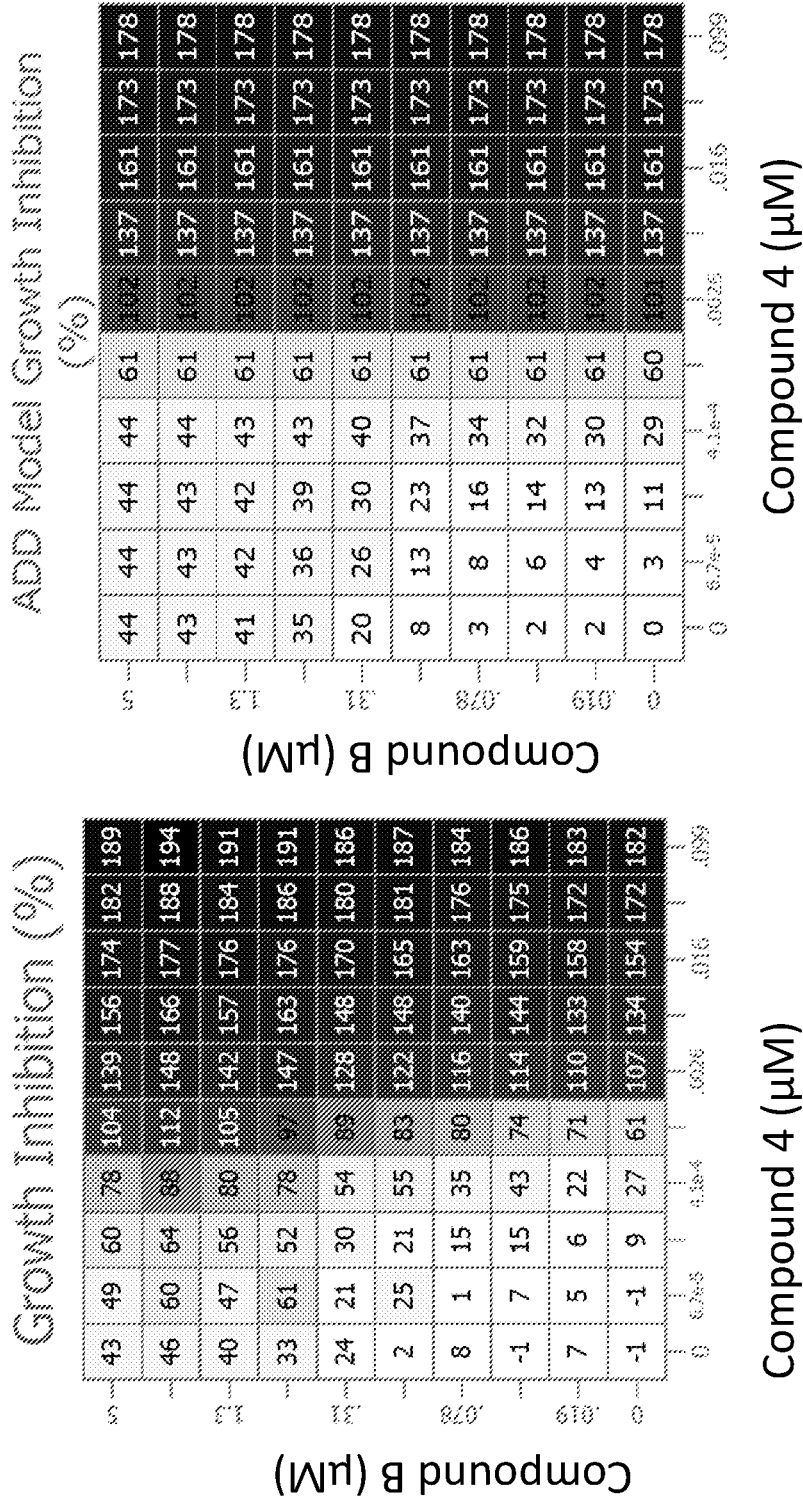
Figure 35-Example 35; SH-4 cells

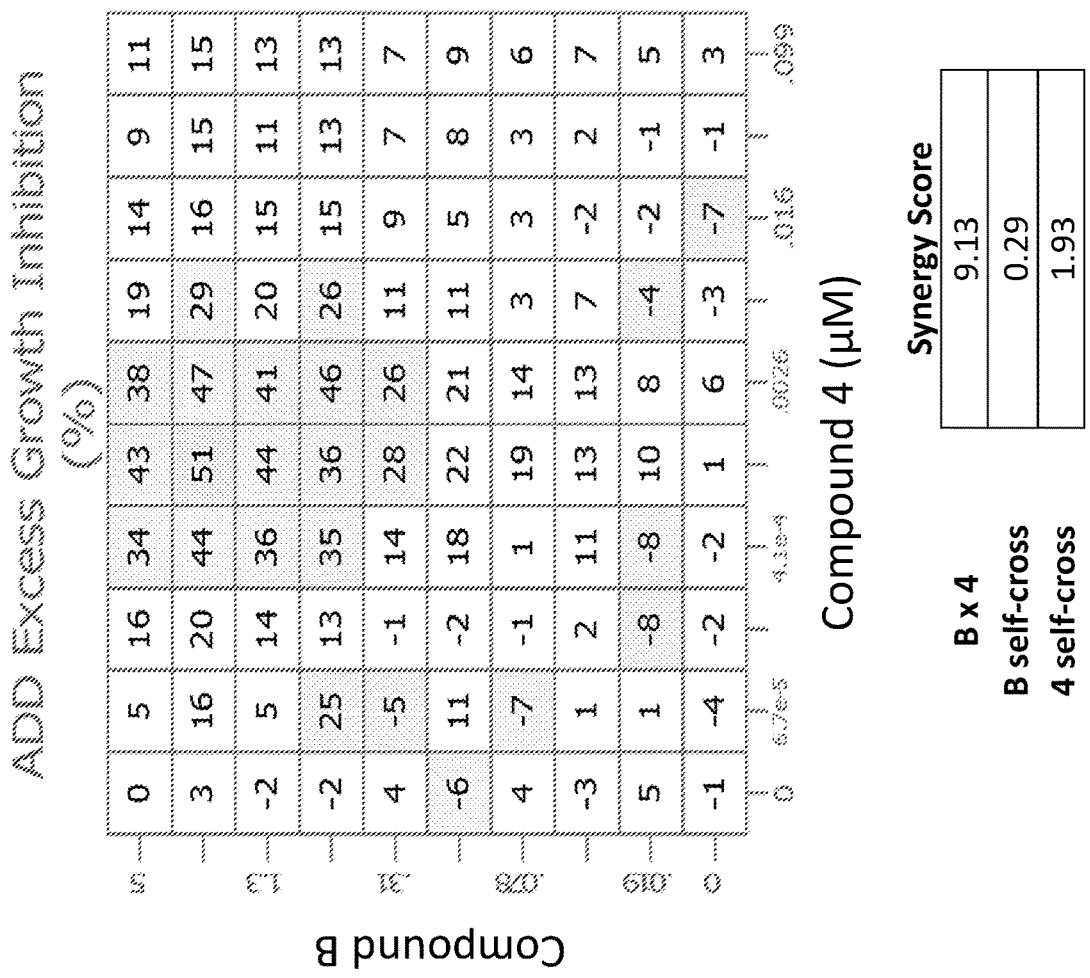
Figure 35a-Example 35; SH-4 cells

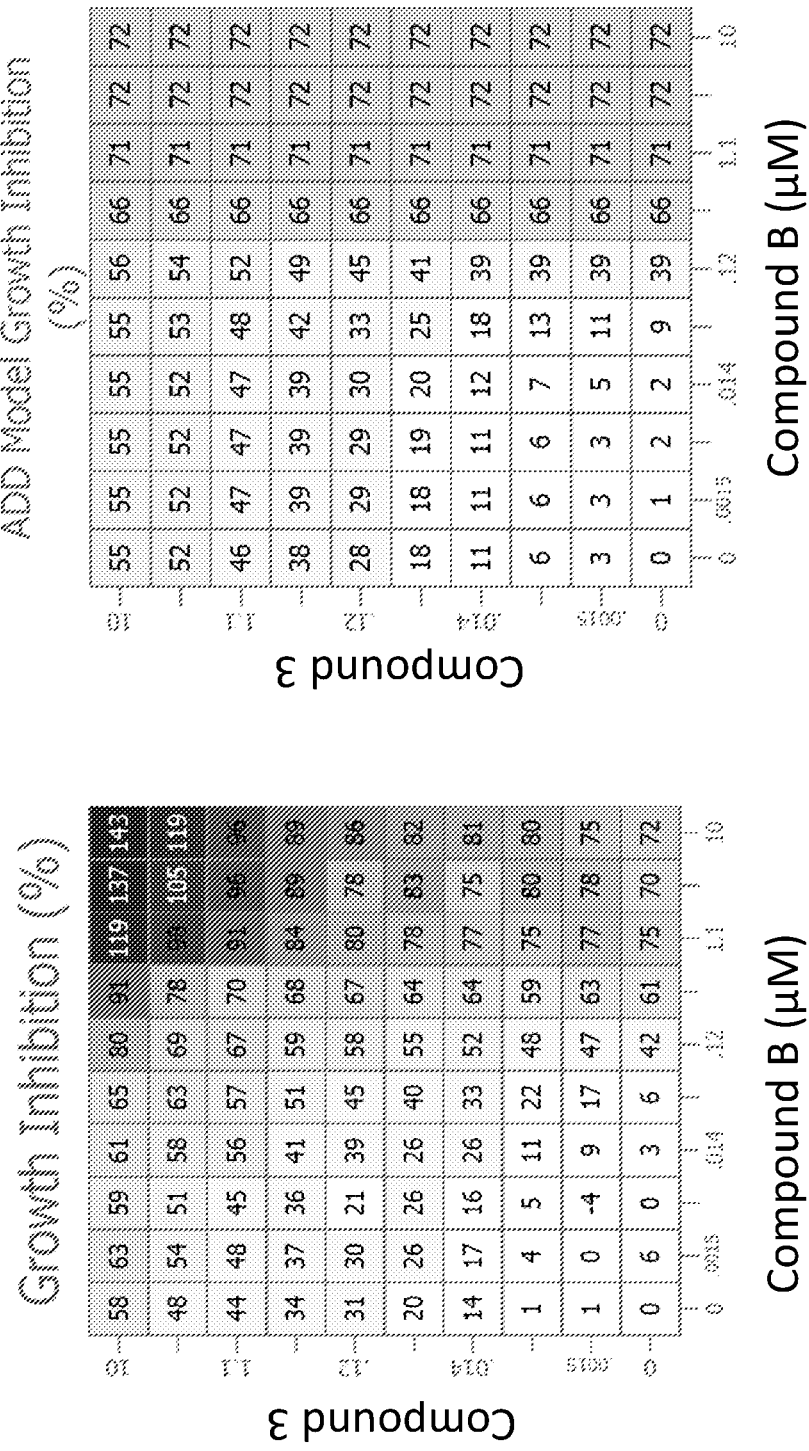
Figure 36-Example 36; SK-HEP-1 cells

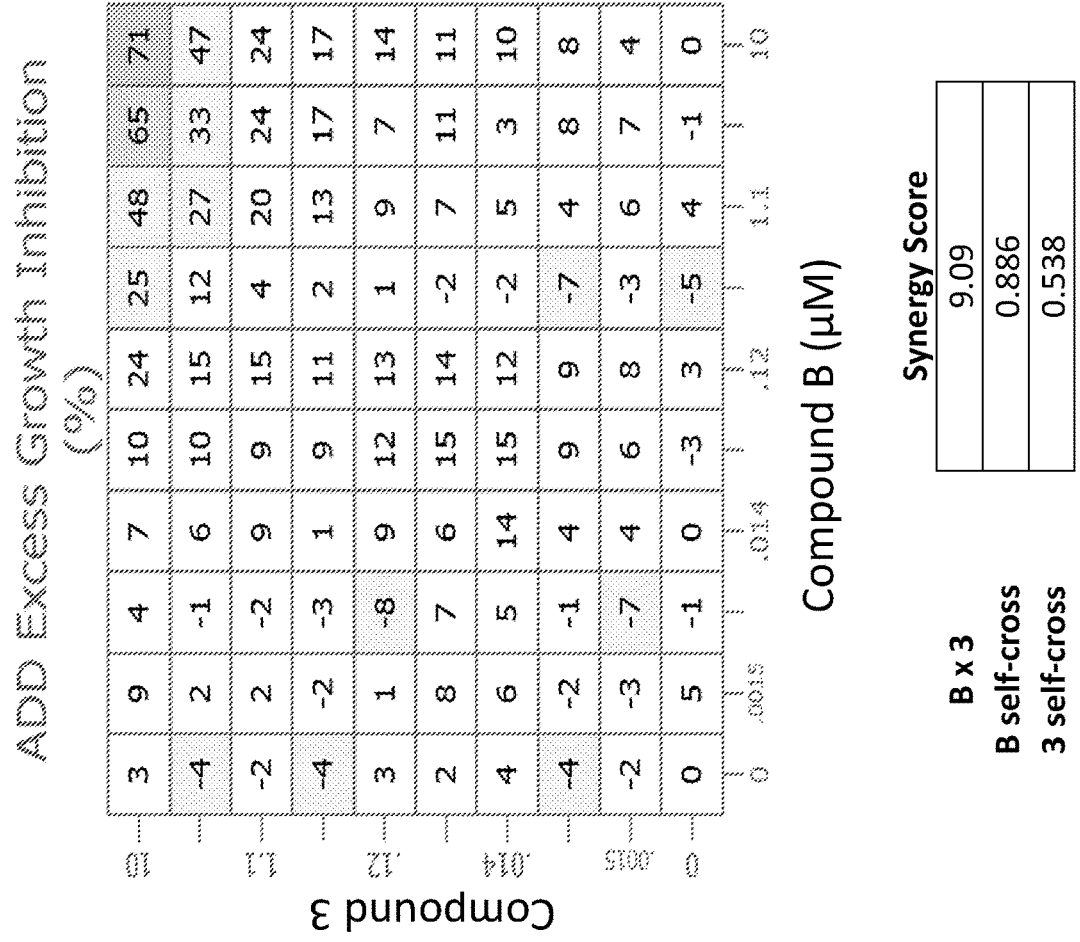
Figure 36a-Example 36; SK-HEP-1 cells

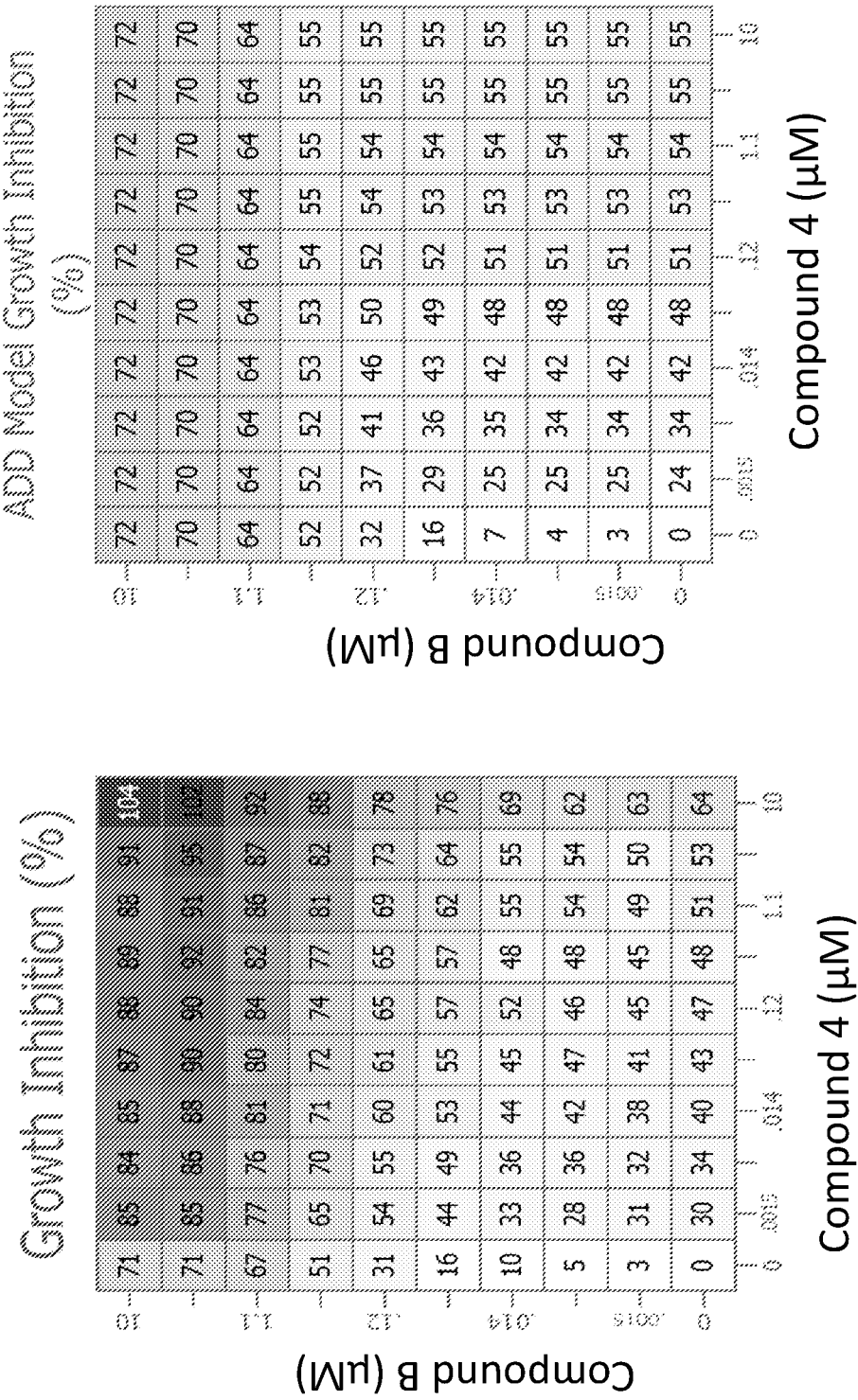
Figure 37-Example 37; SK-HEP-1 cells

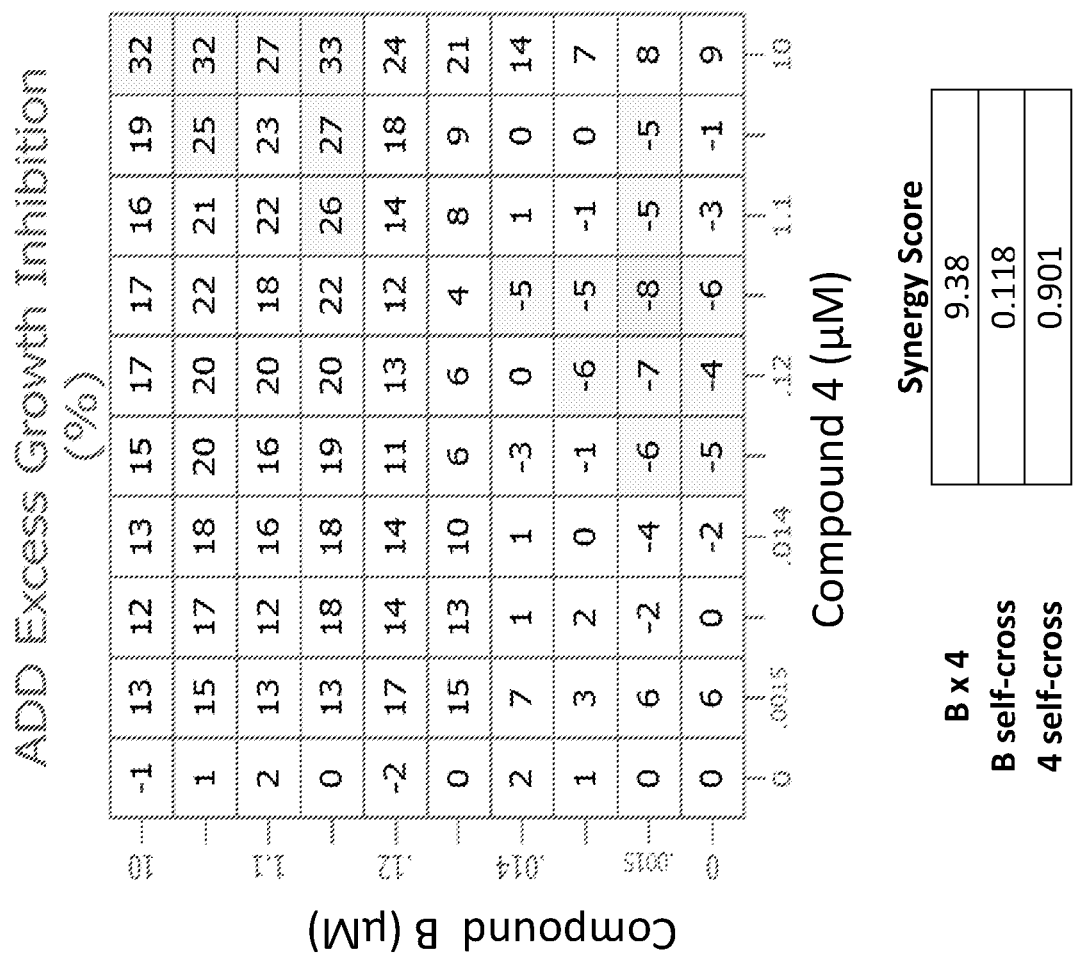
Figure 37a-Example 37; SK-HEP-1 cells

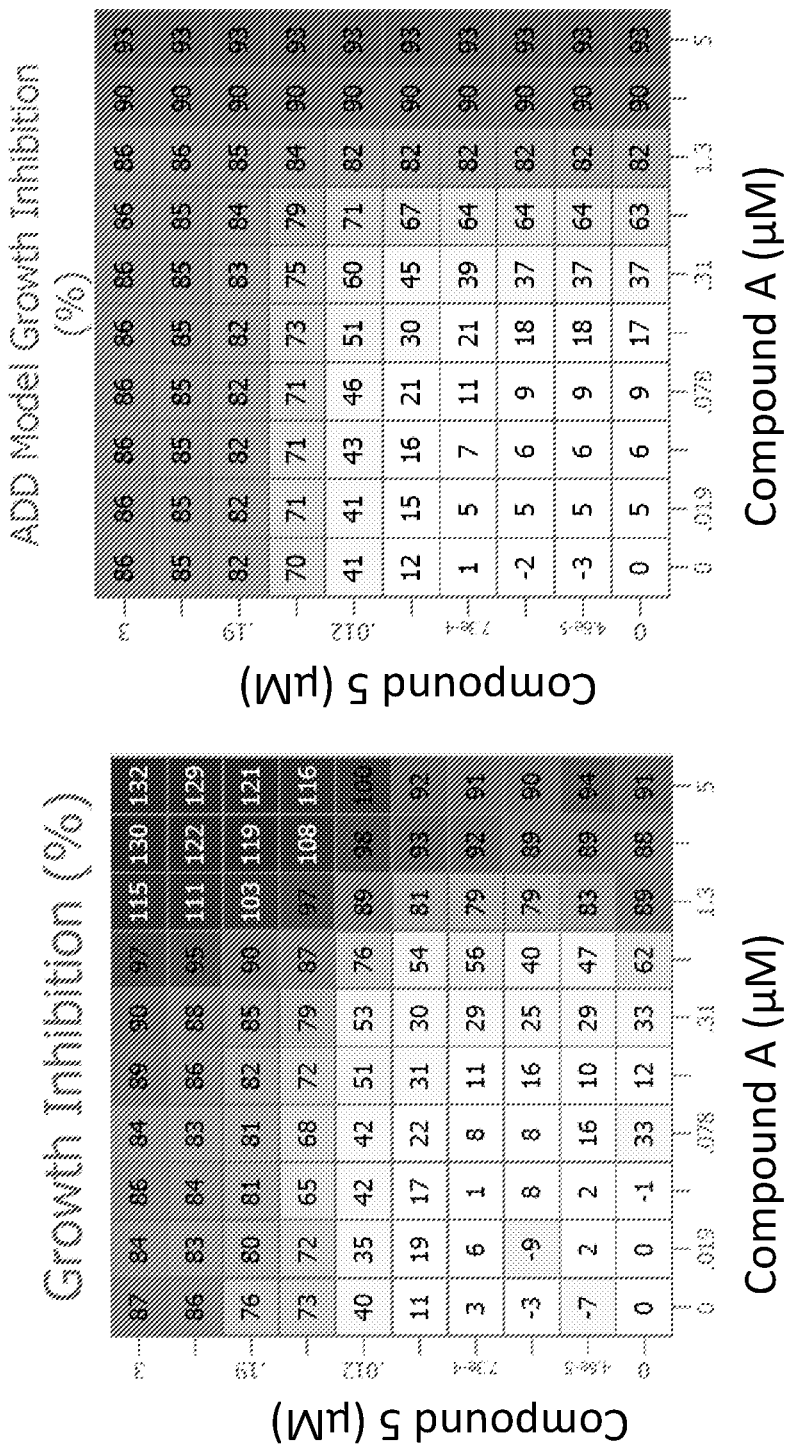
Figure 38-Example 38; A204 cells

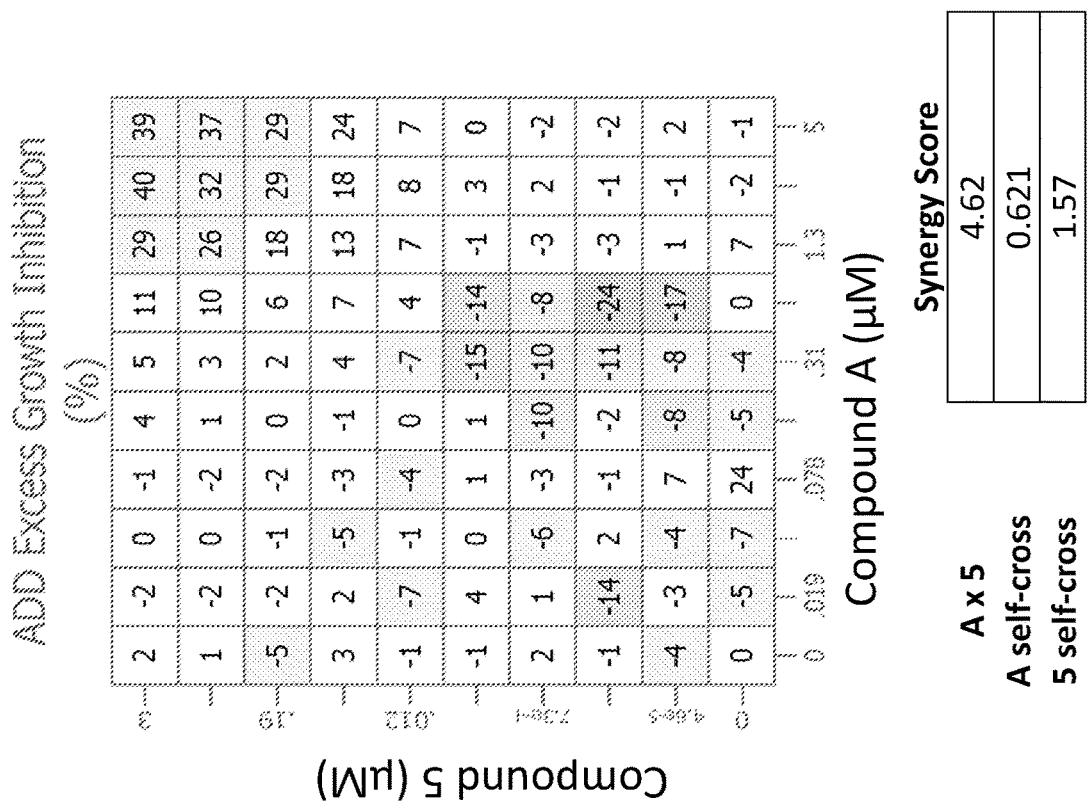
Figure 38a-Example 38; A204 cells

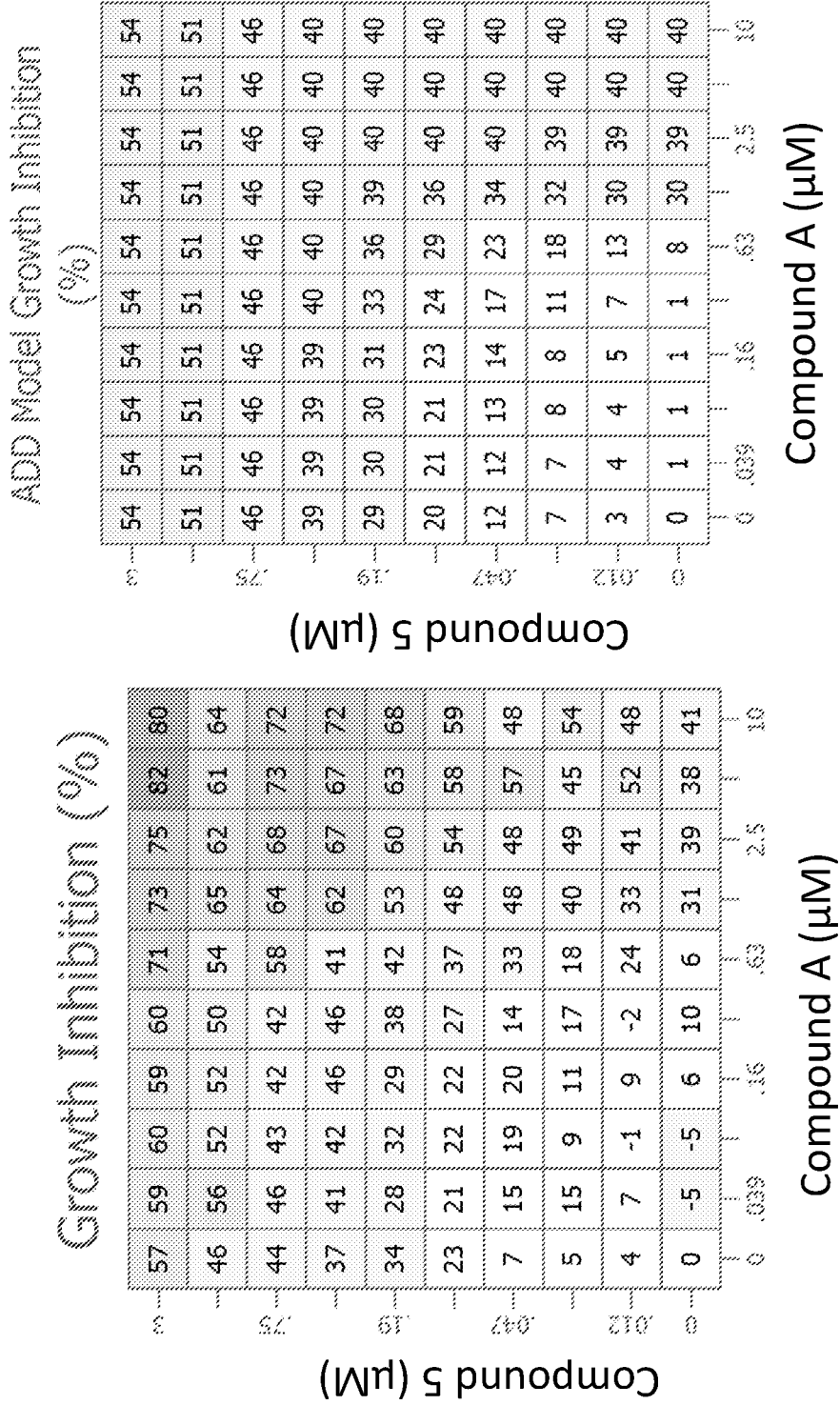
Figure 39-Example 39; A375sq2 cells

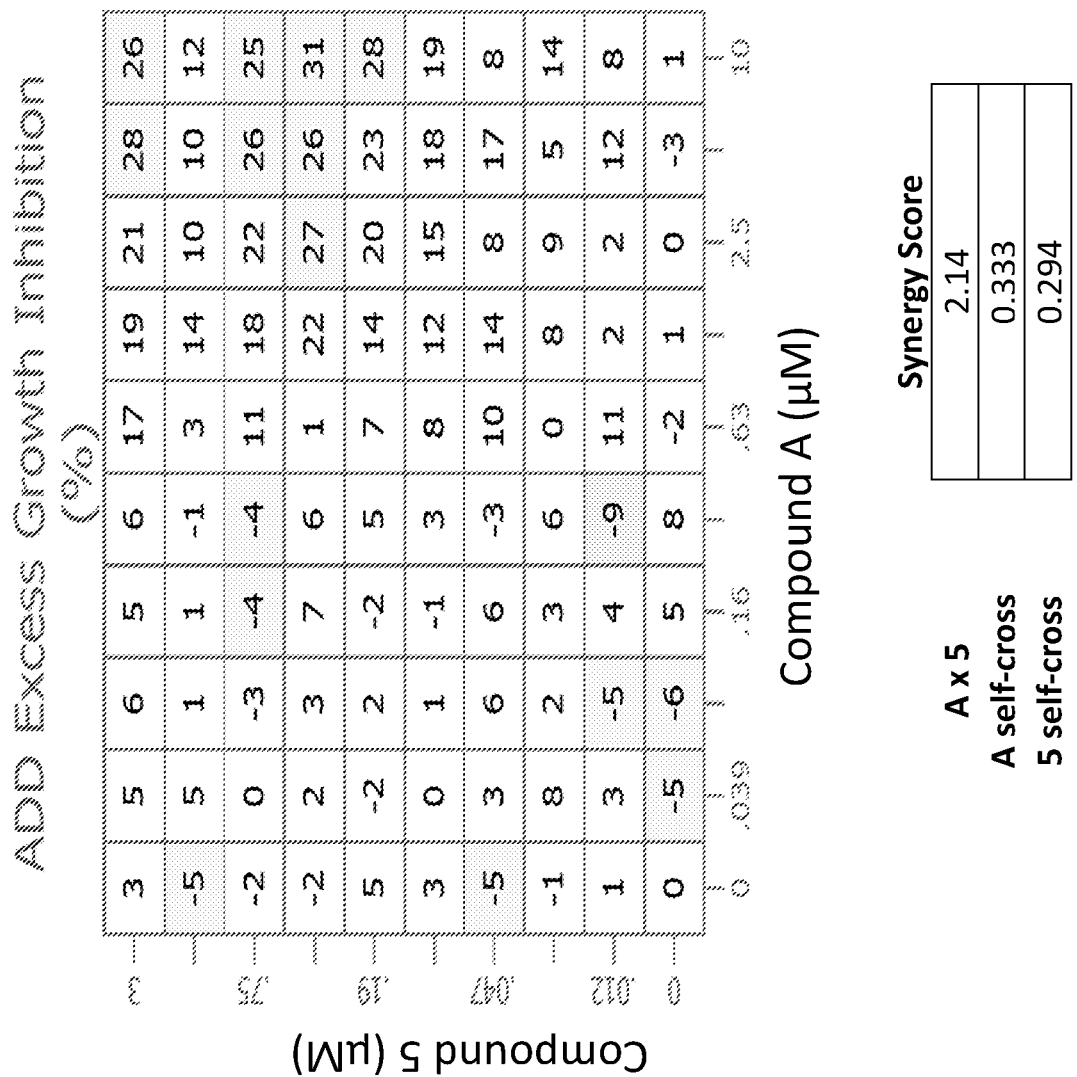
Figure 39a-Example 39; A375sq2 cells

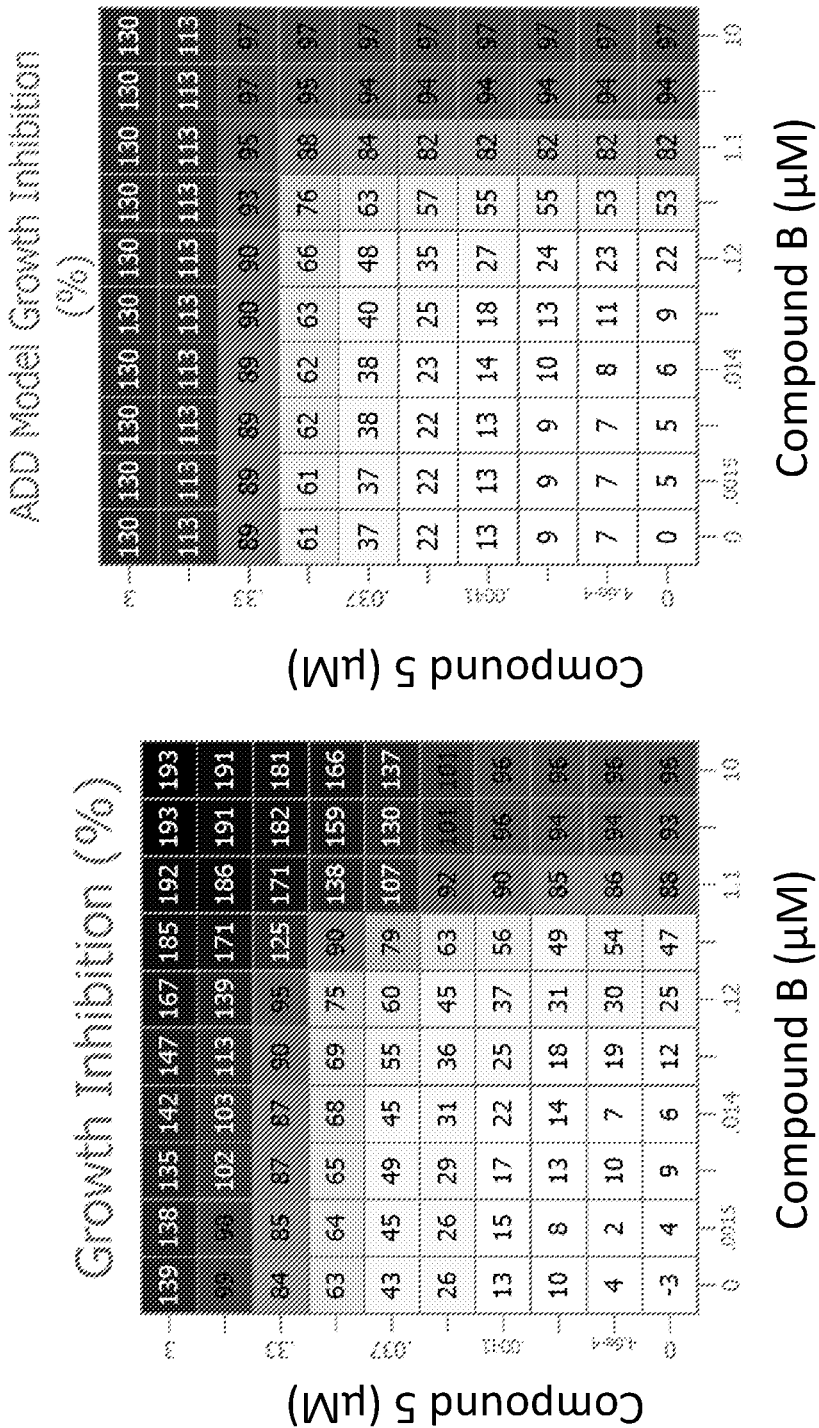
Figure 40-Example 40; CAL-51 cells

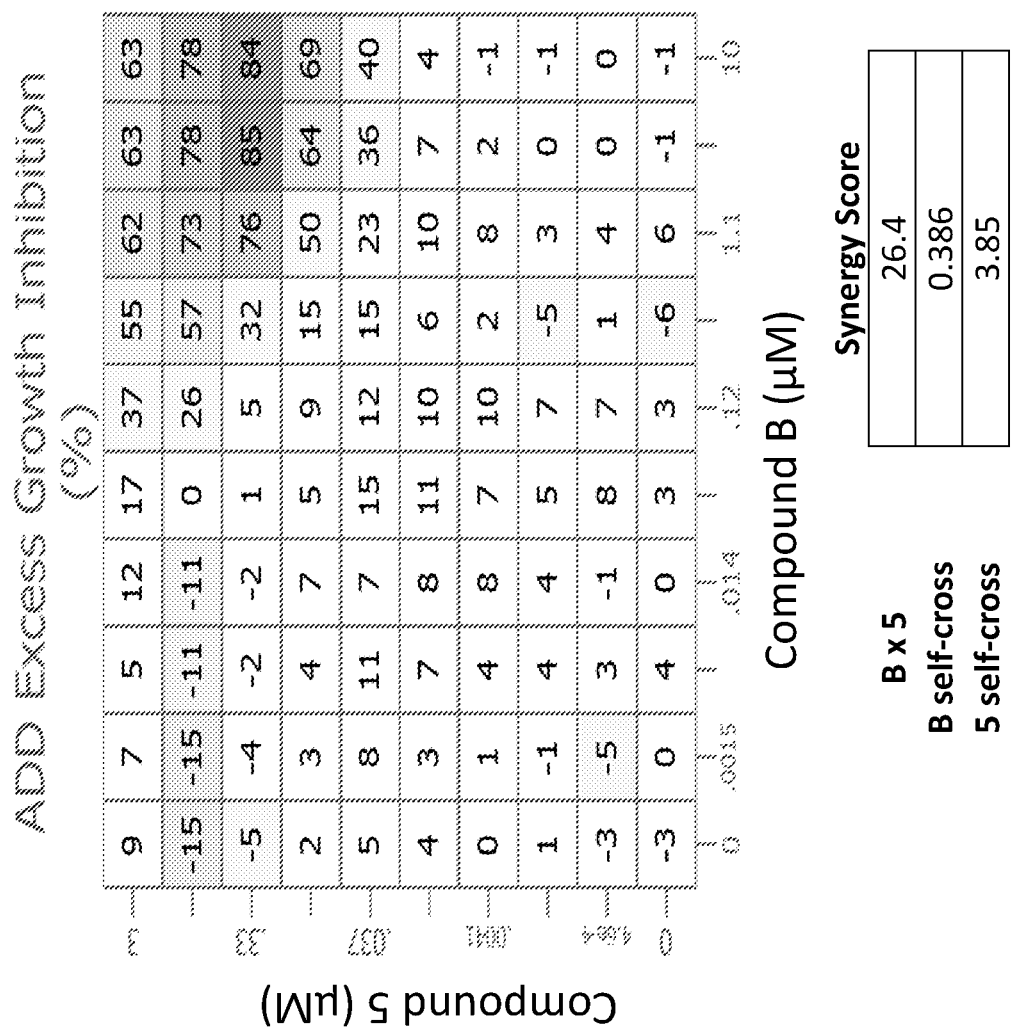
Figure 40a-Example 40; CAL-51 cells

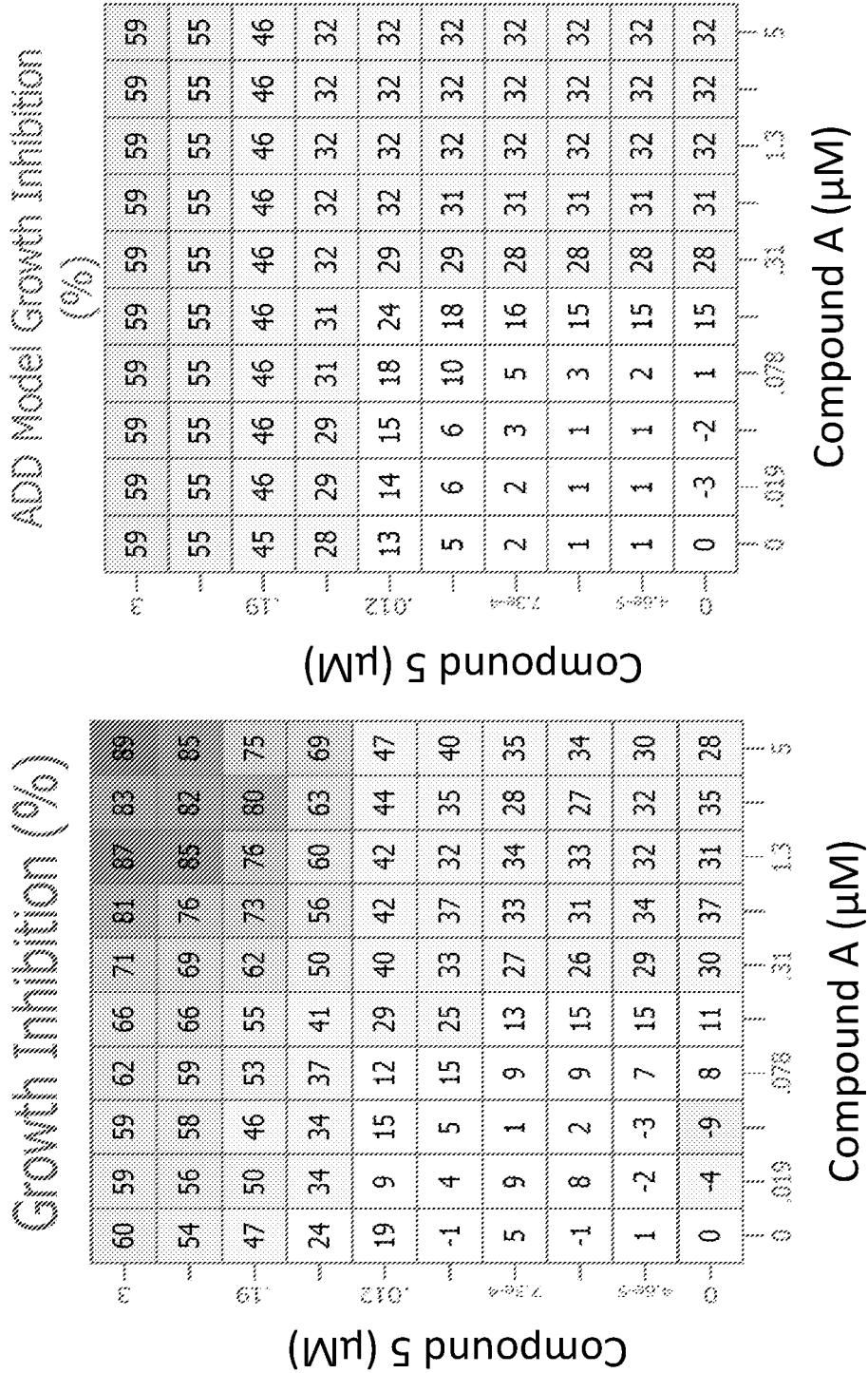
Figure 41-Example 41; G-361 cells

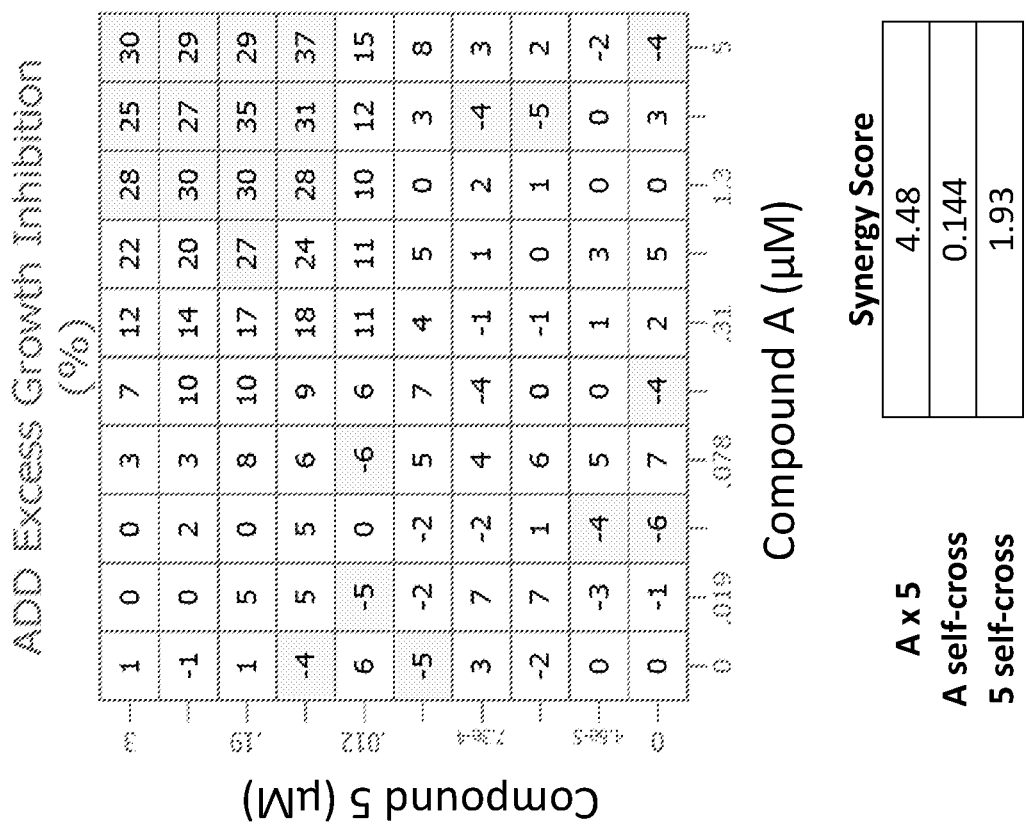
Figure 41a-Example 41; G-361 cells

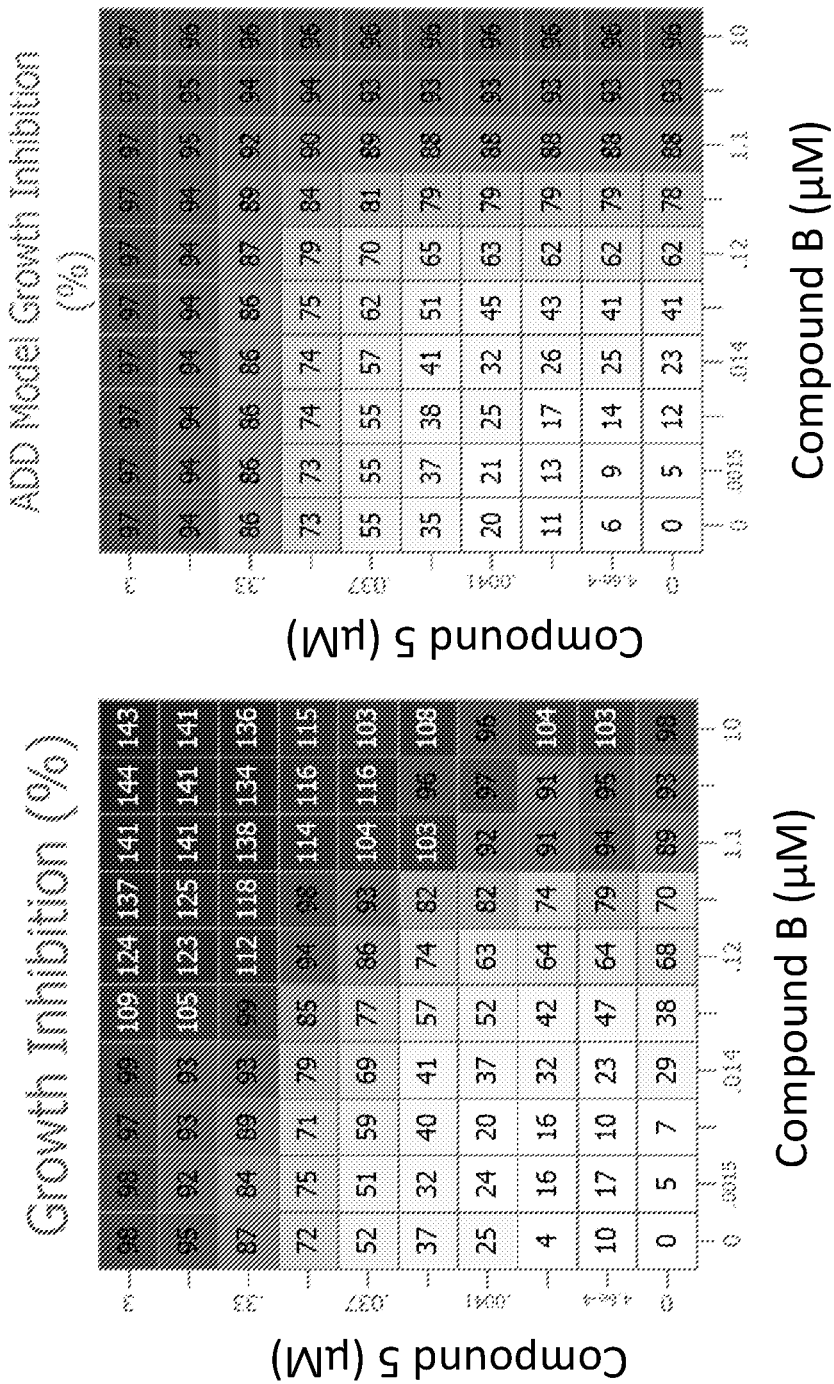
Figure 42-Example 42; HT-1197 cells

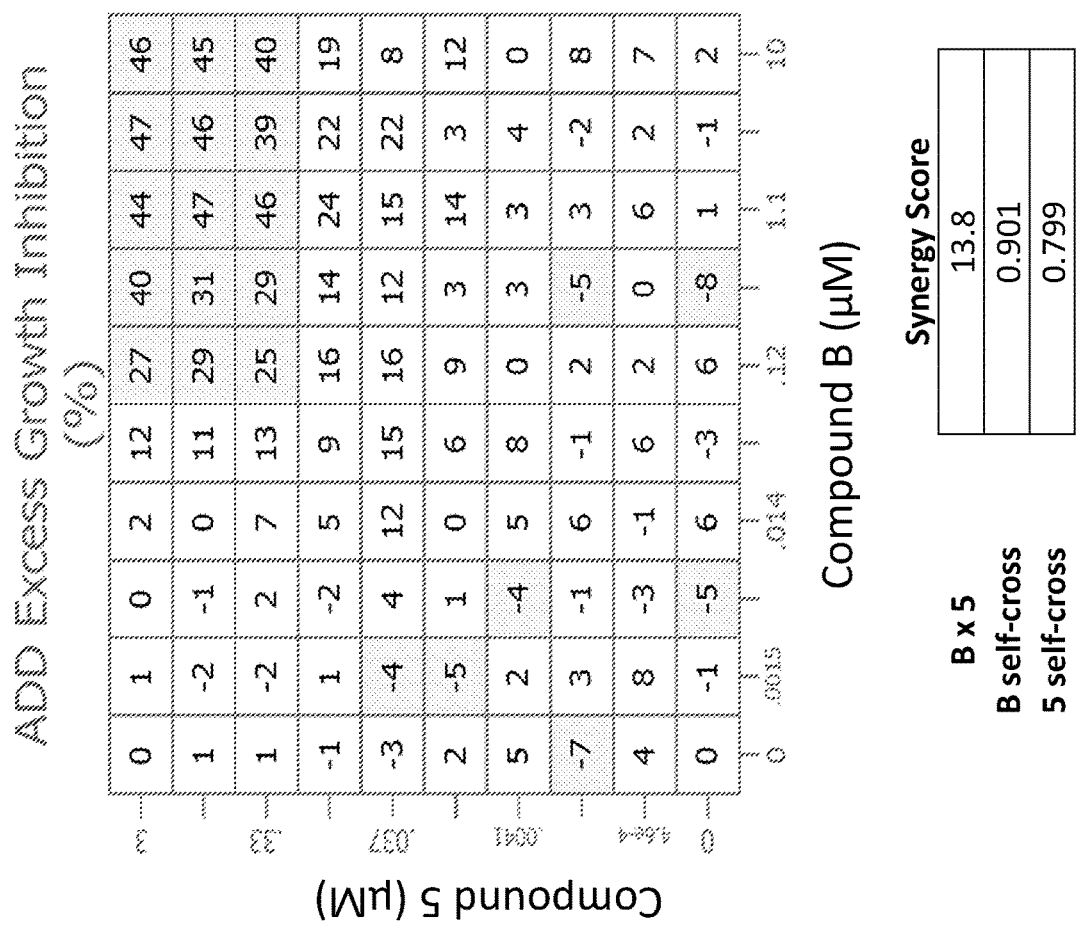
Figure 42a-Example 42; HT1197 cells

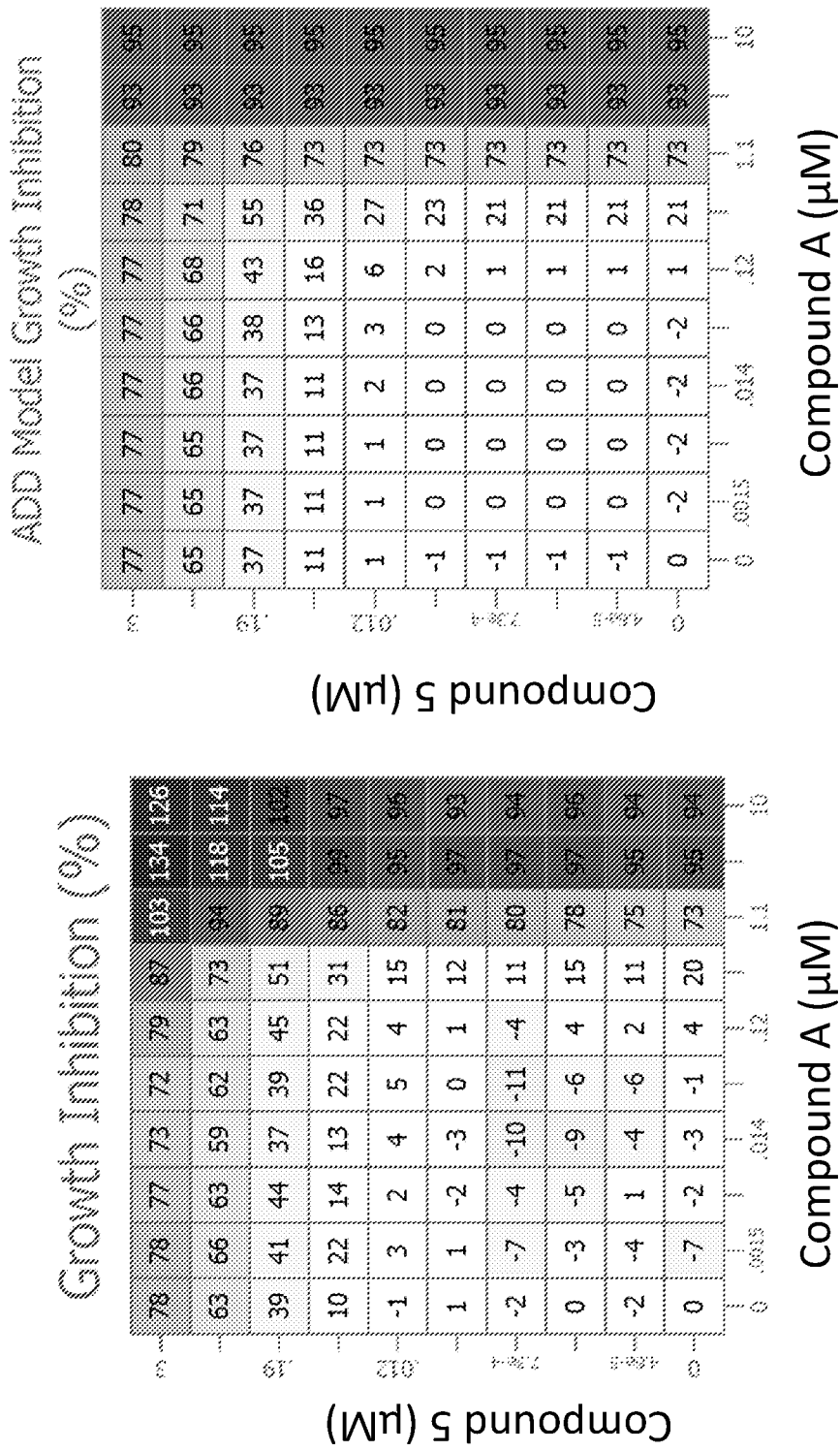
Figure 43-Example 43; LS 174T cells

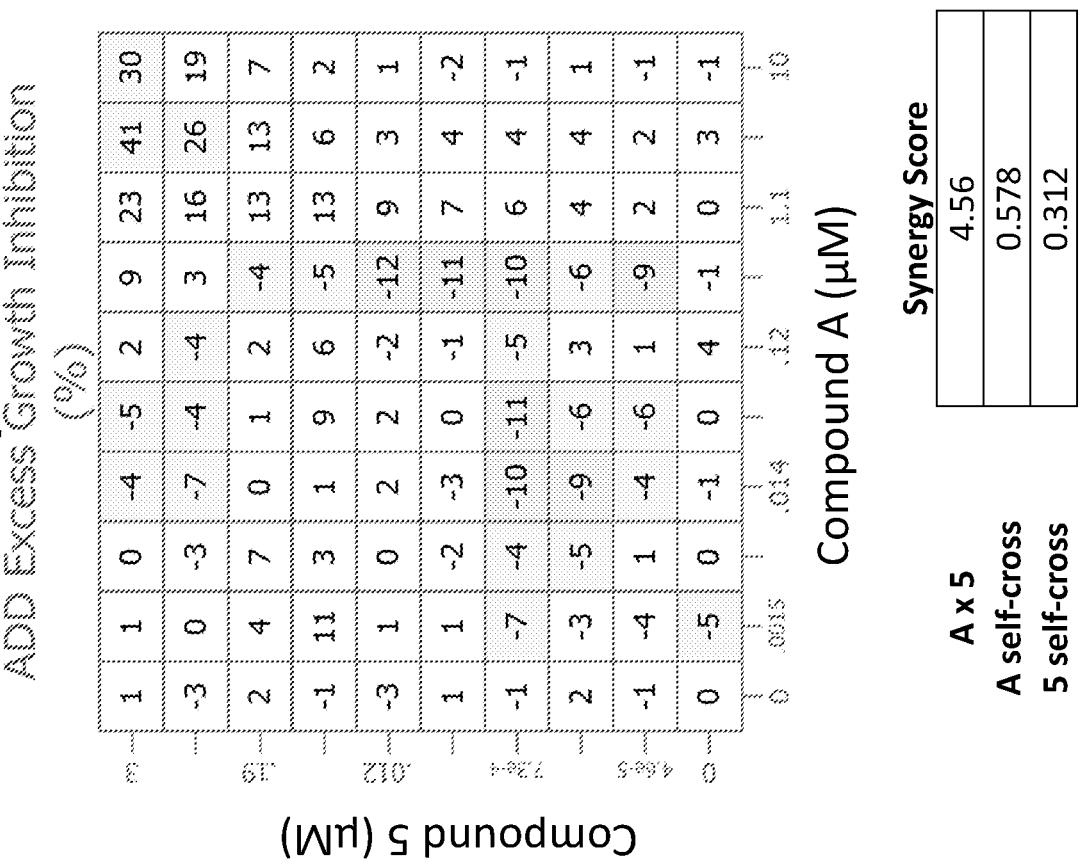
Figure 43a-Example 43; LS 174T cells

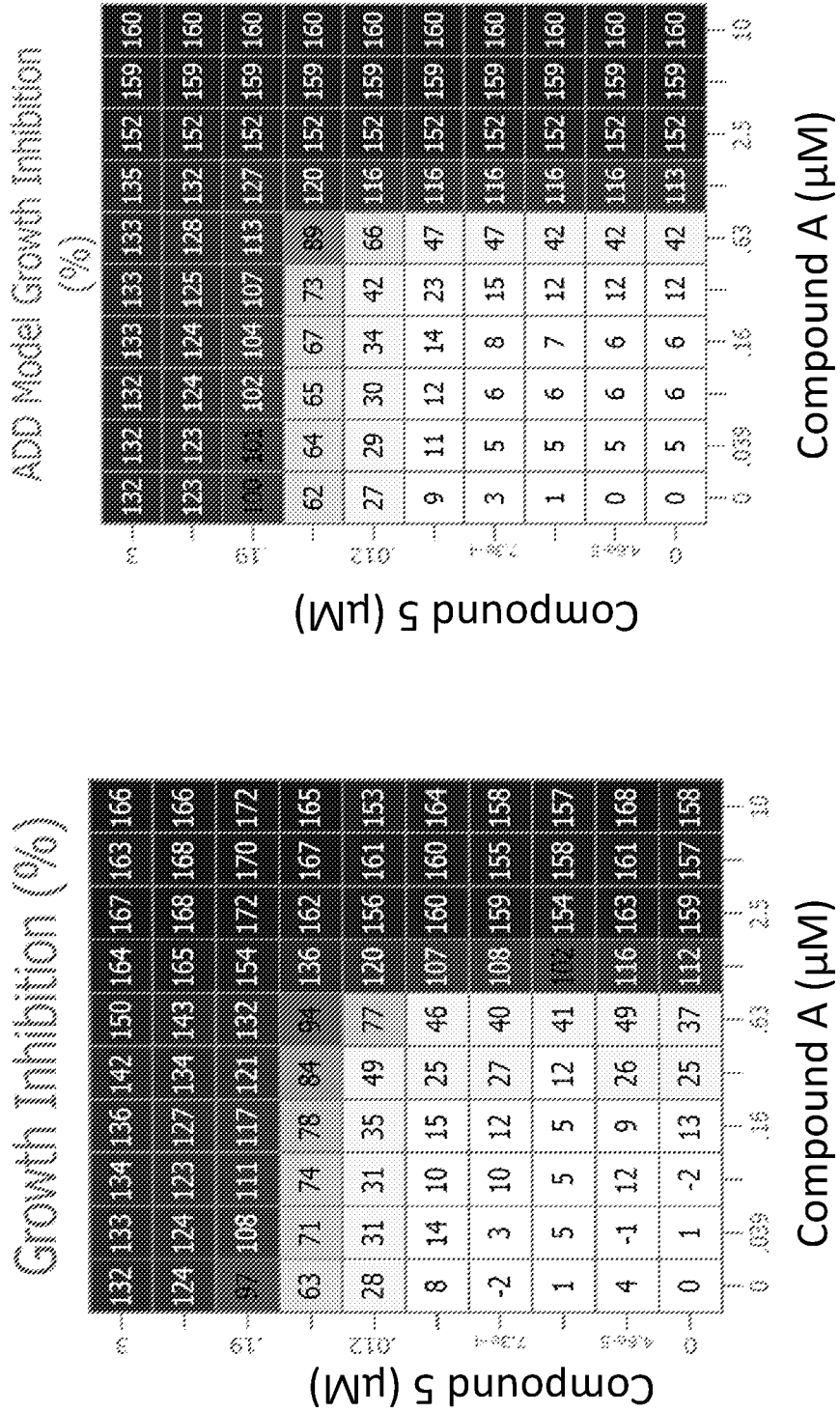
Figure 44-Example 44; MCF7 cells

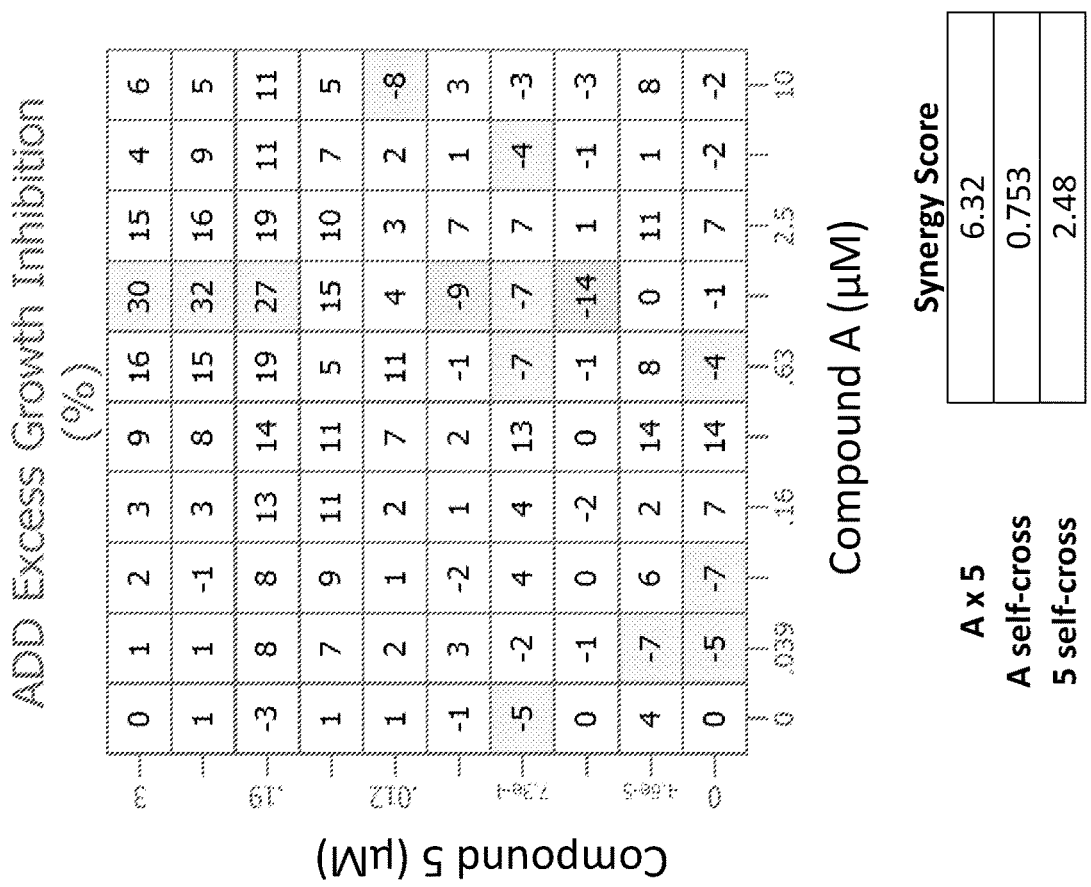
Figure 44a-Example 44; MCF7 cells

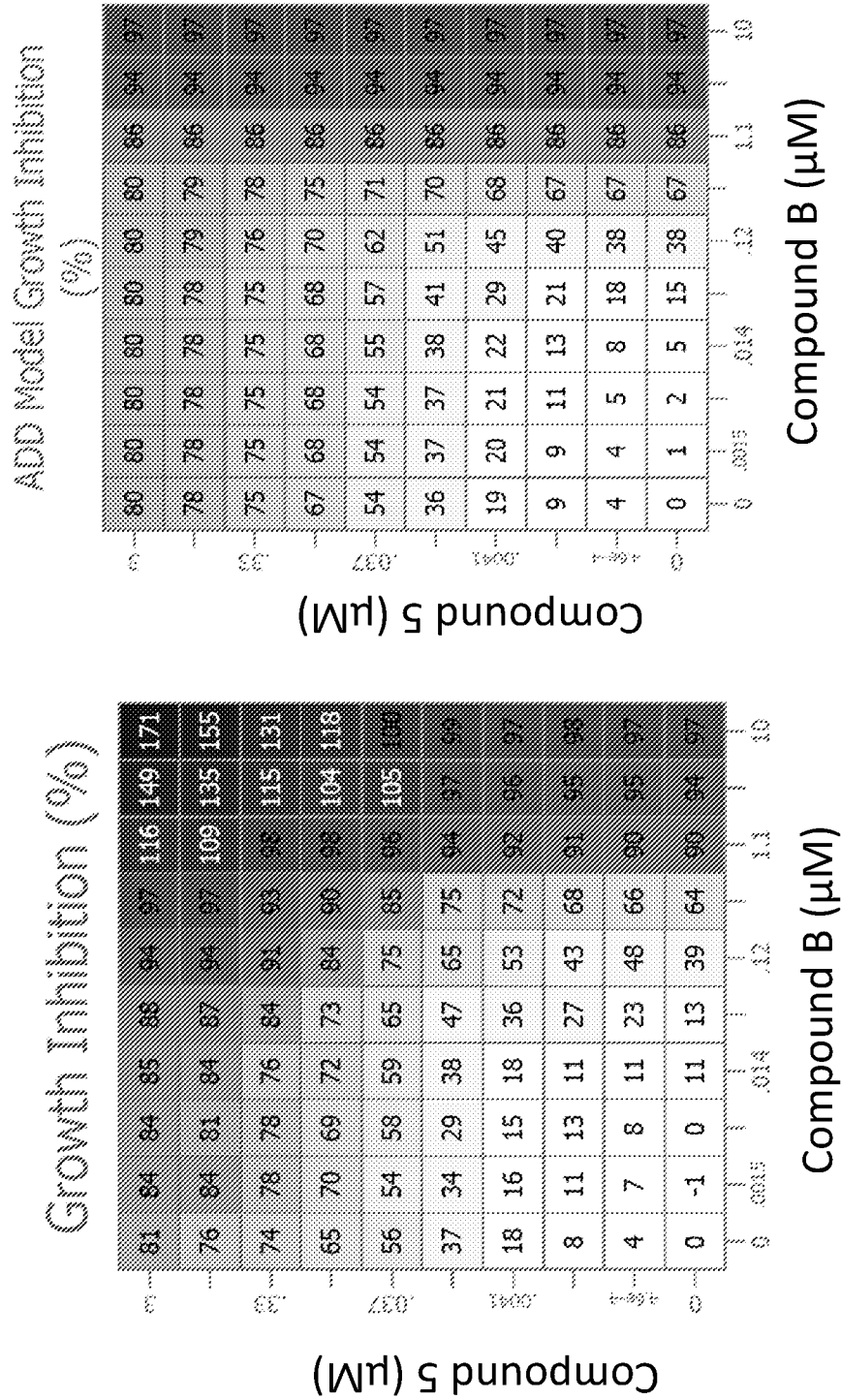
Figure 45-Example 45; NCI-H460 cells

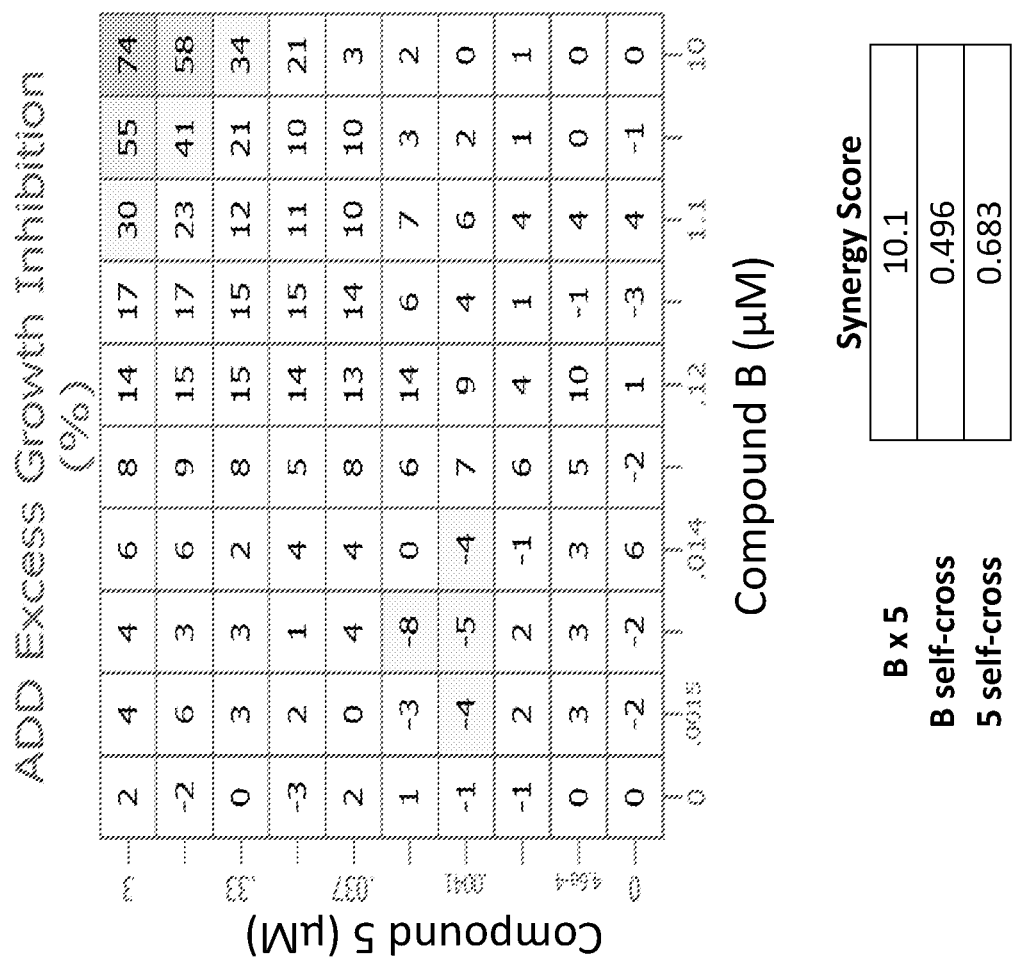
Figure 45a-Example 45; NCI-H460 cells

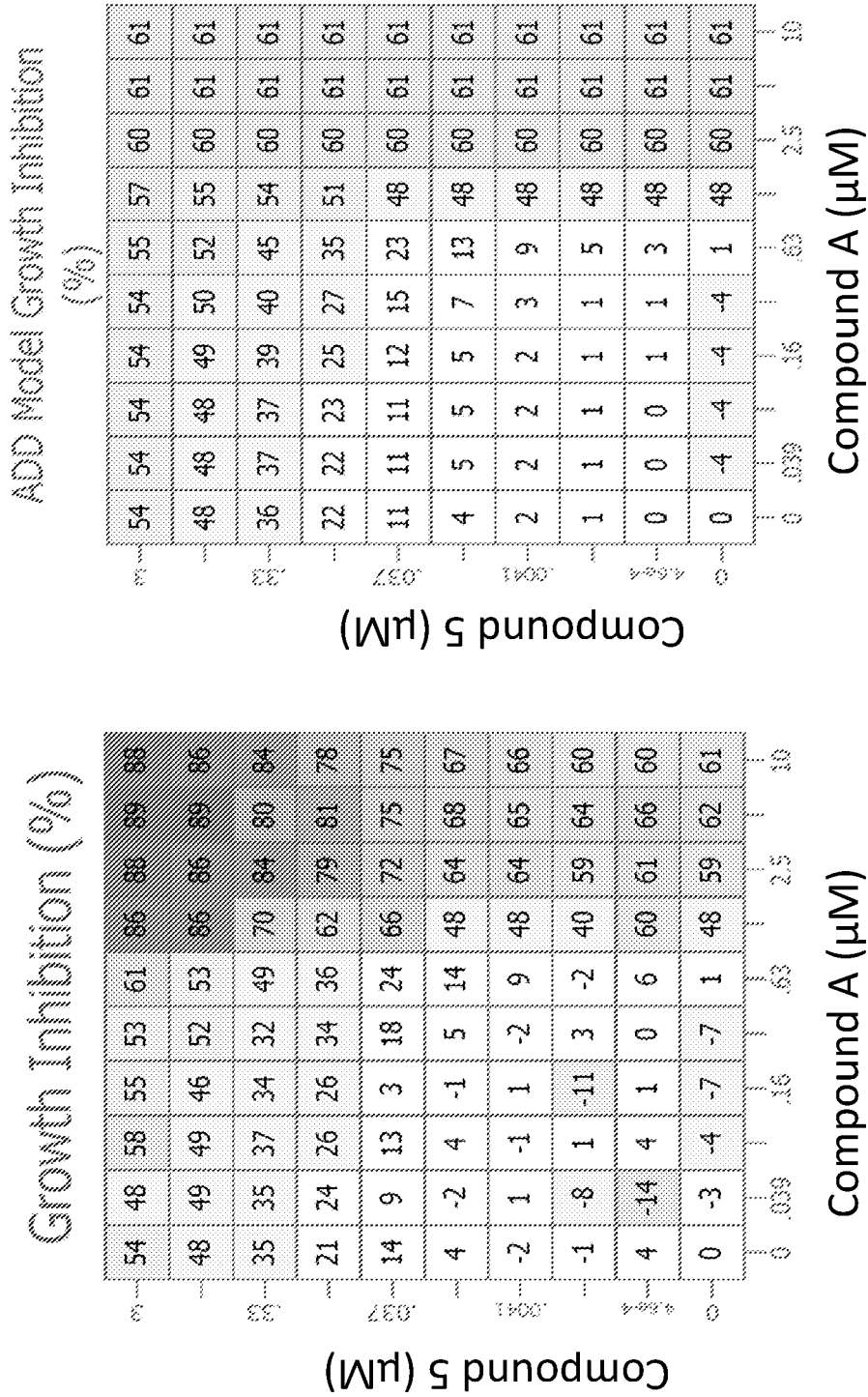
Figure 46-Example 46; RKO cells

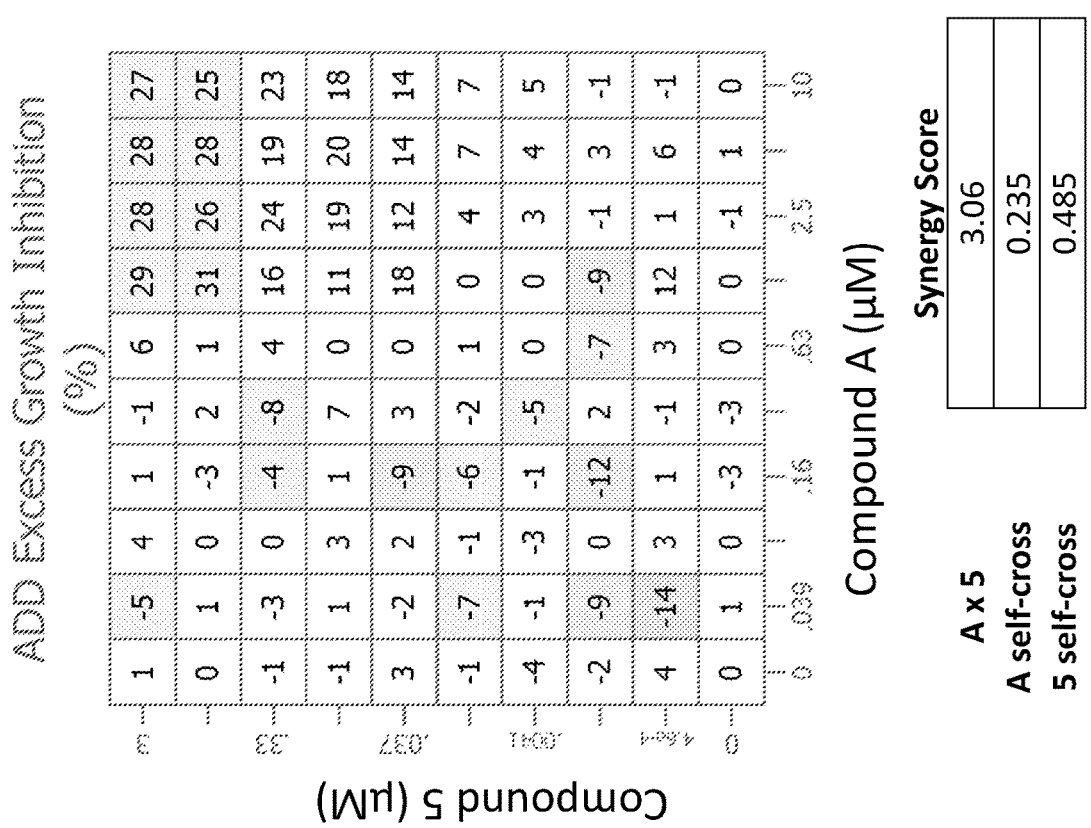
Figure 46a-Example 46; RKO cells

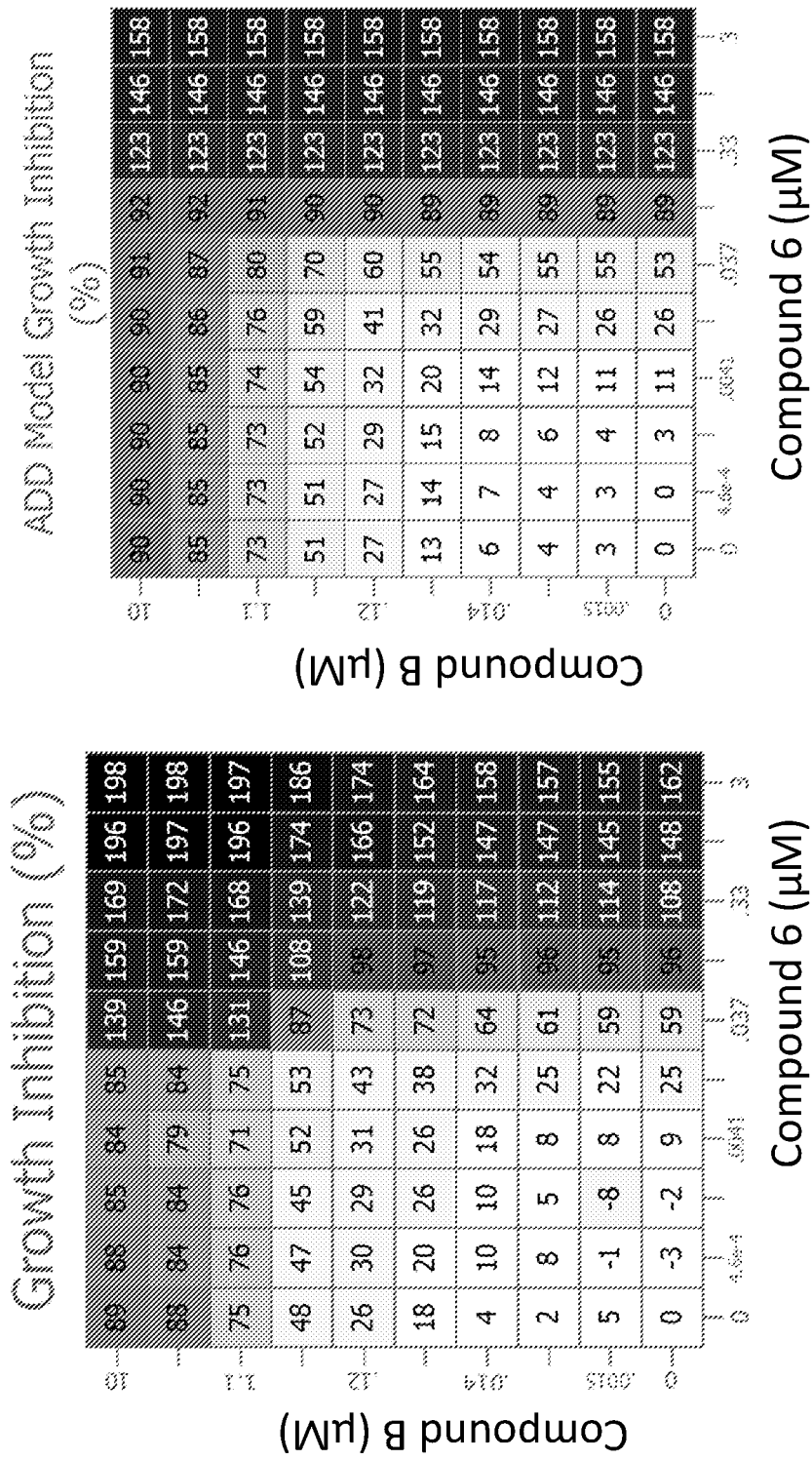
Figure 47-Example 47; A204 cells

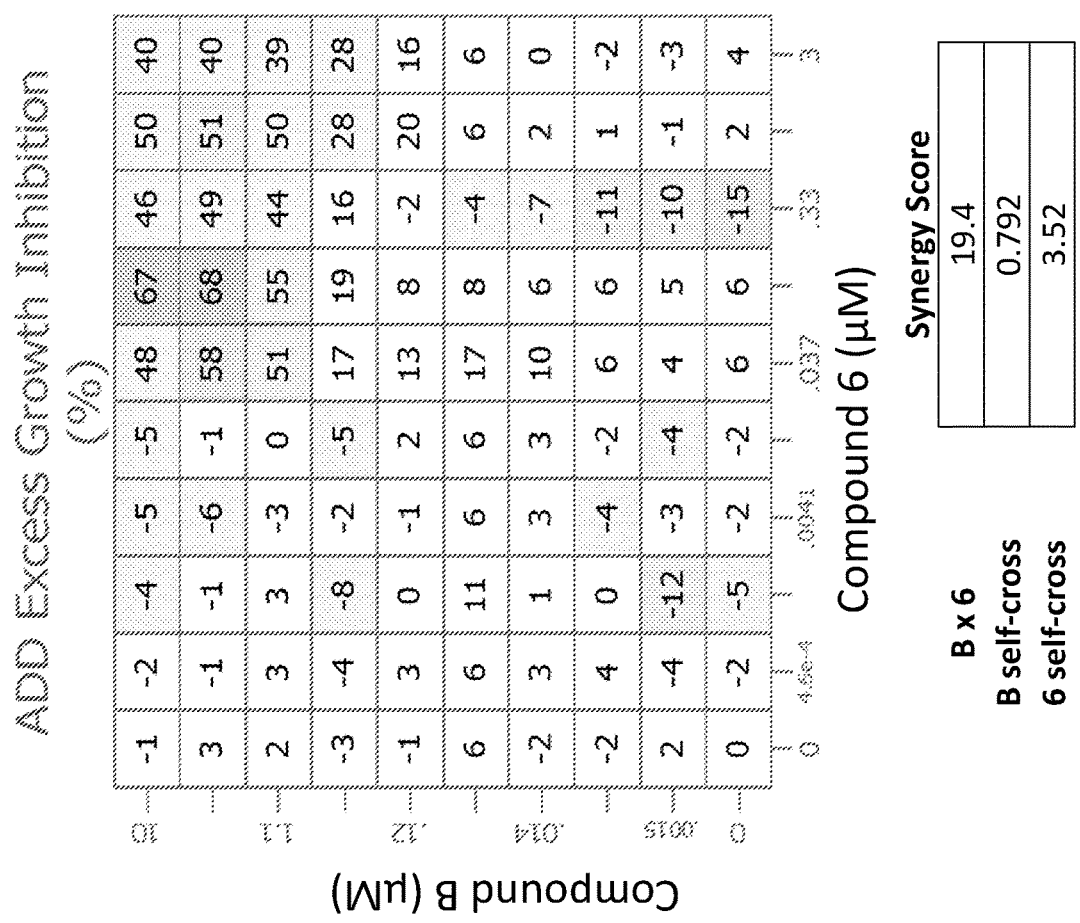
Figure 47a-Example 47; A204 cells

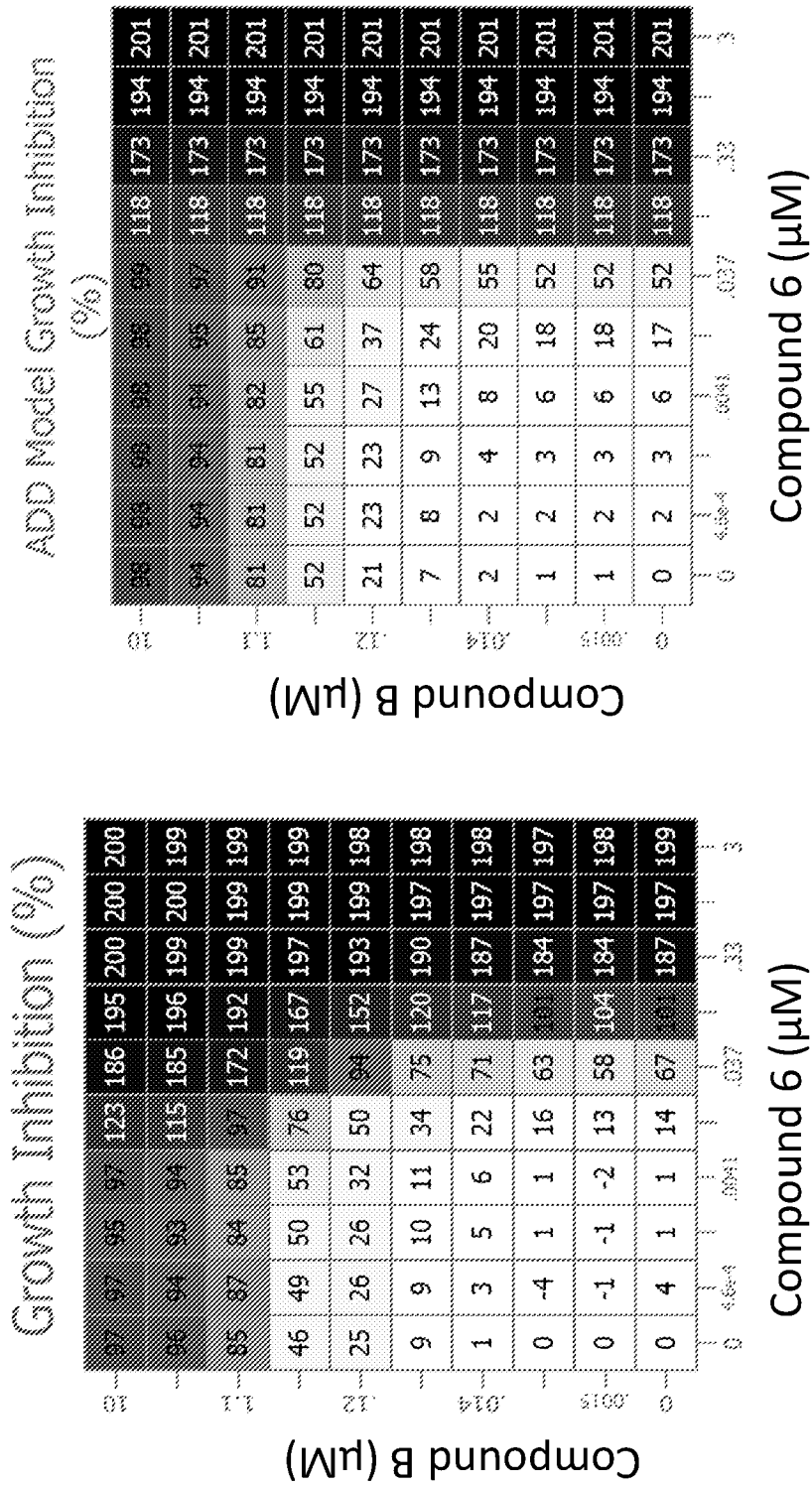
Figure 48-Example 48; A2780 cells

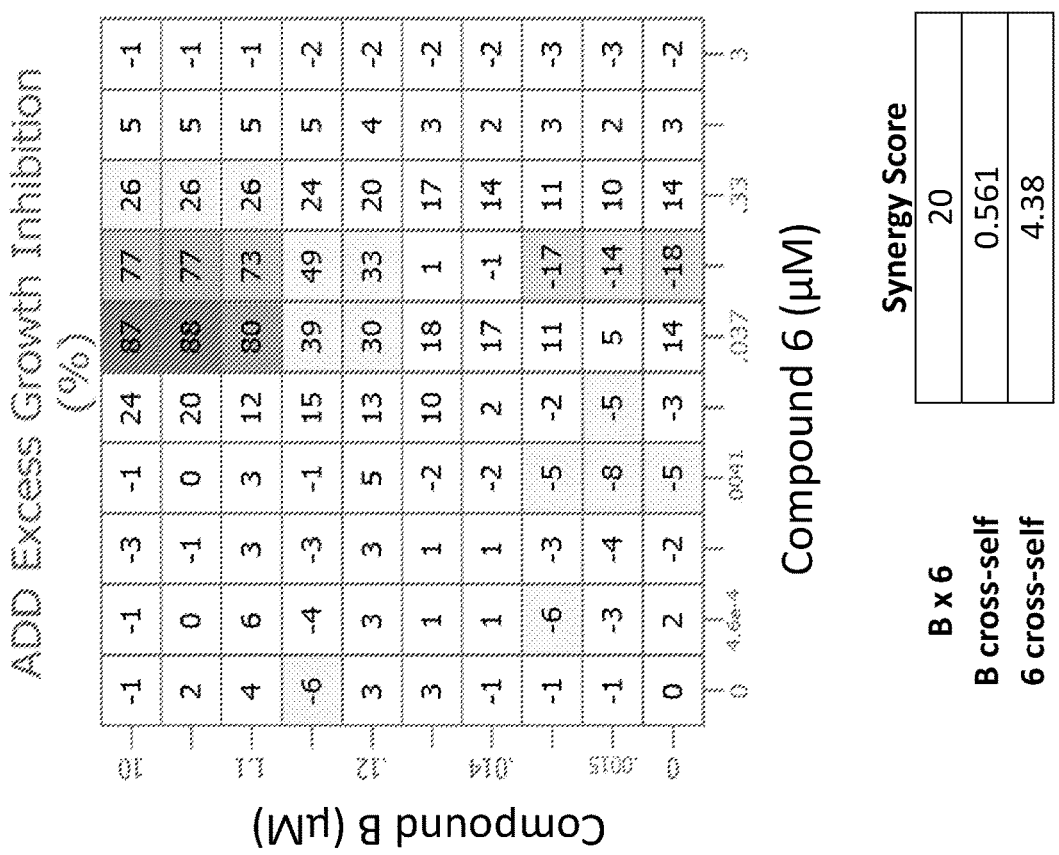
Figure 48a-Example 48; A2780 cells

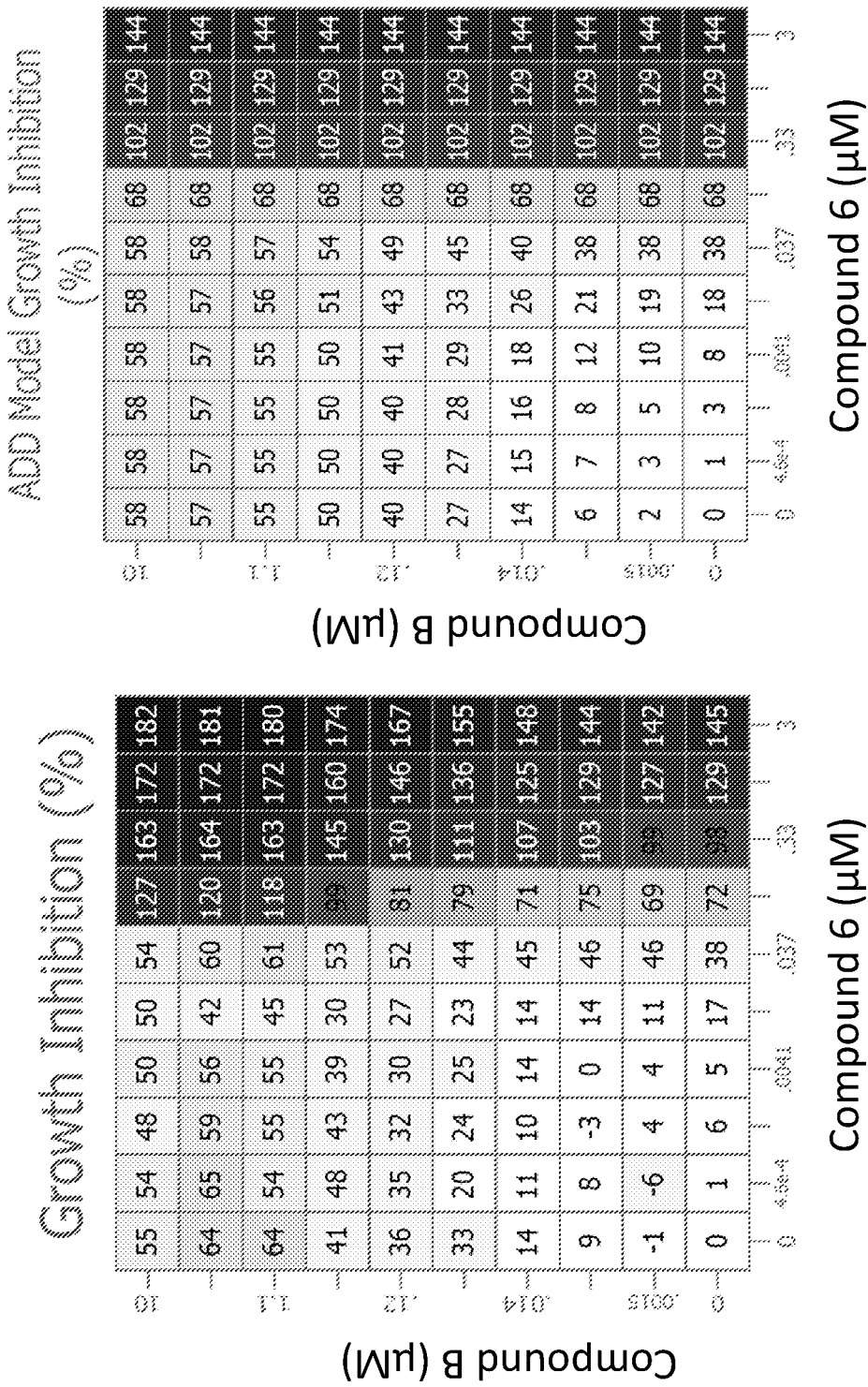
Figure 49-Example 49; C32 cells

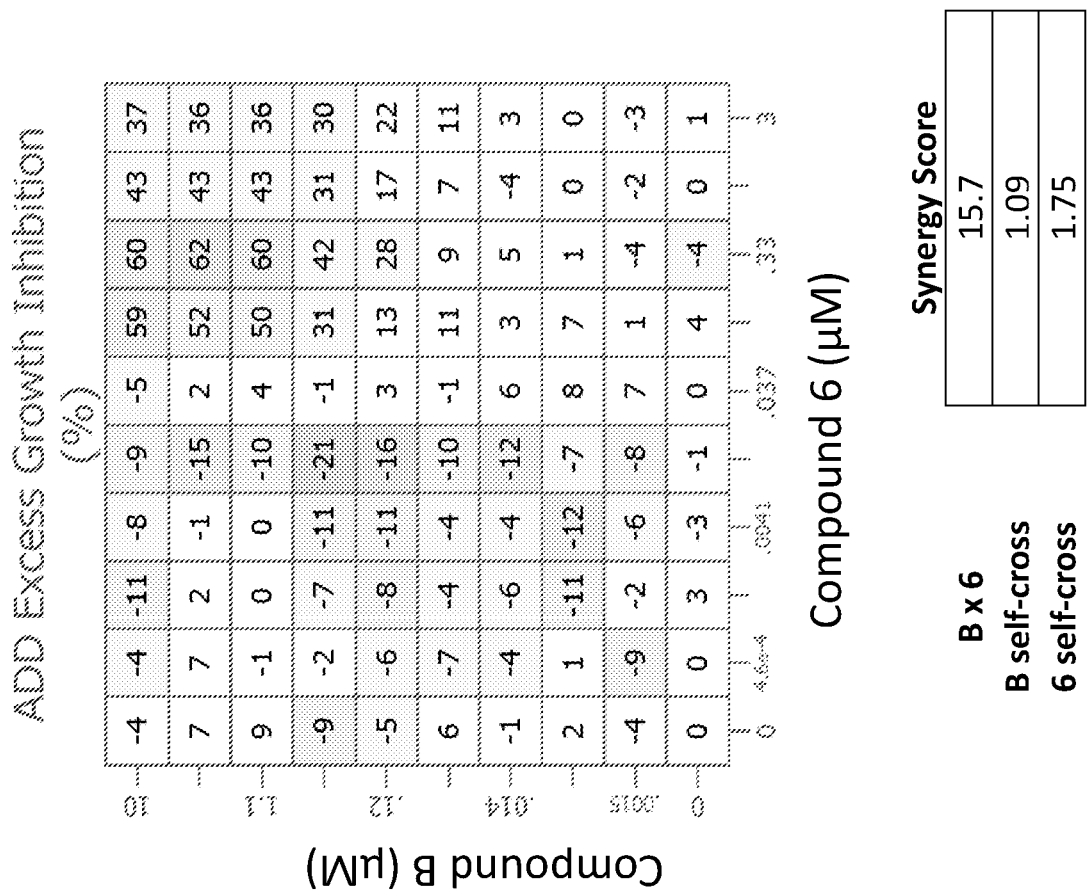
Figure 49a- Example 49; C32 cells

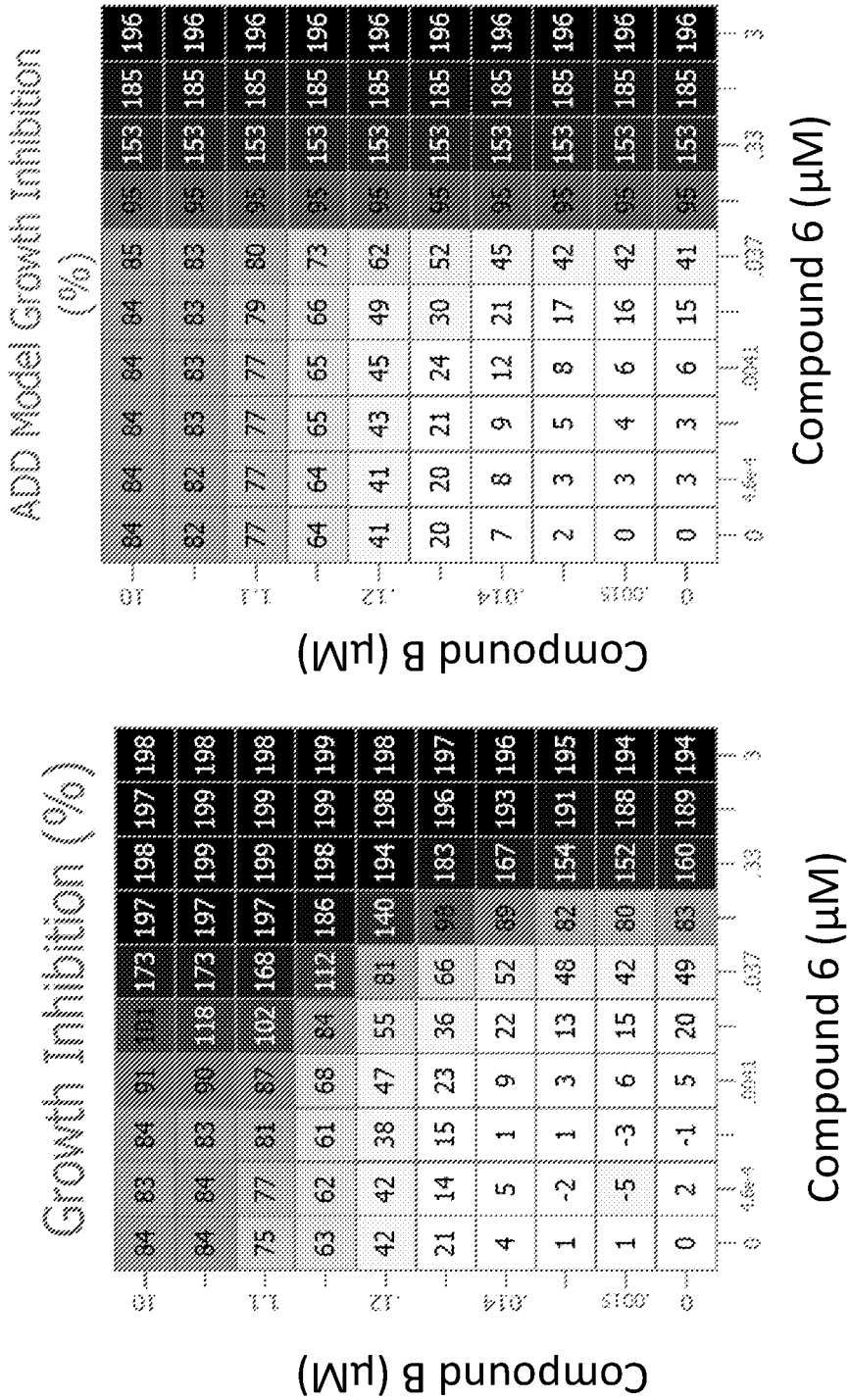
Figure 50-Example 50; G-401 cells

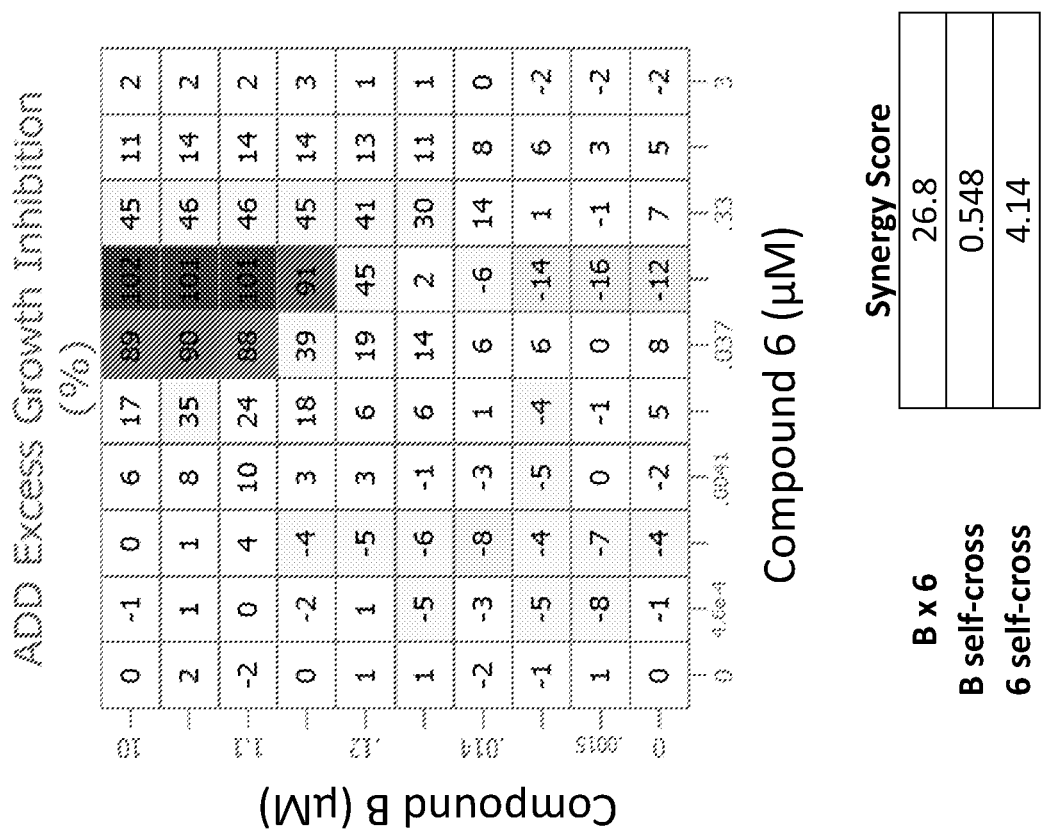
Figure 50a-Example 50; G-401 cells

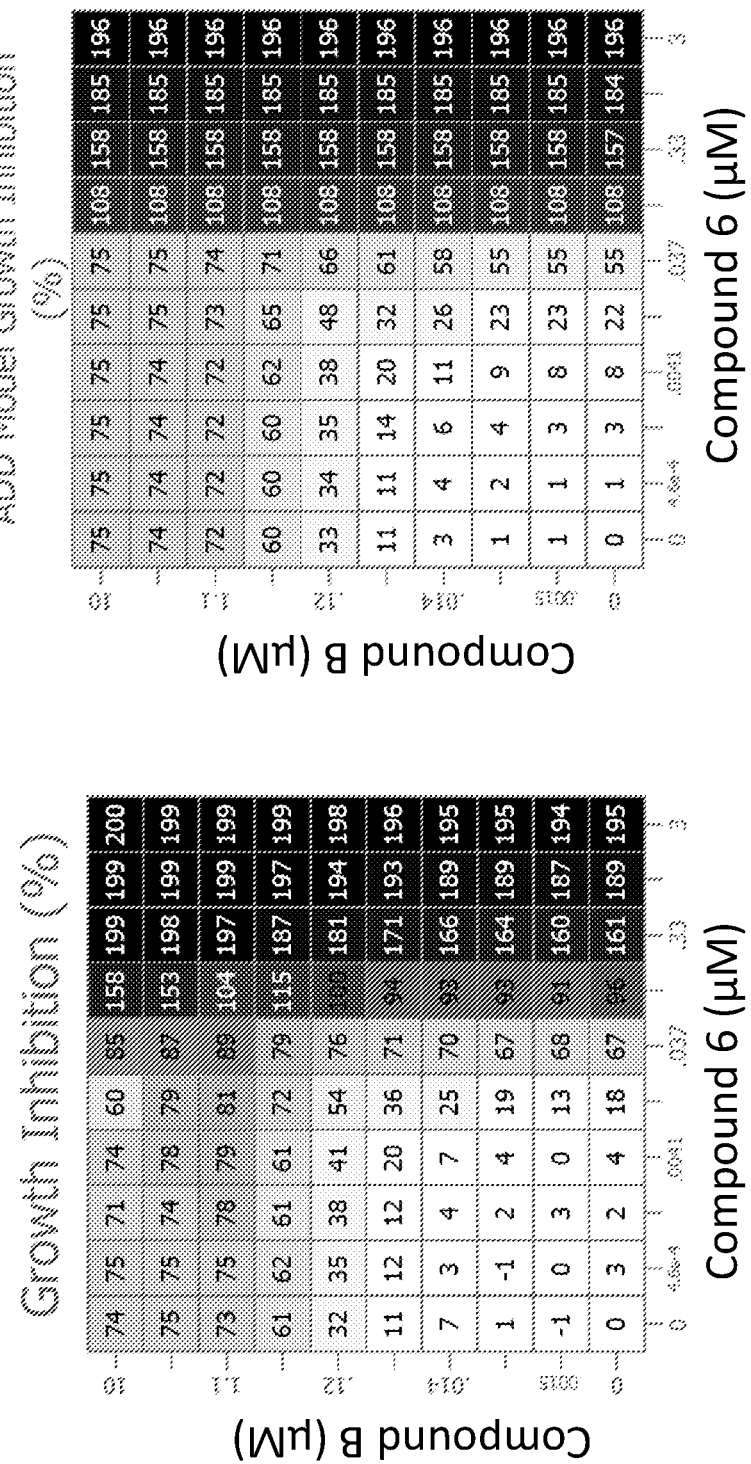
Figure 51-Example 51; SK-HEP-1 cells

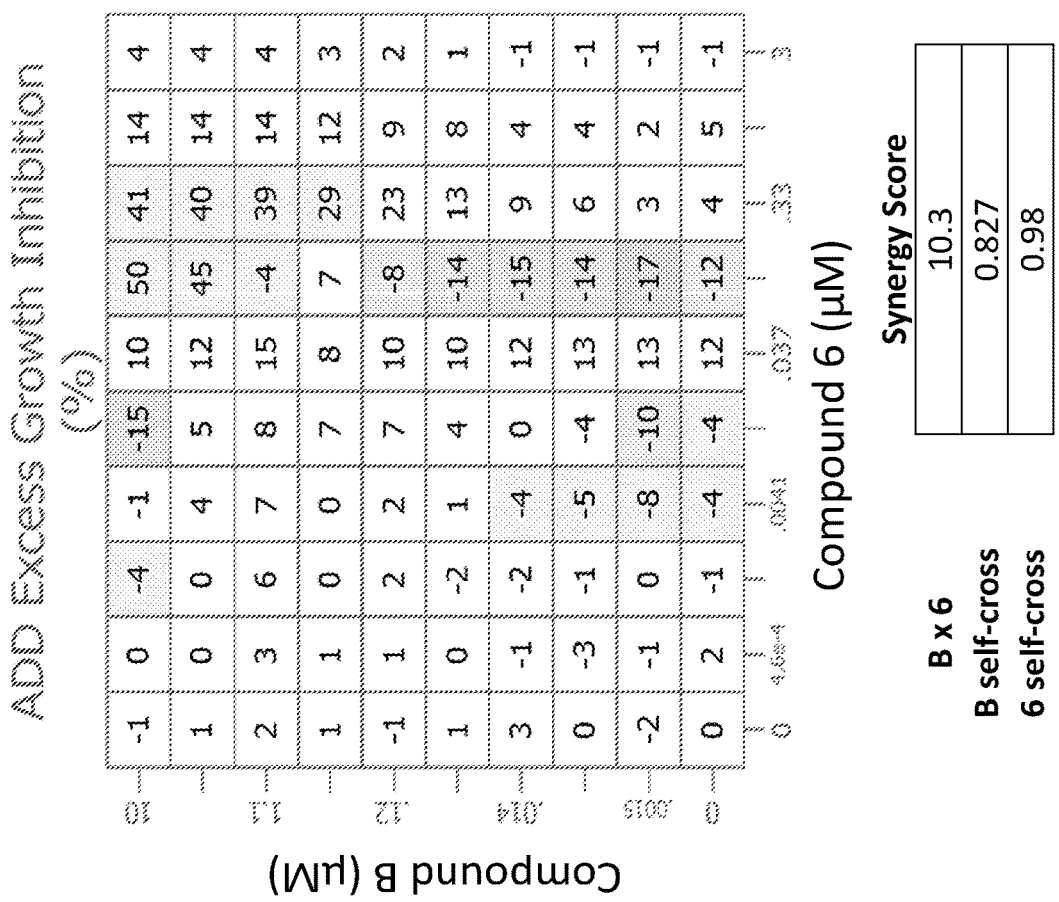
Figure 51a-Example 51; SK-HEP-1 cells

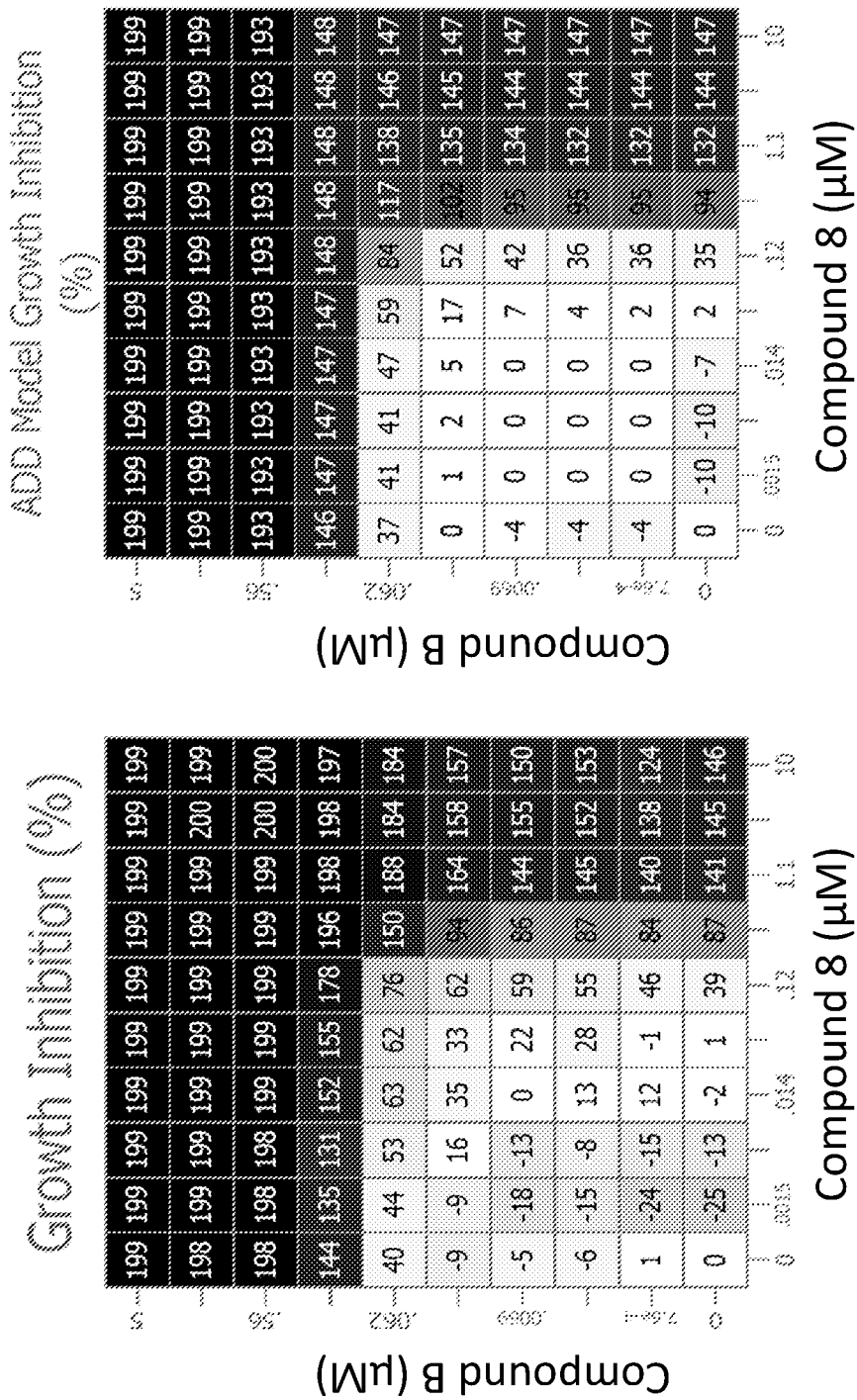
Figure 52-Example 52; BV-173 cells

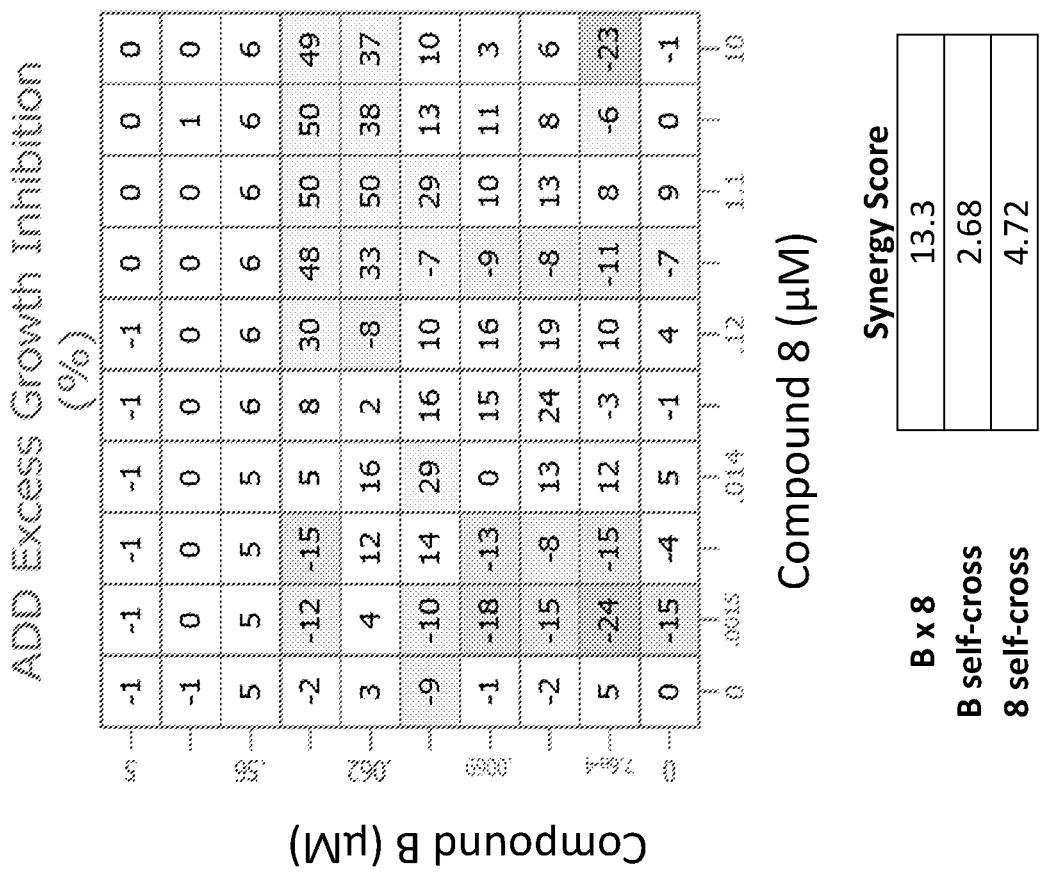
Figure 52a-Example 52; BV-173 cells

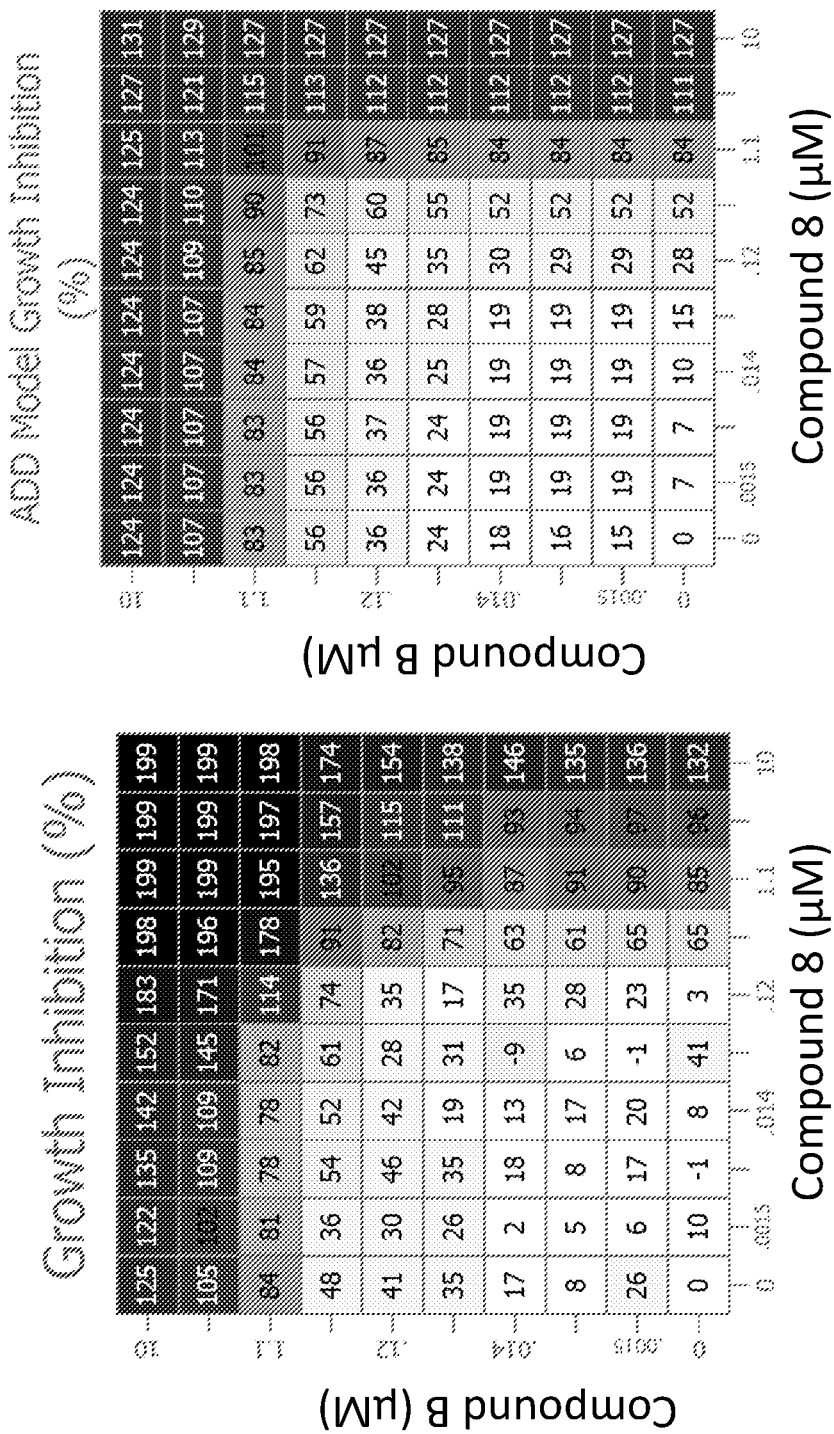
Figure 53-Example 53; CML-T1 cells

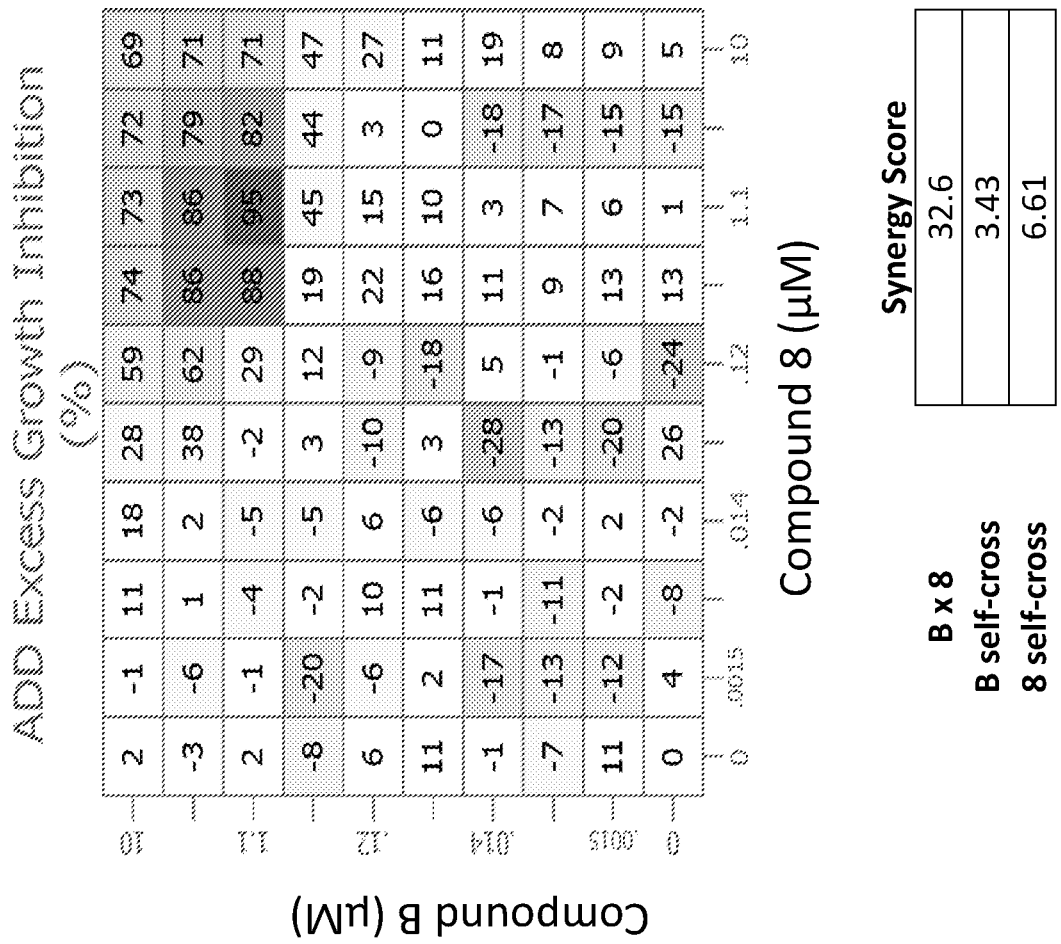
Figure 53a-Example 53; CML-T1 cells

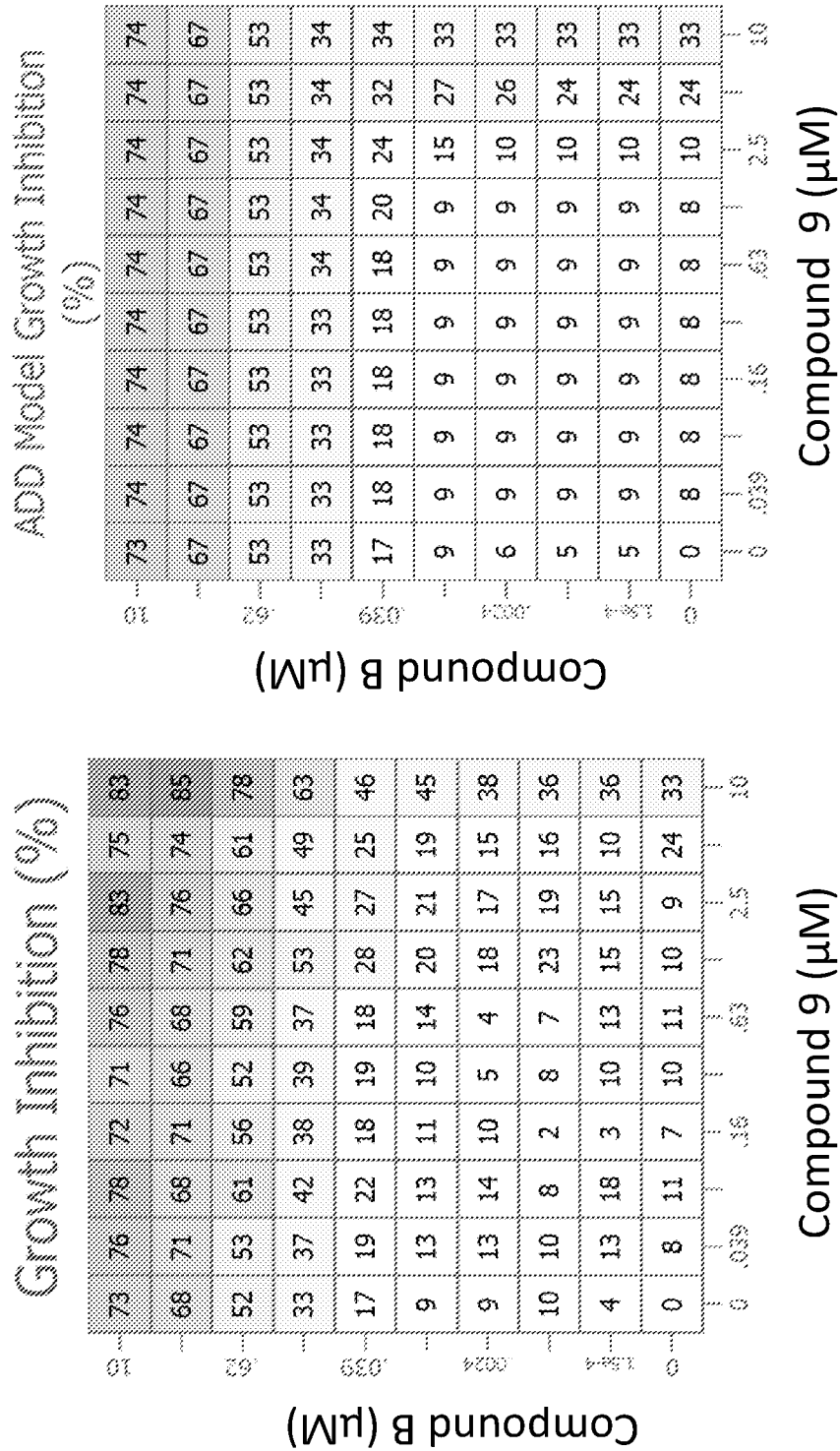
Figure 54-Example 54; KNS-81-FD cells

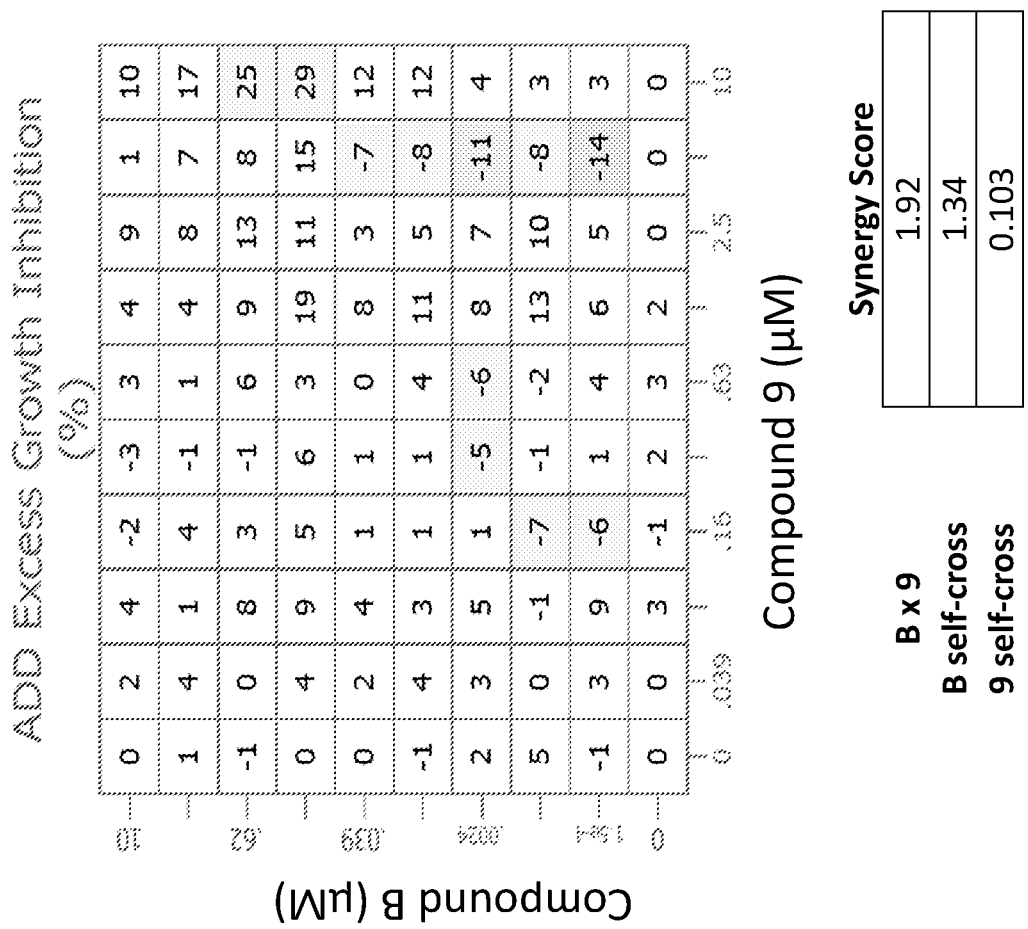
Figure 54a-Example 54; KNS-81-FD cells

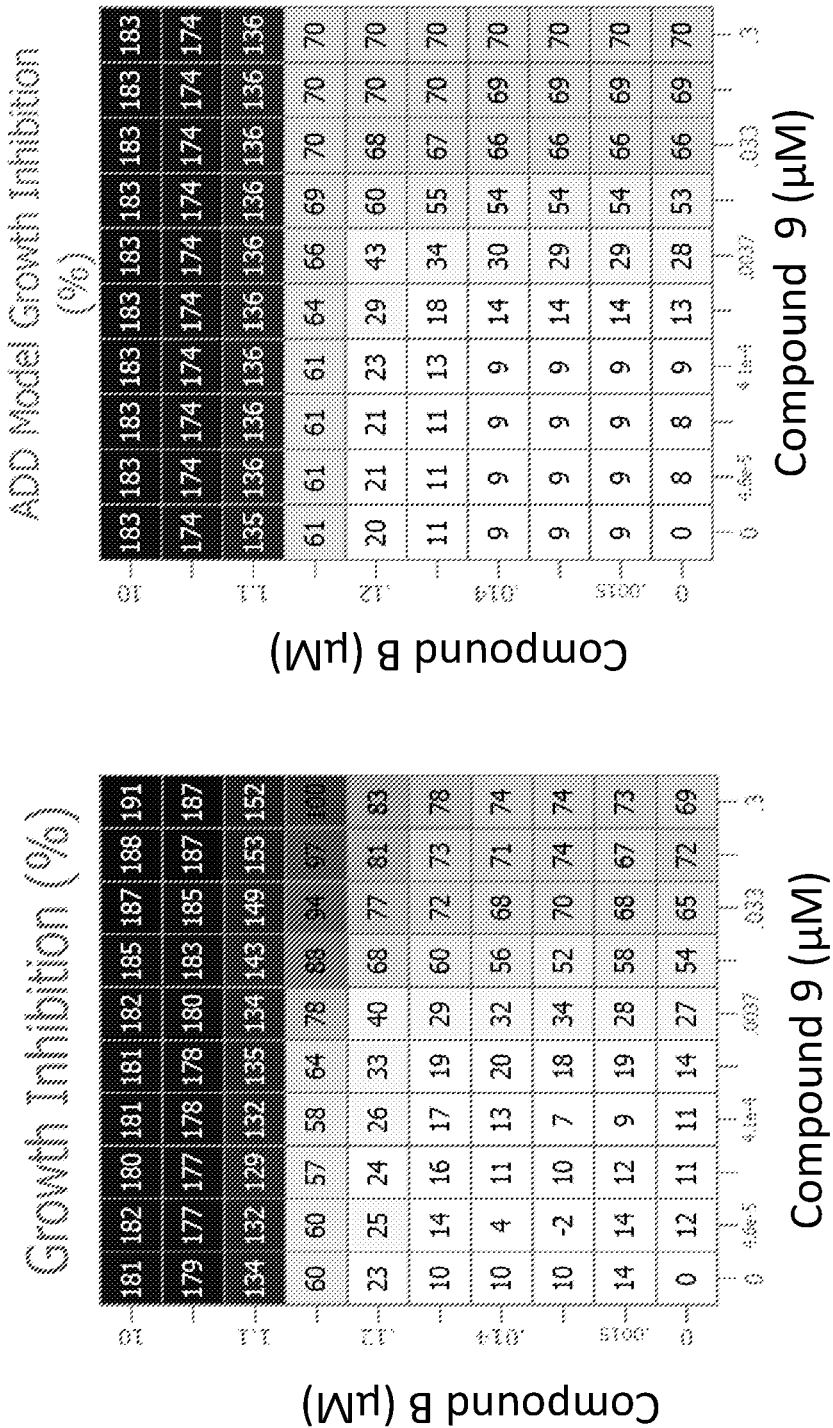
Figure 55-Example 55; SW48 cells

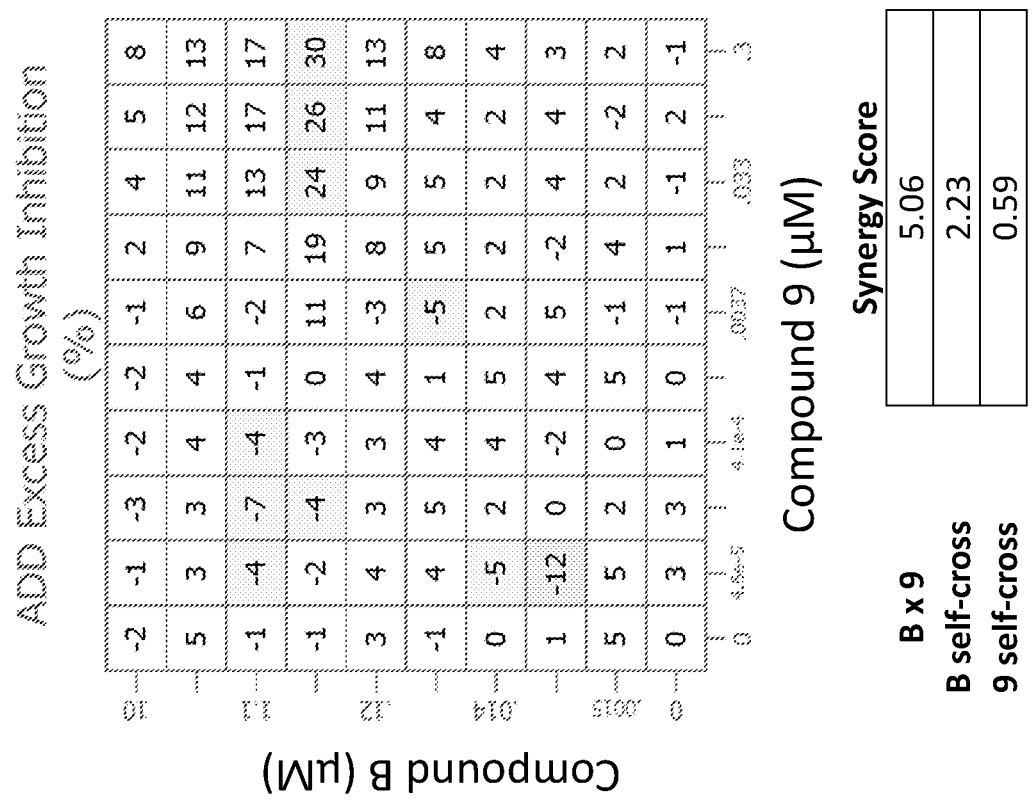
Figure 55a-Example 55; SW48 cells

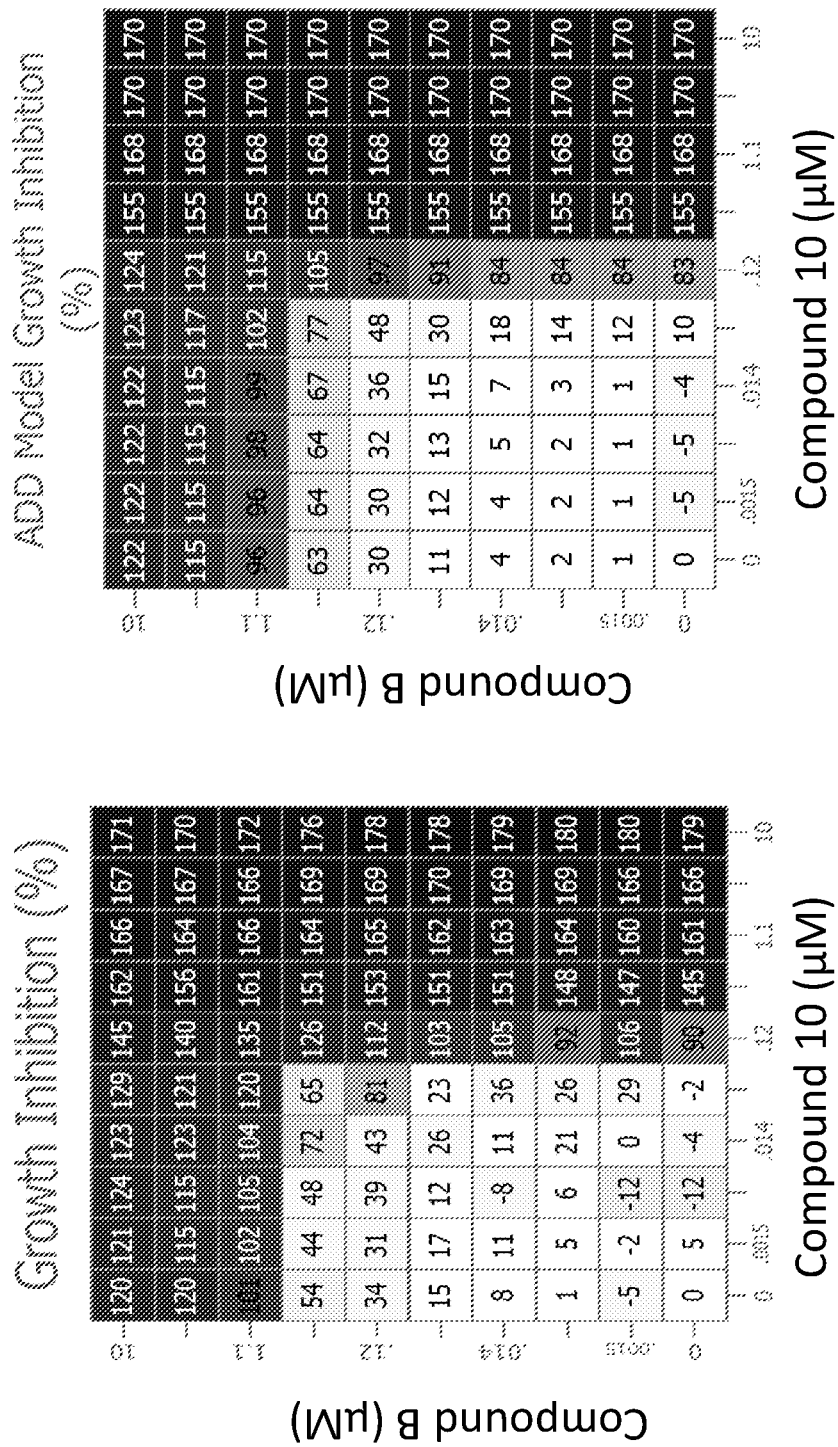
Figure 56-Example 56; MDA-MB-175-VII cells

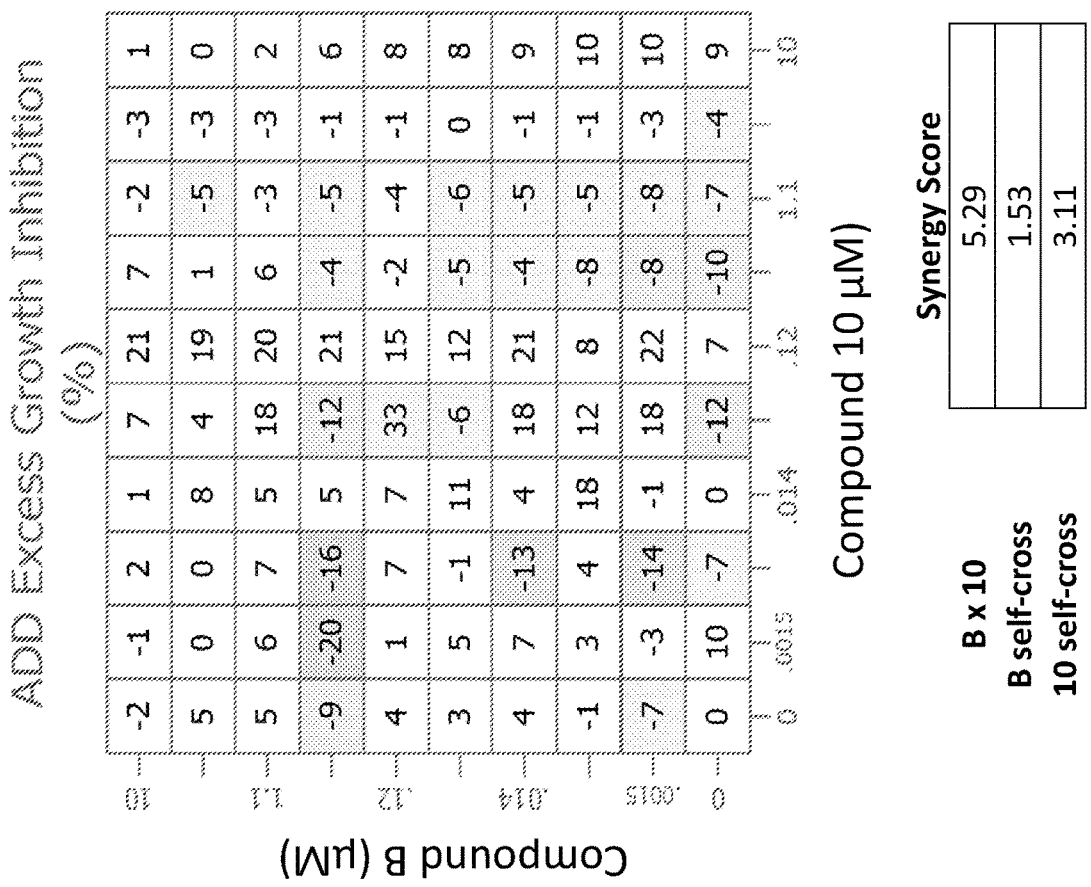
Figure 56a-Example 56; MDA-MB-175-VII cells

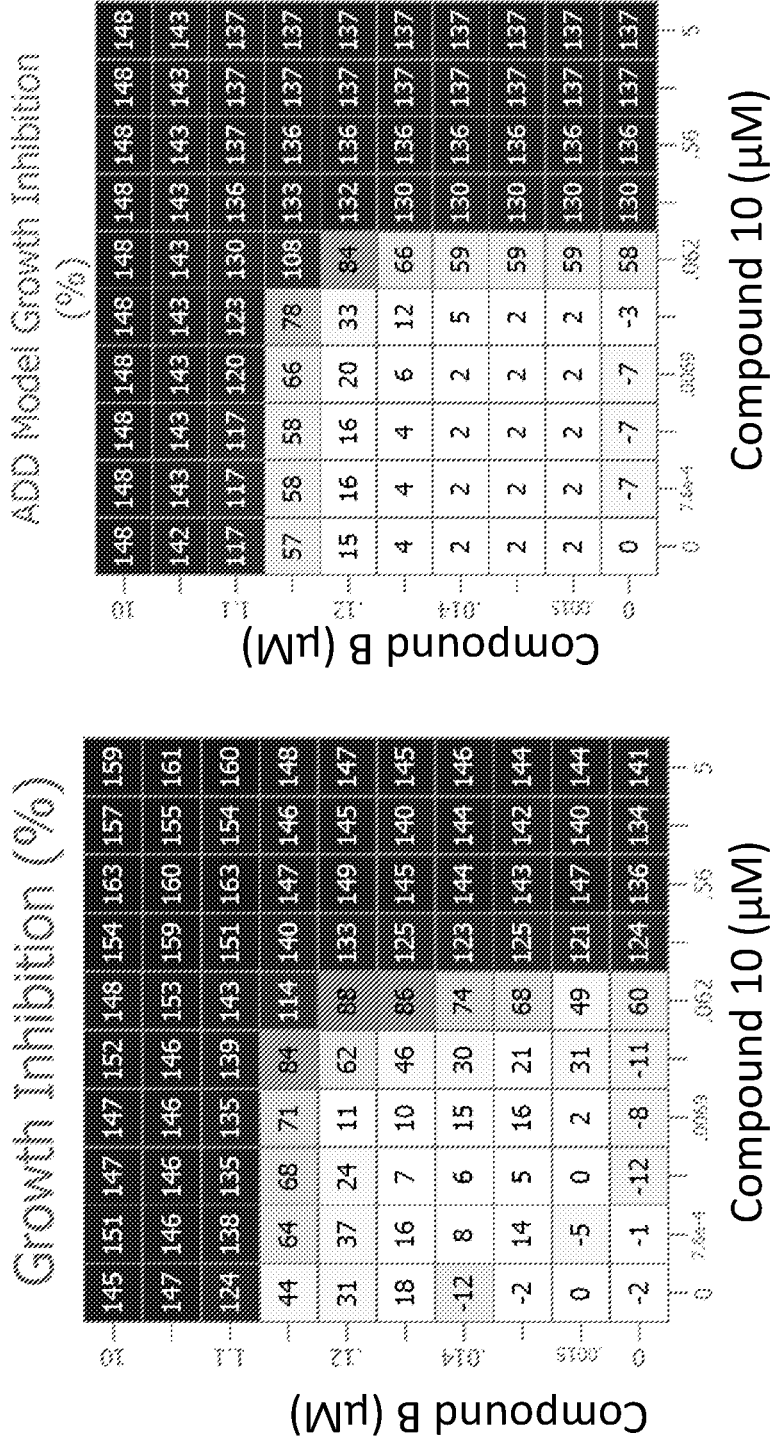
Figure 57-Example 57; UACC-812 cells

Figure 57a-Example 57; UACC-812 cells
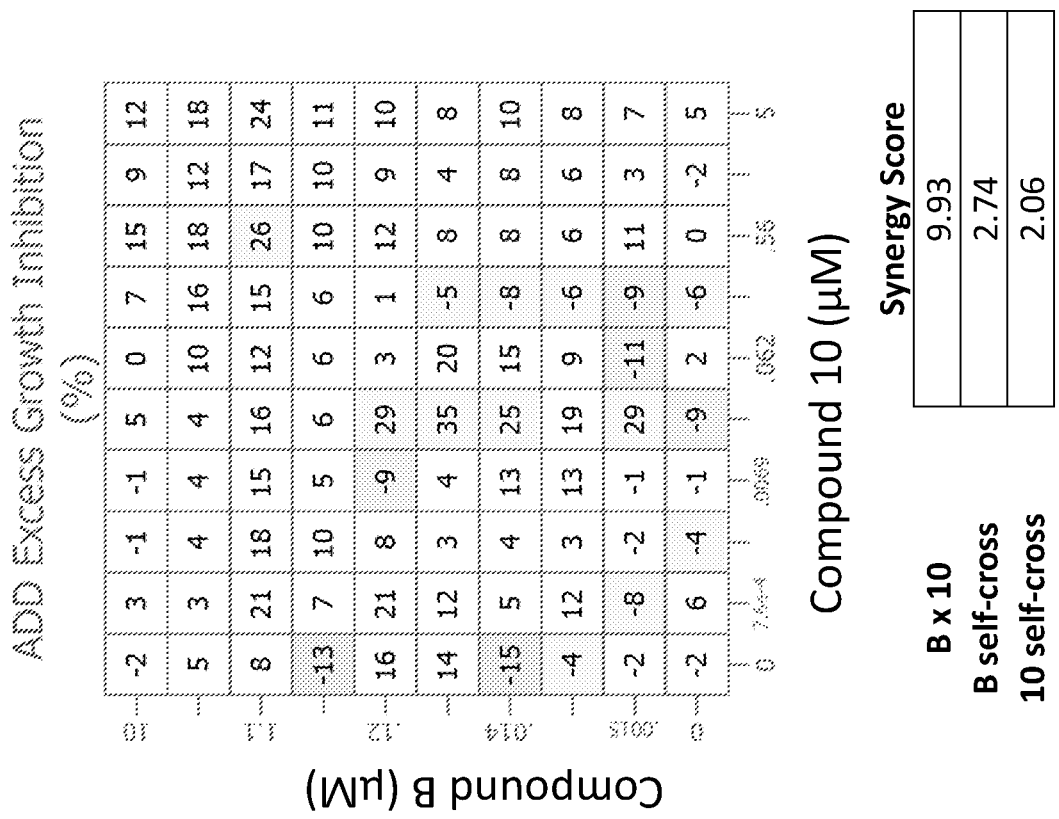

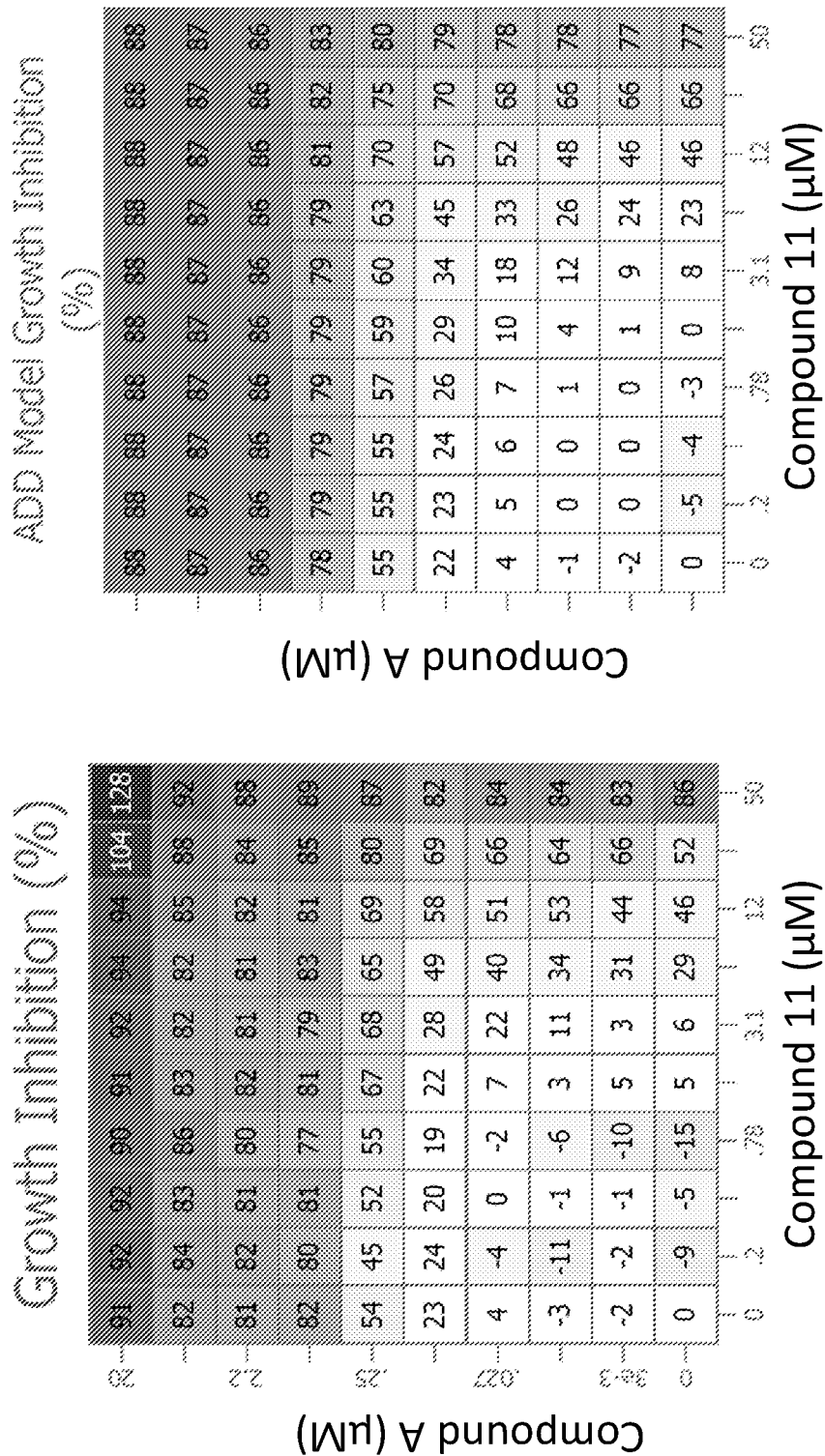
Figure 58-Example 58; HCT 116 cells

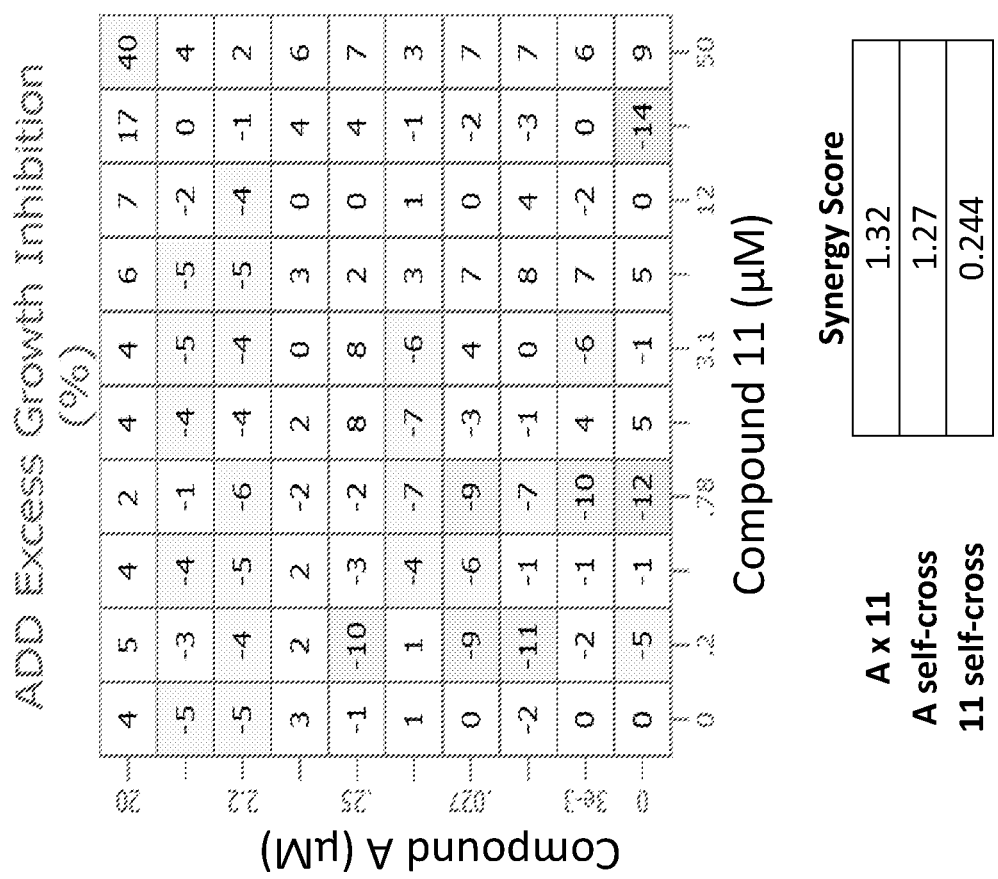
Figure 58a-Example 58; HCT 116 cells

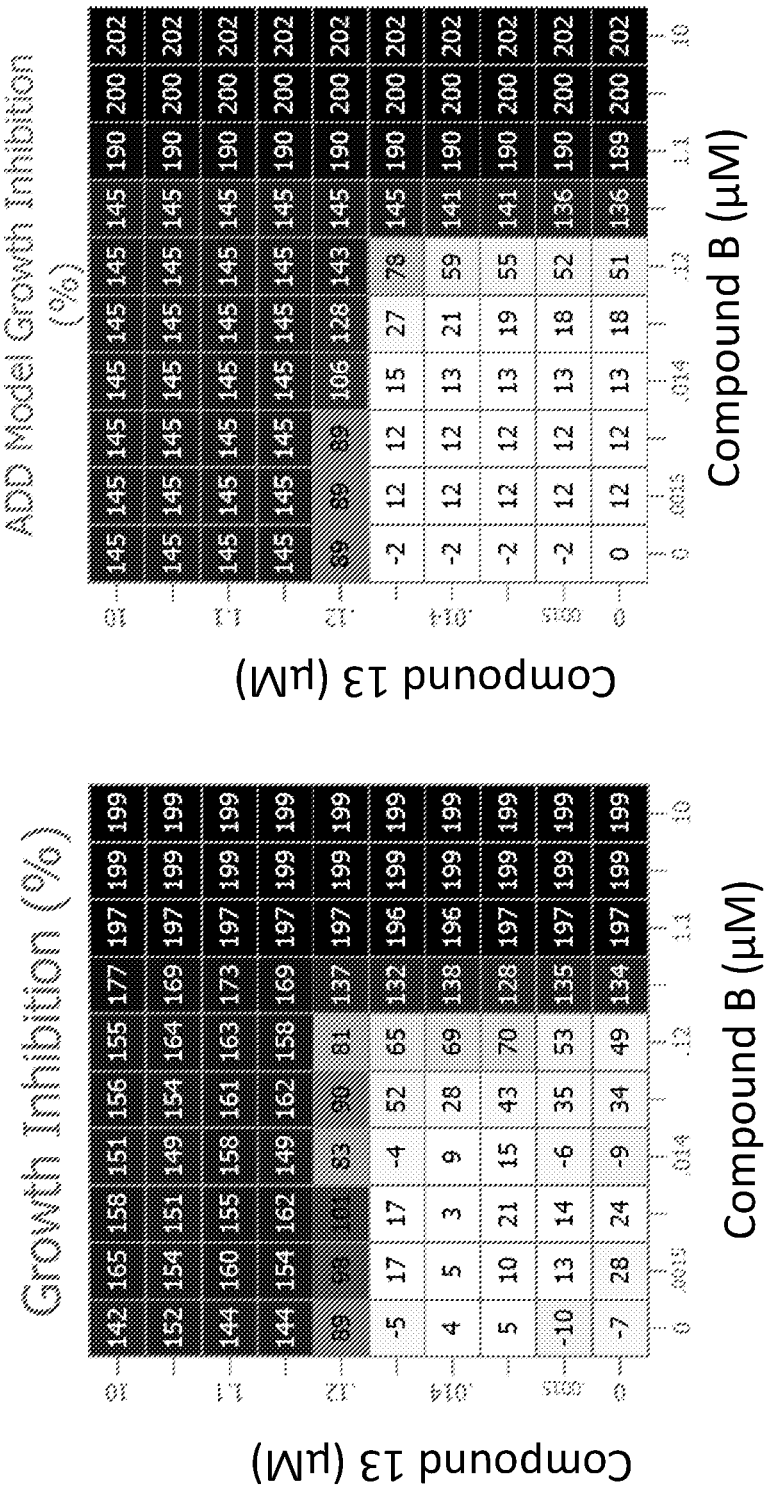
Figure 59-Example 59; GDM-1 cells

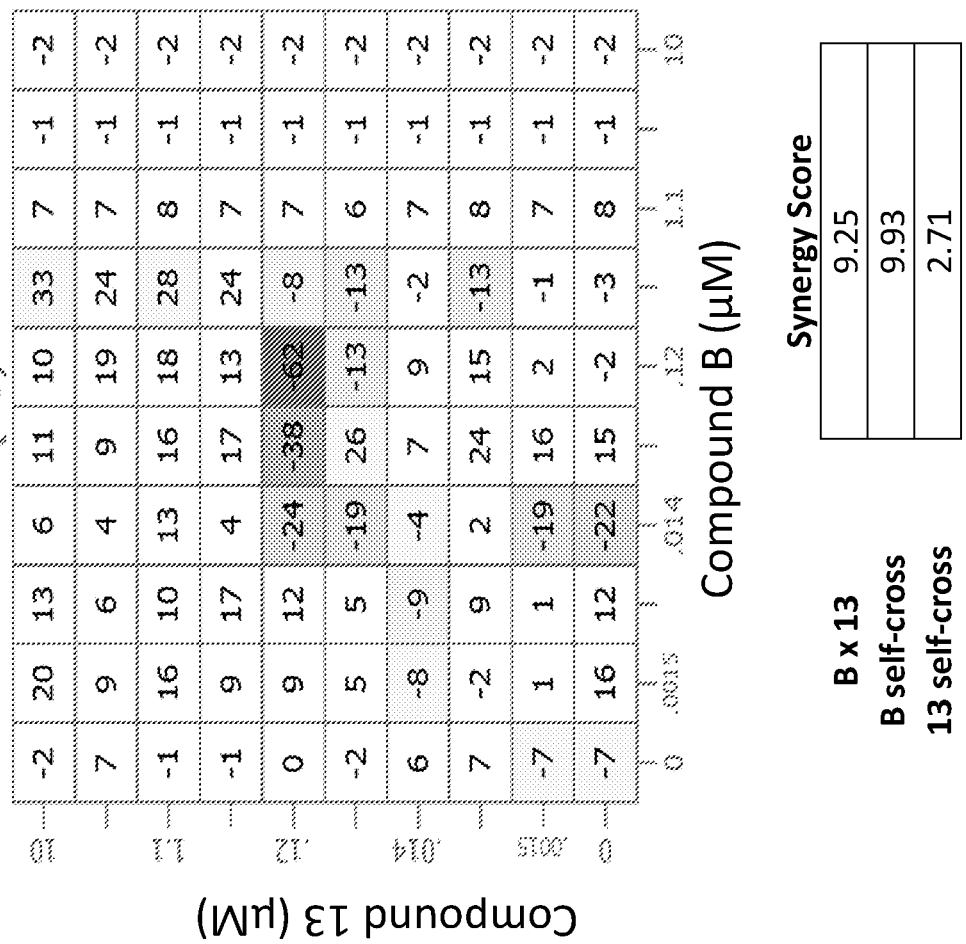
Figure 59a-Example 59; GDM-1 cells

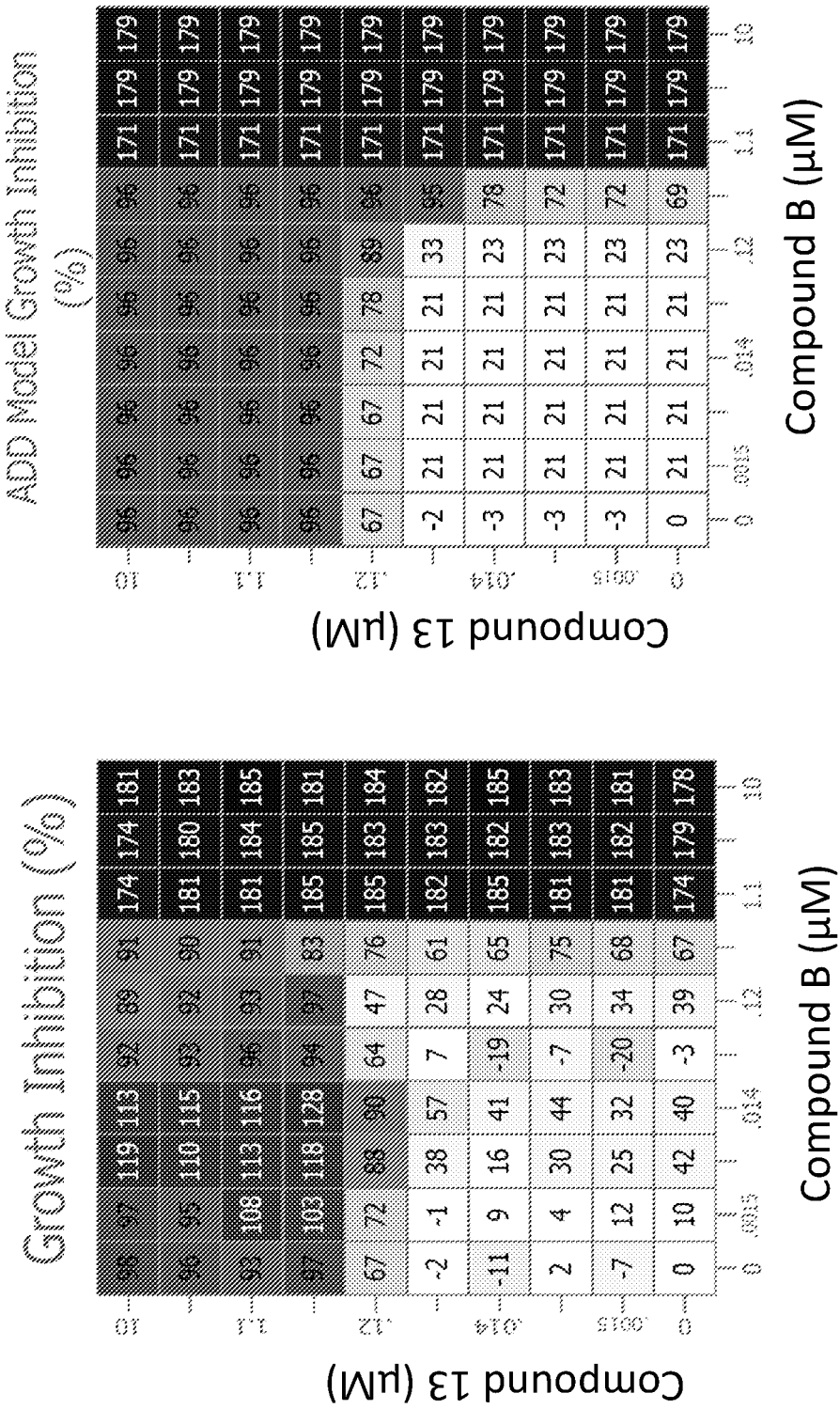
Figure 60-Example 60; ML-2 cells

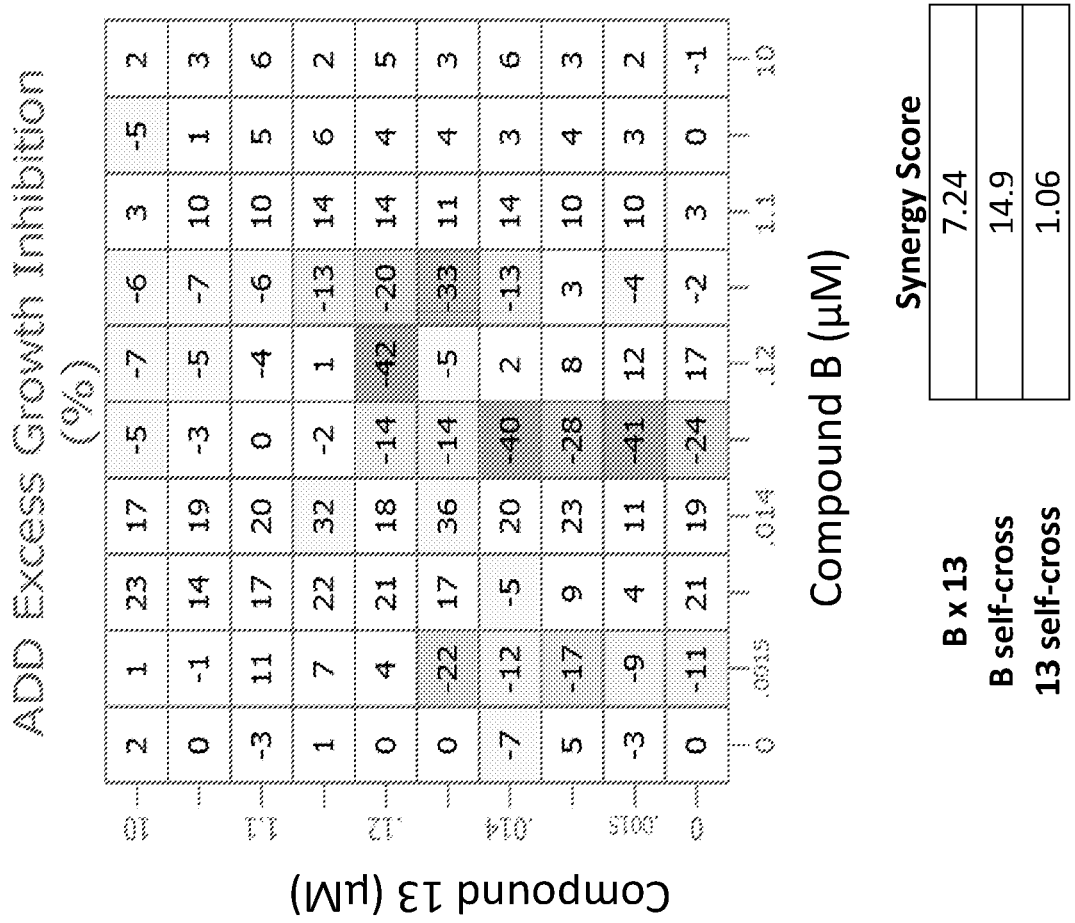
Figure 60a-Example 60; ML-2 cells

Figure 61-Example 61; MOLM-13 cells
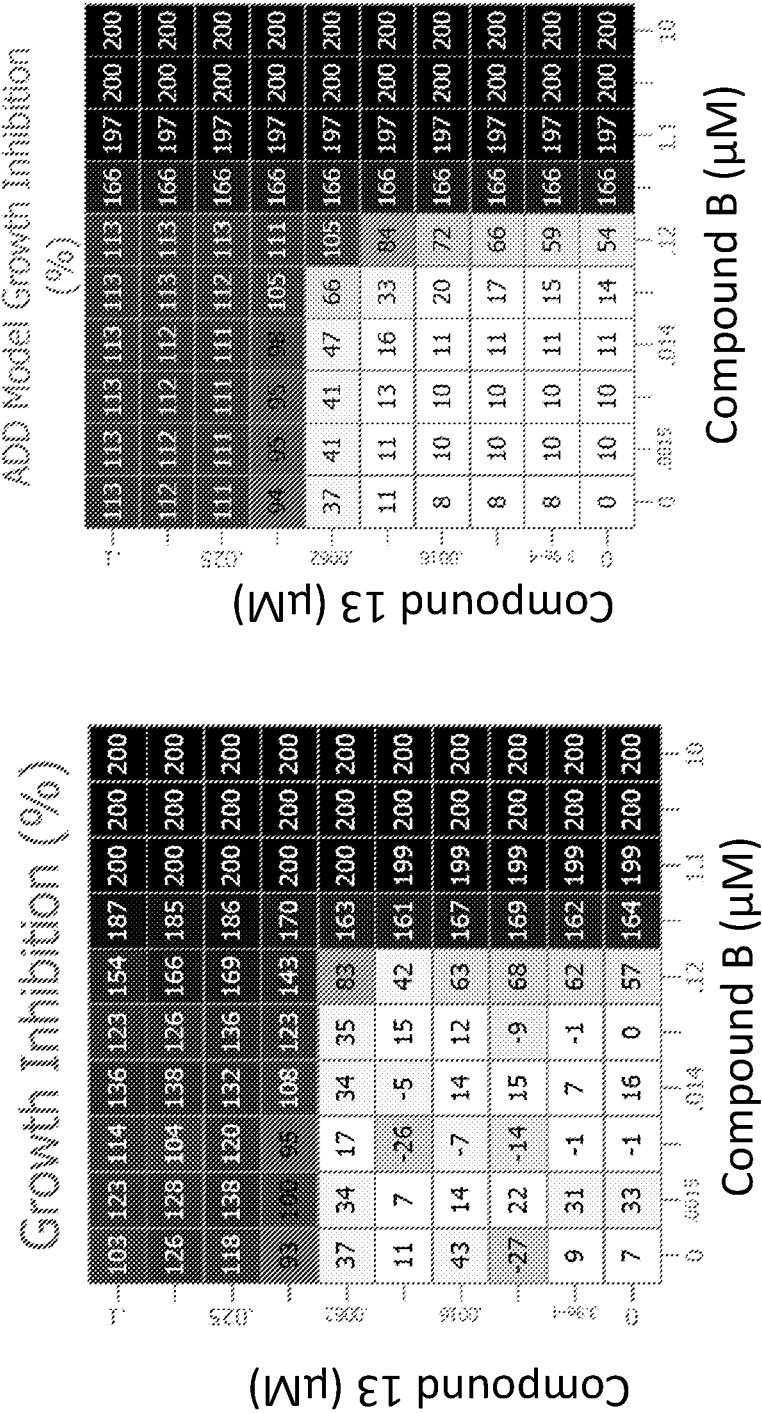

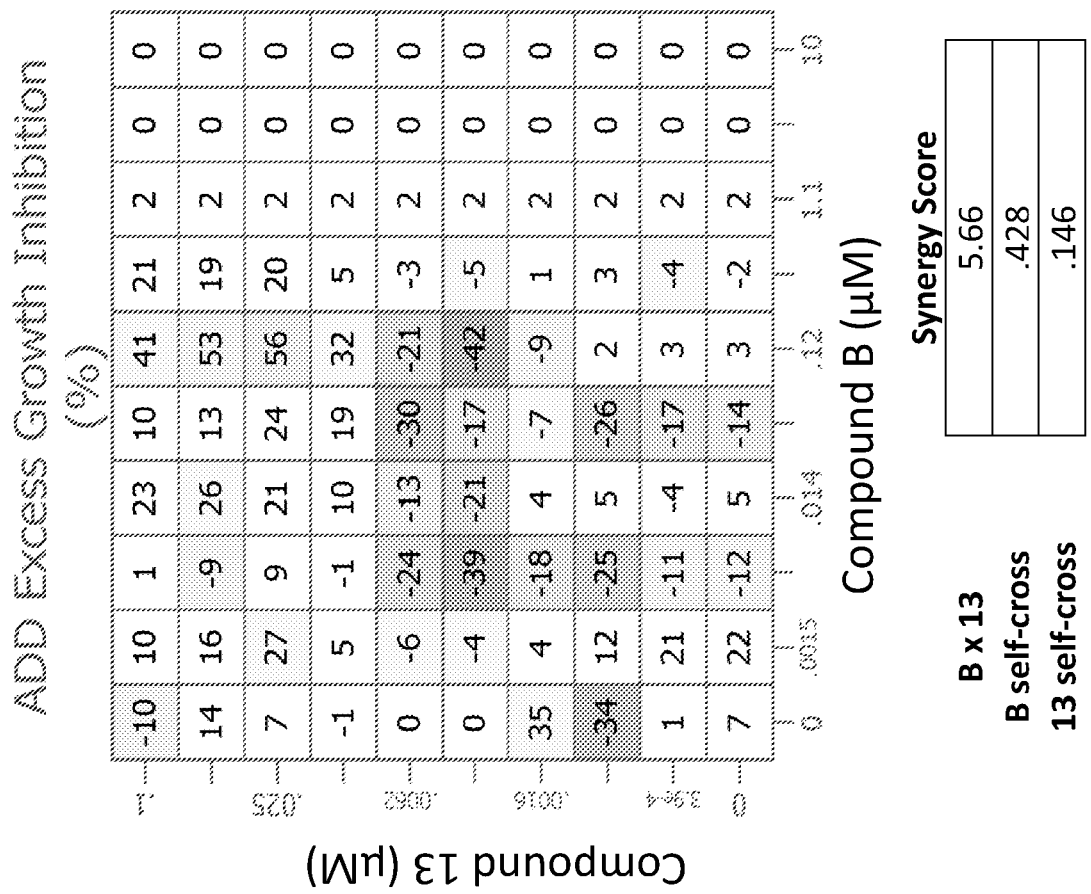
Figure 61a-Example 61; MOLM-13 cells

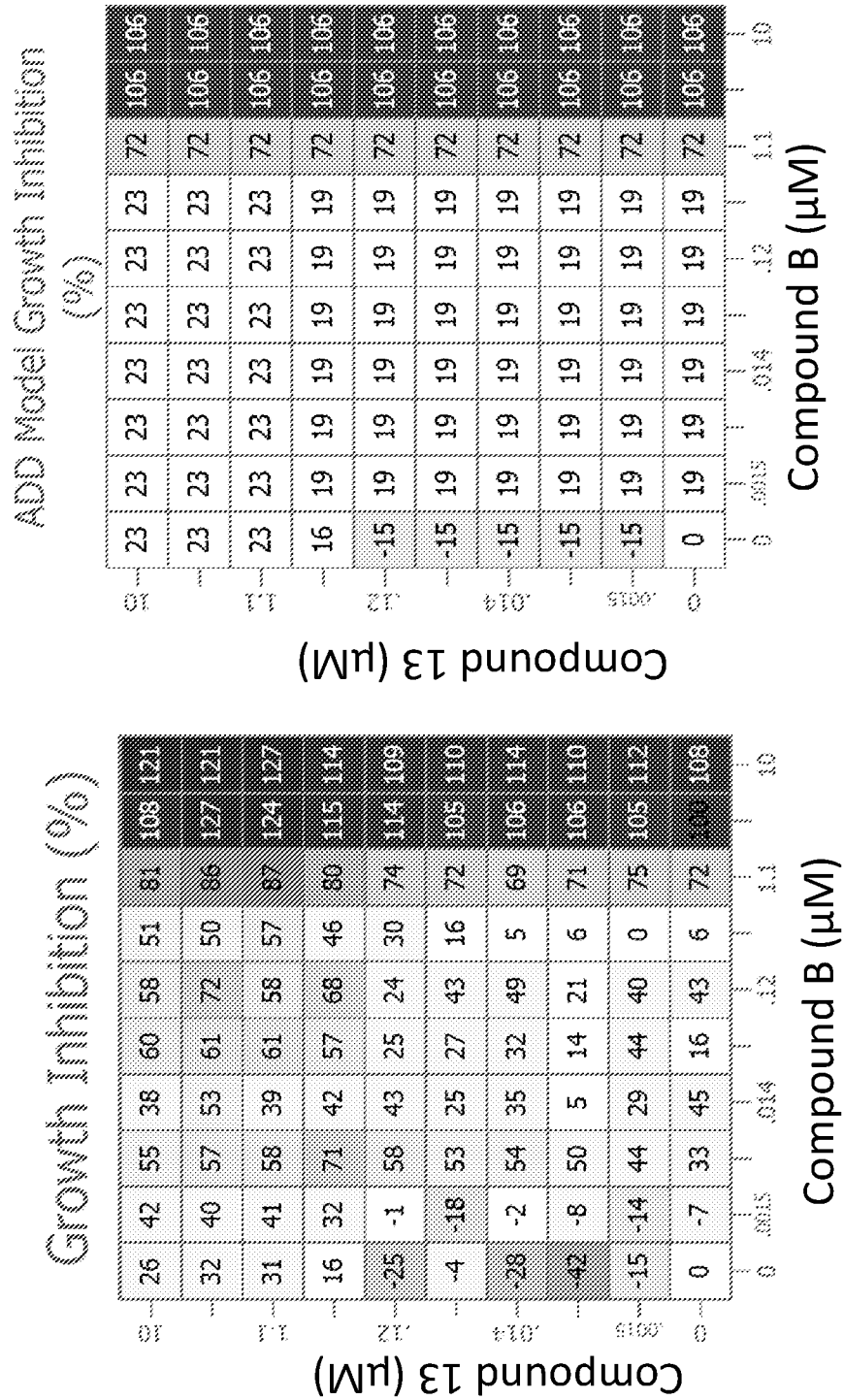
Figure 62-Example 62; OCI-AML3 cells

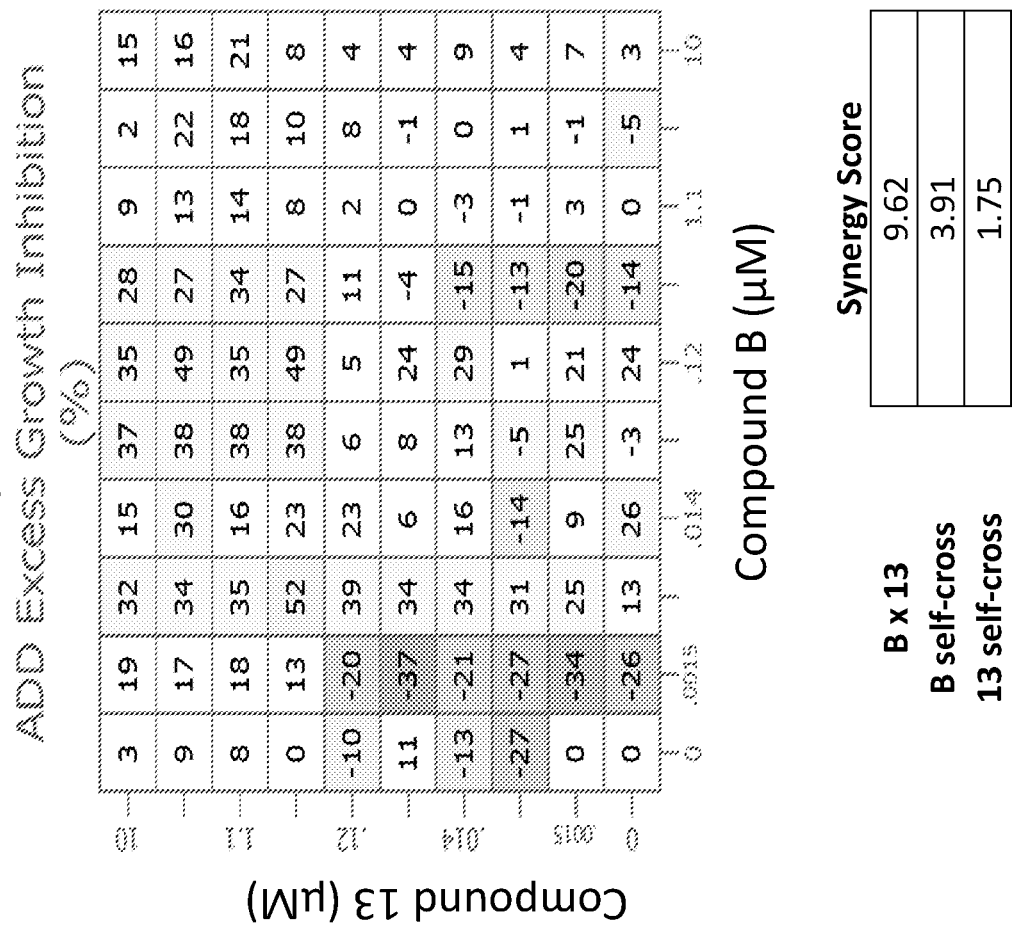
Figure 62a-Example 62; OCI-AML3 cells

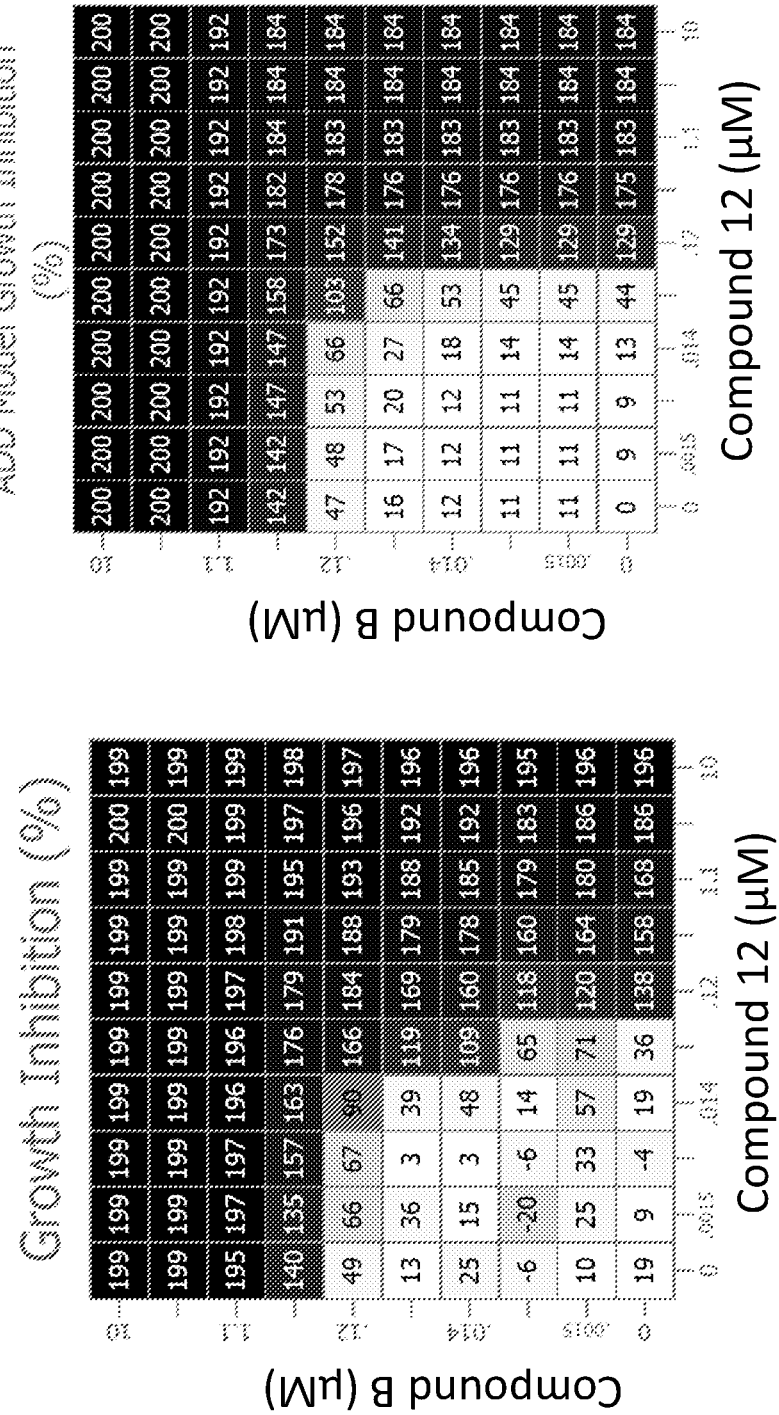
Figure 63-Example 63; GDM-1 cells

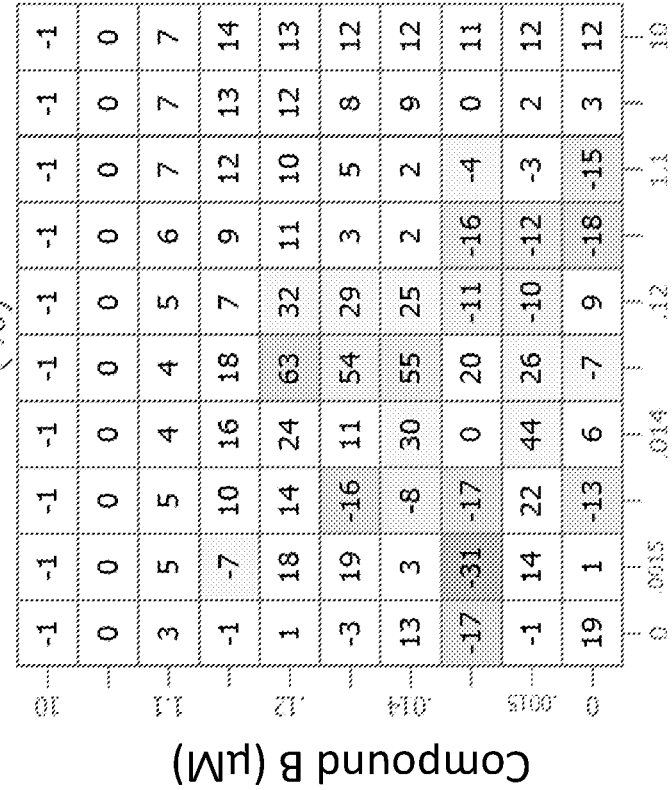
Example 63a-Figure 63; GDM-1 cells

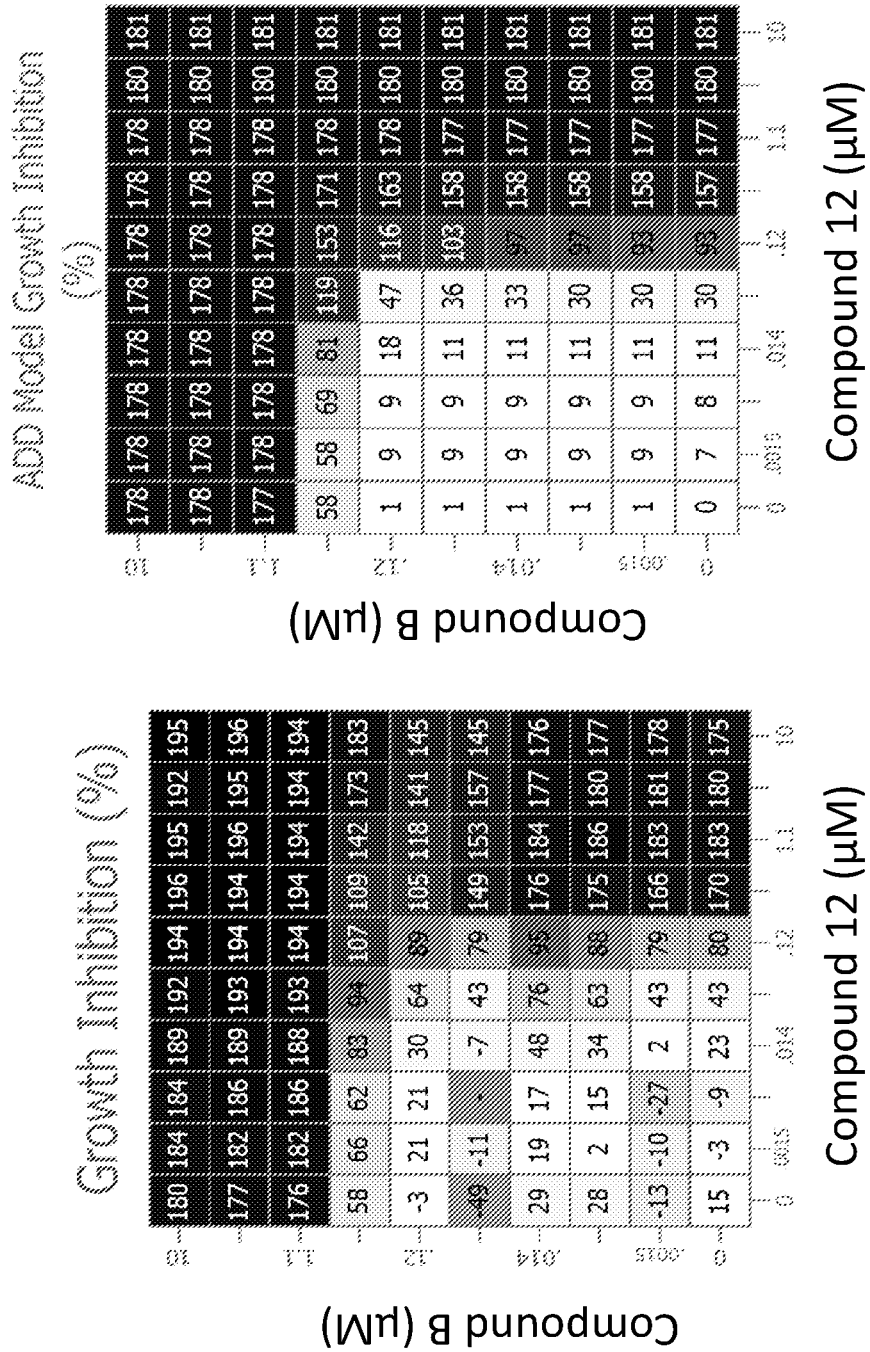
Figure 64-Example 64; ML-2 cells

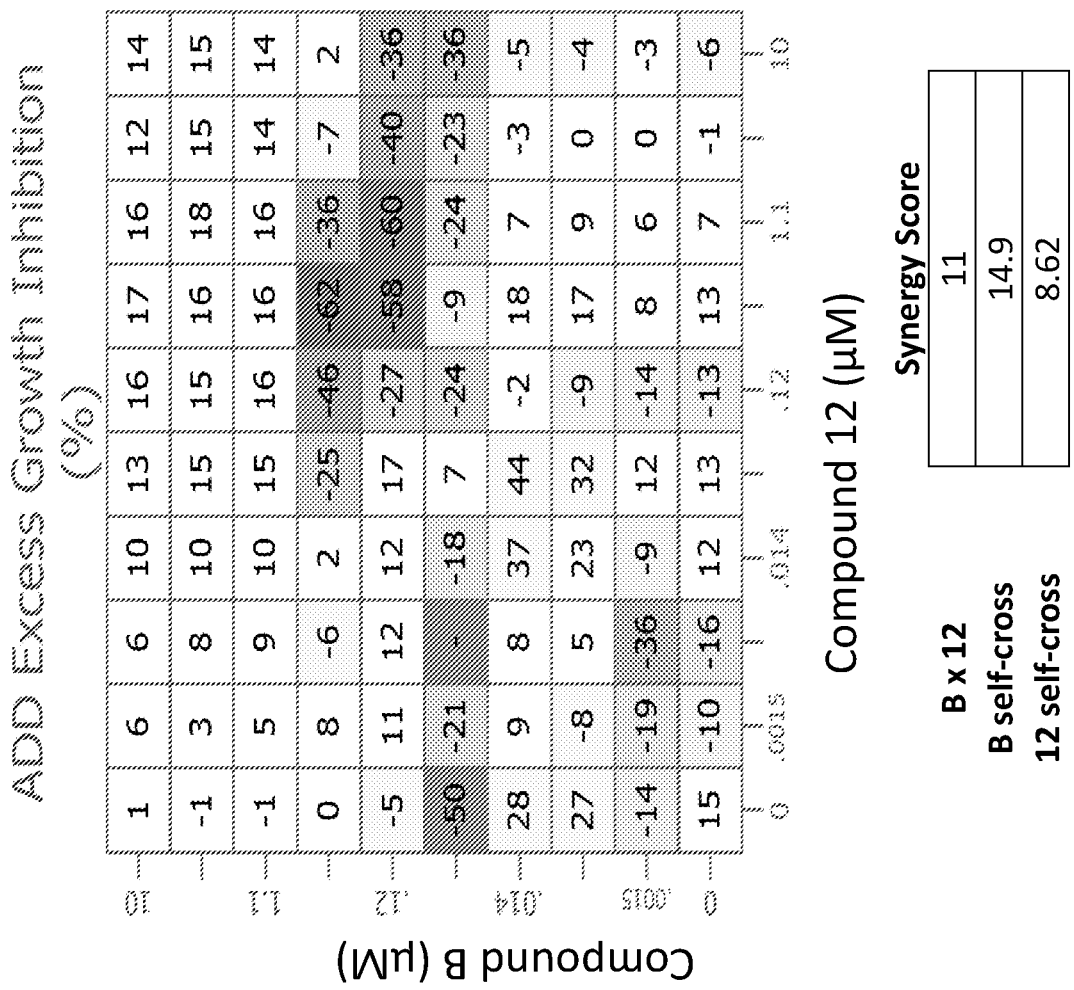
Figure 64a-example 64; ML-2 cells

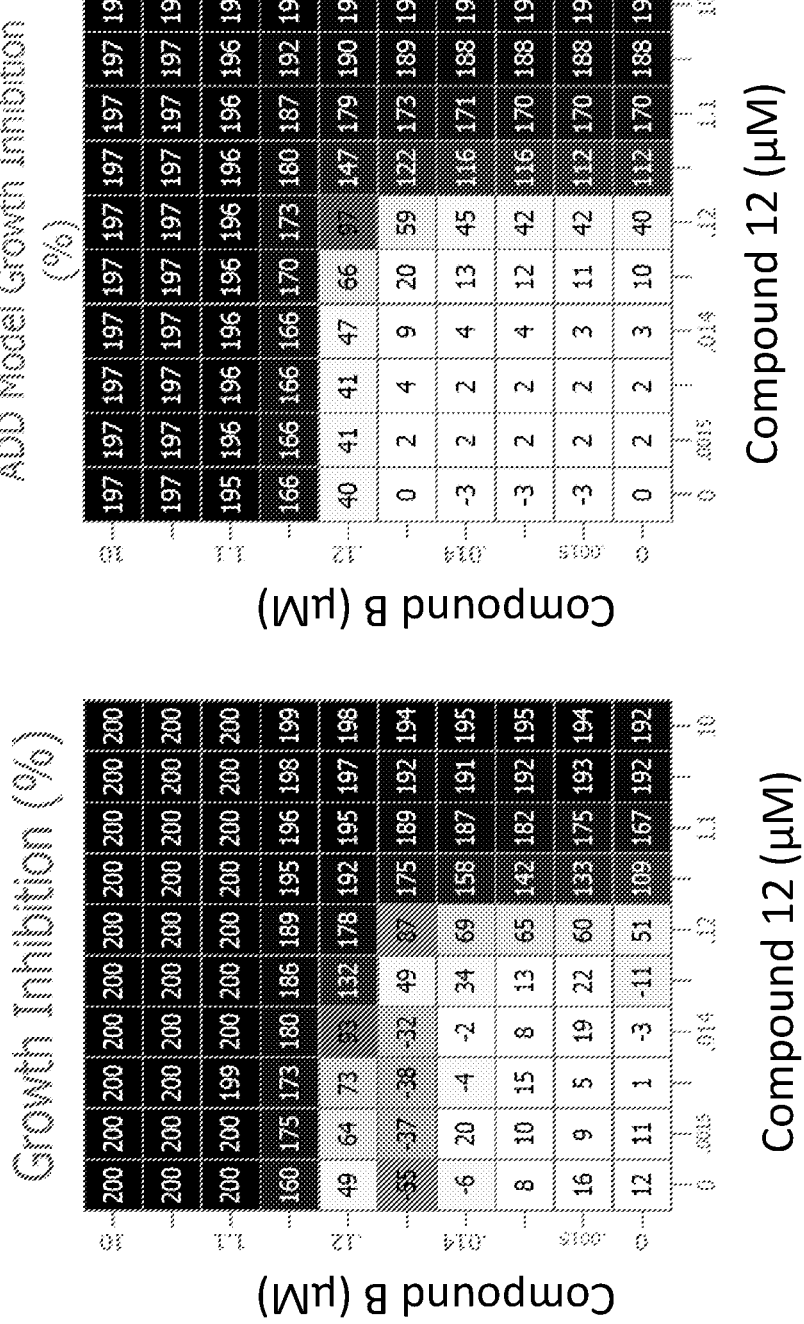
Figure 65-Example 65; MOLM-13 cells

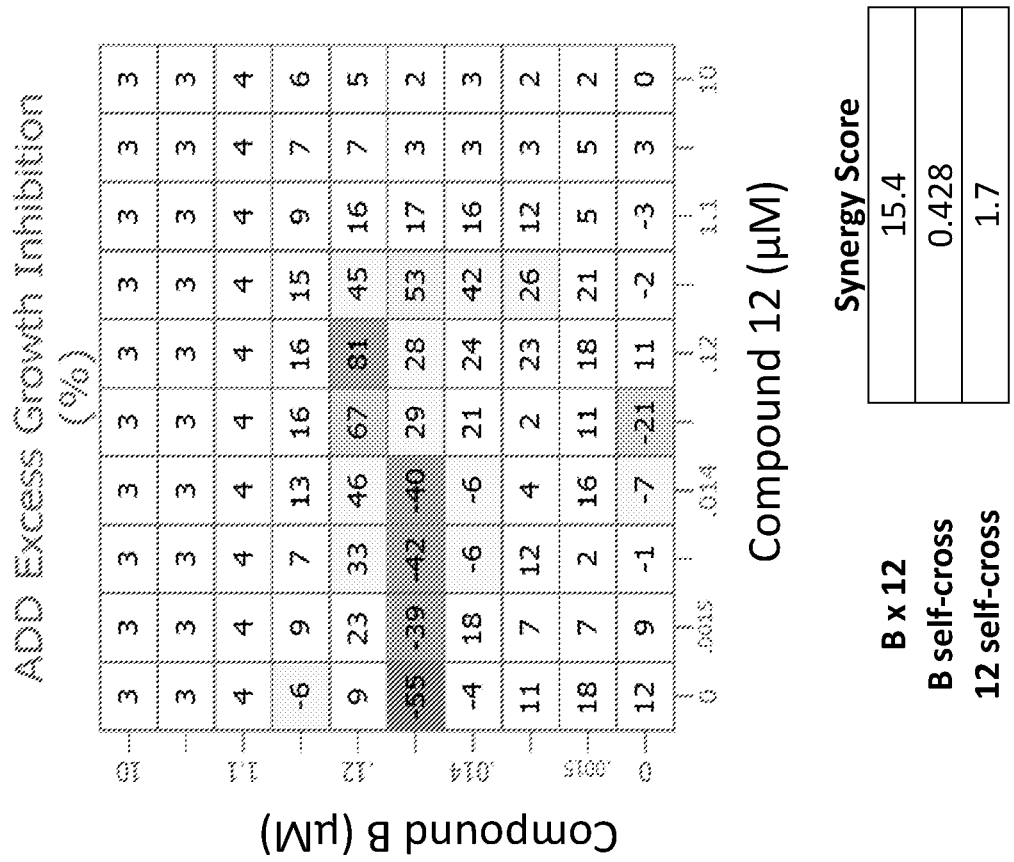
Figure 65a-Example65; MOLM-13 cells

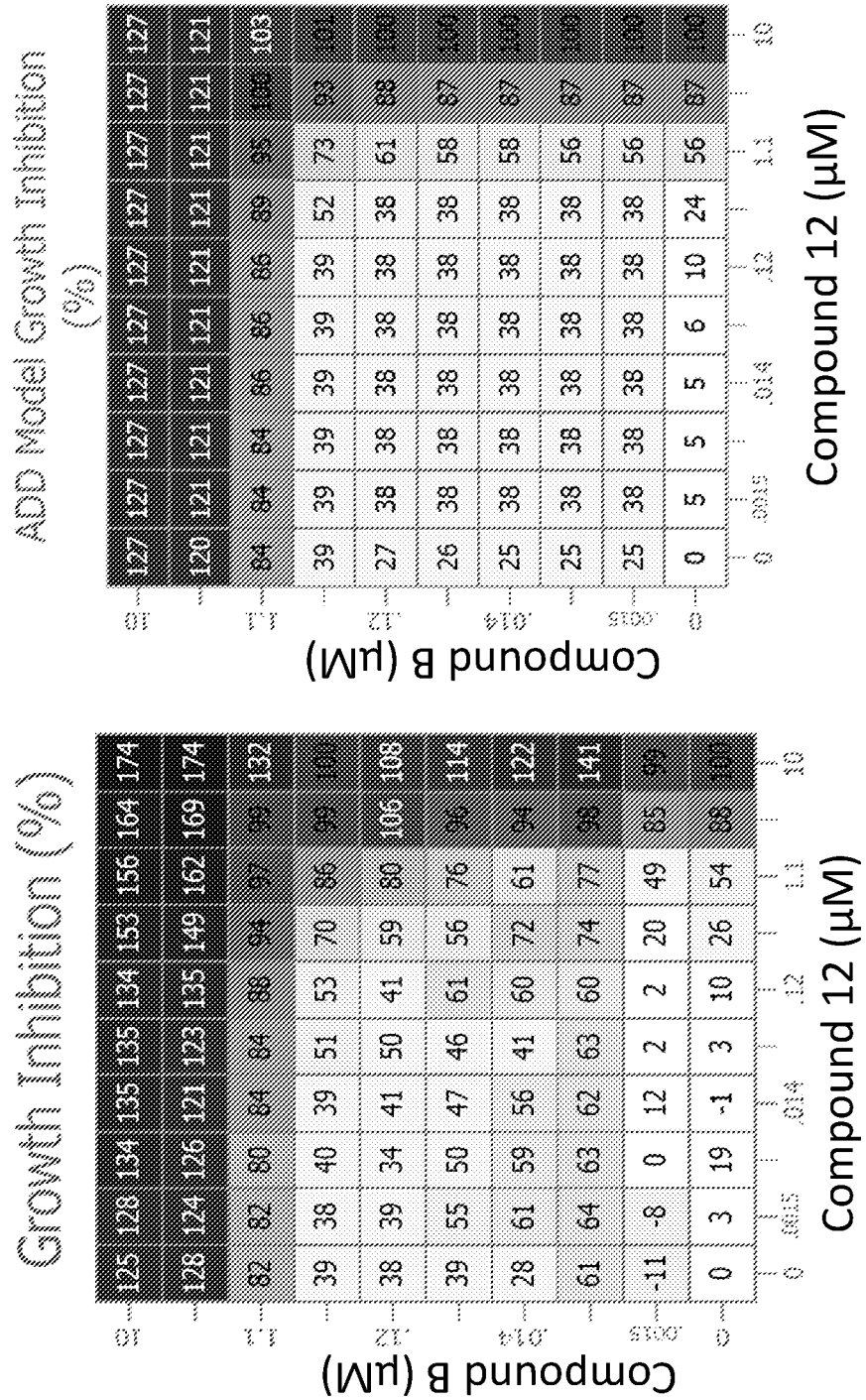
Figure 66-Example 66; OCI-AML3 cells

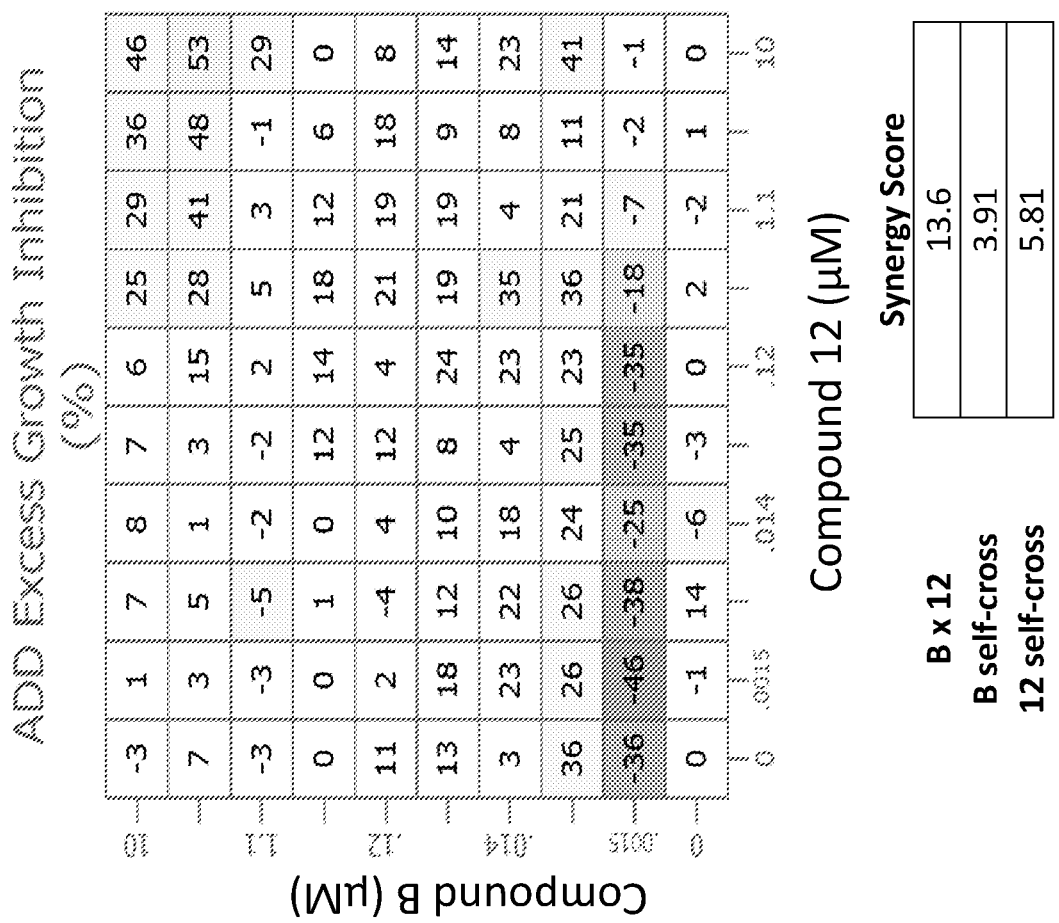
Figure 66a-Example 66; OCI-AML3 cells

Figure 67
AMG 232 – MAPKi Combinations

Figure 68
AM-7209 – MAPKi Combinations

Figure 69
RG7112 – MAPKi Combinations

Figure 70
AMG 232 – PI3Ki Combinations

|  | | Pan-PI3K | Pan-PI3K | PI3Kα | PI3Kβ | AKT | AKT | AKT | PI3K/mTOR | PI3K/mTOR | mTOR |
|---|---|---|---|---|---|---|---|---|---|---|---|
|  | | AMG 232 x BKM120 | AMG 232 x GDC-0941 | AMG 232 x BYL719 | AMG 232 x GSK-2636771 | AMG 232 x MK-2206 | AMG 232 x GDC-0068 | AMG 232 x AZD5363 | AMG 232 x GDC-0980 | AMG 232 x AZD2014 | AMG 232 x MLN0128 |
| PI3K | 22RV1 (Prostate) | 4.74 | 6.91 | 3.97 | 0.59 | 5.47 | 2.63 | 4.26 | 7.08 | 3.90 | 8.56 |
| PI3K | MCF7 (Breast) | 5.18 | 2.94 | 6.27 | 1.67 | 6.56 | 7.54 | 6.13 | 9.59 | 7.32 | 8.56 |
| PI3K | RKO (Colon) | 0.46 | 1.14 | 2.26 | 0.69 | 1.31 | 1.93 | 2.77 | 2.01 | 1.61 | 2.58 |
| PTEN | SNG-M (Endometrium) | 0.61 | 8.04 | 5.48 | 2.20 | 7.88 | 8.58 | 8.28 | 2.92 | 6.41 | 9.08 |
| PTEN | C32 (Melanoma) | 2.11 | 2.42 | 1.18 | 1.26 | 3.00 | 4.00 | 4.53 | 5.15 | 5.60 | 5.97 |
| PTEN | A375 (Melanoma) | 6.82 | 6.04 | 3.30 | 1.62 | 2.18 | 2.70 | 2.20 | 6.00 | 6.54 | 8.82 |
| PTEN | A427 (NSCLC) | 3.10 | 4.18 | 4.11 | 1.06 | 1.99 | 2.04 | 3.41 | 2.53 | 3.61 | 8.52 |
| PTEN | O-401 (Kidney) | 4.62 | 5.00 | 3.73 | 2.35 | 1.72 | 1.36 | 1.37 | 3.66 | 4.41 | 2.51 |
| PTEN | KS-1 (GBM) | 1.96 | 2.27 | 7.91 | 1.24 | 2.96 | 5.24 | 5.86 | 3.00 | 5.70 | 9.26 |
| PTEN | MKN45 (Stomach) | 2.61 | 3.44 | 2.86 | 0.97 | 2.36 | 2.22 | 2.18 | 3.68 | 3.27 | 6.52 |
| PTEN | NCI-SNU-1 (Stomach) | 1.94 | 2.14 | 2.55 | 0.82 | 2.02 | 2.51 | 2.61 | 2.39 | 1.79 | 2.04 |
| PTEN | RPMI-2650 (Head and Neck) | 6.26 | 6.18 | 2.01 | 1.86 | 2.61 | 7.88 | 7.50 | 7.72 | 4.20 | 7.50 |
| PTEN | RT4 (Bladder) | 5.32 | 3.96 | 3.98 | 0.66 | 0.60 | 0.78 | 0.13 | 7.34 | 4.16 | 6.73 |
| PTEN | SJSA-1 (Sarcoma) | 1.67 | 2.69 | 2.52 | 1.81 | 1.93 | 1.11 | 1.82 | 2.13 | 2.12 | 2.52 |
| PTEN | SK-HEP-1 (Liver) | 0.74 | 2.10 | 1.27 | 0.94 | 1.04 | 1.02 | 2.87 | 6.03 | 4.44 | 3.07 |
| PTEN | SW982 (Sarcoma) | 8.56 | 11.52 | 7.92 | 1.67 | 4.88 | 4.58 | 7.24 | 10.38 | 8.10 | 9.19 |
| TP53 | EOL-1 (AML) | 3.10 | 8.88 | 6.11 | 4.59 | 6.60 | 5.30 | 4.64 | 9.36 | 5.35 | 5.00 |
| TP53 | MOLM-13 (AML) | 2.96 | 4.40 | 4.99 | 3.79 | 3.77 | 2.99 | 4.16 | 3.37 | 9.52 | 6.20 |
| TP53 | CML-T1 (CML) | 5.09 | 3.96 | 2.15 | 1.15 | 2.24 | 1.52 | 3.65 | 1.79 | 0.71 | 0.68 |
| TP53 | DOHH-2 (DLBCL) | 2.23 | 5.42 | 4.99 | 5.09 | 4.14 | 3.77 | 5.56 | 5.64 | 4.53 | 5.66 |
| TP53 | HT-29 (Colon) | 0.75 | 0.83 | 1.20 | 0.33 | 0.57 | 0.59 | 0.73 | 0.27 | 0.45 | 0.65 |
| TP53 | PC-3 (Prostate) | 0.44 | 0.42 | 0.38 | 0.57 | 1.17 | 0.43 | 1.60 | 0.64 | 0.68 | 0.73 |

Figure 71
AM-7209 – PI3Ki Combinations

Figure 72

RG7112 – PI3Ki Combinations

Figure 73
AMG 232 – Intrinsic Apoptosis Combinations

Figure 74
AM-7209 – Intrinsic Apoptosis Combinations

Figure 75

RG7112 – Intrinsic Apoptosis Combinations

Figure 76
AMG 232 – Miscellaneous Combinations

Figure 77
AM-7209 – Miscellaneous Combinations

Figure 78
RG7112 – Miscellaneous Combinations

Figure 79

AMG 232 – Chemotherapeutic Combinations

| | | MCF7 (Breast) | RKO (Colon) | KS-1 (GBM) | A427 (NSCLC) | S35A-1 (Sarcoma) | SW982 (Sarcoma) | MKN45 (Stomach) | NCI-SNU-1 (Stomach) | EOL-1 (AML) | MOLM-13 (AML) | HT-29 (Colon) TP53 | PC-3 (Prostate) TP53 |
|---|---|---|---|---|---|---|---|---|---|---|---|---|---|
| Platinums | AMG 232 x Cisplatin | | | | 0.70 | | | | | | | 0.19 | 0.48 |
| | AMG 232 x Oxaliplatin | | 0.85 | | | | | | | | | 0.08 | 0.18 |
| Topoisomerase II | AMG 232 x Doxorubicin | 4.63 | | | | | | | | 4.37 | 8.93 | 1.14 | 2.14 |
| | AMG 232 x Etoposide | | | | | 2.16 | 9.05 | 2.86 | 1.88 | | | 1.92 | 0.52 |
| Topoisomerase I | AMG 232 x Irinotecan | | 1.69 | | | | | | | | | 0.95 | 0.67 |
| DNA Alkylation | AMG 232 x Temozolomide | | | 2.61 | | | | | | | | 0.04 | 0.18 |
| Nucleoside Analogs | AMG 232 x Cytarabine | | | | | | | | | 6.90 | 0.70 | 0.56 | 1.33 |
| | AMG 232 x Decitabine | | | | | | | | | | | 0.07 | 0.86 |

Figure 80

AM-7209 – Chemotherapeutic Combinations

| | | MCF7 (Breast) | RKO (Colon) | KS-1 (GBM) | A427 (NSCLC) | SJSA-1 (Sarcoma) | SW982 (Sarcoma) | MKN45 (Stomach) | NCI-SNU-1 (Stomach) | EOL-1 (AML) | MOLM-13 (AML) | HT-29 (Colon) | PC-3 (Prostate) |
|---|---|---|---|---|---|---|---|---|---|---|---|---|---|
| Platinums | AM-7209 x Cisplatin | | 2.83 | | 1.18 | | | | | | | 0.51 | 0.73 |
| | AM-7209 x Oxaliplatin | | | | | | | | | | | 0.20 | 0.21 |
| Topoisomerase II | AM-7209 x Doxorubicin | | | | | | 17.4 | | | | 1.13 | 2.74 | 1.22 |
| | AM-7209 x Etoposide | | 3.47 | | | 2.01 | | 3.91 | 2.60 | 3.97 | | 1.56 | 0.84 |
| Topoisomerase I | AM-7209 x Irinotecan | | | | | | | | | | | 1.04 | 0.47 |
| DNA Alkylation | AM-7209 x Temozolomide | | | 2.28 | | | | | | | | 0.01 | 0.18 |
| Nucleoside Analogs | AM-7209 x Cytarabine | | | | | | | | | 0.3 | 3.1 | 0.29 | 0.58 |
| | AM-7209 x Decitabine | | | | | | | | | 3.17 | 17.7 | 0.30 | 0.28 |

TP53

Figure 81
RG7112 – Chemotherapeutic Combinations

|  | | MCF7 (Breast) | RKO (Colon) | KS-1 (GBM) | A427 (NSCLC) | S25A-1 (Sarcoma) | SW982 (Sarcoma) | MKN45 (Stomach) | NCI-SNU-1 (Stomach) | EOL-1 (AML) | MOLM-13 (AML) | HT-29 (Colon) | PC-3 (Prostate) |
|---|---|---|---|---|---|---|---|---|---|---|---|---|---|
| Platinums | RG7112 x Cisplatin | | | | 0.64 | | | | | | | 0.42 | 0.24 |
|  | RG7112 x Oxaliplatin | | 1.03 | | | | | | | | | 0.41 | 0.32 |
| Topoisomerase II | RG7112 x Doxorubicin | 2.60 | | | | | | | | | | 4.90 | 2.88 |
|  | RG7112 x Etoposide | | | | | 0.22 | 9.24 | 3.00 | 1.48 | 5.07 | | 3.10 | 1.39 |
| Topoisomerase I | RG7112 x Irinotecan | | 2.56 | | | | | | | | | 1.53 | 0.54 |
| DNA Alkylation | RG7112 x Temozolomide | | | 2.27 | | | | | | | | 0.01 | 0.05 |
| Nucleoside Analogs | RG7112 x Cytarabine | | | | | | | | | 6.29 | | 0.60 | 0.84 |
|  | RG7112 x Decitabine | | | | | | | | | | | 0.19 | 1.45 |

TP53

AMG 232 – Haematopoietic Lines

Figure 83
AM-7209 – Haematopoietic Lines

Figure 84
RG7112 – Haematopoietic Lines

MDM2 Inhibitor and CPT-11 in HCT116 Tumor

MDM2 inhibitor and Doxorubicin in SJSA-1 Tumors

MDM2 Inhibitor and BRAF or MEK Inhibition in RKO Tumors

MDM2 Inhibitor and PI3K Inhibitor in U87 Tumor

MDM2 Inhibitor and MEK Inhibitor in A375 Tumors

MDM2 Inhibitor and BRAF Inhibitor in A375sq2 Tumors

Combination of MDM2, PI3K and BRAF Inhibition in RKO Tumors

Combination of MDM2, PI3K and BRAF Inhibition in the RKO Tumor Model (single agents vs. double combinations)

MDM2 Inhibitor and Doxorubicin in Molm13 Tumors

MDM2 Inhibitor and MEK inhibitor in Molm13 Tumors

MDM2 Inhibitor and Cytarabine in Molm13 Tumors

MDM2 Inhibitor and Decitabine in Molm13 Tumors

MDM2 Inhibition and Sorafenib in Molm13 Tumors

COMBINATION THERAPY INCLUDING AN MDM2 INHIBITOR AND ONE OR MORE ADDITIONAL PHARMACEUTICALLY ACTIVE AGENTS FOR THE TREATMENT OF CANCERS

PRIORITY

This application claims the benefit of U.S. Provisional Patent Application No. 61/902,717, filed on Nov. 11, 2013 which is hereby incorporated herein by reference in its entirety.

FIELD OF THE INVENTION

The present invention provides combination therapy that includes an MDM2 inhibitor and one or more additional pharmaceutically active agents, particularly for the treatment of cancers. The invention also relates to pharmaceutical compositions that contain an MDM2 inhibitor and one or more additional pharmaceutically active agents for the treatment of cancers.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in p53$^{WT}$ tumors (p53 wild type). In support of this concept, some p53$^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are p53$^{WT}$ and studies with small molecule MDM2 inhibitors have yielded promising reductions in tumor growth both in vitro and in vivo. Further, in patients with p53-inactivated tumors, stabilization of wild type p53 in normal tissues by MDM2 inhibition might allow selective protection of normal tissues from mitotic poisons. As used herein, MDM2 means a human MDM2 protein and p53 means a human p53 protein. It is noted that human MDM2 can also be referred to as HDM2 or hMDM2. Several MDM2 inhibitors are in human clinical trials for the treatment of various cancers.

The present invention relates to combination therapy with an MDM2 inhibitor and one or more additional pharmaceutically active agents, which particular combinations show enhanced anti-cancer activity in certain types of cancers over what is expected when the individual members of the combination therapy are used alone.

SUMMARY OF THE INVENTION

In embodiment 1, the present invention provides a method of treating melanoma, the method comprising administering to a patient in need thereof a therapeutically effective amount of an MDM2 inhibitor and a BRAF inhibitor.

In embodiment 2, the present invention provides a method of embodiment 1 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 3, the present invention provides a method of embodiment 1 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 4, the present invention provides a method of any one of embodiments 1 to 3 wherein the BRAF inhibitor is dabrafenib.

In embodiment 5, the present invention provides a method of any one of embodiments 1 to 3 wherein the BRAF inhibitor is AMG 2112819 or vemurafenib.

In embodiment 6, the present invention provides a method of treating melanoma, the method comprising administering to a patient in need thereof a therapeutically effective amount of an MDM2 inhibitor and a pan-Raf inhibitor.

In embodiment 7, the present invention provides a method of embodiment 6 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 8, the present invention provides a method of embodiment 6 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 9, the present invention provides a method of any one of embodiments 6 to 8 wherein the pan-RAF inhibitor is RAF265 or MLN-2480.

In embodiment 10, the present invention provides a method of treating melanoma, the method comprising administering to a patient in need thereof a therapeutically effective amount of an MDM2 inhibitor and a MEK inhibitor.

In embodiment 11, the present invention provides a method of embodiment 10 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 12, the present invention provides a method of embodiment 10 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 13, the present invention provides a method of any one of embodiments 10 to 12 wherein the MEK inhibitor is trametinib.

In embodiment 14, the present invention provides a method of any one of embodiments 10 to 12 wherein the MEK inhibitor is pimasertib, PD0325901, MEK162, TAK-733, GDC-0973 or AZD8330.

In embodiment 15, the present invention provides a method of any one of embodiments 1 to 14 wherein the melanoma has a BRAF V600E or V600K mutation.

In embodiment 16, the present invention provides a method of treating colon cancer, the method comprising administering to a patient in need thereof a therapeutically effective amount of an MDM2 inhibitor and a BRAF inhibitor.

In embodiment 17, the present invention provides a method of embodiment 16 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 18, the present invention provides a method of embodiment 16 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 19, the present invention provides a method of any one of embodiments 16 to 18 wherein the BRAF inhibitor is dabrafenib.

In embodiment 20, the present invention provides a method of any one of embodiments 16 to 18 wherein the BRAF inhibitor is AMG 2112819 or vemurafenib.

In embodiment 21, the present invention provides a method of treating colon cancer, the method comprising administering to a patient in need thereof a therapeutically effective amount of an MDM2 inhibitor and a pan-Raf inhibitor.

In embodiment 22, the present invention provides a method of embodiment 21 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 23, the present invention provides a method of embodiment 21 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 24, the present invention provides a method of any one of embodiments 21 to 23 wherein the pan-RAF inhibitor is RAF265 or MLN-2480.

In embodiment 25, the present invention provides a method of treating colon cancer, the method comprising administering to a patient in need thereof a therapeutically effective amount of an MDM2 inhibitor and a MEK inhibitor.

In embodiment 26, the present invention provides a method of embodiment 25 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 27, the present invention provides a method of embodiment 25 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 28, the present invention provides a method of any one of embodiments 25 to 27 wherein the MEK inhibitor is trametinib.

In embodiment 29, the present invention provides a method of any one of embodiments 25 to 27 wherein the MEK inhibitor is pimasertib, PD0325901, MEK162, TAK-733, GDC-0973 or AZD8330.

In embodiment 30, the present invention provides a method of any one of embodiments 16 to 29 wherein the colon cancer has a BRAF V600E or V600K mutation.

In embodiment 31, the present invention provides a method of treating liver cancer, the method comprising administering to a patient in need thereof a therapeutically effective amount of an MDM2 inhibitor and a BRAF inhibitor.

In embodiment 32, the present invention provides a method of embodiment 31 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 33, the present invention provides a method of embodiment 31 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 34, the present invention provides a method of any one of embodiments 31 to 33 wherein the BRAF inhibitor is dabrafenib, or a pharmaceutically acceptable salt thereof.

In embodiment 35, the present invention provides a method of any one of embodiments 31 to 33 wherein the BRAF inhibitor is AMG 2112819 or vemurafenib.

In embodiment 36, the present invention provides a method of treating liver cancer, the method comprising administering to a patient in need thereof a therapeutically effective amount of an MDM2 inhibitor and a pan-Raf inhibitor.

In embodiment 37, the present invention provides a method of embodiment 36 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 38, the present invention provides a method of embodiment 36 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 39, the present invention provides a method of any one of embodiments 36 to 38 wherein the pan-RAF inhibitor is RAF265 or MLN-2480.

In embodiment 40, the present invention provides a method of treating liver cancer, the method comprising administering to a patient in need thereof a therapeutically effective amount of an MDM2 inhibitor and a MEK inhibitor.

In embodiment 41, the present invention provides a method of embodiment 40 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 42, the present invention provides a method of embodiment 40 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 43, the present invention provides a method of any one of embodiments 40 to 42 wherein the MEK inhibitor is trametinib.

In embodiment 44, the present invention provides a method of any one of embodiments 40 to 42 wherein the MEK inhibitor is pimasertib, PD0325901, MEK162, TAK-733, GDC-0973 or AZD8330.

In embodiment 45, the present invention provides a method of any one of embodiments 31 to 44 wherein the liver cancer has a BRAF V600E or V600K mutation.

In embodiment 46, the present invention provides a method of treating bladder cancer, the method comprising administering to a patient in need thereof a therapeutically effective amount of an MDM2 inhibitor and a MEK inhibitor.

In embodiment 47, the present invention provides a method of embodiment 46 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 48, the present invention provides a method of embodiment 46 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 49, the present invention provides a method of any one of embodiments 46 to 48 wherein the MEK inhibitor is trametinib.

In embodiment 50, the present invention provides a method of any one of embodiments 46 to 48 wherein the MEK inhibitor is pimasertib, PD0325901, MEK 162, TAK-733, GDC-0973 or AZD8330.

In embodiment 51, the present invention provides a method of treating AML, the method comprising administering to a patient in need thereof a therapeutically effective amount of an MDM2 inhibitor and a MEK inhibitor.

In embodiment 52, the present invention provides a method of embodiment 51 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 53, the present invention provides a method of embodiment 51 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 54, the present invention provides a method of any one of embodiments 51 to 53 wherein the MEK inhibitor is trametinib.

In embodiment 55, the present invention provides a method of any one of embodiments 51 to 53 wherein the MEK inhibitor is pimasertib, PD0325901, MEK162, TAK-733, GDC-0973 or AZD8330.

In embodiment 56, the present invention provides a method of any one of embodiments 51 to 55 wherein the AML has a FLT3-ITD mutation.

In embodiment 57, the present invention provides a method of treating NSCLC, the method comprising administering to a patient in need thereof a therapeutically effective amount of an MDM2 inhibitor and a pan-Raf inhibitor.

In embodiment 58, the present invention provides a method of embodiment 57 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 59, the present invention provides a method of embodiment 57 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 60, the present invention provides a method of any one of embodiments 57 to 59 wherein the pan-RAF inhibitor is RAF265 or MLN-2480.

In embodiment 61, the present invention provides a method of treating NSCLC, the method comprising administering to a patient in need thereof a therapeutically effective amount of an MDM2 inhibitor and a MEK inhibitor.

In embodiment 62, the present invention provides a method of embodiment 61 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 63, the present invention provides a method of embodiment 61 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 64, the present invention provides a method of any one of embodiments 61 to 63 wherein the MEK inhibitor is trametinib.

In embodiment 65, the present invention provides a method of any one of embodiments 61 to 63 wherein the MEK inhibitor is pimasertib, PD0325901, MEK162, TAK-733, GDC-0973 or AZD8330, or a pharmaceutically acceptable salt thereof.

In embodiment 66, the present invention provides a method of any one of embodiments 57 to 65 wherein the NSCLC had a KRAS mutation.

In embodiment 67, the present invention provides a method of treating kidney cancer, the method comprising administering to a patient in need thereof a therapeutically effective amount of an MDM2 inhibitor and a MEK inhibitor.

In embodiment 68, the present invention provides a method of embodiment 67 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 69, the present invention provides a method of embodiment 67 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 70, the present invention provides a method of any one of embodiments 67 to 69 wherein the MEK inhibitor is trametinib.

In embodiment 71, the present invention provides a method of any one of embodiments 67 to 69 wherein the MEK inhibitor is pimasertib, PD0325901, MEK162, TAK-733, GDC-0973 or AZD8330, or a pharmaceutically acceptable salt thereof.

In embodiment 72, the present invention provides a method of treating stomach cancer, the method comprising administering to a patient in need thereof a therapeutically effective amount of an MDM2 inhibitor and a MEK inhibitor.

In embodiment 73, the present invention provides a method of embodiment 72 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 74, the present invention provides a method of embodiment 72 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 75, the present invention provides a method of any one of embodiments 72 to 74 wherein the MEK inhibitor is trametinib.

In embodiment 76, the present invention provides a method of any one of embodiments 72 to 74 wherein the MEK inhibitor is pimasertib, PD0325901, MEK162, TAK-733, GDC-0973 or AZD8330.

In embodiment 77, the present invention provides a method of any one of embodiments 72 to 76 wherein the stomach cancer had a KRAS mutation.

In embodiment 78, the present invention provides a method of treating prostate cancer, the method comprising administering to a patient in need thereof a therapeutically effective amount of an MDM2 inhibitor and a PI3K pathway inhibitor.

In embodiment 79, the present invention provides a method of embodiment 78 wherein the PI3K pathway inhibitor is a PI3Kα selective inhibitor.

In embodiment 80, the present invention provides a method of embodiment 79 wherein the PI3Kα selective inhibitor is AMG 511, AMG2520765 or BYL719.

In embodiment 81, the present invention provides a method of embodiment 78 wherein the PI3K pathway inhibitor is a pan-PI3K inhibitor.

In embodiment 82, the present invention provides a method of embodiment 81 wherein the pan-PI3K inhibitor is BKM120 or GDC-0941.

In embodiment 83, the present invention provides a method of embodiment 78 wherein the PI3K pathway inhibitor is an AKT inhibitor.

In embodiment 84, the present invention provides a method of embodiment 83 wherein the AKT inhibitor is MK-2206, GDC-0068 or AZD5363.

In embodiment 85, the present invention provides a method of embodiment 78 wherein the PI3K pathway inhibitor is a dual PI3K/mTOR inhibitor.

In embodiment 86, the present invention provides a method of embodiment 85 wherein the dual PI3K/mTOR inhibitor is GDC-0980.

In embodiment 87, the present invention provides a method of embodiment 78 wherein the PI3K pathway inhibitor is an mTOR inhibitor.

In embodiment 88, the present invention provides a method of embodiment 87 wherein the mTOR inhibitor is AZD2014 or MLN0128.

In embodiment 89, the present invention provides a method of any one of embodiments 78 to 88 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 90, the present invention provides a method of any one of embodiments 78 to 88 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 91, the present invention provides a method of treating breast cancer, the method comprising administering to a patient in need thereof a therapeutically effective amount of an MDM2 inhibitor and a PI3K pathway inhibitor.

In embodiment 92, the present invention provides a method of embodiment 91 wherein the PI3K pathway inhibitor is a PI3Kα selective inhibitor.

In embodiment 93, the present invention provides a method of embodiment 92 wherein the PI3Kα selective inhibitor is AMG 511, AMG2520765 or BYL719.

In embodiment 94, the present invention provides a method of claim 91 wherein the PI3K pathway inhibitor is a pan-PI3K inhibitor.

In embodiment 95, the present invention provides a method of embodiment 94 wherein the pan-PI3K inhibitor is BKM120 or GDC-0941.

In embodiment 96, the present invention provides a method of embodiment 91 wherein the PI3K pathway inhibitor is an AKT inhibitor.

In embodiment 97, the present invention provides a method of embodiment 96 wherein the AKT inhibitor is MK-2206, GDC-0068 or AZD5363.

In embodiment 98, the present invention provides a method of embodiment 91 wherein the PI3K pathway inhibitor is a dual PI3K/mTOR inhibitor.

In embodiment 99, the present invention provides a method of embodiment 98 wherein the dual PI3K/mTOR inhibitor is GDC-0980.

In embodiment 100, the present invention provides a method of embodiment 91 wherein the PI3K pathway inhibitor is an mTOR inhibitor.

In embodiment 101, the present invention provides a method of embodiment 100 wherein the mTOR inhibitor is AZD2014 or MLN0128.

In embodiment 102, the present invention provides a method of any one of embodiments 91 to 101 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 103, the present invention provides a method of any one of embodiments 91 to 101 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 104, the present invention provides a method of any one of embodiments 91 to 103 wherein the breast cancer has a PI3K mutation.

In embodiment 105, the present invention provides a method of treating endometrial cancer, the method comprising administering to a patient in need thereof a therapeutically effective amount of an MDM2 inhibitor and a PI3K pathway inhibitor.

In embodiment 106, the present invention provides a method of embodiment 105 wherein the PI3K pathway inhibitor is a PI3Kα selective inhibitor.

In embodiment 107, the present invention provides a method of embodiment 106 wherein the PI3Kα selective inhibitor is AMG 511, AMG252076 or BYL719.

In embodiment 108, the present invention provides a method of embodiment 105 wherein the PI3K pathway inhibitor is a pan-PI3K inhibitor.

In embodiment 109, the present invention provides a method of embodiment 108 wherein the pan-PI3K inhibitor is BKM120 or GDC-0941.

In embodiment 110, the present invention provides a method of embodiment 105 wherein the PI3K pathway inhibitor is an AKT inhibitor.

In embodiment 111, the present invention provides a method of embodiment 110 wherein the AKT inhibitor is MK-2206, GDC-0068 or AZD5363.

In embodiment 112, the present invention provides a method of embodiment 105 wherein the PI3K pathway inhibitor is a dual PI3K/mTOR inhibitor.

In embodiment 113, the present invention provides a method of embodiment 112 wherein the dual PI3K/mTOR inhibitor is GDC-0980.

In embodiment 114, the present invention provides a method of embodiment 105 wherein the PI3K pathway inhibitor is an mTOR inhibitor.

In embodiment 115, the present invention provides a method of embodiment 114 wherein the mTOR inhibitor is AZD2014 or MLN0128.

In embodiment 116, the present invention provides a method of any one of embodiments 105 to 115 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 117, the present invention provides a method of any one of embodiments 105 to 115 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 118, the present invention provides a method of treating NSCLC, the method comprising administering to a patient in need thereof a therapeutically effective amount of an MDM2 inhibitor and a PI3K pathway inhibitor.

In embodiment 119, the present invention provides a method of embodiment 118 wherein the PI3K pathway inhibitor is a PI3Kα selective inhibitor.

In embodiment 120, the present invention provides a method of embodiment 119 wherein the PI3Kα selective inhibitor is AMG 511, AMG2520765 or BYL719.

In embodiment 121, the present invention provides a method of embodiment 118 wherein the PI3K pathway inhibitor is a pan-PI3K inhibitor.

In embodiment 122, the present invention provides a method of embodiment 121 wherein the pan-PI3K inhibitor is BKM120 or GDC-0941.

In embodiment 123, the present invention provides a method of embodiment 118 wherein the PI3K pathway inhibitor is an AKT inhibitor.

In embodiment 124, the present invention provides a method of embodiment 123 wherein the AKT inhibitor is MK-2206, GDC-0068 or AZD5363.

In embodiment 125, the present invention provides a method of embodiment 118 wherein the PI3K pathway inhibitor is a dual PI3K/mTOR inhibitor.

In embodiment 126, the present invention provides a method of embodiment 125 wherein the dual PI3K/mTOR inhibitor is GDC-0980.

In embodiment 127, the present invention provides a method of embodiment 118 wherein the PI3K pathway inhibitor is an mTOR inhibitor.

In embodiment 128, the present invention provides a method of embodiment 127 wherein the mTOR inhibitor is AZD2014 or MLN0128.

In embodiment 129, the present invention provides a method of any one of embodiments 118 to 128 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 130, the present invention provides a method of any one of embodiments 118 to 128 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 131, the present invention provides a method of treating head and neck cancer, the method comprising administering to a patient in need thereof a therapeutically effective amount of an MDM2 inhibitor and a PI3K pathway inhibitor.

In embodiment 132, the present invention provides a method of embodiment 131 wherein the PI3K pathway inhibitor is a PI3Kα selective inhibitor.

In embodiment 133, the present invention provides a method of embodiment 132 wherein the PI3Kα selective inhibitor is AMG 511, AMG2520765 or BYL719.

In embodiment 134, the present invention provides a method of embodiment 131 wherein the PI3K pathway inhibitor is a pan-PI3K inhibitor.

In embodiment 135, the present invention provides a method of embodiment 134 wherein the pan-PI3K inhibitor is BKM120 or GDC-0941.

In embodiment 136, the present invention provides a method of embodiment 131 wherein the PI3K pathway inhibitor is an AKT inhibitor.

In embodiment 137, the present invention provides a method of embodiment 136 wherein the AKT inhibitor is MK-2206, GDC-0068 or AZD5363.

In embodiment 138, the present invention provides a method of embodiment 131 wherein the PI3K pathway inhibitor is a dual PI3K/mTOR inhibitor.

In embodiment 139, the present invention provides a method of embodiment 138 wherein the dual PI3K/mTOR inhibitor is GDC-0980.

In embodiment 140, the present invention provides a method of embodiment 131 wherein the PI3K pathway inhibitor is an mTOR inhibitor.

In embodiment 141, the present invention provides a method of embodiment 140 wherein the mTOR inhibitor is AZD2014 or MLN0128.

In embodiment 142, the present invention provides a method of any one of embodiments 131 to 141 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 143, the present invention provides a method of any one of embodiments 131 to 141 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 144, the present invention provides a method of treating DLBCL, the method comprising administering to a patient in need thereof a therapeutically effective amount of an MDM2 inhibitor and a PI3K pathway inhibitor.

In embodiment 145, the present invention provides a method of embodiment 144 wherein the PI3K pathway inhibitor is a PI3Kα selective inhibitor.

In embodiment 146, the present invention provides a method of embodiment 145 wherein the PI3Kα selective inhibitor is AMG 511, AMG2520765 or BYL719.

In embodiment 147, the present invention provides a method of embodiment 144 wherein the PI3K pathway inhibitor is a pan-PI3K inhibitor.

In embodiment 148, the present invention provides a method of embodiment 147 wherein the pan-PI3K inhibitor is BKM120 or GDC-0941.

In embodiment 149, the present invention provides a method of embodiment 144 wherein the PI3K pathway inhibitor is an AKT inhibitor.

In embodiment 150, the present invention provides a method of embodiment 149 wherein the AKT inhibitor is MK-2206, GDC-0068 or AZD5363.

In embodiment 151, the present invention provides a method of embodiment 144 wherein the PI3K pathway inhibitor is a dual PI3K/mTOR inhibitor.

In embodiment 152, the present invention provides a method of embodiment 151 wherein the dual PI3K/mTOR inhibitor is GDC-0980.

In embodiment 153, the present invention provides a method of embodiment 144 wherein the PI3K pathway inhibitor is an mTOR inhibitor.

In embodiment 154, the present invention provides a method of embodiment 153 wherein the mTOR inhibitor is AZD2014 or MLN0128.

In embodiment 155, the present invention provides a method of any one of embodiments 144 to 154 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 156, the present invention provides a method of any one of embodiments 144 to 154 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 157, the present invention provides a method of treating glioblastoma, the method comprising administering to a patient in need thereof a therapeutically effective amount of an MDM2 inhibitor and a PI3K pathway inhibitor.

In embodiment 158, the present invention provides a method of embodiment 157 wherein the PI3K pathway inhibitor is a PI3Kα selective inhibitor.

In embodiment 159, the present invention provides a method of embodiment 158 wherein the PI3Kα selective inhibitor is AMG 511, AMG2520765 or BYL719.

In embodiment 160, the present invention provides a method of embodiment 157 wherein the PI3K pathway inhibitor is a pan-PI3K inhibitor.

In embodiment 161, the present invention provides a method of embodiment 160 wherein the pan-PI3K inhibitor is BKM120 or GDC-0941.

In embodiment 162, the present invention provides a method of embodiment 157 wherein the PI3K pathway inhibitor is an AKT inhibitor.

In embodiment 163, the present invention provides a method of embodiment 162 wherein the AKT inhibitor is MK-2206, GDC-0068 or AZD5363.

In embodiment 164, the present invention provides a method of embodiment 157 wherein the PI3K pathway inhibitor is a dual PI3K/mTOR inhibitor.

In embodiment 165, the present invention provides a method of embodiment 164 wherein the dual PI3K/mTOR inhibitor is GDC-0980.

In embodiment 166, the present invention provides a method of embodiment 157 wherein the PI3K pathway inhibitor is an mTOR inhibitor.

In embodiment 167, the present invention provides a method of embodiment 166 wherein the mTOR inhibitor is AZD2014 or MLN0128.

In embodiment 168, the present invention provides a method of any one of embodiments 157 to 167 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 169, the present invention provides a method of any one of embodiments 157 to 167 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 170, the present invention provides a method of treating bladder cancer, the method comprising administering to a patient in need thereof a therapeutically effective amount of an MDM2 inhibitor and a PI3K pathway inhibitor.

In embodiment 171, the present invention provides a method of embodiment 170 wherein the PI3K pathway inhibitor is a PI3Kα selective inhibitor.

In embodiment 172, the present invention provides a method of embodiment 171 wherein the PI3Kα selective inhibitor is AMG 511, AMG2520765 or BYL719.

In embodiment 173, the present invention provides a method of embodiment 170 wherein the PI3K pathway inhibitor is a pan-PI3K inhibitor.

In embodiment 174, the present invention provides a method of embodiment 173 wherein the pan-PI3K inhibitor is BKM120 or GDC-0941.

In embodiment 175, the present invention provides a method of embodiment 170 wherein the PI3K pathway inhibitor is an AKT inhibitor.

In embodiment 176, the present invention provides a method of embodiment 175 wherein the AKT inhibitor is MK-2206, GDC-0068 or AZD5363.

In embodiment 177, the present invention provides a method of embodiment 170 wherein the PI3K pathway inhibitor is a dual PI3K/mTOR inhibitor.

In embodiment 178, the present invention provides a method of embodiment 177 wherein the dual PI3K/mTOR inhibitor is GDC-0980.

In embodiment 179, the present invention provides a method of embodiment 170 wherein the PI3K pathway inhibitor is an mTOR inhibitor.

In embodiment 180, the present invention provides a method of embodiment 179 wherein the mTOR inhibitor is AZD2014 or MLN0128.

In embodiment 181, the present invention provides a method of any one of embodiments 170 to 180 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 182, the present invention provides a method of any one of embodiments 170 to 180 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 183, the present invention provides a method of treating AML, the method comprising administering to a patient in need thereof a therapeutically effective amount of an MDM2 inhibitor and a PI3K pathway inhibitor.

In embodiment 184, the present invention provides a method of embodiment 183 wherein the PI3K pathway inhibitor is a PI3Kα selective inhibitor.

In embodiment 185, the present invention provides a method of embodiment 184 wherein the PI3Kα selective inhibitor is AMG 511, AMG2520765 or BYL719.

In embodiment 186, the present invention provides a method of embodiment 183 wherein the PI3K pathway inhibitor is a pan-PI3K inhibitor.

In embodiment 187, the present invention provides a method of embodiment 186 wherein the pan-PI3K inhibitor is BKM120 or GDC-0941.

In embodiment 188, the present invention provides a method of embodiment 183 wherein the PI3K pathway inhibitor is an AKT inhibitor.

In embodiment 189, the present invention provides a method of embodiment 188 wherein the AKT inhibitor is MK-2206, GDC-0068 or AZD5363.

In embodiment 190, the present invention provides a method of embodiment 183 wherein the PI3K pathway inhibitor is a dual PI3K/mTOR inhibitor.

In embodiment 191, the present invention provides a method of embodiment 190 wherein the dual PI3K/mTOR inhibitor is GDC-0980.

In embodiment 192, the present invention provides a method of embodiment 183 wherein the PI3K pathway inhibitor is an mTOR inhibitor.

In embodiment 193, the present invention provides a method of embodiment 192 wherein the mTOR inhibitor is AZD2014 or MLN0128.

In embodiment 194, the present invention provides a method of any one of embodiments 183 to 193 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 195, the present invention provides a method of any one of embodiments 183 to 193 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 196, the present invention provides a method of any one of embodiments 183 to 195 wherein the AML has a FLT3 ITD mutation.

In embodiment 197, the present invention provides a method of treating bladder cancer, the method comprising administering to a patient in need thereof a therapeutically effective amount of an MDM2 inhibitor and a Bcl2/BclxL inhibitor.

In embodiment 198, the present invention provides a method of embodiment 197 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 199, the present invention provides a method of embodiment 197 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 200, the present invention provides a method of any one of embodiments 197 to 199 wherein the Bcl2/BclxL inhibitor is navitoclax.

In embodiment 201, the present invention provides a method of treating glioblastoma, the method comprising administering to a patient in need thereof a therapeutically effective amount of an MDM2 inhibitor and a Bcl2/BclxL inhibitor.

In embodiment 202, the present invention provides a method of embodiment 201 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 203, the present invention provides a method of embodiment 201 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 204, the present invention provides a method of any one of embodiments 201 to 203 wherein the Bcl2/BclxL inhibitor is navitoclax.

In embodiment 205, the present invention provides a method of treating head and neck cancer, the method comprising administering to a patient in need thereof a therapeutically effective amount of an MDM2 inhibitor and a Bcl2/BclxL inhibitor.

In embodiment 206, the present invention provides a method of embodiment 205 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 207, the present invention provides a method of embodiment 205 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 208, the present invention provides a method of any one of embodiments 205 to 207 wherein the Bcl2/BclxL inhibitor is navitoclax.

In embodiment 209, the present invention provides a method of treating kidney cancer, the method comprising administering to a patient in need thereof a therapeutically effective amount of an MDM2 inhibitor and a Bcl2/BclxL inhibitor.

In embodiment 210, the present invention provides a method of embodiment 209 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 211, the present invention provides a method of embodiment 209 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 212, the present invention provides a method of any one of embodiments 209 to 211 wherein the Bcl2/BclxL inhibitor is navitoclax.

In embodiment 213, the present invention provides a method of treating liver cancer, the method comprising administering to a patient in need thereof a therapeutically effective amount of an MDM2 inhibitor and a Bcl2/BclxL inhibitor.

In embodiment 214, the present invention provides a method of embodiment 213 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 215, the present invention provides a method of embodiment 213 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3 yl)acetamido)-2-methoxybenzoic acid, or a pharmaceutically acceptable salt thereof.

In embodiment 216, the present invention provides a method of any one of embodiments 213 to 215 wherein the Bcl2/BclxL inhibitor is navitoclax.

In embodiment 217, the present invention provides a method of treating sarcoma, the method comprising administering to a patient in need thereof a therapeutically effective amount of an MDM2 inhibitor and a Bcl2/BclxL inhibitor.

In embodiment 218, the present invention provides a method of embodiment 217 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 219, the present invention provides a method of embodiment 217 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 220, the present invention provides a method of any one of embodiments 217 to 219 wherein the Bcl2/BclxL inhibitor is navitoclax.

In embodiment 221, the present invention provides a method of treating AML, the method comprising administering to a patient in need thereof a therapeutically effective amount of an MDM2 inhibitor and a Bcl2/BclxL inhibitor.

In embodiment 222, the present invention provides a method of embodiment 221 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 223, the present invention provides a method of embodiment 221 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 224, the present invention provides a method of any one of embodiments 221 to 223 wherein the Bcl2/BclxL inhibitor is navitoclax.

In embodiment 225, the present invention provides a method of any one of embodiments 221 to 224 wherein the AML has a FLT3 ITD mutation.

In embodiment 226, the present invention provides a method of treating CML, the method comprising administering to a patient in need thereof a therapeutically effective amount of an MDM2 inhibitor and a Bcl2/BclxL inhibitor.

In embodiment 227, the present invention provides a method of embodiment 226 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 228, the present invention provides a method of embodiment 226 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 229, the present invention provides a method of any one of embodiments 226 to 228 wherein the Bcl2/BclxL inhibitor is navitoclax.

In embodiment 230, the present invention provides a method of any one of embodiments 226 to 229 where the CML has a BCR-ABL mutation.

In embodiment 231, the present invention provides a method of treating DLBCL, the method comprising administering to a patient in need thereof a therapeutically effective amount of an MDM2 inhibitor and a Bcl2/BclxL inhibitor.

In embodiment 32, the present invention provides a method of embodiment 231 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 233, the present invention provides a method of embodiment 231 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 234, the present invention provides a method of any one of embodiments 231 to 233 wherein the Bcl2/BclxL inhibitor is navitoclax.

In embodiment 235, the present invention provides a method of treating sarcoma, the method comprising administering to a patient in need thereof a therapeutically effective amount of an MDM2 inhibitor and a BCL2 inhibitor.

In embodiment 236, the present invention provides a method of embodiment 235 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 237, the present invention provides a method of embodiment 235 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 238, the present invention provides a method of any one of embodiments 235 to 237 wherein the BCL2 inhibitor is ABT-199.

In embodiment 239, the present invention provides a method of treating AML, the method comprising administering to a patient in need thereof a therapeutically effective amount of an MDM2 inhibitor and a BCL2 inhibitor.

In embodiment 240, the present invention provides a method of embodiment 239 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 241, the present invention provides a method of embodiment 239 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 242, the present invention provides a method of any one of embodiments 239 to 241 wherein the BCL2 inhibitor is ABT-199.

In embodiment 243, the present invention provides a method of any one of embodiments 239 to 242 wherein the AML has a FLT3 ITD mutation.

In embodiment 244, the present invention provides a method of treating CML, the method comprising administering to a patient in need thereof a therapeutically effective amount of an MDM2 inhibitor and a BCL2 inhibitor.

In embodiment 245, the present invention provides a method of embodiment 244 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 246, the present invention provides a method of embodiment 244 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 247, the present invention provides a method of any one of embodiments 244 to 246 wherein the BCL2 inhibitor is ABT-199.

In embodiment 248, the present invention provides a method of any one of embodiments 244 to 247 where the CML has a BCR-ABL mutation.

In embodiment 249, the present invention provides a method of treating DLBCL, the method comprising administering to a patient in need thereof a therapeutically effective amount of an MDM2 inhibitor and a BCL2 inhibitor.

In embodiment 250, the present invention provides a method of embodiment 249 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 251, the present invention provides a method of embodiment 249 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 252, the present invention provides a method of any one of embodiments 249 to 251 wherein the BCL2 inhibitor is ABT-199.

In embodiment 253, the present invention provides a method of treating endometrial cancer, the method comprising administering to a patient in need thereof a therapeutically effective amount of an MDM2 inhibitor and a BCR-ABL inhibitor.

In embodiment 254, the present invention provides a method of embodiment 253 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 255, the present invention provides a method of embodiment 253 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 256, the present invention provides a method of any one of embodiments 253 to 255 wherein the BCR-ABL inhibitor is dasatinib.

In embodiment 257, the present invention provides a method of treating glioblastoma, the method comprising administering to a patient in need thereof a therapeutically effective amount of an MDM2 inhibitor and a BCR-ABL inhibitor.

In embodiment 258, the present invention provides a method of embodiment 257 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 259, the present invention provides a method of embodiment 257 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 260, the present invention provides a method of any one of embodiments 257 to 259 wherein the BCR-ABL inhibitor is dasatinib.

In embodiment 261, the present invention provides a method of treating CML, the method comprising administering to a patient in need thereof a therapeutically effective amount of an MDM2 inhibitor and a BCR-ABL inhibitor.

In embodiment 262, the present invention provides a method of embodiment 261 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 263, the present invention provides a method of embodiment 261 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 264, the present invention provides a method of any one of embodiments 261 to 263 wherein the BCR-ABL inhibitor is dasatinib.

In embodiment 265, the present invention provides a method of any one of embodiments 261 to 264 where the CML has a BCR-ABL mutation.

In embodiment 266, the present invention provides a method of treating endometrial cancer, the method comprising administering to a patient in need thereof a therapeutically effective amount of an MDM2 inhibitor and a BCR-ABL inhibitor.

In embodiment 267, the present invention provides a method of embodiment 266 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 268, the present invention provides a method of embodiment 266 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 269, the present invention provides a method of any one of embodiments 266 to 268 wherein the BCR-ABL inhibitor is dasatinib.

In embodiment 270, the present invention provides a method of treating bladder cancer, the method comprising administering to a patient in need thereof a therapeutically effective amount of an MDM2 inhibitor and a BCR-ABL inhibitor.

In embodiment 271, the present invention provides a method of embodiment 270 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 272, the present invention provides a method of embodiment 270 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 273, the present invention provides a method of any one of embodiments 270 to 272 wherein the BCR-ABL inhibitor is dasatinib.

In embodiment 274, the present invention provides a method of treating head and neck cancer, the method comprising administering to a patient in need thereof a therapeutically effective amount of an MDM2 inhibitor and a BCR-ABL inhibitor.

In embodiment 275, the present invention provides a method of embodiment 274 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 276, the present invention provides a method of embodiment 274 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 277, the present invention provides a method of any one of embodiments 274 to 276 wherein the BCR-ABL inhibitor is dasatinib.

In embodiment 278, the present invention provides a method of treating kidney cancer, the method comprising administering to a patient in need thereof a therapeutically effective amount of an MDM2 inhibitor and a HDAC inhibitor.

In embodiment 279, the present invention provides a method of embodiment 278 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 280, the present invention provides a method of embodiment 278 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 281, the present invention provides a method of any one of embodiments 278 to 280 wherein the HDAC inhibitor is panobinostat.

In embodiment 282, the present invention provides a method of treating liver cancer, the method comprising administering to a patient in need thereof a therapeutically effective amount of an MDM2 inhibitor and a HDAC inhibitor.

In embodiment 283, the present invention provides a method of embodiment 282 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 284, the present invention provides a method of embodiment 282 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 285, the present invention provides a method of any one of embodiments 282 to 284 wherein the HDAC inhibitor is panobinostat.

In embodiment 286, the present invention provides a method of treating melanoma, the method comprising administering to a patient in need thereof a therapeutically effective amount of an MDM2 inhibitor and a HDAC inhibitor.

In embodiment 287, the present invention provides a method of embodiment 286 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 288, the present invention provides a method of embodiment 286 wherein the MDM2 inhibitor is 4-(2-(((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 289, the present invention provides a method of any one of embodiments 286 to 288 wherein the HDAC inhibitor is panobinostat.

In embodiment 290, the present invention provides a method of treating AML, the method comprising administering to a patient in need thereof a therapeutically effective amount of an MDM2 inhibitor and decitabine.

In embodiment 291, the present invention provides a method of embodiment 290 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 292, the present invention provides a method of embodiment 290 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 293, the present invention provides a method of any one of embodiments 290 to 292 wherein the AML has a FLT3 ITD mutation.

In embodiment 294, the present invention provides a method of treating AML, the method comprising administering to a patient in need thereof a therapeutically effective amount of an MDM2 inhibitor and cytarabine.

In embodiment 295, the present invention provides a method of embodiment 294 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 296, the present invention provides a method of embodiment 294 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 297, the present invention provides a method of any one of embodiments 294 to 296 wherein the AML has a FLT3 ITD mutation.

In embodiment 298, the present invention provides a method of treating AML, the method comprising administering to a patient in need thereof a therapeutically effective amount of an MDM2 inhibitor and doxorubicin.

In embodiment 299, the present invention provides a method of embodiment 298 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 300, the present invention provides a method of embodiment 298 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 301, the present invention provides a method of any one of embodiments 298 to 300 wherein the AML has a FLT3 ITD mutation.

In embodiment 302, the present invention provides a method of treating sarcoma, the method comprising administering to a patient in need thereof a therapeutically effective amount of an MDM2 inhibitor and etoposide.

In embodiment 303, the present invention provides a method of embodiment 302 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 304, the present invention provides a method of embodiment 302 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 305, the present invention provides a method of treating breast cancer, the method comprising administering to a patient in need thereof a therapeutically effective amount of an MDM2 inhibitor and doxorubicin.

In embodiment 306, the present invention provides a method of embodiment 305 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 307, the present invention provides a method of embodiment 305 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 308, the present invention provides a method of treating AML, the method comprising administering to a patient in need thereof a therapeutically effective amount of an MDM2 inhibitor and imatinib.

In embodiment 309, the present invention provides a method of embodiment 308 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 310, the present invention provides a method of embodiment 308 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 311, the present invention provides a method of any one of embodiments 308 to 310 wherein the AML has a FLT3 ITD mutation.

In embodiment 312, the present invention provides a method of treating AML, the method comprising administering to a patient in need thereof a therapeutically effective amount of an MDM2 inhibitor and ponatinib.

In embodiment 313, the present invention provides a method of embodiment 312 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 314, the present invention provides a method of embodiment 312 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 315, the present invention provides a method of any one of embodiments 312 to 314 wherein the AML has a FLT3 ITD mutation.

In embodiment 316, the present invention provides a method of treating AML, the method comprising administering to a patient in need thereof a therapeutically effective amount of an MDM2 inhibitor and bosutinib.

In embodiment 317, the present invention provides a method of embodiment 316 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 318, the present invention provides a method of embodiment 316 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 319, the present invention provides a method of any one of embodiments 316 to 318 wherein the AML has a FLT3 ITD mutation In embodiment 320, the present invention provides a method of treating AML, the method comprising administering to a patient in need thereof a therapeutically effective amount of an MDM2 inhibitor and nilotinib.

In embodiment 321, the present invention provides a method of embodiment 320 wherein the MDM2 inhibitor is 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof.

In embodiment 322, the present invention provides a method of embodiment 320 wherein the MDM2 inhibitor is 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof.

In embodiment 323, the present invention provides a method of any one of embodiments 320 to 322 wherein the AML has a FLT3 ITD mutation In embodiment 324, the present invention provides a method of treating melanoma, the method comprising administering to a patient in need thereof a therapeutically effective amount of 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, dabrafenib and trametinib.

In embodiment 325, the present invention provides a method of treating melanoma, the method comprising administering to a patient in need thereof a therapeutically effective amount of 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, dabrafenib and trametinib.

In embodiment 326, the present invention provides a method of any one of embodiments 324 to 325 wherein the melanoma has a BRAF V600E or V600K mutation.

In embodiment 327, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; dabrafenib; and a pharmaceutically acceptable excipient.

In embodiment 328, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; dabrafenib; and a pharmaceutically acceptable excipient.

In embodiment 329, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AMG 2112819; and a pharmaceutically acceptable excipient.

In embodiment 330, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AMG 2112819; and a pharmaceutically acceptable excipient.

In embodiment 331, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; RAF265; and a pharmaceutically acceptable excipient.

In embodiment 332, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; RAF265; and a pharmaceutically acceptable excipient.

In embodiment 333, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; MLN-2480; and a pharmaceutically acceptable excipient.

In embodiment 334, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; MLN-2480; and a pharmaceutically acceptable excipient.

In embodiment 335, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; trametinib; and a pharmaceutically acceptable excipient.

In embodiment 336, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; trametinib; and a pharmaceutically acceptable excipient.

In embodiment 337, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; nilotinib; and a pharmaceutically acceptable excipient.

In embodiment 338, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; nilotinib; and a pharmaceutically acceptable excipient.

In embodiment 339, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; pimasertinib; and a pharmaceutically acceptable excipient.

In embodiment 340, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2- oxopiperidin-3-yl)acetamido)-2-methoxybenzoic acid, or a pharmaceutically acceptable salt thereof; pimasertinib; and a pharmaceutically acceptable excipient.

In embodiment 341, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; PD0325901; and a pharmaceutically acceptable excipient.

In embodiment 342, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; PD0325901; and a pharmaceutically acceptable excipient.

In embodiment 343, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; MEK 162; and a pharmaceutically acceptable excipient.

In embodiment 344, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; MEK 162; and a pharmaceutically acceptable excipient.

In embodiment 345, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; TAK-733; and a pharmaceutically acceptable excipient.

In embodiment 346, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; TAK-733; and a pharmaceutically acceptable excipient.

In embodiment 347, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; GDC-0973; and a pharmaceutically acceptable excipient.

In embodiment 348, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; GDC-0973; and a pharmaceutically acceptable excipient.

In embodiment 349, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AZD 8330; and a pharmaceutically acceptable excipient.

In embodiment 350, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AZD 8330; and a pharmaceutically acceptable excipient.

In embodiment 351, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; vemurafenib; and a pharmaceutically acceptable excipient.

In embodiment 352, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; vemurafenib; and a pharmaceutically acceptable excipient.

In embodiment 353, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AMG 511; and a pharmaceutically acceptable excipient.

In embodiment 354, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AMG 511; and a pharmaceutically acceptable excipient.

In embodiment 355, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AMG 2520765; and a pharmaceutically acceptable excipient.

In embodiment 356, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AMG 2520765; and a pharmaceutically acceptable excipient.

In embodiment 357, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; BYL719; and a pharmaceutically acceptable excipient.

In embodiment 358, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; BYL719; and a pharmaceutically acceptable excipient.

In embodiment 359, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; BKM120; and a pharmaceutically acceptable excipient.

In embodiment 360, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; BKM120; and a pharmaceutically acceptable excipient.

In embodiment 361, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; GDC-0941; and a pharmaceutically acceptable excipient.

In embodiment 362, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; GDC-0941; and a pharmaceutically acceptable excipient.

In embodiment 363, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; MK-2206; and a pharmaceutically acceptable excipient.

In embodiment 364, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; MK-2206; and a pharmaceutically acceptable excipient.

In embodiment 365, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AZD 5363; and a pharmaceutically acceptable excipient.

In embodiment 366, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AZD 5363; and a pharmaceutically acceptable excipient.

In embodiment 367, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; GDC-0068; and a pharmaceutically acceptable excipient.

In embodiment 368, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; GDC-0068; and a pharmaceutically acceptable excipient.

In embodiment 369, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; GDC-0980; and a pharmaceutically acceptable excipient.

In embodiment 370, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; GDC-0980; and a pharmaceutically acceptable excipient.

In embodiment 371, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; AZD2014; and a pharmaceutically acceptable excipient.

In embodiment 372, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; AZD2014; and a pharmaceutically acceptable excipient.

In embodiment 373, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; MLN0128; and a pharmaceutically acceptable excipient.

In embodiment 374, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; MLN0128; and a pharmaceutically acceptable excipient.

In embodiment 375, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; navitoclax; and a pharmaceutically acceptable excipient.

In embodiment 376, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; navitoclax; and a pharmaceutically acceptable excipient.

In embodiment 377, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; ABT-199; and a pharmaceutically acceptable excipient.

In embodiment 378, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; ABT-199; and a pharmaceutically acceptable excipient.

In embodiment 379, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; dasatinib; and a pharmaceutically acceptable excipient.

In embodiment 380, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; dasatinib; and a pharmaceutically acceptable excipient.

In embodiment 381, the present invention provides a pharmaceutical composition comprising: 2-((3R,5R,6S)-5-

(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; panobinostat; and a pharmaceutically acceptable excipient.

In embodiment 382, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; panobinostat; and a pharmaceutically acceptable excipient.

In embodiment 383, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; decitabine; and a pharmaceutically acceptable excipient.

In embodiment 384, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; decitabine; and a pharmaceutically acceptable excipient.

In embodiment 385, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; cytarabine; and a pharmaceutically acceptable excipient.

In embodiment 386, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; cytarabine; and a pharmaceutically acceptable excipient.

In embodiment 387, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; doxorubicin; and a pharmaceutically acceptable excipient.

In embodiment 388, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; doxorubicin; and a pharmaceutically acceptable excipient.

In embodiment 389, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; etoposide; and a pharmaceutically acceptable excipient.

In embodiment 390, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; etoposide; and a pharmaceutically acceptable excipient.

In embodiment 391, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; imatinib; and a pharmaceutically acceptable excipient.

In embodiment 392, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; imatinib; and a pharmaceutically acceptable excipient.

In embodiment 393, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; ponatinib; and a pharmaceutically acceptable excipient.

In embodiment 394, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; ponatinib; and a pharmaceutically acceptable excipient.

In embodiment 395, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; bosutinib; and a pharmaceutically acceptable excipient.

In embodiment 396, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; bosutinib; and a pharmaceutically acceptable excipient.

In embodiment 397, the present invention provides a pharmaceutical composition comprising: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, or a pharmaceutically acceptable salt thereof; dabrafenib; trametinib; and a pharmaceutically acceptable excipient.

In embodiment 398, the present invention provides a pharmaceutical composition comprising: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid, or a pharmaceutically acceptable salt thereof; dabrafenib; trametinib; and a pharmaceutically acceptable excipient.

In embodiment 399, the present invention provides a method of treating melanoma comprising administering to a patient in need thereof a therapeutically effective amount of 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, and dabrafenib.

In embodiment 400, the present invention provides a combination of an MDM2 inhibitor medicament and a MEK inhibitor medicament for treating a solid tumor.

In embodiment 401, the present invention provides a combination of an MDM2 inhibitor medicament and a MEK inhibitor medicament for treating AML.

In embodiment 402, the present invention provides a combination of an MDM2 inhibitor medicament and a BRAF inhibitor medicament for treating a solid tumor.

In embodiment 403, the present invention provides a combination of an MDM2 inhibitor medicament and a BRAF inhibitor medicament for treating AML.

In embodiment 404, the present invention provides a use of an MDM2 inhibitor in combination with a BRAF inhibitor for manufacture of a medicament for the management or treatment of melanoma, liver cancer, AML or colon cancer in a subject.

In embodiment 405, the present invention provides a use of an MDM2 inhibitor in combination with a MEK inhibitor for manufacture of a medicament for the management or treatment of melanoma, liver cancer, AML or colon cancer in a subject.

A further embodiment of the invention includes the use of a combination comprising an MDM2 inhibitor with another therapeutic agent selected from a RAF inhibitor, a MEK inhibitor, a Pi3K α selective inhibitor, an mTOR inhibitor, an AKT inhibitor or an Aurora kinase inhibitor. A further embodiment of the invention includes the use of a combination for treatment of cancer, the combination comprising an MDM2 inhibitor with another therapeutic agent selected from a RAF inhibitor, an MEK inhibitor, a Pi3K a selective inhibitor, an mTOR inhibitor, an AKT inhibitor or an Aurora kinase inhibitor. A further embodiment of the invention includes a method of using a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor, for the treatment of cancer. A further embodiment of the invention includes the use of a combination for treatment of cancer, the combination comprising an MDM2 inhibitor with another therapeutic agent selected from a RAF inhibitor, an MEK inhibitor, a Pi3K a selective inhibitor, an mTOR inhibitor, an AKT inhibitor or an Aurora kinase inhibitor, wherein the use comprises self-administering the combination.

A further embodiment of the invention includes a method of treating cancer comprising prescribing a combination further comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor. A further embodiment of the invention includes a method of treating cancer comprising prescribing to a subject in need thereof, a combination further comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor. A further embodiment of the invention includes a method of treating cancer comprising prescribing a combination containing an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor.

A further embodiment of the invention includes a method of treating cancer using a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor, wherein such method further comprises listing said combination in a formulary and directing a patient in need of such cancer treatment to administer the combination. A further embodiment of the invention includes a method of treating cancer using a combination comprising an MDM2 inhibitor with another therapeutic agent selected from a RAF inhibitor, a MEK inhibitor, a Pi3K a selective inhibitor, an mTOR inhibitor, an AKT inhibitor, wherein such method further comprises listing said combination in a formulary and directing a patient in need of such cancer treatment to self-administer the combination.

A further embodiment of the invention includes a method of treating cancer using a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor, wherein such method further comprises selling said combination for self-administration to a patient in need of such cancer treatment.

A further embodiment of the invention includes a method of using a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor, for the treatment of cancer, wherein such method comprises purchasing said combination for self-administration by a patient in need of such cancer treatment. A further embodiment of the invention includes a method of using a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor, for the treatment of cancer, wherein such method comprises purchasing said combination for administration by a patient in need of such cancer treatment.

A further embodiment of the invention includes a method of treating cancer comprising instructing a subject in need of such treatment to administer a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor.

A further embodiment of the invention includes a process of treating cancer comprising
A] prescribing
B] selling or advertising to sell,
C] purchasing,
D] instructing to self-administer, or
E] administering
of a combination described herein, wherein the combination has been approved by a regulatory agency for the treatment of cancer, to a subject in need of cancer treatment.

A further embodiment of the invention includes a method of supplying a combination comprising an MDM2 inhibitor with another therapeutic agent selected from a RAF inhibitor, a MEK inhibitor, a Pi3K a selective inhibitor, an mTOR inhibitor, an AKT inhibitor or an Aurora kinase inhibitor for treating cancer, said method comprises reimbursing a physician, a formulary, a patient or an insurance company for the sale of said combination.

For clarity, the term "instructing" is meant to include information on a label approved by a regulatory agency, in addition to its commonly understood definition.

BRIEF DESCRIPTION OF THE DRAWINGS

FIG. 1 shows data for the combination of compound 1 and compound A with A204 cells.
FIG. 1a shows data for the combination of compound 1 and compound A with A204 cells.
FIG. 2 shows data for the combination of compound 1 and compound A with A375sq2 cells.
FIG. 2a shows data for the combination of compound 1 and compound A with A375sq2 cells.
FIG. 3 shows data for the combination of compound 2 and compound B with A-427 cells.

FIG. 3a shows data for the combination of compound 2 and compound B with A-427 cells.

FIG. 4 shows data for the combination of compound 1 and compound B with C32 cells.

FIG. 4a shows data for the combination of compound 1 and compound B with C32 cells.

FIG. 5 shows data for the combination of compound 2 and compound B with C32 cells.

FIG. 5a shows data for the combination of compound 2 and compound B with C32 cells.

FIG. 6 shows data for the combination of compound 1 and compound A with G-361 cells.

FIG. 6a shows data for the combination of compound 1 and compound A with G-361 cells.

FIG. 7 shows data for the combination of compound 1 and compound A with LS174T cells.

FIG. 7a shows data for the combination of compound 1 and compound A with LS 174T cells.

FIG. 8 shows data for the combination of compound 1 and compound A with MCF7 cells.

FIG. 8a shows data for the combination of compound 1 and compound A with MCF7 cells.

FIG. 9 shows data for the combination of compound 1 and compound B with NCI-H1666 cells.

FIG. 9a shows data for the combination of compound 1 and compound B with NCI-H1666 cells.

FIG. 10 shows data for the combination of compound 2 and compound B with NCI-H1666 cells.

FIG. 10a shows data for the combination of compound 2 and compound B with NCI-H1666 cells.

FIG. 11 shows data for the combination of compound 1 and compound A with RKO cells.

FIG. 11a shows data for the combination of compound 1 and compound A with RKO cells.

FIG. 12 shows data for the combination of compound 2 and compound B with RKO cells.

FIG. 12a shows data for the combination of compound 2 and compound B with RKO cells.

FIG. 13 shows data for the combination of compound 1 and compound B with RT4 cells.

FIG. 13a shows data for the combination of compound 1 and compound B with RT4 cells.

FIG. 14 shows the data for the combination of compound 2 and compound B with RT4 cells.

FIG. 14a shows data for the combination of compound 2 and compound B with RT4 cells.

FIG. 15 shows data for the combination of compound 1 and compound B with SH-4 cells.

FIG. 15a shows data for the combination of compound 1 and compound B with SH-4 cells.

FIG. 16 shows data for the combination of compound 2 and compound B with SH-4 cells.

FIG. 16a shows data for the combination of compound 2 and compound B with SH-4 cells.

FIG. 17 shows data for the combination of compound 1 and compound B with SK-HEP-1 cells.

FIG. 17a shows data for the combination of compound 1 and compound B with SK-HEP-1 cells.

FIG. 18 shows data for the combination of compound 2 and compound B with SK-HEP-1 cells.

FIG. 18a shows data for the combination of compound 2 and compound B with SK-HEP-1 cells.

FIG. 19 shows data for the combination of compound 3 and compound A with A204 cells.

FIG. 19a shows data for the combination of compound 3 and compound A with A204 cells.

FIG. 20 shows data for the combination of compound 3 and compound A with A375sq2 cells.

FIG. 20a shows data for the combination of compound 3 and compound A with A375sq2 cells.

FIG. 21 shows data for the combination of compound 3 and compound B with A-427 cells.

FIG. 21a shows data for the combination of compound 3 and compound B with A-427 cells.

FIG. 22 shows data for the combination of compound 4 and compound B with A-427 cells.

FIG. 22a shows data for the combination of compound 4 and compound B with A-427 cells.

FIG. 23 shows data for the combination of compound 3 and compound B with C32 cells.

FIG. 23a shows data for the combination of compound 3 and compound B with C32 cells.

FIG. 24 shows data for the combination of compound 4 and compound B with C32 cells.

FIG. 24a shows data for the combination of compound 4 and compound B with C32 cells.

FIG. 25 shows data for the combination of compound 3 and compound A with G-361 cells.

FIG. 25a shows data for the combination of compound 3 and compound A with G-361 cells.

FIG. 26 shows data for the combination of compound 3 and compound A with LS 174T cells.

FIG. 26a shows data for the combination of compound 3 and compound A with LS 174T cells.

FIG. 27 shows data for the combination of compound 3 and compound A with MCF7 cells.

FIG. 27a shows data for the combination of compound 3 and compound A with MCF7 cells.

FIG. 28 shows data for the combination of compound 3 and compound B with NCI-H1666 cells.

FIG. 28a shows data for the combination of compound 3 and compound B with NCI-H1666 cells.

FIG. 29 shows data for the combination of compound 4 and compound B with NCI-H1666 cells.

FIG. 29a shows data for the combination of compound 4 and compound B with NCI-H1666 cells.

FIG. 30 shows data for the combination of compound 3 and compound A with RKO cells.

FIG. 30a shows data for the combination of compound 3 and compound A with RKO cells.

FIG. 31 shows data for the combination of compound 4 and compound B with RKO cells.

FIG. 31a shows data for the combination of compound 4 and compound B with RKO cells.

FIG. 32 shows data for the combination of compound 3 and compound B with RT4 cells.

FIG. 32a shows data for the combination of compound 3 and compound B with RT4 cells.

FIG. 33 shows data for the combination of compound 4 and compound B with RT4 cells.

FIG. 33a shows data for the combination of compound 4 and compound B with RT4 cells.

FIG. 34 shows data for the combination of compound 3 and compound B with SH-4 cells.

FIG. 34a shows data for the combination of compound 3 and compound B with SH-4 cells.

FIG. 35 shows data for the combination of compound 4 and compound B with SH-4 cells.

FIG. 35a shows data for the combination of compound 4 and compound B with SH-4 cells.

FIG. 36 shows data for the combination of compound 3 and compound B with SK-HEP-1 cells.

FIG. 36a shows data for the combination of compound 3 and compound B with SK-HEP-1 cells.
FIG. 37 shows data for the combination of compound 4 and compound B with SK-HEP-1 cells.
FIG. 37a shows data for the combination of compound 4 and compound B with SK-HEP-1 cells.
FIG. 38 shows data for the combination of compound 5 and compound A with A204 cells.
FIG. 38a shows data for the combination of compound 5 and compound A with A204 cells.
FIG. 39 shows data for the combination of compound 5 and compound A with A375sq2 cells.
FIG. 39a shows data for the combination of compound 5 and compound A with A375sq2 cells.
FIG. 40 shows data for the combination of compound 5 and compound B with CAL-51 cells.
FIG. 40a shows data for the combination of compound 5 and compound B with CAL-51 cells.
FIG. 41 shows data for the combination of compound 5 and compound A with G-361 cells.
FIG. 41a shows data for the combination of compound 5 and compound A with G-361 cells.
FIG. 42 shows data for the combination of compound 5 and compound B with HT-1197 cells.
FIG. 42a shows data for the combination of compound 5 and compound B with HT-1197 cells.
FIG. 43 shows data for the combination of compound 5 and compound A with LS 174T cells.
FIG. 43a shows data for the combination of compound 5 and compound A with LS174T cells.
FIG. 44 shows data for the combination of compound 5 and compound A with MCF7 cells.
FIG. 44a shows data for the combination of compound 5 and compound A with MCF7 cells.
FIG. 45 shows data for the combination of compound 5 and compound B with NCI-H460 cells.
FIG. 45a shows data for the combination of compound 5 and compound B with NCI-H460 cells.
FIG. 46 shows data for the combination of compound 5 and compound A with RKO cells.
FIG. 46a shows data for the combination of compound 5 and compound A with RKO cells.
FIG. 47 shows data for the combination of compound 6 and compound B with A204 cells.
FIG. 47a shows data for the combination of compound 6 and compound B with A204 cells.
FIG. 48 shows data for the combination of compound 6 and compound B with A2780 cells.
FIG. 48a shows data for the combination of compound 6 and compound B with A2780 cells.
FIG. 49 shows data for the combination of compound 6 and compound B with C32 cells.
FIG. 49a shows data for the combination of compound 6 and compound B with C32 cells.
FIG. 50 shows data for the combination of compound 6 and compound B with G-401 cells.
FIG. 50a shows data for the combination of compound 6 and compound B with G-401 cells.
FIG. 51 shows data for the combination of compound 6 and compound B with SK-HEP-1 cells.
FIG. 51a shows data for the combination of compound 6 and compound B with SK-HEP-1 cells.
FIG. 52 shows data for the combination of compound 8 and compound B with BV-173 cells.
FIG. 52a shows data for the combination of compound 8 and compound B with BV-173 cells.
FIG. 53 shows data for the combination of compound 8 and compound B with CML-T1 cells.
FIG. 53a shows data for the combination of compound 8 and compound B with CML-T1 cells.
FIG. 54 shows data for the combination of compound 9 and compound B with KNS-81-FD cells.
FIG. 54a shows data for the combination of compound 9 and compound B with KNS-81-FD cells.
FIG. 55 shows data for the combination of compound 9 and compound B with SW48 cells.
FIG. 55a shows data for the combination of compound 9 and compound B with SW48 cells.
FIG. 56 shows data for the combination of compound 10 and compound B with MDA-MB-175 VII cells.
FIG. 56a shows data for the combination of compound 10 and compound B with MDA-MB-175 VII cells.
FIG. 57 shows data for the combination of compound 10 and compound B with UACC-812 cells.
FIG. 57a shows data for the combination of compound 10 and compound B UACC-812 cells.
FIG. 58 shows data for the combination of compound 11 and compound A with HCT-116 cells.
FIG. 58a shows data for the combination of compound 11 and compound A HCT-116 cells.
FIG. 59 shows data for the combination of compound 13 and compound B with GDM-1 cells.
FIG. 59a shows data for the combination of compound 13 and compound B with GDM-1 cells.
FIG. 60 shows data for the combination of compound 13 and compound B with ML-2 cells.
FIG. 60a shows data for the combination of compound 13 and compound B ML-2 cells.
FIG. 61 shows data for the combination of compound 13 and compound B with MOLM-13 cells.
FIG. 61a shows data for the combination of compound 13 and compound B with MOLM-13 cells.
FIG. 62 shows data for the combination of compound 13 and compound B with OCI-AML3 cells.
FIG. 62a shows data for the combination of compound 13 and compound B with OCI-AML3 cells.
FIG. 63 shows data for the combination of compound 12 and compound B with GDM-1 cells.
FIG. 63a shows data for the combination of compound 12 and compound B with GDM-1 cells.
FIG. 64 shows data for the combination of compound 12 and compound B with ML-2 cells.
FIG. 64a shows data for the combination of compound 12 and compound B with ML-2 cells.
FIG. 65 shows data for the combination of compound 12 and compound B with MOLM-13 cells.
FIG. 65a shows data for the combination of compound 12 and compound B with MOLM-13 cells.
FIG. 66 shows data for the combination of compound 12 and compound B with OCI-AML3 cells.
FIG. 66a shows data for the combination of compound 12 and compound B with OCI-AML3 cells.
FIG. 67 shows data for combinations of AMG 232 and various MAP kinase pathway inhibitors.
FIG. 68 shows data for combinations of AM-7209 and various MAP kinase pathway inhibitors.
FIG. 69 shows data for combinations of RG7112 and various MAP kinase pathway inhibitors.
FIG. 70 shows data for combinations of AMG 232 and various PI3 kinase pathway inhibitors.
FIG. 71 shows data for combinations of AM-7209 and various PI3 kinase pathway inhibitors.

Figure 72:
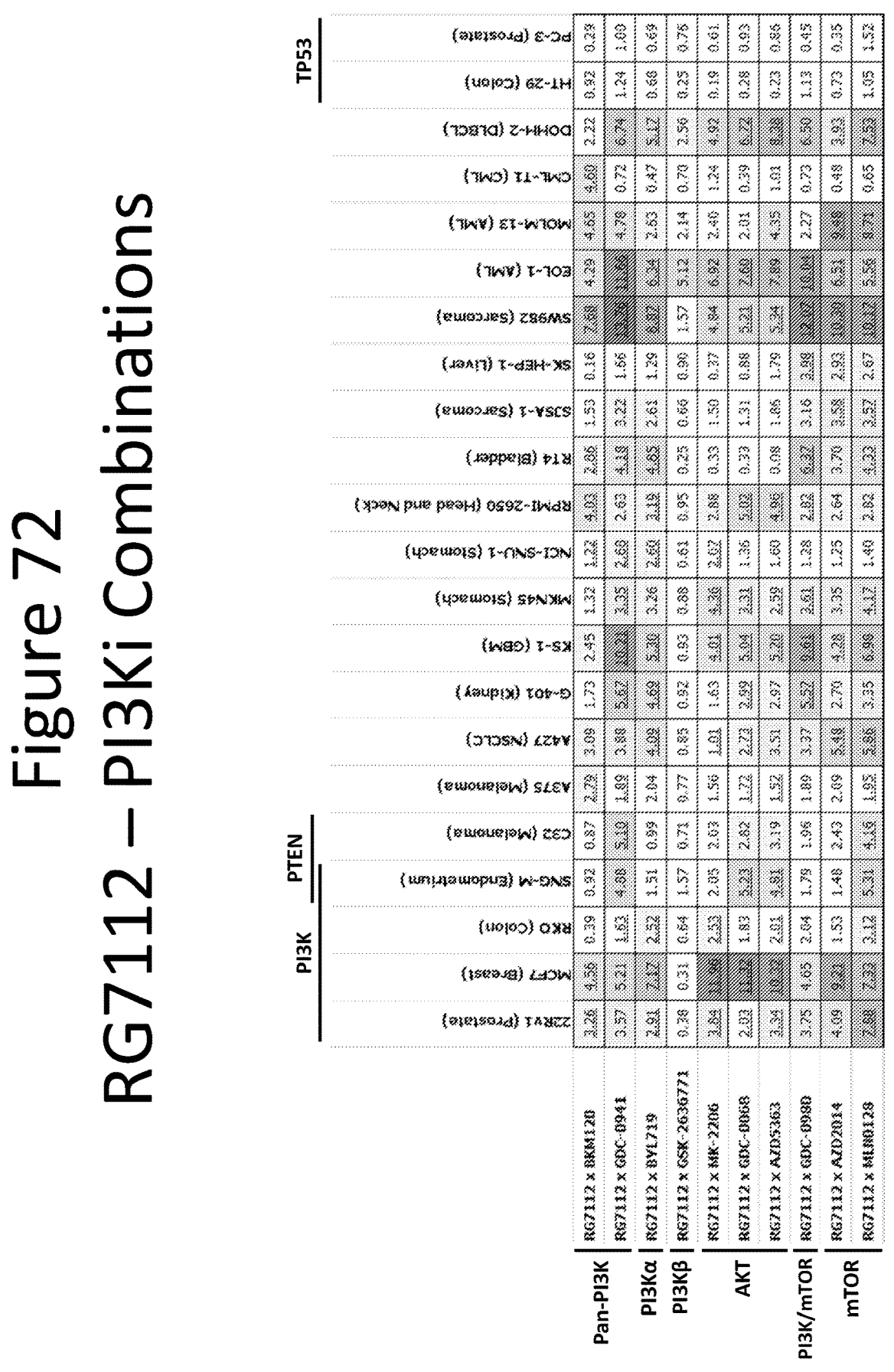

FIG. 72 shows data for combinations of RG7112 and various PI3 kinase pathway inhibitors.

FIG. 73 shows data for combinations of AMG 232 and various compounds active in the intrinsic apoptosis pathway.

FIG. 74 shows data for combinations of AM-7209 and various compounds active in the intrinsic apoptosis pathway.

Figure 75:
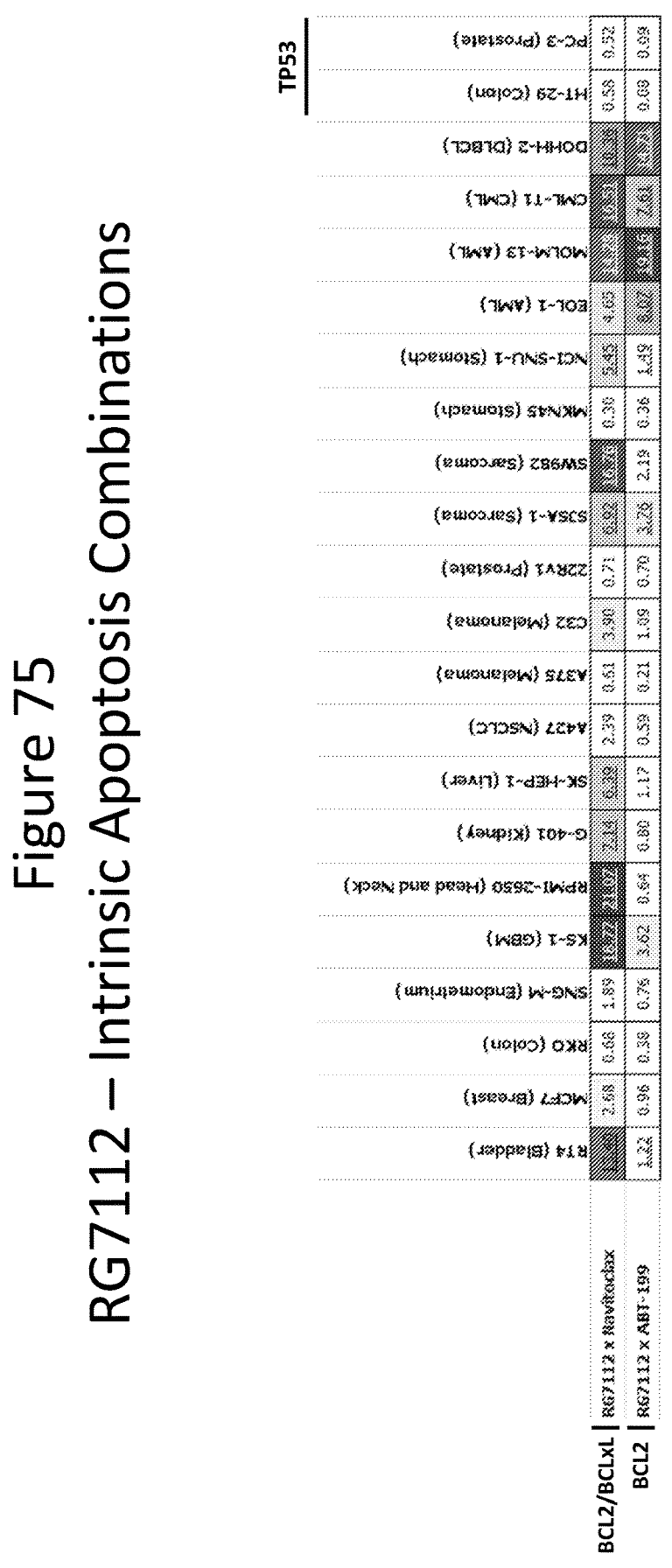

FIG. 75 shows data for combinations of RG7112 and various compounds active in the intrinsic apoptosis pathway.

FIG. 76 shows data for combinations of AMG 232 and various chemotherapeutic compounds.

FIG. 77 shows data for combinations of AM-7209 and various chemotherapeutic compounds.

FIG. 78 shows data for combinations of RG7112 and various chemotherapeutic compounds.

FIG. 79 shows data for combinations of AMG 232 and various chemotherapeutic compounds.

FIG. 80 shows data for combinations of AM-7209 and various chemotherapeutic compounds.

FIG. 81 shows data for combinations of RG7112 and various chemotherapeutic compounds.

Figure 83:
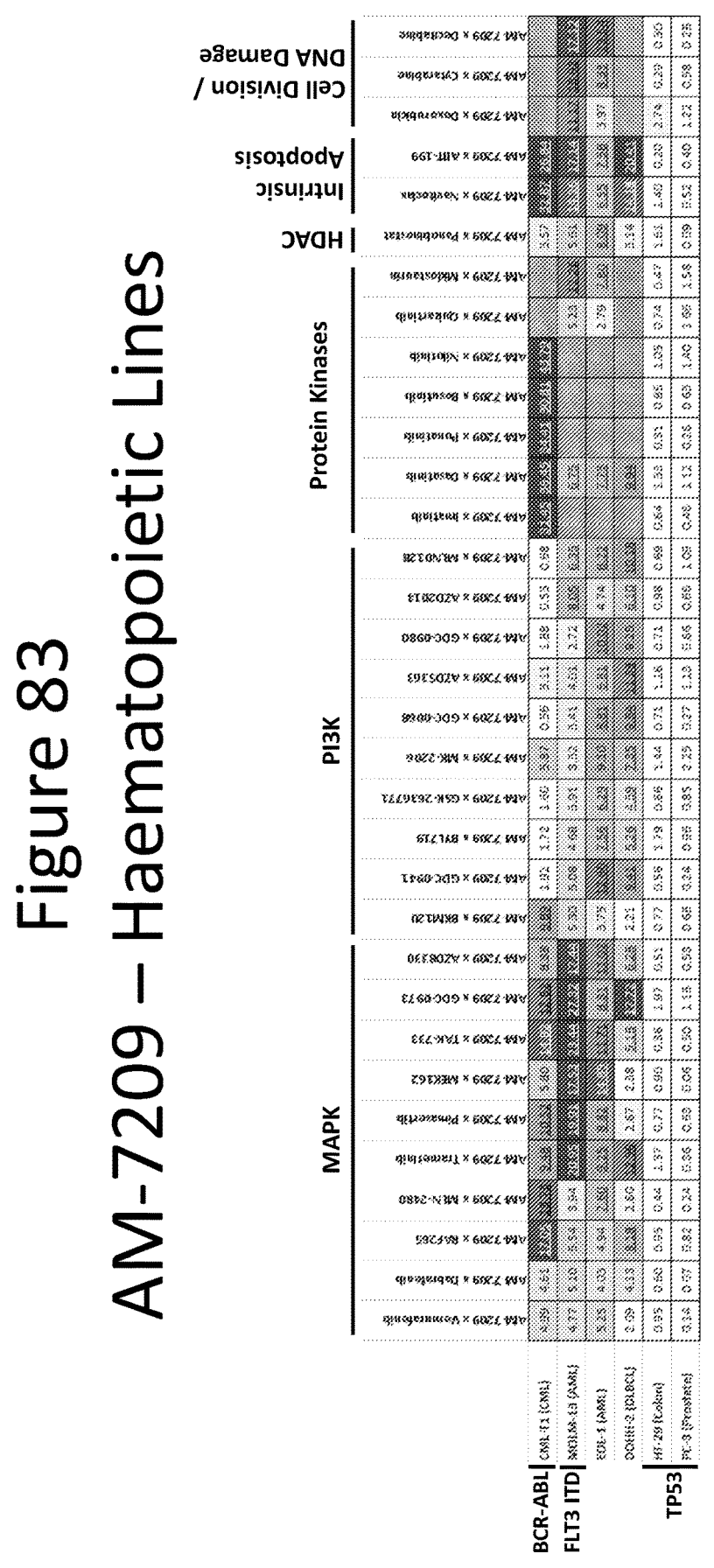

FIG. 83 shows data for combinations of AM-7209 and various compounds in hematopoietic cell lines.

Figure 84:
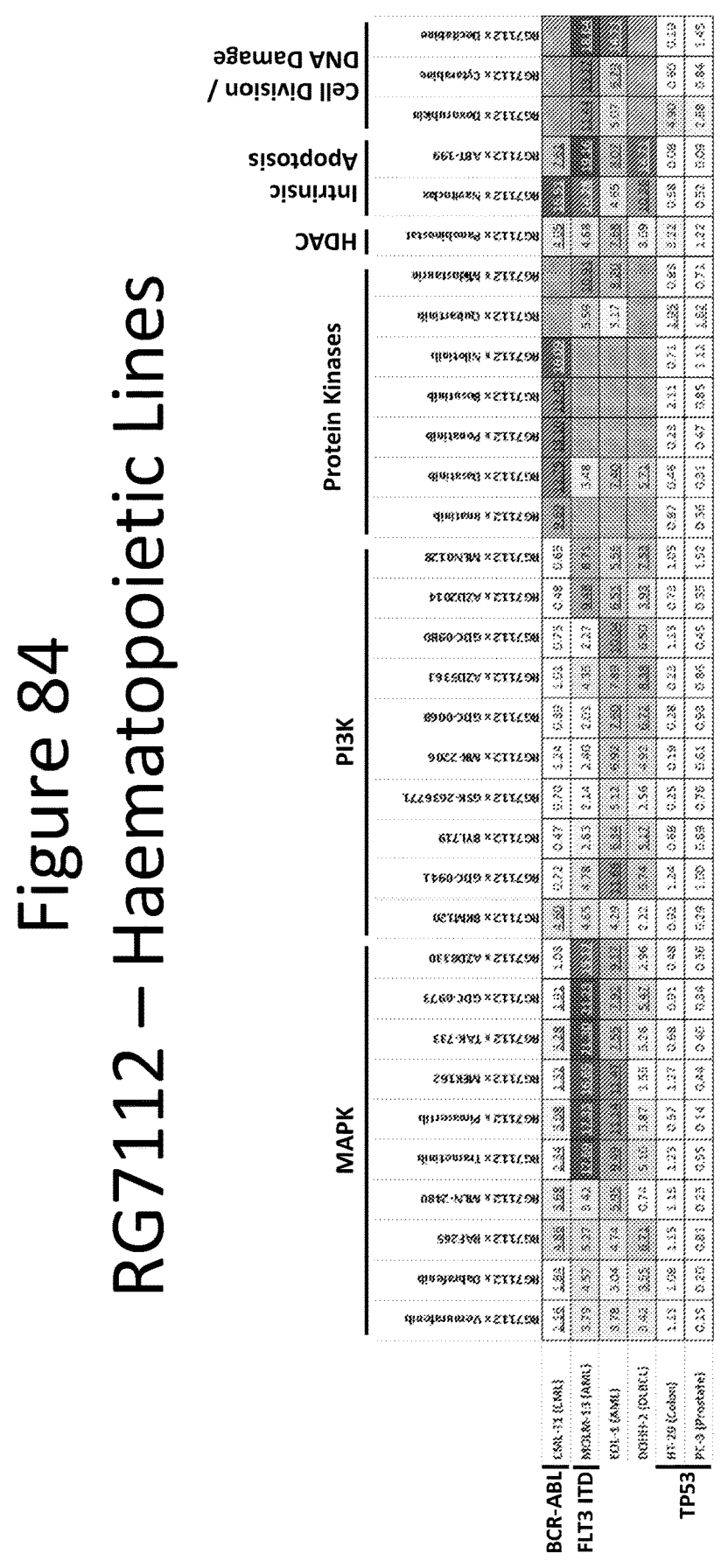

FIG. 84 shows data for combinations of RG7112 and various compounds in hematopoietic cell lines.

DETAILED DESCRIPTION OF THE INVENTION

Figure 82:
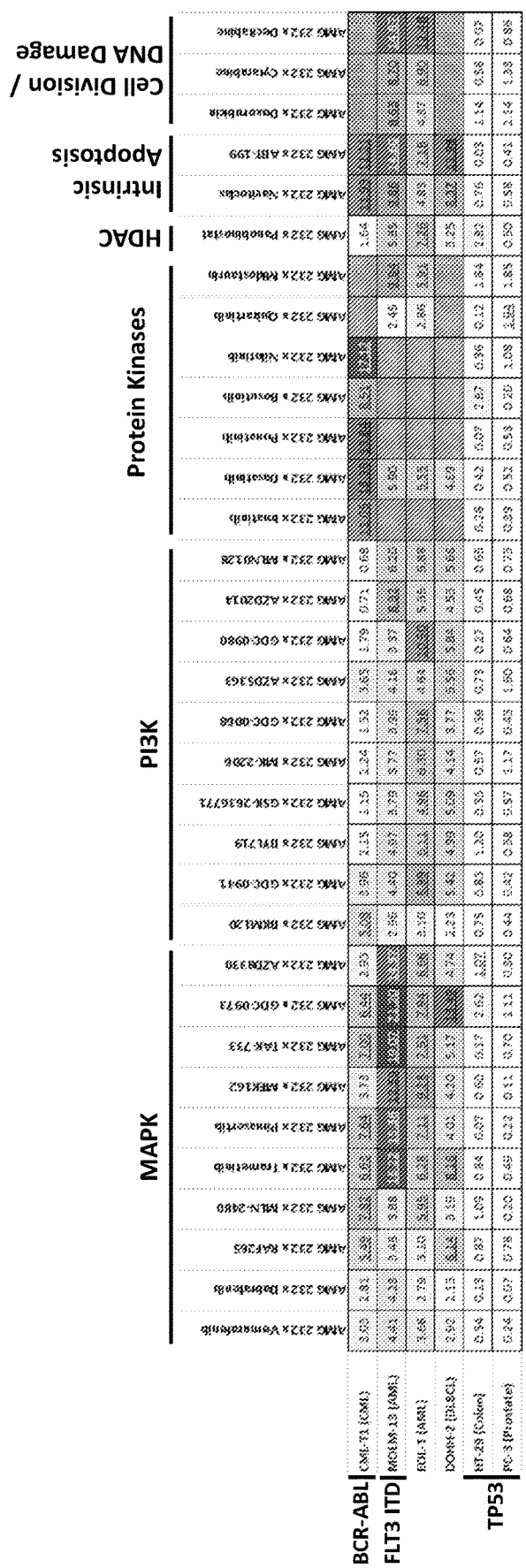
FIG. 82 shows data for combinations of AMG 232 and various compounds in hematopoietic cell lines.
Figure 85:
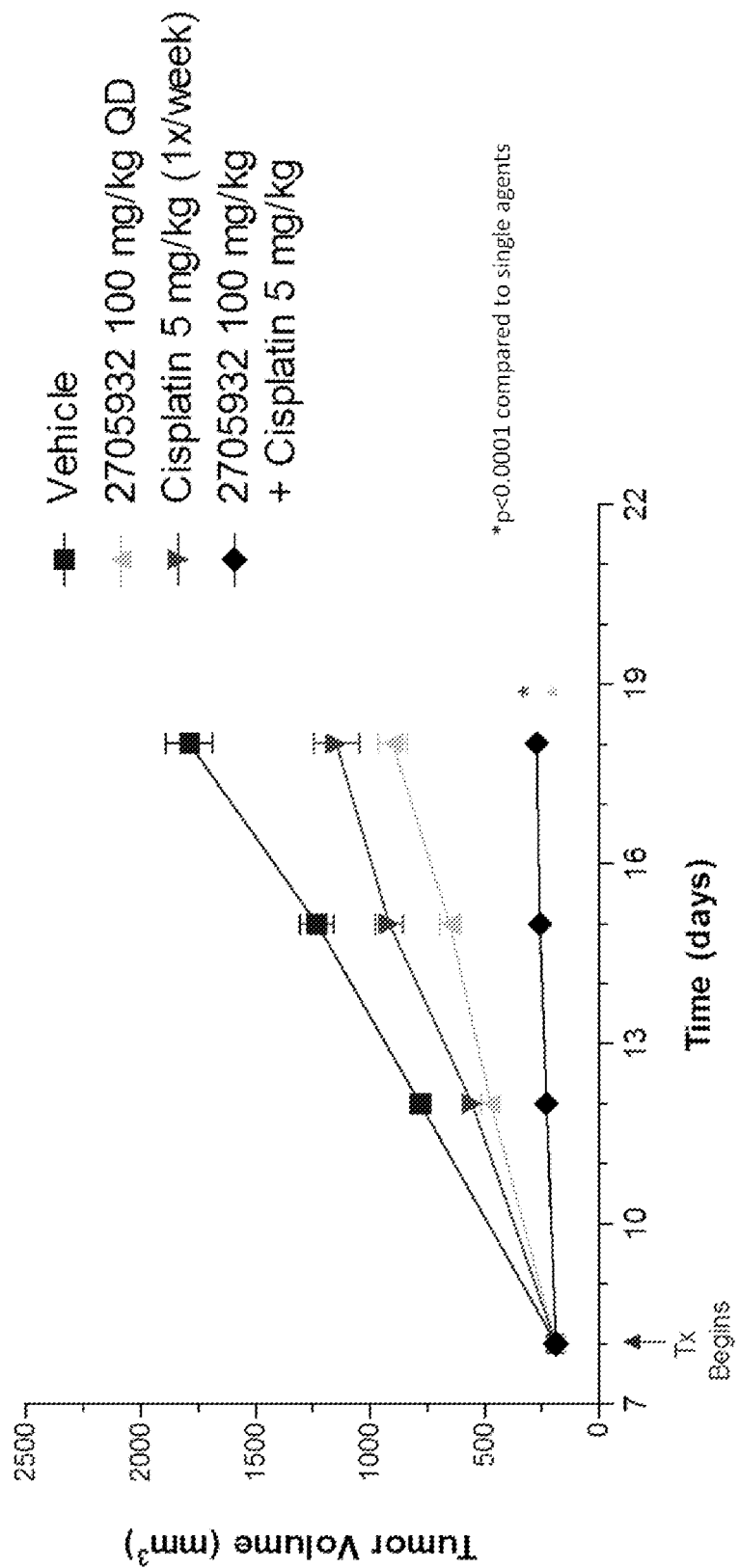
FIG. 85 shows tumor xenograft data for the combination of AMG 232 and cisplatin in an H460 tumor.
Figure 86:
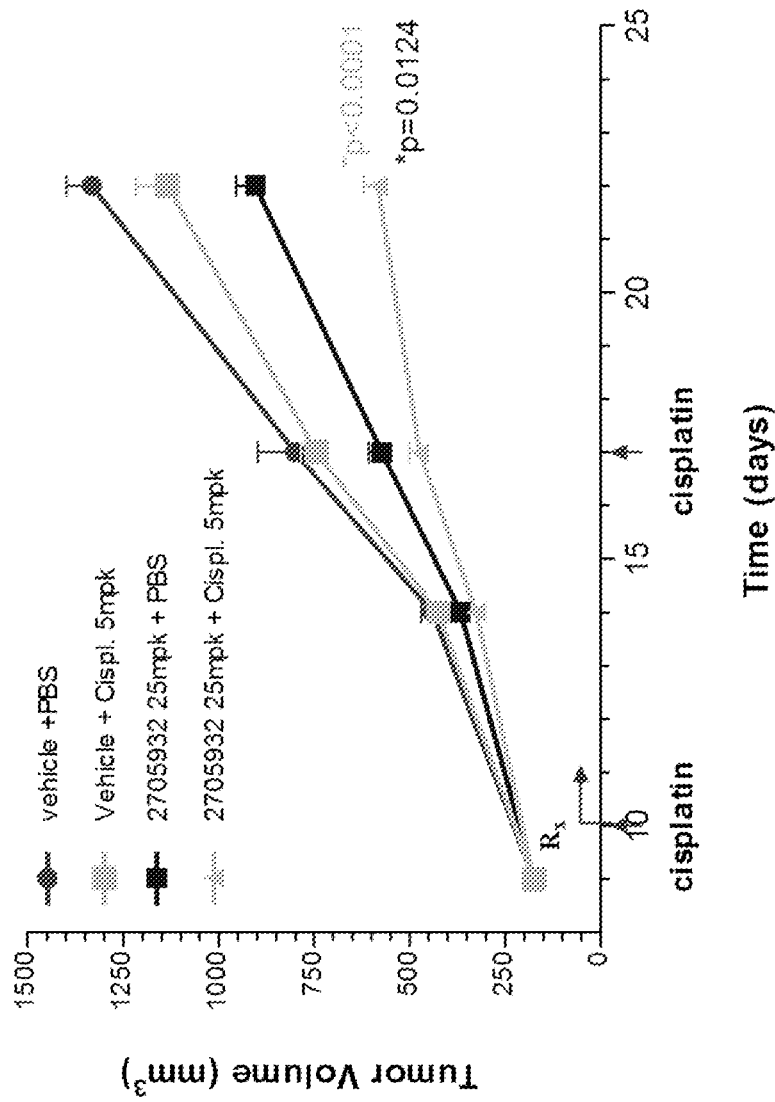
FIG. 86 shows tumor xenograft data for the combination of AMG 232 and cisplatin in an HCT116 tumor.
Figure 87:
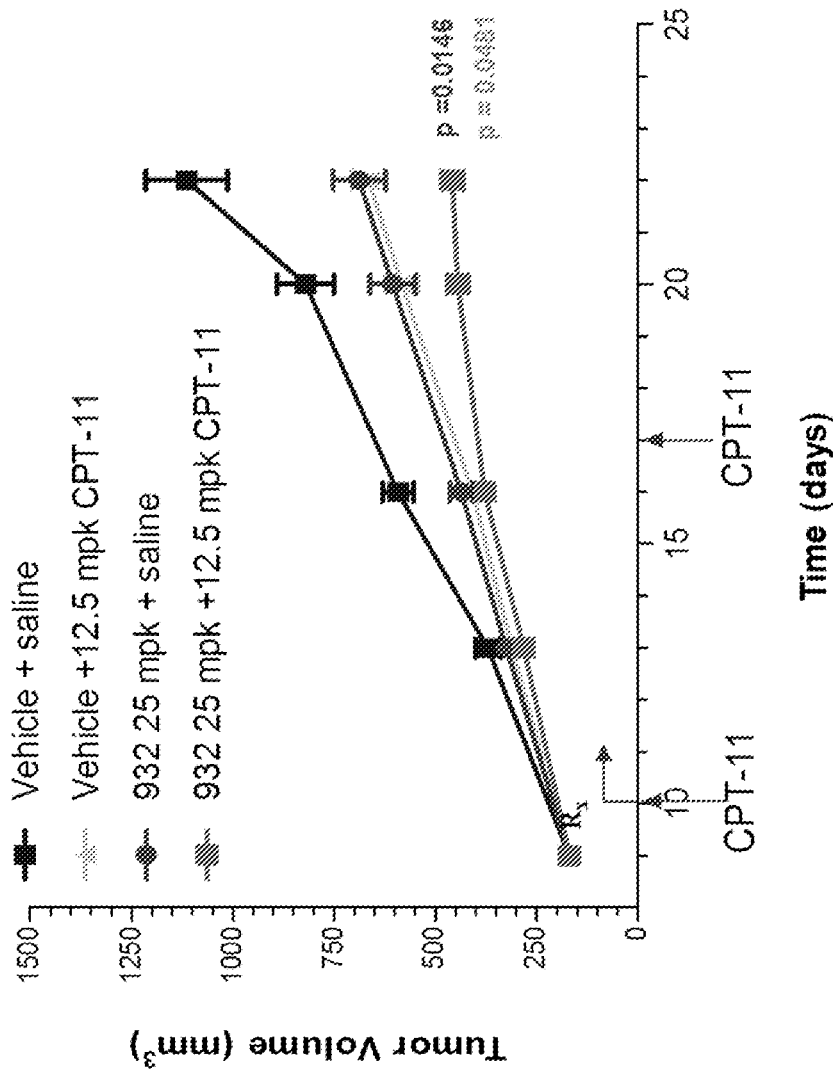
FIG. 87 shows tumor xenograft data for the combination of AMG 232 and CPT-11 (irinotecan) in an HCT116 tumor.
Figure 88:
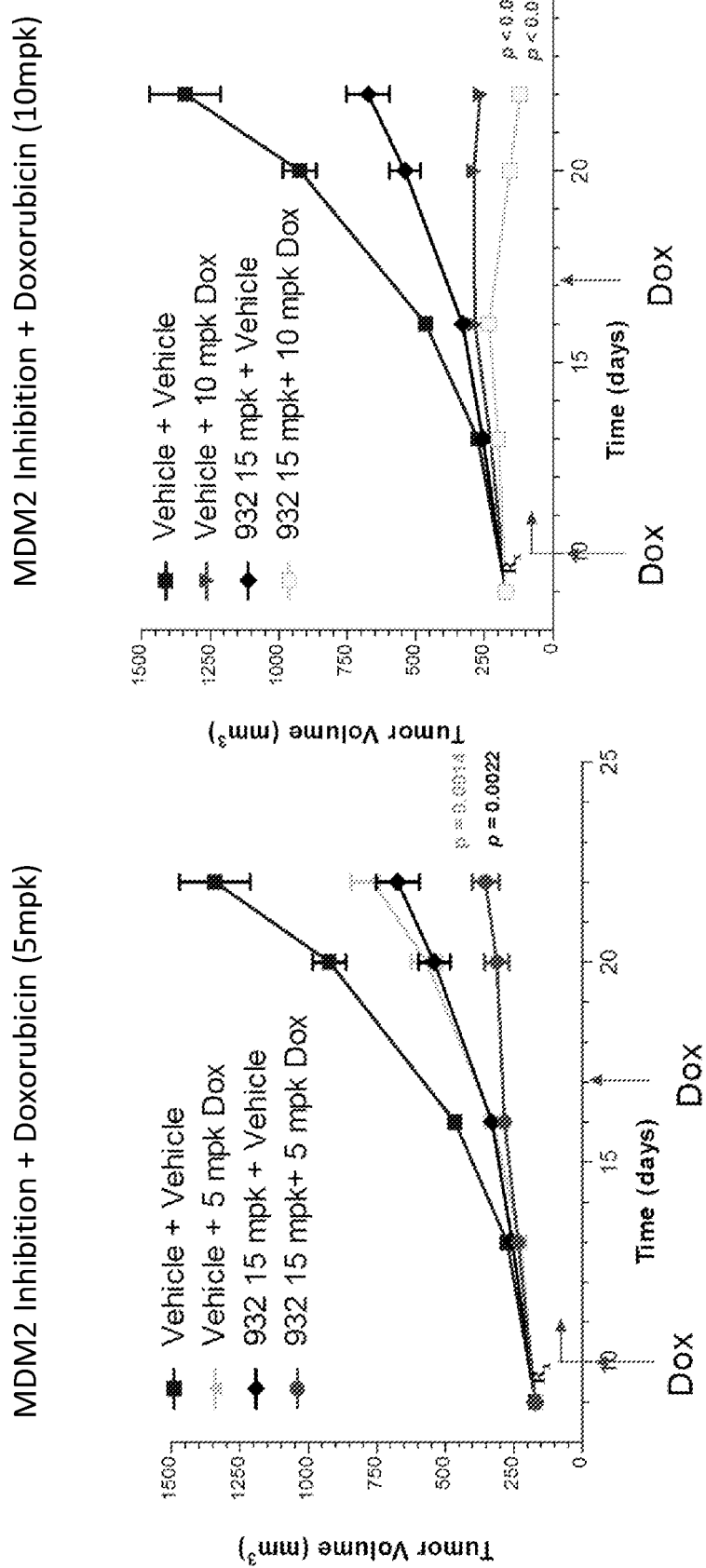
FIG. 88 shows tumor xenograft data for the combination of AMG 232 and doxorubicin in a SJSA-1 tumor.

The present invention provides combination therapy that includes an MDM2 inhibitor and one or more additional pharmaceutically active agents, particularly for the treatment of cancers. The invention also relates to pharmaceutical compositions that contain an MDM2 inhibitor and one or more additional pharmaceutically active agents for the treatment of cancers.

The term "comprising" is meant to be open ended, including the indicated component but not excluding other elements.

The term "therapeutically effective amount" means an amount of a compound, or combination of compounds, that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound, or a salt of the compound, or a formulation containing the compound, or a particular excipient, are suitable for administration to a patient.

The terms "treating", "treat" or "treatment" and the like include preventative (e.g., prophylactic) and palliative treatment. The term"treating" and the like, in accordance with the present invention, means reducing or eliminating cancers cells in a patient.

The term "excipient" means any pharmaceutically acceptable additive, carrier, diluent, adjuvant, or other ingredient, other than the active pharmaceutical ingredient (API), which is typically included for formulation and/or administration to a patient.

The phrase "compound(s) of the present invention" includes MDM2 inhibitors and/or the one or more additional pharmaceutically active agents according to the context of the use.

An "MDM2 inhibitor" is defined as a compound with a molecular weight less than about 1000 that binds MDM2 as shown with in vitro testing or by other means.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compounds can be varied over time.

If the patient is to receive or is receiving multiple pharmaceutically active compounds, the compounds can be administered simultaneously or sequentially. For example, in the case of tablets, the active compounds may be found in one tablet or in separate tablets, which can be administered at once or sequentially in any order. In addition, it should be recognized that the compositions may be different forms. For example, one or more compounds may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of one or more compounds, or pharmaceutically acceptable salts of any of the compounds.

The compounds of the present invention can be used to treat tumors. The methods of treating a tumor comprise administering to a patient in need thereof a therapeutically effective amount of one or more compounds of the present invention, or pharmaceutically acceptable salts of any of the compounds.

The invention also concerns the use of the compounds in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with the compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myelogenous leukemia (AML).

In a particular embodiment of the invention that relates to the treatment of cancers, the cancer is identified as p53 wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p537^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. In still another aspect, the patient has a cancer that is $p53^{WT}$ and exhibits MDM2 amplification. The taking of cancer cells for analyses is well known to those skilled in the art. The term "$p53^{WT}$" means a protein encoded by genomic DNA sequence no. NC_000017 version 9 (7512445 . . . 7531642)(GenBank); a protein encoded by cDNA sequence no. NM_000546 (GenBank); or a protein having the GenBank sequence no. NP_000537.3. The term "CDNK2A mutant" means a CDNK2A protein that in not wild type. The term "CDKN2A wild type" means a protein encoded by genomic DNA sequence no. 9:21957751-21984490 (Ensembl ID); a protein encoded by cDNA sequence no. NM_000077 (GenBank) or NM_058195 9 GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention may be designated as follows in the application and figures.

| | |
|---|---|
| Compound A | AMG 232 |
| Compound B | AMG 2653149 |
| Compound C | AM-7209 |
| Compound 1 | AMG 2112819 |
| Compound 2 | dabrafenib |
| Compound 3 | PD0325901* |
| Compound 4 | trametinib |
| Compound 5 | AMG 511 |
| Compound 6 | panobinostat |
| Compound 7 | not used |
| Compound 8 | imatinib |
| Compound 9 | erlotinib |
| Compound 10 | lapatinib |
| Compound 11 | cisplatin |
| Compound 12 | cytarabine |
| Compound 13 | AMG 900 |

*AMG 1009089 (also called herein 1009089 or Compound 3) is PD0325901.

The MDM2 inhibitors of the present invention include those disclosed in published PCT application WO2011/153,509. A particular compound disclosed in the application is AMG 232 (Example 362) having the structure and name shown below.

2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid

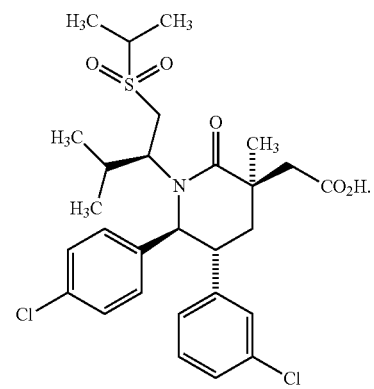 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

A particular synthesis of AMG 232 is set forth in U.S. provisional patent application No. 61/833,196, filed Jun. 10, 2013.

Procedures to Make Certain Intermediates and Starting Materials
Method for Making

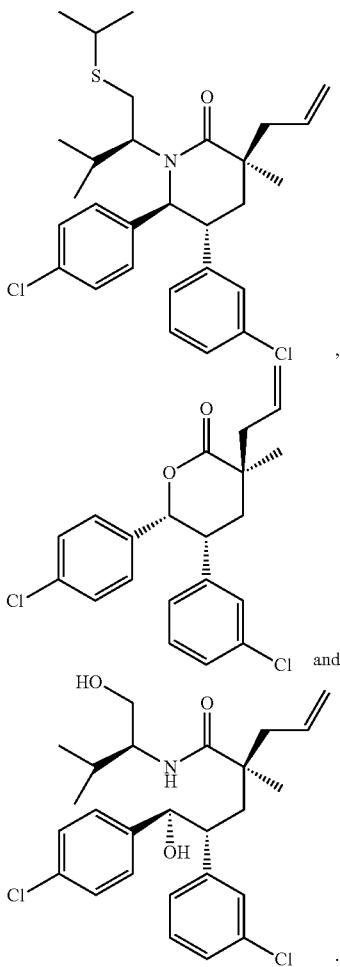

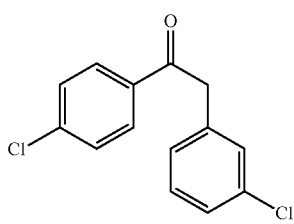 [SMILES: O=C(Cc1cccc(Cl)c1)c1ccc(Cl)cc1]

Step A.
2-(3-Chlorophenyl)-1-(4-chlorophenyl)ethanone

Sodium bis(trimethylsilyl)amide (1 M in tetrahydrofuran, 117 mL) was slowly added to a −78° C. solution of 2-(3-chlorophenyl) acetic acid (10 g, 58.6 mmol) in tetrahydrofuran (58 mL) over 1 hour. After stirring at −78° C. for 40 minutes, a solution of methyl 4-chlorobenzoate (10 g, 58.6 mmol) in tetrahydrofuran (35 mL) was added over a period of 10 minutes. The reaction was stirred at −78° C. for 3 hours then allowed to warm to 25° C. After two hours at 25° C., the reaction was quenched with saturated aqueous ammonium chloride solution, and most of the tetrahydrofuran was removed under reduced pressure. The residue was extracted with ethyl acetate (2×100 mL). The combined organic layers were washed with saturated sodium chloride solution, dried over sodium sulfate, filtered and the filtrate was concentrated. The product was recrystallized from ether/pentane to provide the title compound as a white solid. $^1$H NMR (500 MHz, DMSO-$d_6$, δ ppm): 8.05 (m, 2H), 7.62 (m, 2H), 7.33 (m, 3H), 7.21 (br d, J=7.3 Hz, 1H), 4.45 (s, 2H). MS (ESI)=265.1 [M+H]$^+$.

Step B: Methyl 4-(3-chlorophenyl)-5-(4-chlorophenyl)-2-methyl-5-oxopentanoate

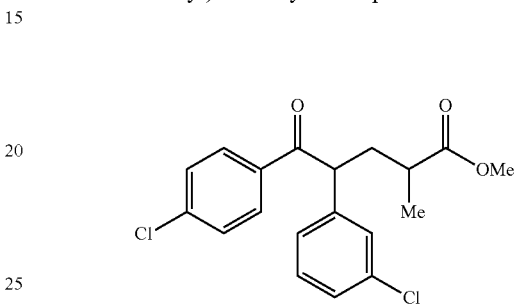

Methyl methacrylate (12.65 mL, 119 mmol) was added to a solution of 2-(3-chlorophenyl)-1-(4-chlorophenyl)ethanone (30 g, 113 mmol) in tetrahydrofuran (283 mL). Potassium tert-butoxide (1.27 g, 11.3 mmol) was then added and the reaction was stirred at room temperature for 2 days. The solvent was removed under a vacuum and replaced with 300 mL of ethyl acetate. The organic phase was washed with brine (50 mL), water (3×50 mL), and brine (50 mL). The organic phase was dried over magnesium sulfate, filtered and concentrated under a vacuum to afford methyl 4-(3-chlorophenyl)-5-(4-chlorophenyl)-2-methyl-5-oxopentanoate as an approximately 1:1 mixture of diastereomers. $^1$H NMR (400 MHz, CDCl$_3$, δ ppm): 7.87 (m, 2H), 7.38 (m, 2H), 7.27-7.14 (series of m, 4H), 4.61 (m, 1H), 3.69 (s, 1.5H), 3.60 (s, 1.5H), 2.45 (m, 1H), 2.34 (m, 1H), 2.10 (ddd, J=13.9, 9.4, 5.5 Hz, 0.5H), 1.96 (ddd, J=13.7, 9.0, 4.3 Hz, 0.5H), 1.22 (d, J=7.0 Hz, 1.5H), 1.16 (d, J=7.0, 1.5H). MS (ESI)=387.0 [M+23]$^+$.

Step C: (3S, 5R,6R)-5-(3-Chlorophenyl)-6-(4-chlorophenyl)-3-methyltetrahydro-2H-pyran-2-one and (3R, 5R,6R)-5-(3-chlorophenyl)-6-(4-chlorophenyl)-3-methyltetrahydro-2H-pyran-2-one

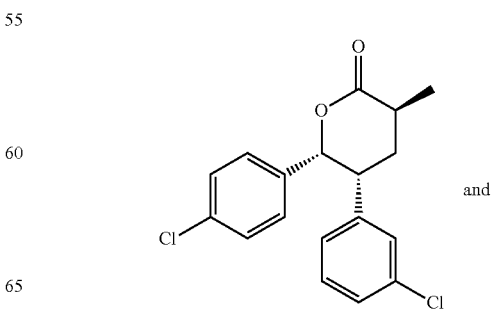

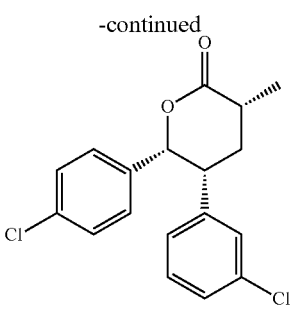

Methyl 4-(3-chlorophenyl)-5-(4-chlorophenyl)-2-methyl-5-oxopentanoate (40 g, 104.0 mmol) was dissolved in 200 mL of anhydrous toluene and concentrated under a vacuum. The residue was placed under high vacuum for 2 hours before use. The compound was split into 2×20 g batches and processed as follows: methyl 4-(3-chlorophenyl)-5-(4-chlorophenyl)-2-methyl-5-oxopentanoate (20 g, 52.0 mmol) in anhydrous 2-propanol (104 mL) was treated with potassium tert-butoxide (2.33 g, 20.8 mmol) in a 250 mL glass hydrogenation vessel. RuCl$_2$(S-xylbinap)(S-DAIPEN) (0.191 g, 0.156 mmol, Strem Chemicals, Inc., Newburyport, Mass.) in 3.8 mL of toluene was added. After 1.5 hours, the vessel was pressurized to 50 psi (344.7 kPa) and purged with hydrogen five times and allowed to stir at room temperature. The reaction was recharged with additional hydrogen as needed. After 3 days, the reactions were combined and partitioned between 50% saturated ammonium chloride solution and ethyl acetate. The aqueous layer was extracted with ethyl acetate. The combined organic phases were washed with brine, dried over magnesium sulfate, filtered, and concentrated.

The crude product (predominantly, (4R,5R)-isopropyl 4-(3-chlorophenyl)-5-(4-chlorophenyl)-5-hydroxy-2-methylpentanoate) was dissolved in tetrahydrofuran (450 mL) and methanol (150 mL). Lithium hydroxide (1.4 M, 149 mL, 208 mmol) was added, and the solution was stirred at room temperature for 24 hours. The mixture was concentrated under a vacuum and the residue was redissolved in ethyl acetate. Aqueous 1N hydrochloric acid was added with stirring until the aqueous layer had a pH of about 1. The layers were separated and the organic phase was washed with brine, dried over magnesium sulfate, filtered and concentrated. The material was dissolved in 200 mL of anhydrous toluene and treated with pyridinium p-toluenesulfonate (PPTS, 0.784 g, 3.12 mmol). The reaction was heated to reflux under Dean-Stark conditions until the seco-acid was consumed (about 2 hours). The reaction was cooled to room temperature and washed with saturated sodium bicarbonate (50 mL) and brine (50 mL). The solution was dried over sodium sulfate, filtered and concentrated. The crude material was purified by flash chromatography on silica gel (120 g column; eluting with 100% dichloromethane). The title compounds were obtained as a white solid with an approximate 94:6 enantiomeric ratio and a 7:3 mixture of methyl diastereomers. $^1$H NMR (400 MHz, CDCl$_3$, δ ppm): 7.22-6.98 (series of m, 5H), 6.91 (dt, J=7.4, 1.2 Hz, 0.3H), 6.81 (m, 2H), 6.73 (dt, J=7.6, 1.4 Hz, 0.7H), 5.76 (d, J=4.1 Hz, 0.3H), 5.69 (d, J=4.7 Hz, 0.7H), 3.67 (dt, J=6.6, 4.3 Hz, 0.3H), 3.55 (td, J=7.8, 4.7 Hz, 0.7H), 2.96 (d of quintets, J=13.5, 6.7 Hz, 0.7H), 2.81 (m, 0.3H), 2.56 (dt, J=14.3, 8.0 Hz, 0.7H), 2.32 (dt, J=13.69, 7.0 Hz, 0.3H), 2.06 (ddd, J=13.7, 8.4, 4.1, 0.3H), 1.85 (ddd, J=14.1, 12.5, 7.4, 0.7H), 1.42 (d, J=7.0 Hz, 0.9H), 1.41 (d, J=6.7 Hz, 2.1H). MS (ESI)=357.0 [M+23]$^+$. [α]$_D$ (22° C., c=1.0, CH$_2$Cl$_2$)=−31.9°; m.p. 98-99° C.

Step D. (3S,5R,6R)-3-Allyl-5-(3-chlorophenyl)-6-(4-chlorophenyl)-3-methyltetrahydro-2H-pyran-2-one

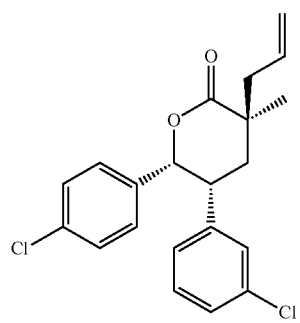 [SMILES: C=CC[C@@]1(C)C[C@H](c2cccc(Cl)c2)[C@H](c2ccc(Cl)cc2)OC1=O]

A solution of (3S, 5R,6R)-5-(3-chlorophenyl)-6-(4-chlorophenyl)-3-methyltetrahydro-2H-pyran-2-one and (3R,5S,6S)-5-(3-chlorophenyl)-6-(4-chlorophenyl)-3-methyltetrahydro-2H-pyran-2-one (4.5 g, 13.4 mmol) and allyl bromide (3.48 mL, 40.3 mmol) in tetrahydrofuran (22 mL) at −35° C. (acetonitrile/dry ice bath) was treated with a solution of lithium bis(trimethylsilyl)amide in tetrahydrofuran (1.0 M, 17.45 mL, 17.45 mmol). The reaction was allowed to warm to −5° C. over 1 hour and then was quenched with 50% saturated ammonium chloride. The reaction was diluted with 100 mL of ethyl acetate and the layers were separated. The organic phase was washed with brine, dried over magnesium sulfate, filtered and concentrated under a vacuum to afford the title compound as a white solid upon standing under a vacuum. Chiral SFC (92% CO$_2$, 8% methanol (20 mM ammonia), 5 mL/min, Phenomenex Lux-2 column (Phenomenex, Torrance, Calif.), 100 bar (10,000 kPa), 40° C., 5 minute method) was used to determine that the compound had an enantiomeric ratio of 96:4. (Major enantiomer:title compound, retention time=2.45 minutes, 96%; minor enantiomer (structure not shown, retention time=2.12 min, 4%). The title compound was recrystallized by adding to heptane (4.7 g slurried in 40 mL) at reflux and 1.5 mL of toluene was added dropwise to solubilize. The solution was cooled to 0° C. The white solid was filtered and rinsed with 20 mL of cold heptanes to afford a white powder. Chiral SFC (92% CO$_2$, 8% methanol, Phenomenex Lux-2 column, same method as above) indicated an enantiomeric ratio of 99.2:0.8. (major enantiomer, 2.45 min, 99.2%; minor enantiomer: 2.12 min, 0.8%). $^1$H NMR (400 MHz, CDCl$_3$, δ ppm): 7.24 (ddd, J=8.0, 2.0, 1.2 Hz, 1H), 7.20-7.15 (series of m, 3H), 6.91 (t, J=2.0 Hz, 1H), 6.78 (br d, J=7.6 Hz, 1H), 6.60 (m, 2H), 5.84 (ddt, J=17.6, 10.2, 7.4 Hz, 1H), 5.70 (d, J=5.3 Hz, 1H), 5.21-5.13 (series of m, 2H), 3.82 (dt, J=11.7, 4.5 Hz, 1H), 2.62 (ABX J$_{AB}$=13.7 Hz, J$_{AX}$=7.6 Hz, 1H), 2.53 (ABX, J$_{AB}$=13.9 Hz, J$_{BX}$=7.2 Hz, 1H). 1.99 (dd, J=14.1, 11.9 Hz, 1H), 1.92 (ddd, J=13.9, 3.9, 1.2 Hz, 1H). $^{13}$C NMR (CDCl$_3$, 100 MHz, 6 ppm): 175.9, 140.2, 134.5, 134.3, 134.0, 132.2, 129.8, 128.6, 128.0, 127.9, 127.8, 126.4, 119.9, 83.9, 44.5, 42.4, 40.7, 31.8, 26.1. MS (ESI)=375.2 [M+H]$^+$. IR=1730 cm$^{-1}$. [α]$_D$ (24° C., c=1.0, CH$_2$Cl$_2$)=−191°. m.p. 111-114° C.

Step E. (S)-2-((2R,3R)-2-(3-Chlorophenyl)-3-(4-chlorophenyl)-3-hydroxypropyl)-N—((S)-1-hydroxy-3-methylbutan-2-yl)-2-methylpent-4-enamide

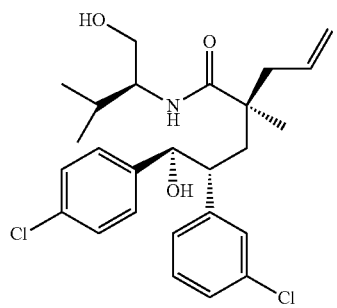 [SMILES: C=CC[C@@](C)(C[C@H](c1cccc(Cl)c1)[C@@H](O)c1ccc(Cl)cc1)C(=O)N[C@H](CO)C(C)C]

(3S,5R,6R)-3-Allyl-5-(3-chlorophenyl)-6-(4-chlorophenyl)-3-methyltetrahydro-2H-pyran-2-one (113 g, 300.0 mmol) was combined with (S)-2-amino-3-methyllbutan-1-ol (93 g, 900.0 mmol) and the suspension was heated at 100° C. for 5 hours. The reaction mixture was cooled to room temperature, diluted with ethyl acetate (1000 mL) and washed with 1N hydrochloric acid (2×), water, and brine. The organic layer was dried over magnesium sulfate and concentrated under a vacuum to give the title compound as white solid which was used in next step without further purification.

Step F. (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate

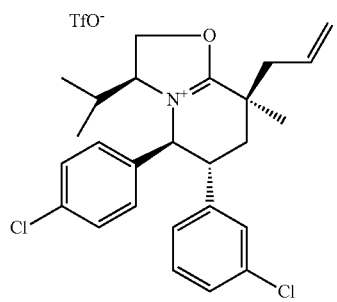 [SMILES: "TfO-" ; C=CC[C@@]1(C)C[C@H](c2cccc(Cl)c2)[C@@H](c2ccc(Cl)cc2)[N+]2=C1OC[C@@H]2C(C)C]

Trifluoromethanesulfonic anhydride (57 mL, 339 mmol) was added dropwise over 60 minutes via addition funnel to a solution of (S)-2-((2R,3R)-2-(3-chlorophenyl)-3-(4-chlorophenyl)-3-hydroxypropyl)-N—((S)-1-hydroxy-3-methylbutan-2-yl)-2-methylpent-4-enamide (73.7 g, 154 mmol) and 2,6-dimethylpyridine (78 mL, 678 mmol) in dichloromethane (700 mL) at −50° C. The reaction mixture was stirred at −50° C. for one additional hour and concentrated under a vacuum to provide the title compound as a reddish solid which was used in next step without further purification.

Step G. (3S,5R,6S)-3-Allyl-5-(3-chlorophenyl)-6-(4-chlorophenyl)-1-((S)-1-(isopropylthio)-3-methylbutan-2-yl)-3-methylpiperidin-2-one

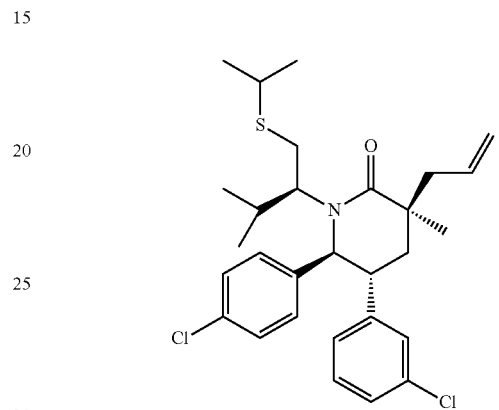

(3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (736 mg, 1.242 mmol) was weighed into an oven dried 50 mL pear-bottom flask and dissolved in 20 mL dry toluene. The toluene was removed under a vacuum to remove trace water in the solid. The process was repeated twice, and the resulting residue was dried under a strong vacuum.

A solution of sodium isopropyl sulfide was prepared by adding potassium 2-methylpropan-2-olate (3.0 mL, 3.00 mmol, 1 M solution in tetrahydrofuran) to a solution of propane-2-thiol (331 mg, 4.35 mmol) in 8 mL dimethylformamide that had been prepared under nitrogen and cooled to 0° C. The sulfide solution was allowed to stir at room temperature for five minutes and was cooled to 0° C. The dry (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (736 mg, 1.242 mmol) was dissolved in dimethylformamide (8 mL total) and transferred (3 transfers total) via syringe to the sulfide solution over the course of 5 minutes. After 5 minutes, the ice bath was removed and the pale orange solution was allowed to warm to room temperature.

After stirring overnight, the mixture was partitioned between ethyl acetate and saturated ammonium chloride solution. The aqueous phase was saturated in sodium chloride and back-extracted three times. The combined organics were washed twice with saturated sodium bicarbonate, twice with brine, dried over sodium sulfate, filtered, and concentrated under a vacuum to provide a residue that was purified by silica gel column chromatography (80 g column, gradient elution of 0% to 50% ethyl acetate in hexanes).

Method for Making

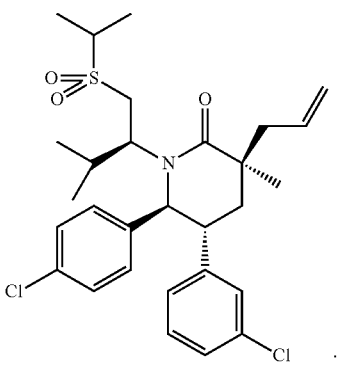 [SMILES: C=CC[C@@]1(C)C[C@H](c2cccc(Cl)c2)[C@@H](c2ccc(Cl)cc2)N([C@H](CS(=O)(=O)C(C)C)C(C)C)C1=O]

Step A. (3S,5R,6S)-3-Allyl-5-(3-chlorophenyl)-6-(4-chlorophenyl)-1-((S)-1-hydroxy-3-methylbutan-2-yl)-3-methylpiperidin-2-one

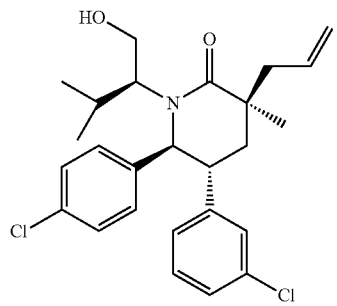 [SMILES: C=CC[C@@]1(C)C[C@H](c2cccc(Cl)c2)[C@@H](c2ccc(Cl)cc2)N([C@H](CO)C(C)C)C1=O]

Lithium hydroxide hydrate (64.6 g, 1540 mmol) was added portionwise, over a 5 minute period, to a solution of (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (Step F above) dissolved in tetrahydrofuran (500 ml) and water (300 ml). The reaction mixture was stirred at room temperature for 1 hour and concentrated under a vacuum. The residue was dissolved in ethyl acetate (ca. 1.3 L) and the layers were separated. The organic layer was washed with 1N hydrochloric acid (ice cooled, with enough hydrochloric acid to protonate and remove any remaining 2,6-dimethylpyridine (300 mL×2)), water and brine. The solvent was removed under a vacuum to give a residue which was purified by silica gel column chromatography (1500 g column, gradient elution of 0% to 50% ethyl acetate in hexanes. The product was also crystallized from cyclohexane.

Step B. (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium 4-methylbenzenesulfonate

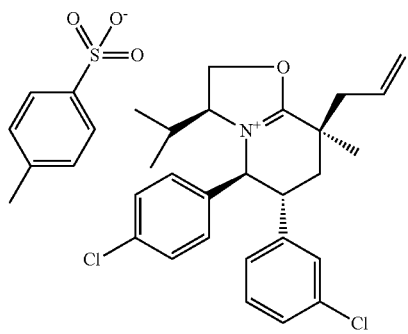 [SMILES: Cc1ccc(S(=O)(=O)[O-])cc1 ; C=CC[C@@]1(C)C[C@H](c2cccc(Cl)c2)[C@@H](c2ccc(Cl)cc2)[N+]2=C1OC[C@@H]2C(C)C]

(3S,5R,6S)-3-Allyl-5-(3-chlorophenyl)-6-(4-chlorophenyl)-1-((S)-1-hydroxy-3-methylbutan-2-yl)-3-methylpiperidin-2-one (49.77 g, 98 mmol) was transferred to a 1000 mL flask containing 4-methylbenzenesulfonic acid hydrate (19.27 g, 101 mmol) and a stirring bar. The reactants were suspended in toluene (230 mL). The flask was equipped with a Dean Stark trap and reflux condenser, and the stirred mixture was heated at reflux in a preheated bath. After 1 hour, the solvent was carefully removed under a vacuum and the resulting residue was further dried under high vacuum. The title compound was taken to the next step without purification.

Step C. (3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one

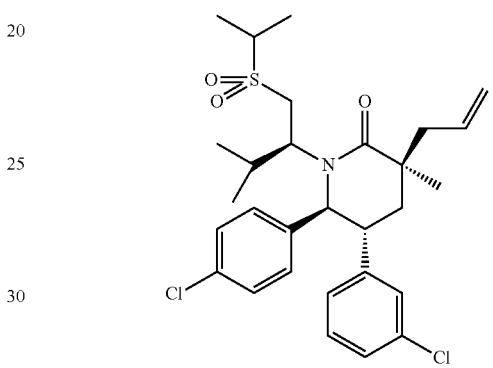

(3S,5S,6R,8S)-8-Allyl-6-(3-chlorophenyl)-5-(4-chlorophenyl)-3-Isopropyl-8-methyl-2,3,5,6,7,8-hexahydrooxazolo[3,2-a]pyridin-4-ium 4-methylbenzenesulfonate, dry, powdered potassium carbonate (26.9 g, 195 mmol) and propane-2-thiol (14 ml, 150 mmol) were added along with 200 mL freshly sparged dimethylformamide. The mixture was heated under argon at 50° C. After about 21 hours, a solution of meta-chloroperbenzoic acid (68.2 g, 77% pure by weight, in 100 mL dimethylformamide) was transferred to a dropping funnel and rapidly added to the stirred reaction mixture while the flask was immersed in an ice bath. After 5 minutes, the resulting yellow solution was allowed to warm to room temperature. After 10 minutes, additional meta-chloroperbenzoic acid (12 g, 77% wt %) was added as a solid and the mixture was stirred at room temperature. Upon completion, the mixture was poured into ethyl acetate and washed with 1 M sodium hydroxide (500 mL) that had been poured into ice. The aqueous phase was back-extracted three times and washed with additional 1 M NaOH ((500 mL, also poured into ice). The aqueous layer was washed once with ethyl acetate and the organics were combined. Sodium thiosulfate (1 M in water, 250 mL) was added to the organics in a large Erlenmeyer flask, and the mixture was stirred for twenty minutes. The organic phase was washed again with sodium thiosulfate (1 M in water, 250 mL) and the mixture was allowed to stand over the weekend. The organics were concentrated to ca. 500 mL, then sequentially washed with 10% aqueous citric acid, 1 M sodium hydroxide, and brine. The organics were dried over sodium sulfate, filtered, and concentrated to give the crude product. The residue was purified by flash column chromatography (1.5 kg silica gel column, gradient elution of 0% to 50% ethyl acetate in hexanes) to give the title compound as a white solid.

Synthesis of Compound AMG 232 (Alternative 1)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

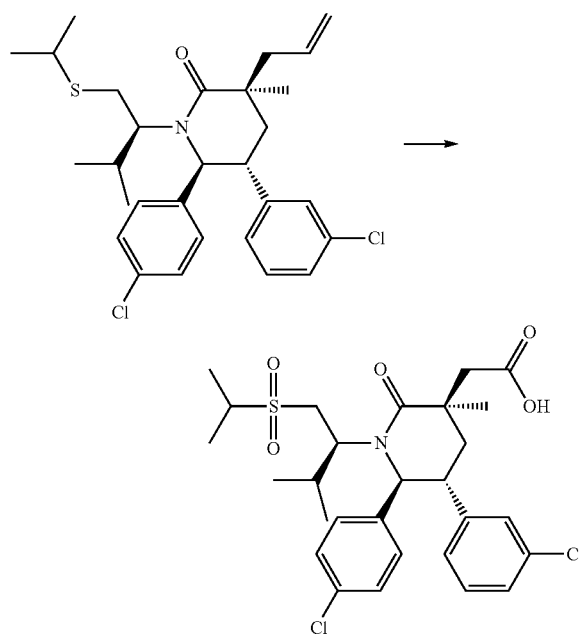

Ruthenium(III) chloride trihydrate 22 mg, 0.84 mmol) and sodium periodate (1.12 g, 5.24 mmol) were added to a mixture of (3S,5R,6S)-3-allyl-5-(3-chlorophenyl)-6-(4-chlorophenyl)-1-((S)-1-(isopropylthio)-3-methylbutan-2-yl)-3-methylpiperidin-2-one (390 mg, 0.752 mmol) in acetonitrile (4.0 mL), carbon tetrachloride (4.0 mL), and water (6.0 mL). The resulting dark brown mixture was vigorously stirred at ambient temperature overnight. The mixture was filtered through a pad of diatomaceous earth, washing with ethyl acetate. The filtrate was partitioned between 2 M HCl and ethyl acetate. The aqueous phase was back-extracted twice with ethyl acetate, and the combined organics were washed with brine, dried over sodium sulfate, filtered, and concentrated under a vacuum to a residue that was purified by flash chromatography (40 g silica gel column, gradient elution of 0% to 15% isopropanol in hexanes). Fractions containing the desired product were combined, stripped of solvent, redissolved in minimal ACN/water, frozen, and lyophilized to give a white powder.

Subsequently, a mixture of (3S,5R,6S)-3-allyl-5-(3-chlorophenyl)-6-(4-chlorophenyl)-1-((S)-1-(isopropylthio)-3-methylbutan-2-yl)-3-methylpiperidin-2-one (388 mg, 0.748 mmol), ruthenium(III) chloride trihydrate (19.56 mg, 0.075 mmol), and sodium periodate (1.15 g, 5.38 mmol) in acetonitrile (4 mL), carbon tetrachloride (4.00 mL), and water (4.00 mL) was vigorously stirred at ambient temperature. After four hours, the mixture was filtered through a pad of diatomaceous earth, and the filtrate was partitioned between ethyl acetate and 2 M HCl. The aqueous phase was back-extracted twice with ethyl acetate, and the combined organics were washed with brine, dried over sodium sulfate, filtered, and concentrated under a vacuum to a residue. The residue was purified by flash chromatography (40 g silica gel column, gradient elution of 0% to 15% isopropanol in hexanes). Fractions containing the product were concentrated and combined with the solid obtained in the prior experiment. The combined material was dissolved in minimal acetonitrile/water, frozen, and lyophilized overnight to give a white solid.

Synthesis of AMG 232 (Alternative 2)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

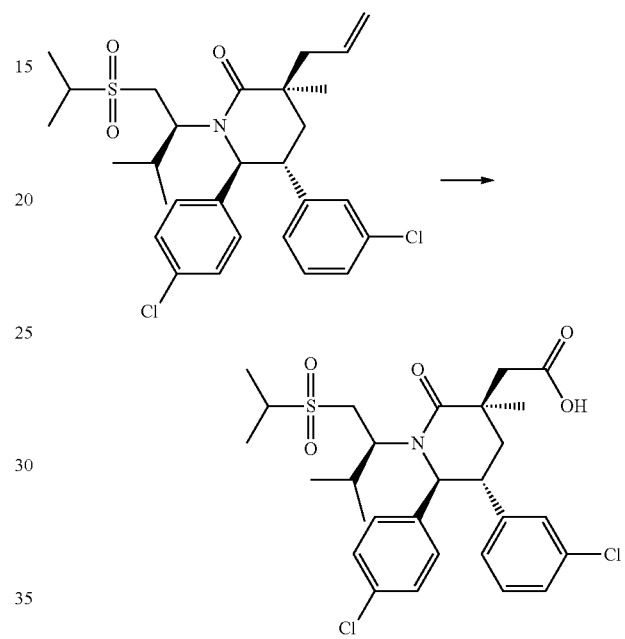

Sodium periodate (2.85 g, 13.32 mmol) and ruthenium (III) chloride trihydrate (0.049 g, 0.189 mmol) were added to a mixture of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (1.73 g, 3.14 mmol) in acetonitrile (18 mL), carbon tetrachloride (18 mL), and water (27 mL). The mixture was stirred vigorously at room temperature for 25 hours. The mixture was diluted with 2M HCl and filtered through a pad of diatomaceous earth and rinsed with ethyl acetate. The organic layer was separated, washed with brine, dried over sodium sulfate, filtered, and concentrated under a vacuum. The material was purified twice by flash chromatography (120 g silica gel, gradient elution of 0% to 20% isopropanol in hexanes; 120 g column, gradient elution of 0% to 15% gradient isopropanol in hexanes). It was purified once more by flash chromatography (220 g silica gel; gradient elution 0% to 20% isopropanol in hexanes, 45 minutes) using a method in which the purest fractions were concentrated and set aside and mixed fractions were pooled and resubjected to the chromatography.

Subsequently, a mixture of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (4.1 g, 7.45 mmol), ruthenium(III) chloride trihydrate (0.120 g, 0.459 mmol), and sodium periodate (6.73 g, 31.5 mmol) in acetonitrile (40 mL), carbon tetrachloride (40 mL), and water (60 mL) was vigorously stirred at ambient temperature for 23 hours. The reaction was diluted by addition of 2 M aqueous HCl and filtered through a diatomaceous earth pad, washing with copious ethyl acetate. Most of the organics were removed under a vacuum. The crude product was extracted into ethyl acetate, washed with brine, dried over sodium sulfate, filtered, and concentrated to a residue that was purified twice by flash chromatography (330 g silica gel column, gradient elution of 0% to 20% isopropanol in hexanes; 330 g silica gel column, gradient elution of 0% to 20% isopropanol in hexanes) to give an off-white foam. The material was purified by flash chromatography three additional times (220 g silica gel column; gradient elution 0% to 20% isopropanol in hexanes, 45 minutes) using a method in which the purest fractions were concentrated and set aside and mixed fractions were pooled and resubjected to the chromatography.

Mixed fractions from both experiments were combined and purified by flash chromatography twice more (220 g silica gel column; gradient elution 0% to 20% isopropanol in hexanes, 45 minutes), and again the pure fractions were set aside.

All of the pure fractions were combined, concentrated under a vacuum, dissolved in minimal acetonitrile/water and lyophilized.

Synthesis of AMG 232 (Alternative 3)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid Three portions of sodium periodate (2.08 g, 2.07 g and 2.08 g) were slowly added on 15 minute intervals. The temperature was kept below 19° C., and ice was quickly added to the bath if the internal temperature began to rise. The mixture was stirred at ambient temperature overnight. The mixture was filtered through a pad of diatomaceous earth and the filter cake was washed copiously with ethyl acetate. The filtrate was concentrated under a vacuum and partitioned between 2 M HCl (100 mL) and ethyl acetate (200 mL).

Two rounds of flash column chromatography (330 g silica gel, then 220 g silica gel, gradient elution of 0% to 20% isopropanol in hexanes) provided the title compound. A portion of this material was lyophilized from acetonitrile and water. The less pure fractions were repurified by two additional rounds of flash column chromatography (220 g then 330 g silica gel columns, gradient elution of 0% to 20% isopropanol in hexanes). The most pure fractions from both runs were combined, concentrated under a vacuum and lyophilized from acetonitrile and water to give the title compound.

Another particular MDM2 inhibitor is AM-7209 (Compound C herein), which is disclosed in U.S. provisional patent application No. 61/770,901, filed Feb. 28, 2013. (See Example No. 5 therein and below). AM-7209 has the following chemical name and structure: 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid

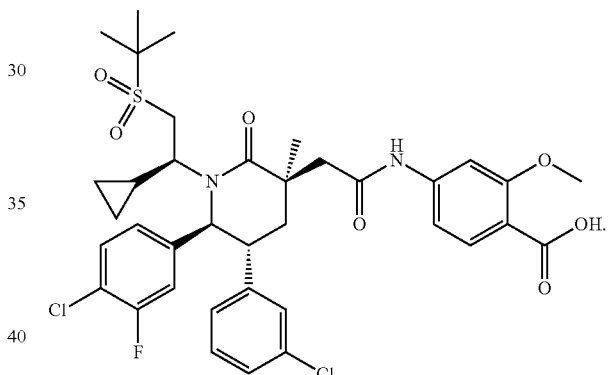

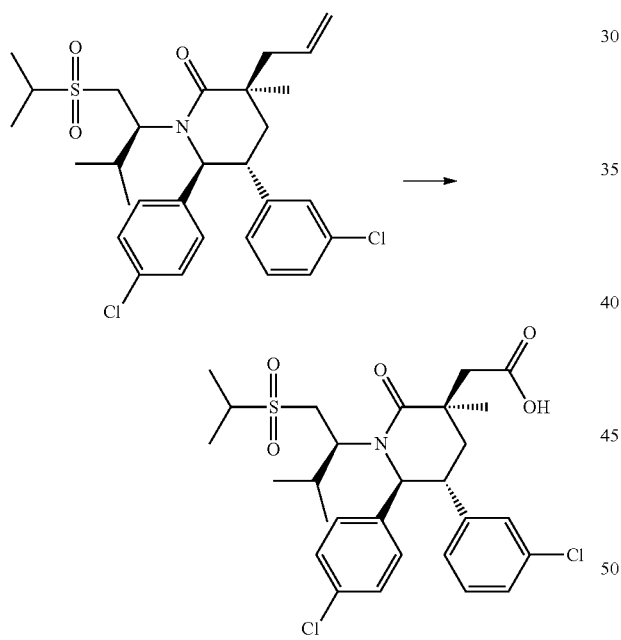

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (5.05 g, 9.17 mmol) was weighed into a 500 mL round bottom flask containing a large stir bar and 2.04 g sodium periodate (2.04 g). The mixture was diluted with carbon tetrachloride (52 mL), acetonitrile, (52 mL) and water (78 mL). The flask was immersed in a room temperature water bath and the internal temperature was monitored with a digital thermocouple.

Ruthenium chloride hydrate (approximately 50 mg) was added in a single portion. The internal temperature rose to 22° C., then ice was added to the bath to cool the mixture. Additional ruthenium chloride hydrate (25 mg) was added 3 minutes later. After stirring for a total of thirty minutes, Example 1

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetic acid (Example 351 of WO2011/153509 (Amgen Inc.), Published Dec. 8, 2011

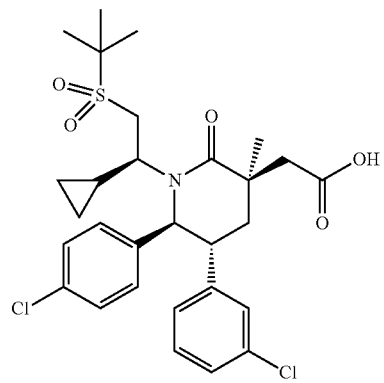 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)cc1]

Step A.
2-(3-Chlorophenyl)-1-(4-chlorophenyl)ethanone

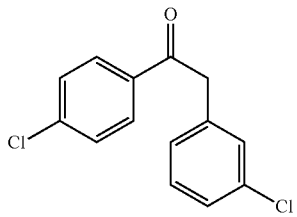 [SMILES: O=C(Cc1cccc(Cl)c1)c1ccc(Cl)cc1]

Sodium bis(trimethylsilyl)amide (1 M in tetrahydrofuran, 117 mL) slowly added to a −78° C. solution of 2-(3-chlorophenyl) acetic acid (10 g, 58.6 mmol) in tetrahydrofuran (58 mL) over 1 hour. After stirring at −78° C. for 40 minutes, a solution of methyl 4-chlorobenzoate (10 g, 58.6 mmol) in tetrahydrofuran (35 mL) was added over a period of 10 minutes. The reaction was stirred at −78° C. for 3 hours then allowed to warm to 25° C. After two hours at 25° C., the reaction was quenched with saturated aqueous ammonium chloride solution, and most of the tetrahydrofuran was removed under reduced pressure. The residue was extracted with ethyl acetate (2×100 mL). The combined organic layers were washed with saturated sodium chloride solution, dried over sodium sulfate, filtered and the filtrate was concentrated. The product was recrystallized from ether/pentane to provide the title compound as a white solid. $^1$H NMR (500 MHz, DMSO-d$_6$, δ ppm): 8.05 (m, 2H), 7.62 (m, 2H), 7.33 (m, 3H), 7.21 (br d, J=7.3 Hz, 1H), 4.45 (s, 2H). MS (ESI)=265.1 [M+H]$^+$.

Step B: Methyl 4-(3-chlorophenyl-5-(4-chlorophenyl)-2-met-5-oxopentanoate

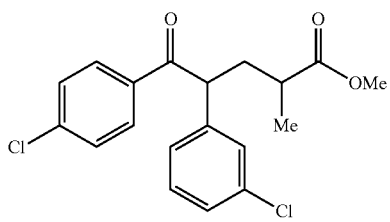 [SMILES: COC(=O)C(C)CC(C(=O)c1ccc(Cl)cc1)c1cccc(Cl)c1]

Methyl methacrylate (12.65 mL, 119 mmol) was added to a solution of 2-(3-chlorophenyl)-1-(4-chlorophenyl)ethanone (30 g, 113 mmol, Example 1, Step A) in tetrahydrofuran (283 mL). Potassium tert-butoxide (1.27 g, 11.3 mmol) was then added and the reaction was stirred at room temperature for 2 days. The solvent was removed under a vacuum and replaced with 300 mL of ethyl acetate. The organic phase was washed with brine (50 mL), water (3×50 mL), and brine (50 mL). The organic phase was dried over magnesium sulfate, filtered and concentrated under a vacuum to afford methyl 4-(3-chlorophenyl)-5-(4-chlorophenyl)-2-methyl-5-oxopentanoate as an approximately 1:1 mixture of diastereomers. $^1$H NMR (400 MHz, CDCl$_3$, δ ppm): 7.87 (m, 2H), 7.38 (m, 2H), 7.27-7.14 (series of m, 4H), 4.61 (m, 1H), 3.69 (s, 1.5H), 3.60 (s, 1.5H), 2.45 (m, 1H), 2.34 (m, 1H), 2.10 (ddd, J=13.9, 9.4, 5.5 Hz, 0.5H), 1.96 (ddd, J=13.7, 9.0, 4.3 Hz, 0.5H), 1.22 (d, J=7.0 Hz, 1.5H), 1.16 (d, J=7.0, 1.5H). MS (ESI)=387.0 [M+23]$^+$.

Step C: (3S, 5R,6R)-5-(3-Chlorophenyl)-6-(4-chlorophenyl)-3-methyltetrahydro-2H-pyran-2-one and (3R, 5R,6R)-5-(3-chlorophenyl)-6-(4-chlorophenyl)-3-methyltetrahydro-2H-pyran-2-one

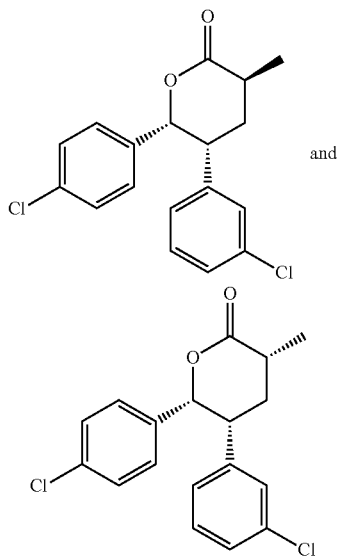

Methyl 4-(3-chlorophenyl)-5-(4-chlorophenyl)-2-methyl-5-oxopentanoate (40 g, 104.0 mmol, Example 1, Step B) was dissolved in 200 mL of anhydrous toluene and concentrated under a vacuum. The residue was placed under high vacuum for 2 hours before use. The compound was split into 2×20 g batches and processed as follows: methyl 4-(3-chlorophenyl)-5-(4-chlorophenyl)-2-methyl-5-oxopentanoate (20 g, 52.0 mmol) in anhydrous 2-propanol (104 mL) was treated with potassium tert-butoxide (2.33 g, 20.8 mmol) in a 250 mL glass hydrogenation vessel. RuCl$_2$(S-xylbinap)(S-DAIPEN) (0.191 g, 0.156 mmol, Strem Chemicals, Inc., Newburyport, Mass.) in 3.8 mL of toluene was added. After 1.5 hours, the vessel was pressurized to 50 psi (344.7 kPa) and purged with hydrogen five times and allowed to stir at room temperature. The reaction was recharged with additional hydrogen as needed. After 3 days, the reactions were combined and partitioned between 50% saturated ammonium chloride solution and ethyl acetate. The aqueous layer was extracted with ethyl acetate. The combined organic phases were washed with brine, dried over magnesium sulfate, filtered, and concentrated. The crude product (predominantly, (4R,5R)-isopropyl 4-(3-chlorophenyl)-5-(4-chlorophenyl)-5-hydroxy-2-methylpentanoate) was dissolved in tetrahydrofuran (450 mL) and methanol (150 mL). Lithium hydroxide (1.4 M, 149 mL, 208 mmol) was added, and the solution was stirred at room temperature for 24 hours. The mixture was concentrated under a vacuum and the residue was redissolved in ethyl acetate. Aqueous 1N hydrochloric acid was added with stirring until the aqueous layer had a pH of about 1. The layers were separated and the organic phase was washed with brine, dried over magnesium sulfate, filtered and concentrated. The material was dissolved in 200 mL of anhydrous toluene and treated with pyridinium p-toluenesulfonate (PPTS, 0.784 g, 3.12 mmol). The reaction was heated to reflux under Dean-Stark conditions until the seco-acid was consumed (about 2 hours). The reaction was cooled to room temperature and washed with saturated sodium bicarbonate (50 mL) and brine (50 mL). The solution was dried over sodium sulfate, filtered and concentrated. The crude material was purified by flash chromatography on silica gel (120 g column; eluting with 100% dichloromethane). The title compounds were obtained as a white solid with an approximate 94:6 enantiomeric ratio and a 7:3 mixture of methyl diastereomers. $^1$H NMR (400 MHz, CDCl$_3$, δ ppm): 7.22-6.98 (series of m, 5H), 6.91 (dt, J=7.4, 1.2 Hz, 0.3H), 6.81 (m, 2H), 6.73 (dt, J=7.6, 1.4 Hz, 0.7H), 5.76 (d, J=4.1 Hz, 0.3H), 5.69 (d, J=4.7 Hz, 0.7H), 3.67 (dt, J=6.6, 4.3 Hz, 0.3H), 3.55 (td, J=7.8, 4.7 Hz, 0.7H), 2.96 (d of quintets, J=13.5, 6.7 Hz, 0.7H), 2.81 (m, 0.3H), 2.56 (dt, J=14.3, 8.0 Hz, 0.7H), 2.32 (dt, J=13.69, 7.0 Hz, 0.3H), 2.06 (ddd, J=13.7, 8.4, 4.1, 0.3H), 1.85 (ddd, J=14.1, 12.5, 7.4, 0.7H), 1.42 (d, J=7.0 Hz, 0.9H), 1.41 (d, J=6.7 Hz, 2.1H). MS (ESI)=357.0 [M+23]. [c]D (22° C., c=1.0, CH$_2$Cl$_2$)=−31.9°; m.p. 98-99° C.

Step D. (3S,5R,6R)-3-Allyl-5-(3-chlorophenyl)-6-(4-chlorophenyl)-3-methyltetrahydro-2H-pyran-2-one

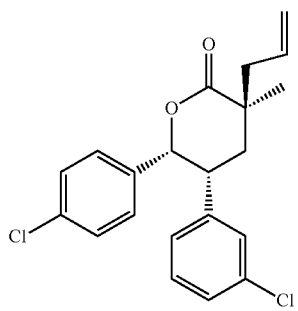 [SMILES: C=CC[C@@]1(C)C[C@H](c2cccc(Cl)c2)[C@H](c2ccc(Cl)cc2)OC1=O]

A solution of (3S, 5R,6R)-5-(3-chlorophenyl)-6-(4-chlorophenyl)-3-methyltetrahydro-2H-pyran-2-one and (3R,5S,6S)-5-(3-chlorophenyl)-6-(4-chlorophenyl)-3-methyltetrahydro-2H-pyran-2-one (4.5 g, 13.4 mmol, Example 1, Step C) and allyl bromide (3.48 mL, 40.3 mmol) in tetrahydrofuran (22 mL) at −35° C. (acetonitrile/dry ice bath) was treated with a solution of lithium bis(trimethylsilyl)amide in tetrahydrofuran (1.0 M, 17.45 mL, 17.45 mmol). The reaction was allowed to warm to −5° C. over 1 hour and then was quenched with 50% saturated ammonium chloride. The reaction was diluted with 100 mL of ethyl acetate and the layers were separated. The organic phase was washed with brine, dried over magnesium sulfate, filtered and concentrated under a vacuum to afford the title compound as a white solid upon standing under a vacuum. Chiral SFC (92% CO$_2$, 8% methanol (20 mM ammonia), 5 mL/min, Phenomenex Lux-2 column (Phenomenex, Torrance. Calif.), 100 bar (10,000 kPa), 40° C., 5 minute method) was used to determine that the compound had an enantiomeric ratio of 96:4. (Major enantiomer:title compound, retention time=2.45 minutes, 96%; minor enantiomer (structure not shown, retention time=2.12 min, 4%). The title compound was recrystallized by adding to heptane (4.7 g slurried in 40 mL) at reflux and 1.5 mL of toluene was added dropwise to solubilize. The solution was cooled to 0° C. The white solid was filtered and rinsed with 20 mL of cold heptanes to afford a white powder. Chiral SFC (92% CO$_2$, 8% methanol, Phenomenex Lux-2 column, same method as above) indicated an enantiomeric ratio of 99.2:0.8. (major enantiomer, 2.45 min, 99.2%; minor enantiomer: 2.12 min, 0.8%). $^1$H NMR (400 MHz, CDCl$_3$, δ ppm): 7.24 (ddd, J=8.0, 2.0, 1.2 Hz, 1H), 7.20-7.15 (series of m, 3H), 6.91 (t, J=2.0 Hz, 1H), 6.78 (br d, J=7.6 Hz, 1H), 6.60 (m, 2H), 5.84 (ddt, J=17.6, 10.2, 7.4 Hz, 1H), 5.70 (d, J=5.3 Hz, 1H), 5.21-5.13 (series of m, 2H), 3.82 (dt, J=11.7, 4.5 Hz, 1H), 2.62 (ABX J$_{AB}$=13.7 Hz, J$_{AX}$=7.6 Hz, 1H), 2.53 (ABX, J$_{AB}$=13.9 Hz, J$_{BX}$=7.2 Hz, 1H). 1.99 (dd, J=14.1, 11.9 Hz, 1H), 1.92 (ddd, J=13.9, 3.9, 1.2 Hz, 1H). $^{13}$C NMR (CDCl$_3$, 100 MHz, δ ppm): 175.9, 140.2, 134.5, 134.3, 134.0, 132.2, 129.8, 128.6, 128.0, 127.9, 127.8, 126.4, 119.9, 83.9, 44.5, 42.4, 40.7, 31.8, 26.1. MS (ESI)=375.2 [M+H]$^+$. IR=1730 cm$^{-1}$. [α]$_D$ (24° C., c=1.0, CH$_2$Cl$_2$)=−191°. m.p. 111-114° C.

Step E. (2S)-2-((2R)-2-(3-Chlorophenyl)-3-(4-chlorophenyl)-3-hydroxypropyl)-N—((S)-1-cyclopropyl-2-hydroxyethyl)-2-methylpent-4-enamide

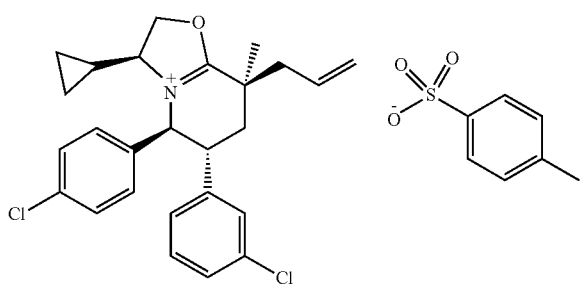

(3S,5R,6R)-3-Allyl-5-(3-chlorophenyl)-6-(4-chlorophenyl)-3-methyltetrahydro-2H-pyran-2-one (125.0 g, 333 mmol, Example 1, Step D) was added to (S)-2-amino-2-cyclopropylethanol (101 g, 999 mmol) and the reaction mixture was heated at 110° C. under argon for 25 hours. The reaction mixture was diluted with isopropyl acetate, cooled to room temperature, and 3 M hydrochloric acid (400 mL) was added slowly. The mixture was stirred at room temperature for 20 minutes, and the layers were separated. The organic layer was washed with 1 M hydrochloric acid (200 mL) and brine, then dried over magnesium sulfate, filtered and concentrated under a vacuum to provide the desired product as a brown oil (159 g).

Step F. (3S,5S,6R,8S)-8-Allyl-6-(3-chlorophenyl)-5-(4-chlorophenyl)-3-cyclopropyl-8-methyl-2,3,5,6,7,8-hexahydrooxazolo[3,2-a]pyridin-4-ium 4-methylbenzenesulfonate A 2 L 4-necked round-bottomed flask equipped with a magnetic stir bar, addition funnel, septa and internal temperature sensor was charged with p-toluenesulfonic anhydride (240 g, 734 mmol) and anhydrous dichloromethane (600 mL). The internal temperature was adjusted to 14° C. and the mixture was stirred for 10 minutes. A solution of (S)-2-((2R,3R)-2-(3-chlorophenyl)-3-(4-chlorophenyl)-3-hydroxypropyl)-N—((S)-1-cyclopropyl-2-hydroxyethyl)-2-methylpent-4-enamide (159.0 g, 334 mmol, Example 1, Step E) in anhydrous dichloromethane (400 mL) was added to the reaction mixture. The temperature increased to 17° C. before returning to 14° C. The reaction mixture was cooled to 7° C. and 2,6-lutidine (160 mL, 1372 mmol) (dried over activated 4 Å molecular sieves) was added dropwise via addition funnel to the reaction mixture. The addition was complete after 1 hour. The reaction mixture was removed from the water bath and stirred at room temperature for 1 hour. The reaction mixture was heated at reflux for 16 hours. LCMS indicated that some intermediate remained. Additional p-toluenesulfonic anhydride (0.25 equiv) and lutidine (0.5 equiv) were added and the reaction mixture was heated at reflux for 8 hours. LCMS indicated that the reaction was complete. The reaction mixture was cooled to room temperature and added via addition funnel to 1 M aqueous sulfuric acid (764 mL, 764 mmol) with stirring. The addition took 30 minutes, and the solution was stirred at room temperature for 30 minutes thereafter. The layers were separated and the organic layer was dried over magnesium sulfate, filtered and concentrated under a vacuum to provide a brown syrup. To remove any dichloromethane from the syrup it was taken up in ethyl acetate and concentrated under a vacuum twice to provide a thick brown syrup. Ethyl acetate (2 L) was added and the mixture was heated at 60° C. until all of the syrup was dissolved (about 45 minutes). The solution was stirred while cooling to room temperature. Crystals had formed after 2 hours and the mixture was cooled to 10° C. for 1 hour before collecting the solid by vacuum filtration and washing with cold (10° C.) ethyl acetate. This provided 70 g of the desired product as an off-white crystalline solid. The filtrate was concentrated under a vacuum to 1.5 L and the mixture was stirred at 10° C. for 1.5 hours. The mixture was filtered under vacuum to provide a light brown crystalline solid that was shown to be lutidinium tosylate by NMR. The filtrate was concentrated under vacuum to provide a brown syrup (161 g). Heptane was added to the syrup and the mixture was heated. A minimal amount of ethyl acetate was added until the material dissolved. The solution was cooled to room temperature and then placed in the freezer. The resulting solid was collected by vacuum filtration and washed with cold (0° C.) ethyl acetate to provide the desired product as an off-white crystalline solid (34 g). The filtrate was concentrated to provide a dark brown oil and purified by flash chromatography on silica gel (1.5 kg SiO₂ column, gradient elution of 20% to 100% acetone in hexanes) to provide the desired product as a light brown syrup (73 g). $^1$H NMR (500 MHz, CDCl₃, δ ppm): −0.3 to −0.2 (m, 2H), 0.06-0.11 (m, 1H), 0.31-0.36 (m, 1H), 0.38-0.43 (m, 1H), 1.57 (s, 3H), 1.91 (dd, J=3.7 and 13.9 Hz, 1H), 2.36 (s, 3H), 2.64 (dd, J=7.3 and 13.7 Hz, 1H), 2.72 (dd, J=7.6 and 13.7 Hz, 1H), 2.95 (t, J=13.9 Hz, 1H), 3.32 (dt, J=3.7 and 10.8 Hz, 1H), 4.47 (t, J=8.6 Hz, 1H), 4.57-4.62 (m, 1H), 5.32 (d, J=16.9 Hz, 1H), 5.35 (d, J=10.3 Hz, 1H), 5.46 (t, J=9.5 Hz, 1H), 5.82 (d, J=10.5 Hz, 1H), 5.84-5.93 (m, 1H), 6.94 (br s, 1H), 7.04 (s, 1H), 7.14-7.20 (m, 5H), 7.28-7.40 (m, 3H), 7.88 (d, J=8.1 Hz, 2H)). MS (ESI) 440.1 [M+H].

Step G. (3S,5R,6S)-3-Allyl-1-((S)-2-(tert-butylthio)-1-cyclopropylethyl)-5-(3-chlorophenyl)-6-(4-chlorophenyl)-3-methylpiperidin-2-one

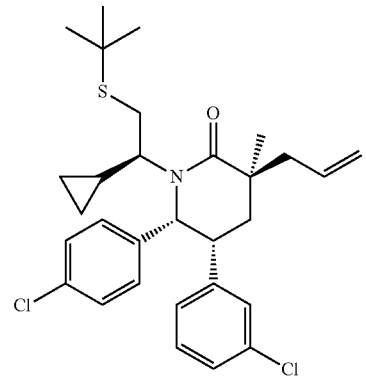 [SMILES: C=CC[C@@]1(C)C[C@H](c2cccc(Cl)c2)[C@H](c2ccc(Cl)cc2)N([C@H](CSC(C)(C)C)C2CC2)C1=O]

2-Methyl-2-propanethiol (0.195 mL, 1.796 mmol, dried over activated 4 Å molecular sieves) was added to a solution of lithium bis(trimethylsilyl)amide in tetrahydrofuran (1.0 M, 1.8 mL, 1.8 mmol) in anhydrous tetrahydrofuran (4 mL) at room temperature. The reaction mixture was heated at 60° C. After 15 minutes at 60° C., (3S,5S,6R,8S)-8-allyl-6-(3-chlorophenyl)-5-(4-chlorophenyl)-3-cyclopropyl-8-methyl-2,3,5,6,7,8-hexahydrooxazolo[3,2-a]pyridin-4-ium 4-methylbenzenesulfonate (1.00 g, 1.632 mmol, Example 1, Step F) was added as a solid. The reaction mixture was heated at 60° C. for 12 hours and then cooled to room temperature and diluted with water. The solution was extracted with ethyl acetate thrice and the organics were pooled, washed with brine, dried over sodium sulfate, decanted and concentrated under a vacuum to provide a brown oil. Purification by flash chromatography (80 g SiO₂ column, gradient elution of 10 to 60% ethyl acetate in hexanes provided the desired product as a colorless syrup. $^1$H NMR (500 MHz, CDCl₃, δ ppm): −0.88 to −0.85 (m, 1H), −0.16 to −0.13 (m, 1H), 0.22-0.27 (m, 1H), 0.39-0.44 (m, 1H), 1.28 (s, 3H), 1.35 (s, 9H), 1.66-1.71 (m, 1H), 1.86 (dd, J=3.2 and 13.5 Hz, 1H), 2.16 (t, J=13.7, 1H), 2.21-2.27 (m, 1H), 2.60 (dd, J=4.4 and 12.0 Hz, 1H), 2.65 (d, J=7.6 Hz, 2H), 3.12 (dt, J=3.2 and 10.3 Hz, 1H), 3.60 (t, J=11.3 Hz, 1H), 4.68 (d, J=10.3 Hz, 1H), 5.16-5.19 (m, 2H), 5.83-5.92 (m, 1H), 6.79 (d, J=7.6 Hz, 1H), 6.93-7.04 (m, 3H), 7.09-7.16 (m, 2H), 7.19-7.24 (m, 2H). MS (ESI) 530.2 [M+H]⁺.

Step H. 2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetic acid

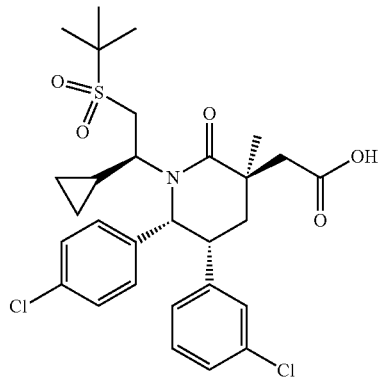 [SMILES: CC(C)(C)S(=O)(=O)C[C@H](C1CC1)N1C(=O)[C@@](C)(CC(=O)O)C[C@H](c2cccc(Cl)c2)[C@@H]1c1ccc(Cl)cc1]

Ruthenium(III) chloride hydrate (30.0 mg, 0.135 mmol) was added to a solution of (3S,5R,6S)-3-allyl-1-((S)-2-(tert-butylthio)-1-cyclopropylethyl)-5-(3-chlorophenyl)-6-(4-chlorophenyl)-3-methylpiperidin-2-one (3.25 g, 6.13 mmol, Example 1, Step H) and sodium periodate (1.33 g) in ethyl acetate (12 mL), acetonitrile (12 mL) and water (18 mL) at 18° C. The temperature rose to 25° C. upon addition. Additional sodium periodate was added in five 1.33 g portions over 30 minutes while maintaining the temperature below 22° C. LCMS after 1.5 hours indicated that the reaction was incomplete, and sodium periodate (1 equivalent) was added. After 1.5 hours the reaction mixture was vacuum filtered, washed with ethyl acetate, and the layers were separated. The aqueous layer was extracted with ethyl acetate and the organics were combined, washed with brine, dried over magnesium sulfate, filtered and concentrated under a vacuum to provide a green oil. Purification by flash chromatography (330 g SiO$_2$ column, gradient elution of 0% to 20% isopropanol in hexanes provided the title compound as a white solid. $^1$H NMR (500 MHz, CDCl$_3$, δ ppm): −1.15 to −1.05 (m, 1H), −0.35 to −0.25 (m, 1H), 0.18-0.28 (m, 1H), 0.33-0.40 (m, 1H), 1.45 (s, 9H), 1.51 (s, 3H), 1.86 (dd, J=2.7 and 13.7 Hz, 1H), 1.87-1.93 (m, 1H), 2.47 (t, J=13.9, 1H), 2.72-2.76 (m, 1H), 2.76 (d, J=15.5 Hz, 1H), 2.93 (d, J=13.7 Hz, 1H), 3.12 (d, J=15.1 Hz, 1H), 3.12 (dt, J=2.7 and 12.5 Hz, 1H), 4.29 (t, J=11.5 Hz, 1H), 4.95 (d, J=10.8 Hz, 1H), 6.86-6.89 (m, 1H), 6.96 (br s, 1H), 7.08-7.14 (m, 3H), 7.15-7.35 (m, 3H). MS (ESI) 580.2 [M+H]$^+$.

Example 2

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)acetamide

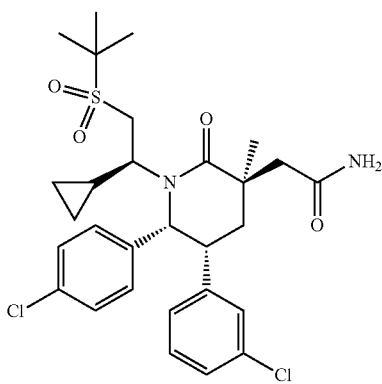 [SMILES: CC(C)(C)S(=O)(=O)C[C@H](C1CC1)N1C(=O)[C@@](C)(CC(N)=O)C[C@H](c2cccc(Cl)c2)[C@@H]1c1ccc(Cl)cc1]

Oxalyl chloride (0.033 mL, 0.379 mmol) was added to a solution of 2-((3R,5R,6S)-1-((S)-2-(tert-butylsulfonyl)-1-cyclopropylethyl)-5-(3-chlorophenyl)-6-(4-chlorophenyl)-3-methyl-2-oxopiperidin-3-yl)acetic acid (0.200 g, 0.344 mmol, Example 1, Step H) in anhydrous dichloromethane (1.5 mL) at room temperature. The reaction mixture was stirred at room temperature for 1 hour and then concentrated under a vacuum to provide the acid chloride as a white foam (206 mg). Lithium bis(trimethylsilyl)amide (1.0 M in tetrahydrofuran, 0.516 mL, 0.516 mmol) and anhydrous tetrahydrofuran (0.5 mL) were added at room temperature. The reaction mixture was stirred at room temperature for 5.5 hours and was then diluted with 1 N hydrochloric acid and extracted with ethyl acetate thrice. The organics were pooled, washed with brine, dried over sodium sulfate, decanted and concentrated under a vacuum to provide a yellow foam. Purification by flash chromatography (12 g SiO$_2$ column; gradient elution of 35% to 100% ethyl acetate) provided the title compound as an off-white foam. $^1$H NMR (500 MHz, CDCl$_3$, δ ppm): −1.10 to −1.00 (in, 1H), −0.38 to −0.325 (m, 1H), 0.17-0.26 (m, 1H), 0.30-0.38 (m, 1H), 1.43 (s, 3H), 1.44 (s, 9H), 1.85-1.92 (m, 1H), 2.00 (dd, J=2.7 and 13.5 Hz, 1H), 2.39 (t, J=13.7 Hz, 1H), 2.65-2.75 (m, 1H), 2.73-2.80 (m, 2H), 2.90-2.96 (m, 1H), 3.31 (dt, J=2.9 and 10.8 Hz, 1H), 4.30-4.38 (m, 1H), 4.96 (d, J=10.8 Hz, 1H), 5.63 (br s, 1H), 6.64 (br s, 1H), 6.90-6.91 (m, 1H), 7.00 (s, 2H), 7.06-7.11 (m, 3H), 7.12-7.29 (m, 2H). MS (ESI) 579.2 [M+H]$^+$.

Example 3

2-((3R,5R,6S)-1-((S)-2-(tert-Butylsulfonyl)-1-cyclopropylethyl)-5-(3-chlorophenyl)-6-(4-chlorophenyl)-3-methyl-2-oxopiperidin-3-yl)-N-phenylacetamide

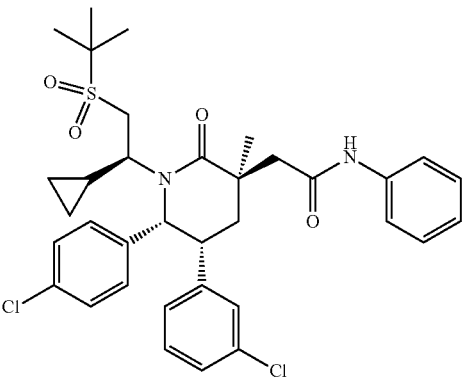 [SMILES: CC(C)(C)S(=O)(=O)C[C@H](C1CC1)N1C(=O)[C@@](C)(CC(=O)Nc2ccccc2)C[C@H](c2cccc(Cl)c2)[C@@H]1c1ccc(Cl)cc1]

N-(3-Dimethylaminopropyl)-N'-ethylcarbodiimide hydrochloride (EDC, 0.117 g, 0.612 mmol) was added to a solution of 2-((3R,5R,6S)-1-((S)-2-(tert-butylsulfonyl)-1-cyclopropylethyl)-5-(3-chlorophenyl)-6-(4-chlorophenyl)-3-methyl-2-oxopiperidin-3-yl)acetic acid (0.118 g, 0.204 mmol, Example 1, Step H) and aniline (0.020 mL, 0.225 mmol) at 0° C. After the addition was complete, the reaction mixture was removed from the ice bath and stirred at room temperature for 19 hours. The reaction mixture was diluted with ice-cold 1 M hydrochloric acid to adjust the pH to 1 and the solution was extracted twice with ether. The combined organic layer was washed with brine, dried over sodium sulfate, decanted and concentrated under a vacuum to provide an orange oil. Purification by flash chromatography (12 g SiO$_2$ column, gradient elution of 15% to 100% ethyl acetate in hexanes provided the title compound as a white foam. $^1$H NMR (500 MHz, CDCl$_3$, δ ppm): −1.32 to −1.20 (m, 1H), −0.40 to −0.28 (m, 1H), −0.28 to −0.10 (m, 1H), 0.30-0.40 (m, 1H), 1.45 (s, 9H), 1.47 (s, 3H), 1.94 (br s, 1H), 2.07 (dd, J=2.7 and 13.7 Hz, 1H), 2.39 (t, J=13.7, 1H), 2.67-2.73 (m, 2H), 2.95 (t, J=13.5 Hz, 2H), 3.30 (dt, J=2.7 and 11.0 Hz, 1H), 4.31 (br t, J=11.7 Hz, 1H), 4.94 (d, J=10.8 Hz, 1H), 6.86-6.89 (m, 1H), 6.99 (s, 1H), 7.02-7.09 (m, 6H), 7.17 (t, J=7.3 Hz, 1H), 7.38 (t, J=8.3 Hz, 2H), 7.66 (d, J=7.8 Hz, 2H). MS (ESI) 655.3 [M+H]$^+$.

Example 4

2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetic acid

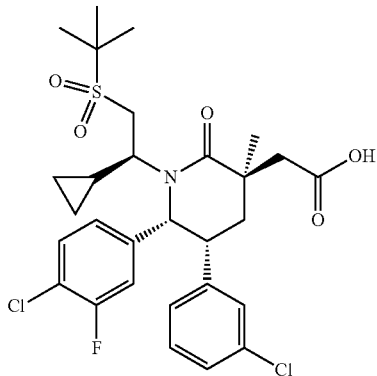 [SMILES: CC(C)(C)S(=O)(=O)C[C@H](C1CC1)N1C(=O)[C@@](C)(CC(=O)O)C[C@H](c2cccc(Cl)c2)[C@@H]1c1ccc(Cl)c(F)c1]

Step A. Methyl-4-chloro-3-fluorobenzoate

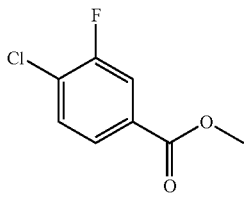

A solution of 4-chloro-3-fluoro benzoic acid (450.0 g, 2.586 mol, Fluorochem, Derbyshire, UK) in methanol (4.5 L) was cooled to 0° C. and thionyl chloride (450.0 mL) was added over 30 minutes. The reaction mixture was stirred for 12 hours at ambient temperature. The reaction was monitored by TLC. Upon completion, the solvent was removed under reduced pressure and the residue was quenched with 1.0 M sodium bicarbonate solution (500 mL). The aqueous layer was extracted with dichloromethane (2×5.0 L). The combined organic layer was washed with brine (2.5 L), dried over anhydrous sodium sulfate and concentrated under reduced pressure afforded the title compound as light brown solid. The crude compound was used in the next step without further purification. $^1$H NMR (400 MHz, CDCl$_3$, δ ppm): 7.82-7.74 (m, 2H), 7.46 (dd, J=8.2, 7.5 Hz, 1H), 3.92 (s, 3H).

Step B. 1-(4-chloro-3-fluorophenyl)-2-(3-chlorophenyl)ethanone

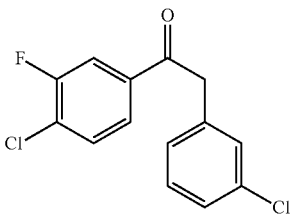 [SMILES: O=C(Cc1cccc(Cl)c1)c1ccc(Cl)c(F)c1]

Sodium bis(trimethylsilyl)amide (1 M in tetrahydrofuran, 4 L, 4000 mmol) was added over 1 hour to a solution of 3-chlorophenyl acetic acid (250.0 g, 1465 mmol) in anhydrous tetrahydrofuran (1.75 L) at −78° C. under nitrogen. The resulting reaction mixture was stirred for an additional hour at −78° C. Then, a solution of methyl-4-chloro-3-fluorobenzoate (221.0 g, 1175 mmol, Example 4, Step A) in tetrahydrofuran (500 mL) was added over 1 hour at −78° C., and the resulting reaction mixture was stirred at the same temperature for 2 hours. The reaction was monitored by TLC. On completion, reaction mixture was quenched with 2 N hydrochloric acid (2.5 L) and aqueous phase was extracted with ethyl acetate (2×2.5 L). The combined organic layer was washed with brine (2.5 L), dried over anhydrous sodium sulfate and concentrated under reduced pressure to provide the crude material which was purified by flash column chromatography (silica gel: 100 to 200 mesh, product eluted in 2% ethyl acetate in hexane) to afford the title compound as a white solid. $^1$H NMR (400 MHz, CDCl$_3$, δ ppm): 7.74 (ddd, J=10.1, 8.9, 1.8 Hz, 2H), 7.56-7.48 (m, 1H), 7.26 (t, J=6.4 Hz, 3H), 7.12 (d, J=5.7 Hz, 1H), 4.22 (s, 2H). MS (ESI) 282.9 [M+H]$^+$.

Step C. Methyl 5-(4-chloro-3-fluorophenyl)-4-(3-chlorophenyl)-2-methyl-5-oxopentanoate

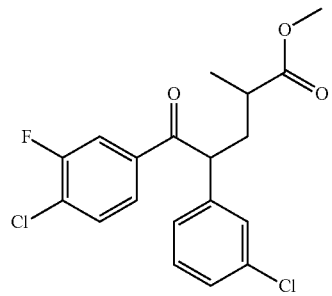 [SMILES: COC(=O)C(C)CC(C(=O)c1ccc(Cl)c(F)c1)c1cccc(Cl)c1]

Methyl methacrylate (125.0 g, 1097 mmol) and potassium tert-butoxide (1 M in tetrahydrofuran, 115 mL, 115 mmol) were sequentially added to a solution of 1-(4-chloro-3-fluorophenyl)-2-(3-chlorophenyl)ethanone (327.0 g, 1160 mmol, Example 4, Step B) in anhydrous tetrahydrofuran (2.61 L), at 0° C. The reaction mixture was stirred for 1 hour at 0° C. and then warmed to ambient temperature and stirred for 12 hours. On completion, the reaction was quenched with water (1.0 L) and extracted with ethyl acetate (2×2.5 L). The combined organic layer was washed with brine, dried over anhydrous sodium sulfate and concentrated under reduced pressure to get the crude material which was purified by flash column chromatography (silica gel: 60 to 120 mesh, product eluted in 4% ethyl acetate in hexane) affording the title compound (mixture of diastereomers) as light yellow liquid. $^1$H NMR (400 MHz, CDCl$_3$, δ ppm): 7.74-7.61 (m, 4H), 7.47-7.40 (m, 2H), 7.28-7.18 (m, 6H), 7.16-7.10 (m, 2H), 4.56 (m, 2H), 3.68 (s, 3H), 3.60 (s, 3H), 2.50-2.39 (m, 2H), 2.37-2.25 (m, 2H), 2.10-2.02 (m, 1H), 1.94 (ddd, J=13.6, 9.1, 4.2 Hz, 1H), 1.21 (d, J=7.0 Hz, 3H), 1.15 (d, J=7.0 Hz, 3H). MS (ESI) 383.0 [M+H]$^+$.

Step D. (3S,5R,6R)-6-(4-Chloro-3-fluorophenyl)-5-(3-chlorophenyl)-3-methyltetrahydro-2H-pyran-2-one and (3R,5R,6R)-6-(4-chloro-3-fluorophenyl)-5-(3-chlorophenyl)-3-methyltetrahydro-2H-pyran-2-one

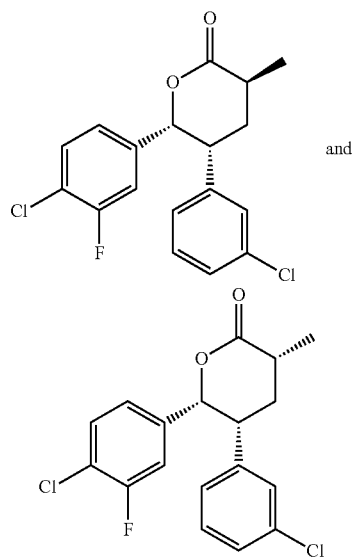

and

In a 2000 mL reaction vessel charged with methyl 5-(4-chloro-3-fluorophenyl)-4-(3-chlorophenyl)-2-methyl-5-oxopentanoate (138.0 g, 360 mmol, Example 4, Step C) (which was cooled on ice for 10 minutes before transferring to a glove bag) anhydrous 2-propanol (500 mL), and potassium tert-butoxide (16.16 g, 144 mmol) were sequentially added while in a sealed glove bag under argon. This mixture was allowed to stir for 30 minutes. RuCl$_2$(S-xylbinap)(S-DAIPEN) (1.759 g, 1.440 mmol, Strem Chemicals, Inc., Newburyport, Mass., weighed in the glove bag) in 30.0 mL toluene was added. The reaction was vigorously stirred at room temperature for 2 hours. The vessel was set on a hydrogenation apparatus, purged with hydrogen 3 times and pressurized to 50 psi (344.7 kPa). The reaction was allowed to stir overnight at room temperature. On completion, the reaction was quenched with water (1.5 L) and extracted with ethyl acetate (2×2.5 L). The organic layer was washed with brine (1.5 L), dried over anhydrous sodium sulfate and concentrated under reduced pressure to get crude material which was purified by flash column chromatography (silica gel; 60-120 mesh; product eluted in 12% ethyl acetate in hexane) to provide a dark colored liquid as a mixture of diastereomers.

The product was dissolved in (240.0 g, 581 mmol) in tetrahydrofuran (1.9 L) and methanol (480 mL), and lithium hydroxide monohydrate (2.5 M aqueous solution, 480.0 mL) was added. The reaction mixture was stirred at ambient temperature for 12 hours. On completion, the solvent was removed under reduced pressure and the residue was acidified with 2 N hydrochloric acid to a pH between 5 and 6. The aqueous phase was extracted with ethyl acetate (2×1.0 L). The combined organic layer was washed with brine (750 mL), dried over anhydrous sodium sulfate, filtered, and concentrated under reduced pressure to provide a dark colored liquid, which was used without further purification.

A portion of the crude intermediate (25.4 g, predominantly seco acid) was added to a 500 mL round bottom flask, equipped with a Dean-Stark apparatus. Pyridinium p-toluenesulfonate (0.516 g, 2.053 mmol) and toluene (274 mL) were added, and the mixture was refluxed for 1 hour (oil bath temperature about 150° C.). The reaction was cooled to room temperature and concentrated under reduced pressure. The reaction was diluted with saturated aqueous sodium bicarbonate (150 mL), extracted with diethyl ether (2×150 mL), and washed with brine (150 mL). The combined organic layer was dried over magnesium sulfate, filtered and concentrated under reduced pressure. Purification by flash column chromatography (divided into 3 portions, 330 g SiO$_2$/each, gradient elution of 0% to 30% acetone in hexanes, 35 minutes) provided the title compounds as a pale yellow solid and a 1:1.6 mixture of diastereomers at C2. MS (ESI) 353.05 [M+H].

Step E. (3S,5R,6R)-3-Allyl-6-(4-chloro-3-fluorophenyl)-5-(3-chlorophenyl)-3-methyltetrahydro-2H-pyran-2-one

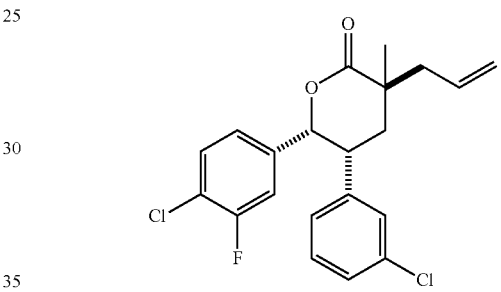

(3S,5R,6R)-6-(4-Chloro-3-fluorophenyl)-5-(3-chlorophenyl)-3-methyltetrahydro-2H-pyran-2-one and (3R,5R,6R)-6-(4-chloro-3-fluorophenyl)-5-(3-h enyl)-3-methyltetrahydro-2H-pyran-2-one (18 g, 51.0 mmol, Example 4, Step D) was added to an oven dried 500 mL round-bottom flask. The solid was dissolved in anhydrous toluene and concentrated to remove adventitious water. 3-Bromoprop-1-ene (11.02 mL, 127 mmol, passed neat through basic alumina prior to addition) in tetrahydrofuran (200 mL) was added and the reaction vessel was evacuated and refilled with argon three times. Lithium bis(trimethylsilyl)amide (1.0 M, 56.1 mL, 56.1 mmol) was added dropwise at −40° C. (dry ice/acetonitrile bath) and stirred under argon. The reaction was allowed to gradually warm to −10° C. and stirred at −10° C. for 3 hours. The reaction was quenched with saturated ammonium chloride (10 mL), concentrated, and the crude product was diluted in water (150 mL) and diethyl ether (200 mL). The layers were separated and the aqueous layer was washed twice more with diethyl ether (200 mL/each). The combined organic layer was washed with brine (100 mL), dried over magnesium sulfate, filtered, and concentrated under reduced pressure to a residue. The residue was purified by flash chromatography (2×330 g silica gel columns, gradient elution of 0% to 30% acetone in hexanes) to provide the title compound as a white solid. The product can alternatively be crystallized from a minimum of hexanes in dichloromethane. Enantiomeric excess was determined to be 87% by chiral SFC (90% CO$_2$, 10% methanol (20 mM ammonia), 5.0 mL/min, 100 bar (10,000 kPa), 40° C., 5 minute method, Phenomenex Lux-2 (Phenomenex, Torrance, Calif.) (100 mm×4.6 mm, 5 μm column), retention times: 1.62 min. (minor) and 2.17 min. (major)). The purity could be upgraded to >98% through recrystallization in hexanes and dichloromethane. ¹H NMR (400 MHz, CDCl₃, δ ppm): 7.24-7.17 (m, 3H), 6.94 (s, 1H), 6.80 (d, J=7.5 Hz, 1H), 6.48 (dd, J=10.0, 1.9 Hz, 1H), 6.40 (d, J=8.3 Hz, 1H), 5.90-5.76 (m, 1H), 5.69 (d, J=5.2 Hz, 1H), 5.20-5.13 (m, 2H), 3.81 (dd, J=13.9, 6.9 Hz, 1H), 2.62 (dd, J=13.8, 7.6 Hz, 1H), 2.50 (dd, J=13.8, 7.3 Hz, 1H), 1.96 (d, J=8.4 Hz, 2H), 1.40 (s, 3H). MS (ESI) 393.1 [M+H]⁺.

Step F. (2S)-2-((2R)-3-(4-Chloro-3-fluorophenyl)-2-(3-chlorophenyl)-3-hydroxypropyl)-N—((S)-1-cyclopropyl-2-hydroxyethyl)-2-methylpent-4-enamide

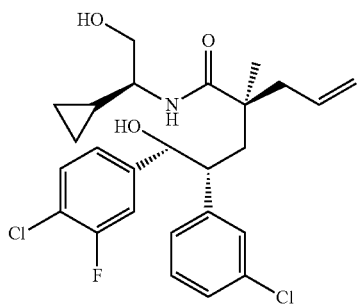 [SMILES: C=CC[C@@](C)(C[C@H](c1cccc(Cl)c1)[C@H](O)c1ccc(Cl)c(F)c1)C(=O)N[C@H](CO)C1CC1]

Sodium methoxide (25% in methanol, 60.7 ml, 265 mmol) was added to a solution of (S)-2-amino-2-cyclopropylethanol hydrochloride (36.5 g, 265 mmol, NetChem Inc., Ontario, Canada) in methanol (177 mL) at 0° C. A precipitate formed during the addition. After the addition was complete, the reaction mixture was removed from the ice bath and warmed to room temperature. The reaction mixture was filtered under a vacuum and the solid was washed with dichloromethane. The filtrate was concentrated under a vacuum to provide a cloudy brown oil. The oil was taken up in dichloromethane (150 mL), filtered under a vacuum and the solid phase washed with dichloromethane to provide the filtrate as a clear orange solution. The solution was concentrated under a vacuum to provide (S)-2-amino-2-cyclopropylethanol as a light brown liquid.

(3S,5R,6R)-3-Allyl-6-(4-chloro-3-fluorophenyl)-5-(3-chlorophenyl)-3-methyltetrahydro-2H-pyran-2-one (32 g, 81 mmol, Example 4, Step E) was combined with (S)-2-amino-2-cyclopropylethanol (26.7 g, 265 mmol) and the suspension was heated at 100° C. overnight. The reaction mixture was cooled to room temperature, diluted with ethyl acetate and washed with 1 N hydrochloric acid (2×), water, and brine. The organic layer was dried over magnesium sulfate and concentrated under vacuum to provide the title compound as a white solid. ¹H NMR (500 MHz, CDCl₃, δ ppm): 0.23-0.30 (m, 2H), 0.45-0.56 (m, 2H), 0.81 (m, 1H), 1.12 (s, 3H), 1.92-2.09 (m, 3H), 2.39 (dd, J=13.6, 7.2 Hz, 1H), 2.86 (br s, 1H), 2.95 (dtd, J=9.5, 6.3, 6.3, 2.9 Hz, 1H), 3.44 (dd, J=11.0, 5.6 Hz, 1H), 3.49 (m, 1H), 3.61 (dd, J=11.0, 2.9 Hz, 1H), 4.78 (d, J=5.6 Hz, 1H), 4.95-5.13 (m, 2H), 5.63 (m, 1H), 5.99 (d, J=6.4 Hz, 1H), 6.94-7.16 (m, 3H), 7.16-7.32 (m, 4H). MS (ESI) 494 [M+H]⁺.

Step G. (3S,5R,6S)-3-Allyl-6-(4-chloro-3-fluorophenyl)-5-(3-chlorophenyl)-1-((S)-1-cyclopropyl-2-hydroxyethyl)-3-methylpiperidin-2-one

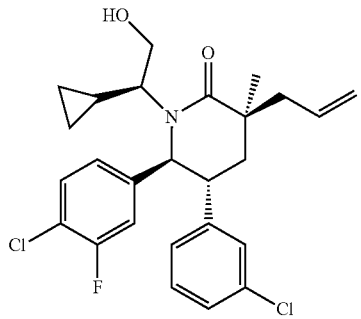 [SMILES: C=CC[C@@]1(C)C[C@H](c2cccc(Cl)c2)[C@@H](c2ccc(Cl)c(F)c2)N([C@H](CO)C2CC2)C1=O]

A solution of (2S)-2-((2R)-3-(4-chloro-3-fluorophenyl)-2-(3-chlorophenyl)-3-hydroxypropyl)-N—((S)-1-cyclopropyl-2-hydroxyethyl)-2-methylpent-4-enamide (40.2 g, 81 mmol, Example 4, Step F) in dichloromethane (80 mL) was added p-toluenesulfonic anhydride (66.3 g, 203 mmol) in dichloromethane (220 mL) at 0° C., and the reaction mixture was stirred for 10 minutes at same the temperature. 2,6-Lutidine (43.6 mL, 374 mmol, Aldrich, St. Louis, Mo.) was added dropwise via addition funnel at 0° C. The reaction mixture was slowly warmed to room temperature, and then it was stirred at reflux. After 24 hours, sodium bicarbonate (68.3 g, 814 mmol) in water (600 mL) and 1,2-dichloroethane (300 mL) were added in succession. The reaction mixture was heated at reflux for an hour and then cooled to room temperature. The layers were separated and the aqueous layer was extracted with dichloromethane. The combined organic layer was washed with 1 N hydrochloric acid, water, and brine, then concentrated under reduced pressure. The residue was purified by flash chromatography (1.5 kg SiO₂ column, gradient elution of 10% to 50% ethyl acetate in hexanes) to provide the title compound as a white solid. ¹H NMR (500 MHz, CDCl₃, δ ppm): 0.06 (m, 1H), 0.26 (m, 1H), 0.57-0.67 (m, 2H), 0.85 (m, 1H), 1.25 (s, 3H), 1.85-2.20 (m, 2H), 2.57-2.65 (m, 2H), 3.09 (ddd, J=11.8, 9.8, 4.8 Hz, 1H), 3.19 (t, J=10.0 Hz, 1H), 3.36 (td, J=10.3, 4.6 Hz, 1H), 3.63 (dd, J=11.0, 4.6 Hz, 1H), 4.86 (d, J=10.0 Hz, 1H), 5.16-5.19 (m, 2H), 5.87 (m, 1H), 6.77 (dd, J=7.7, 1.6 Hz, 1H), 6.80-6.90 (m, 2H), 7.02 (t, J=2.0 Hz, 1H), 7.16 (dd, J=10.0, 7.7 Hz, 1H), 7.21 (dd, J=10.0, 1.6 Hz, 1H), 7.29 (t, J=10.0 Hz, 1H). MS (ESI) 476 [M+H]⁺.

Step H. (3S,5S,6R,8S)-8-Allyl-5-(4-chloro-3-fluorophenyl)-6-(3-chlorophenyl)-3-cyclopropyl-8-methyl-2,3,5,6,7,8-hexahydrooxazolo[32-a]pyridin-4-ium-methylbenzenesulfonate

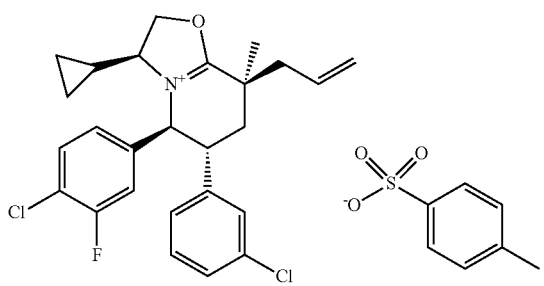

p-Toluenesulfonic acid monohydrate (30.3 g, 159 mmol, Aldrich, St. Louis, Mo.) was added to a solution of (3S,5R,6S)-3-allyl-6-(4-chloro-3-fluorophenyl)-5-(3-chlorophenyl)-1-((S)-1-cyclopropyl-2-hydroxyethyl)-3-methylpiperidin-2-one (73.6 g, 154 mmol) in toluene (386 mL). The reaction mixture was heated at reflux using a Dean-Stark apparatus. After 4 hours, the reaction was cooled and concentrated under reduced pressure to provide the title compound as a pale yellow syrup. The crude product was used in next step without further purification. $^1$H NMR (500 MHz, CDCl$_3$, δ ppm): −0.25 to −0.10 (m, 2H), 0.08-0.18 (m, 1H), 0.33-0.50 (m, 2H), 1.57 (s, 3H), 1.92 (dd, J=3.7 and 13.9 Hz, 1H), 2.37 (s, 3H), 2.63 (dd, J=7.3 and 13.7 Hz, 1H), 2.72 (dd, J=7.6 and 13.7 Hz, 1H), 2.93 (t, J=13.7 Hz, 1H), 3.29 (m, 1H), 4.51 (t, J=8.6 Hz, 1H), 4.57-4.63 (m, 1H), 5.33 (d, J=17.1 Hz, 1H), 5.37 (d, J=10.5 Hz, 1H), 5.47 (dd, J=9.1 and 10.0 Hz, 1H), 5.75-5.93 (m, 2H), 6.80 (br s, 1H), 7.08 (s, 1H), 7.16-7.20 (m, 5H), 7.25-7.32 (m, 2H), 7.87 (d, J=8.3 Hz, 2H). MS (ESI) 458 [M+H]$^+$.

Step I. (3S,5R,6S)-3-Allyl-1-((S)-2-(tert-butylthio)-1-cyclopropylethyl)-6-(4-chloro-3-fluorophenyl)-5-(3-chlorophenyl)-3-methylpiperidin-2-one

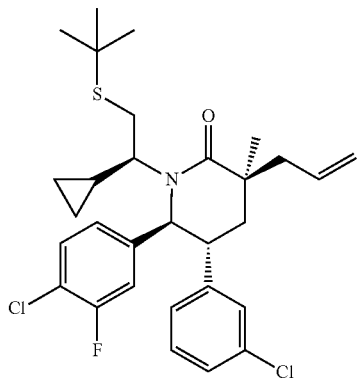 [SMILES: C=CC[C@@]1(C)C[C@H](c2cccc(Cl)c2)[C@@H](c2ccc(Cl)c(F)c2)N([C@H](CSC(C)(C)C)C2CC2)C1=O]

2-Methyl-2-propanethiol (15.25 mL, 135 mmol, dried over activated 4 Å molecular sieves) was added to a solution of lithium bis(trimethylsilyl)amide in tetrahydrofuran (1.0 M, 135 mL, 135 mmol) at room temperature under argon in a 500 mL round-bottomed flask. The reaction mixture was heated to 60° C. After 30 minutes, a solution of (3S,5S,6R,8S)-8-allyl-5-(4-chloro-3-fluorophenyl)-6-(3-chlorophenyl)-3-cyclopropyl-8-methyl-2,3,5,6,7,8-hexahydrooxazolo[3,2-a]pyridin-4-ium 4-methylbenzenesulfonate (78 g, 123 mmol, Example 4, Step H) in anhydrous tetrahydrofuran (100 mL) was added via cannula. The reaction mixture was heated at 60° C. for 3 hours and then cooled to room temperature. The reaction mixture was quenched with water and extracted thrice with ethyl acetate. The organics were pooled, washed with brine, dried over magnesium sulfate, filtered and concentrated under a vacuum to provide a yellow foam. Purification by flash column chromatography (1.5 kg SiO$_2$ column, gradient elution with 5% to 30% ethyl acetate in hexanes provided the title compound as an off-white foam. $^1$H NMR (400 MHz, CDCl$_3$, δ ppm): −0.89 to −0.80 (m, 1H), −0.15 to −0.09 (m, 1H), 0.27-0.34 (m, 1H), 0.41-0.48 (m, 1H), 1.28 (s, 3H), 1.35 (s, 9H), 1.70-1.77 (m, 1H), 1.86 (dd, J=3.1 and 13.5 Hz, 1H), 2.16 (t, J=13.7 Hz, 1H), 2.17-2.23 (m, 1H), 2.60-2.63 (m, 3H), 3.09 (dt, J=3.1 and 10.4 Hz, 1H), 3.62 (t, J=11.1 Hz, 1H), 4.70 (d, J=10.1 Hz, 1H), 5.16 (s, 1H), 5.19-5.21 (m, 1H), 5.82-5.93 (m, 1H), 6.65-6.80 (m, 1H), 6.80-6.83 (m, 1H), 6.84-6.98 (m, 1H), 7.05-7.07 (m, 1H), 7.12-7.18 (m, 2H), 7.19-7.26 (m, 1H). MS (ESI) 548.2 [M+H]$^+$.

Step J. 2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetic acid

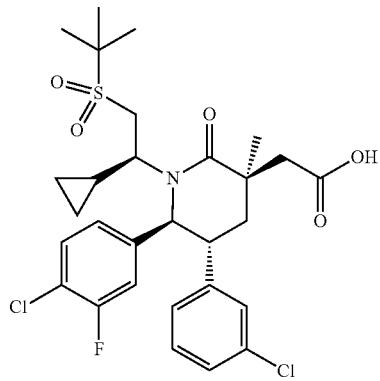 [SMILES: CC(C)(C)S(=O)(=O)C[C@H](C1CC1)N1C(=O)[C@@](C)(CC(=O)O)C[C@H](c2cccc(Cl)c2)[C@H]1c1ccc(Cl)c(F)c1]

Ruthenium(III) chloride hydrate (0.562 mg, 2.493 mmol) was added to a mixture of (3S,5R,6S)-3-allyl-1-((S)-2-(tert-butylthio)-1-cyclopropylethyl)-6-(4-chloro-3-fluorophenyl)-5-(3-chlorophenyl)-3-methylpiperidin-2-one (62.17 g, 113 mmol, Example 4, Step I) and sodium periodate (24.67 g) in ethyl acetate (216 mL), acetonitrile (216 mL) and water (324 mL) at 20° C. The temperature quickly rose to 29° C. The reaction mixture was cooled to 20° C. and the remaining equivalents of sodium periodate were added in five 24.67 g portions over 2 hours, being careful to maintain an internal reaction temperature below 25° C. The reaction was incomplete, so additional sodium periodate (13 g) was added. The temperature increased from 22° C. to 25° C. After stirring for an additional 1.5 hours, the reaction mixture was filtered under a vacuum and washed with ethyl acetate. The layers were separated and the aqueous layer was extracted with ethyl acetate. The organics were pooled, washed with brine, dried over magnesium sulfate, filtered and concentrated under a vacuum to provide a dark green foam. Purification by flash column chromatography (1.5 kg SiO$_2$ column, gradient elution of 0% to 20% isopropanol in hexanes) provided an off-white foam. 15% Ethyl acetate in heptanes (970 mL) was added to the foam, and the mixture was heated at 80° C. until the foam dissolved. The solution was then cooled slowly, and at 60° C. the solution was seeded with previously obtained crystalline material. The mixture was cooled to room temperature and then allowed to stand at room temperature for 2 hours before collecting the solid by vacuum filtration to provide a white solid with a very pale pink hue (57.1 g). The mother liquor was concentrated under a vacuum to provide a pink foam (8.7 g). 15% ethyl acetate in heptanes (130 mL) was added to the foam, and it was heated at 80° C. to completely dissolve the material. The solution was cooled, and at 50° C., it was seeded with crystalline material. After cooling to room temperature the solid was collected by vacuum filtration to provide a white crystalline solid with a very pale pink hue. $^1$H NMR (500 MHz, CDCl$_3$, δ ppm): −1.10 to −1.00 (m, 1H), −0.30 to −0.22 (m, 1H), 0.27-0.37 (m, 1H), 0.38-0.43 (In, 1H), 1.45

(s, 9H), 1.50 (s, 3H), 1.87 (dd, J=2.7 and 13.7 Hz, 1H), 1.89-1.95 (m, 1H), 2.46 (t, J=13.7, 1H), 2.69-2.73 (m, 1H), 2.78 (d, J=14.9 Hz, 1H), 2.93 (dd, J=2.0 and 13.7 Hz, 1H), 3.07 (d, J=14.9 Hz, 1H), 3.11 (dt, J=2.7 and 11.0 Hz, 1H), 4.30 (t, J=13.5 Hz, 1H), 4.98 (d, J=10.8 Hz, 1H), 6.75-6.87 (m, 1H), 6.88-6.90 (m, 1H), 6.98 (br s, 1H), 7.02-7.09 (m, 1H), 7.11-7.16 (m, 2H), 7.16-7.25 (m, 1H). MS (ESI) 598.1 [M+H]$^+$.

Example 5

4-(2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid

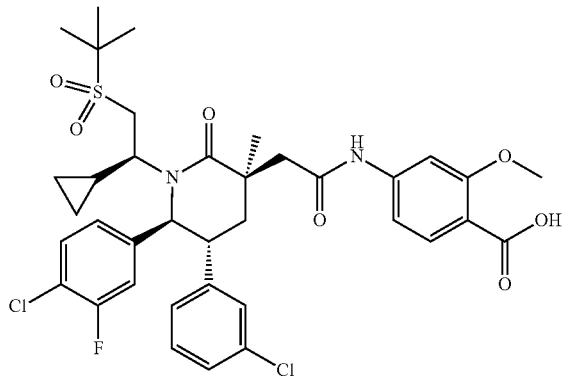 [SMILES: COc1cc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)ccc1C(=O)O]

Step A. Methyl 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoate

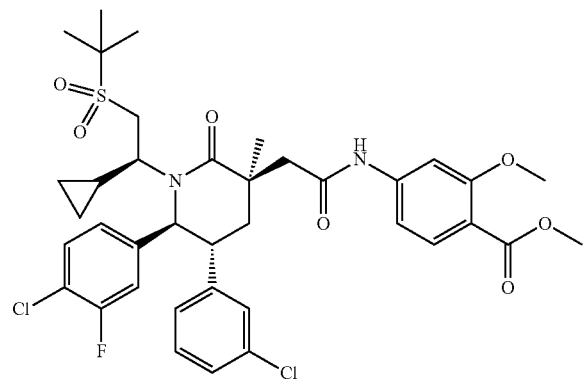 [SMILES: COC(=O)c1ccc(NC(=O)C[C@@]2(C)C[C@H](c3cccc(Cl)c3)[C@@H](c3ccc(Cl)c(F)c3)N([C@H](CS(=O)(=O)C(C)(C)C)C3CC3)C2=O)cc1OC]

N-(3-Dimethylaminopropyl)-N'-ethylcarbodiimide hydrochloride (EDC, 76 g, 398 mmol) was added to a mixture of 2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetic acid (79.4 g, 133 mmol, Example 4, Step J) and methyl 4-amino-2-methoxybenzoate (26.4 g, 146 mmol) in pyridine (332 mL) at 3° C. The mixture was allowed to warm to room temperature and was stirred at room temperature for 16 hours. The reaction mixture was cooled to 0° C. and added to an ice-cold solution of 1 M hydrochloric acid (1 L). Ether (1 L) was added and the layers were agitated and then separated. The organic layer was washed with 1 M hydrochloric acid (6×500 mL), saturated aqueous sodium bicarbonate (500 mL), brine (500 mL), dried over magnesium sulfate, filtered and concentrated under a vacuum to provide an off-white foam. $^1$H NMR (400 MHz, CDCl$_3$, δ ppm): −1.20 to −1.12 (m, 1H), −0.35 to −0.20 (m, 1H), 0.05-0.20 (m, 1H), 0.32-0.45 (m, 1H), 1.45 (s, 9H), 1.48 (s, 3H), 1.86-1.98 (m, 1H), 2.03 (dd, J=2.7 and 13.7 Hz, 1H), 2.43 (t, J=13.7, 1H), 2.64-2.75 (m, 1H), 2.80 (d, J=14.3 Hz, 1H), 2.89-2.96 (m, 2H), 3.24 (dt, J=2.5 and 10.8 Hz, 1H), 3.89 (s, 3H), 3.96 (s, 3H), 4.28-4.36 (m, 1H), 4.98 (d, J=10.8 Hz, 1H), 6.85-6.93 (m, 3H), 6.99 (br s, 1H), 7.06-7.18 (m, 4H), 7.82 (br s, 1H), 7.85 (d, J=8.4 Hz, 1H), 8.81 (br s, 1H). MS (ESI) 761.2 [M+H]$^+$.

Step B. 4-(2-((3R,5R,6S)-1-((S)-2-(tert-Butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoic acid

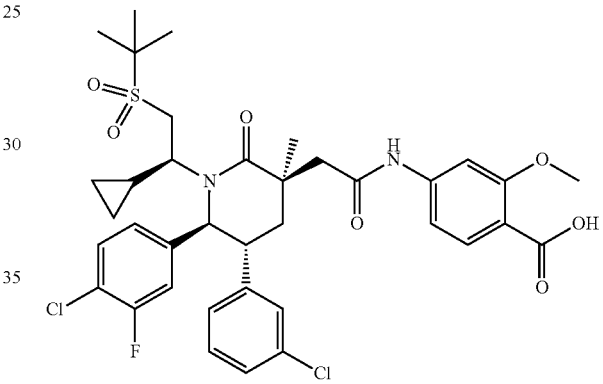

A solution of lithium hydroxide monohydrate (18.2 g, 433 mmol) in water (295 mL) was added to a solution of methyl 4-(2-((3R,5R,6S)-1-((S)-2-(tert-butylsulfonyl)-1-cyclopropylethyl)-6-(4-chloro-3-fluorophenyl)-5-(3-chlorophenyl)-3-methyl-2-oxopiperidin-3-yl)acetamido)-2-methoxybenzoate (164.9 g, 217 mmol, Example 5, Step A) in tetrahydrofuran (591 mL) and methanol (197 mL) at room temperature. After stirring for 15 hours at room temperature, a trace amount of the ester remained, so the reaction mixture was heated at 50° C. for 1 hour. When the reaction was complete, the mixture was concentrated under a vacuum to remove the tetrahydrofuran and methanol. The thick mixture was diluted with water (1 L) and 1 M hydrochloric acid (1 L) was added. The resulting white solid was collected by vacuum filtration in a Büchner funnel. The vacuum was removed, and water (1 L) was added to the filter cake. The material was stirred with a spatula to suspend it evenly in the water. The liquid was then removed by vacuum filtration. This washing cycle was repeated three more times to provide a white solid. The solid was dried under vacuum at 45° C. for 3 days to provide the title compound as a white solid. $^1$H NMR (500 MHz, DMSO-d$_6$) δ ppm −1.30 to −1.12 (m, 1H), −0.30 to −0.13 (m, 1H), 0.14-0.25 (m, 1H), 0.25-0.38 (m, 1H), 1.30 (s, 3H), 1.34 (s, 9H), 1.75-1.86 (m, 1H), 2.08-2.18 (m, 2H), 2.50-2.60 (m, 1H), 2.66 (d, J=13.7, 1H), 3.02-3.16 (m, 2H), 3.40-3.50 (m, 1H), 3.77 (s, 3H), 4.05-4.20 (m, 1H), 4.89 (d, J=10.5 Hz, 1H), 6.90-6.93 (m, 3H), 7.19 (d, J=8.8 Hz, 1H), 7.22-7.26 (m, 3H), 7.40-7.50 (m, 1H), 7.54 (br s, 1H), 7.68 (d, J=8.6 Hz, 1H) 10.44 (s, 1H), 12.29 (br s, 1H). MS (ESI) 747.2 [M+H]$^+$.

Another particular MDM2 inhibitor is Compound B (also known as AMG 2653149 or 2653149), which is Example 256 of published PCT application WO2011/153,509. Other MDM2 inhibitors that can be used in the combinations of the present invention include those disclosed in published PCT application WO2013/049250; U.S. provisional patent application No. 61/766,635; and U.S. provisional patent application No. 61/784,230. Still other MDM2 inhibitors that can be used in the combinations of the present invention include RG7112 (also known as RO504337), RG7388 (also known as idasanutin, and RO5503781), SAR405838 (also known as MI-773), SAR299155, MK-8242 (also known as SCH 900242), CGM097 and DS 3032. The structures of RG7112 and SAR299155 as well as other inhibitors of MDM2 that can be used in the present invention are shown in Bioorganic & Medicinal Chemistry Letters 23 (2013) 2480-2485, which summarizes pathways to the clinic for MDM2 inhibitors. Still other MDM2 inhibitors that can be used in the combinations of the present invention include RG7775 and Novartis CGM097.

The MDM2 inhibitors of the present invention can be used in combination with Aurora kinase inhibitors, such as those found in published PCT application WO2011/031842. A particular compound is AMG 900 (Example 1).

The MDM2 inhibitors of the present invention can be used in combination with MAP kinase pathway inhibitors. Examples of proteins in the MAP kinase pathway that can be inhibited and the inhibitors of such proteins used in combination with an MDM2 inhibitors are BRAF inhibitors, Pan-RAF inhibitors, and MEK inhibitors. There are three main RAF isoforms: ARAF, BRAF and CRAF. A pan-RAF inhibitor shows inhibitory activity on more than one RAF isoform. In contrast, a BRAF inhibitor exhibits more inhibitor activity (or selectivity) towards BRAF than the other RAF proteins.

The MDM2 inhibitors of the present invention can be used in combination with MEK inhibitors, such as those found in published PCT application WO2002/006213. A particular compound is N-(((2R)-2,3-dihydroxypropyl)oxy)-3,4-difluoro-2-((2-fluoro-4-iodophenyl)amino)benzamide, also known as AMG 1009089 or 1009089, (Example 39).

The MDM2 inhibitors of the present invention can be used in combination with BRAF inhibitors, such as those found in published PCT application WO2008/153,947. A particular compound is AMG 2112819 (also known as 2112819) (Example 56). Another particular BRAF inhibitor that can be used in the combinations of the present invention is dabrafenib. Another BRAF inhibitor that can be used in the combinations of the present invention is vemurafenib.

Pan-RAF inhibitors can also be used along with MDM2 inhibitors in the combinations of the present invention. Particular Pan-Raf inhibitor include RAF265 and MLN-2480.

The MDM2 inhibitors of the present invention can be used in combination with MEK inhibitors. Particular MEK inhibitors that can be used in the combinations of the present invention include PD0325901, trametinib, pimasertib, MEK162 [also known as binimetinib], TAK-733, GDC-0973 and AZD8330. A particular MEK inhibitor that can be used along with MDM2 inhibitor in the combinations of the present invention is trametinib (also called AMG 2712849 or 2712849). Another particular MEK inhibitor is N-(((2R)-2,3-dihydroxypropyl)oxy)-3,4-difluoro-2-((2-fluoro-4-iodophenyl)amino)benzamide, also known as AMG 1009089, 1009089 or PD0325901. Another particular MEK inhibitor that can be used in the combinations of the present invention includes cobimetinib.

In another aspect, the present invention relates to the use of the compound of the present invention in combination with one or more pharmaceutical agent that is an inhibitor of a protein in the phosphatidylinositol 3-kinase (PI3K) pathway. Examples of proteins in the PI3K pathway include PI3K, mTOR and PKB (also known as Akt or AKT). The PI3K protein exists in several isoforms including α, β, δ, or γ. It is contemplated that a PI3K inhibitor that can be used in the present invention can be selective for one or more isoform. By selective it is meant that the compounds inhibit one or more isoform more than other isoforms. Selectivity is a concept well known to those is the art and can be measured with well-known in vitro or cell-based activity assays. Preferred selectivity includes greater than 2-fold, preferably 10-fold, or more preferably 100-fold greater selectivity for one or more isoform over the other isoforms. In one aspect, the PI3K inhibitors that can be used in combination with compounds of the present invention are PI3K α selective inhibitors. In another aspect the compound is a PI3K δ selective inhibitor. In still another aspect the compound is a PI3K β selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with the compound of the present invention include:

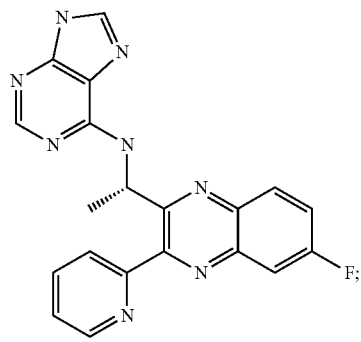

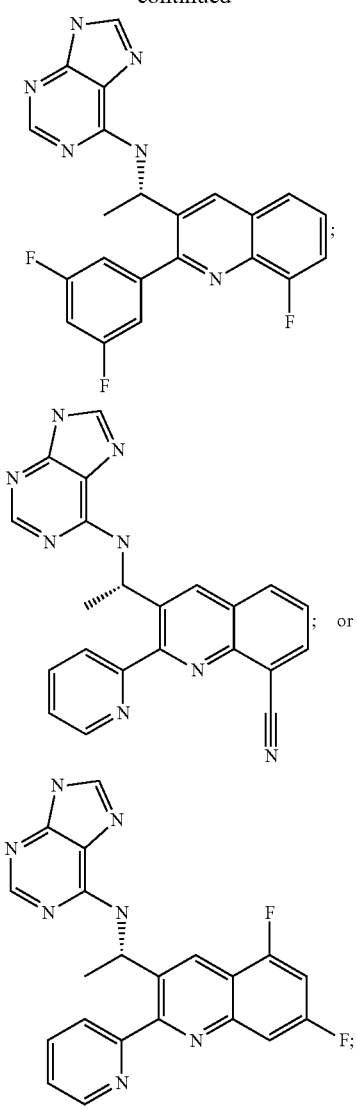

or a pharmaceutically acceptable salt thereof.

Also preferred is a compound of Formula IIa below, or a pharmaceutically acceptable salt thereof, wherein $X^1$ is fluorine or hydrogen; $Y^1$ is hydrogen or methyl; and $Z^1$ is hydrogen or methyl. A particular PI3K inhibitor that can be used in the combinations of the present invention is AMG 511 (also known as AMG 2539965 or 2539965), which is Example 148 of published PCT application WO2010/126895.

Other PI3K inhibitors that can be used in combination with MDM2 inhibitors in the combinations of the present invention include Pan-PI3K inhibitors such as BKM120 and GDC-0941; PI3Kα selective inhibitors such as AMG 511 and BYL719; and PI3K R selective inhibitors such as GSK-2636771.

Compounds that inhibit both PI3K and mTOR (dual inhibitors) are known. In still another aspect, the present invention provides the use of dual PI3K and mTOR inhibitors for use in combination with MDM2 inhibitors. An example of a particular dual inhibitor is GDC-0980.

mTOR is a protein in the PI3K pathway. It is another aspect of the present invention to use an mTOR inhibitor in combination with MDM2 inhibitors, mTOR inhibitors that can be used in combination with the compound of the present invention include those disclosed in the following documents: PCT published application no. WO2010/132598 and PCT published application no. WO2010/096314. mTOR inhibitors that can be used in combination with MDM2 inhibitors in the combinations of the present invention include AZD2014 and MLN0128.

PKB (AKT) is also a protein in the PI3K pathway. It is another aspect of the present invention to use an AKT inhibitor in combination with an MDM2 inhibitor. AKT inhibitors that can be used in combination with the compound of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1. Particular AKT inhibitors that can be used in combination with MDM2 inhibitors in the combinations of the present invention include MK-2206, GDC-0068 and AZD5363.

MDM2 inhibitors can also be used in combination with CDK4 and/or 6 inhibitors in the present invention CDK 4 and/or 6 inhibitors that can be used in the present combinations include those disclosed in the following documents: PCT published application no. WO 2009/085185 or U.S. patent application publication no. US2011/0097305.

Other compounds that can be used in combination with MDM2 inhibitors in the combinations of the present invention include compounds that inhibit proteins that are part of the intrinsic apoptosis pathway. Examples of such compounds include Bcl2/BclxL inhibitors such as navitoclax and Bcl2 inhibitors as such as ABT-199.

Other compounds that can be used in combination with MDM2 inhibitors in the combinations of the present invention include BCR-ABL inhibitors such as dasatinib and HDAC inhibitors such as panobinostat.

Other compounds that can be used in combination with MDM2 inhibitors in the combinations of the present invention include platinums, such as Cisplatin, Carboplatin and Oxaliplatin; Topoisomerase II inhibitors, typically of the anthracycline class, such as doxorubicin, daunorubicin, idarubicin, epirubicin, pegylated liposomal doxorubicin hydrochloride, myocet and etoposide; Topoisomerase I inhibitors such as irinotecan (CPT-11); DNA alkylation agents such as temozolomide; and nucleoside analogs such as cytarabine and decitabine.

Other compounds that can be used in combination with MDM2 inhibitors in the combinations of the present invention include receptor and non-receptor kinase inhibitors including tyrosine kinase inhibitors. Example of such compounds include imatinib, dasatinib, ponatinib, bosutinib, nilotininb, quizartinib, midostaurin, erlotinib and lapatinib.

The compound of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compound of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpylrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of the compound of the present invention include ointments, powders, sprays and inhalants. The active compound or compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. A particular dosage of a compound of the present invention is the FDA approved dosage, if the compound has been approved.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compound of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compound of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compound of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, because the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy) ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

The compounds of the present invention may contain asymmetric or chiral centers, and therefore, exist in different stereoisomeric forms. It is contemplated that all stereoisomeric forms of the compound as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that the compounds of the present invention may exist in different tautomeric forms. All tautomers of the compound of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{18}O$, $^{31}P$, $^{32}P$, $^{35}S$, $^{18}F$, and $^{36}Cl$. In one aspect, the present invention relates to compounds wherein one or more hydrogen atom is replaced with deuterium ($^{2}H$) atoms.

The compounds of the present invention that contains the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing the compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, patent applications and other documents recited herein are hereby incorporated by reference in their entirety.

The examples presented below illustrate specific embodiments of the present invention. These examples are meant to be representative and are not intended to limit the scope of the claims in any manner The following abbreviations may be used herein:

| | |
|---|---|
| 932 or 2705932 | AMG 232 |
| ADD | additivity |
| AML | acute myelogenous leukemia |
| ATP | adenosine triphosphate |
| Cispl | cisplatin |
| CML | chronic myelogenous leukemia |
| CPT-11 | irinotecan |
| DIC | drug in capsules |
| DLBCL | diffuse large B-cell lymphoma |
| Dox | doxorubicin |
| GBM | glioblastoma |
| HPβCD | hydroxypropyl beta cyclodextrin |
| HPMC | hydroxypropyl methylcellulose |
| MDS | myelodysplastic syndrome |
| mpk | milligrams per kilogram |
| NHL | non-Hodgkin's lymphoma |
| NMR | nuclear magnetic resonance |
| NSCLC | non-small cell lung cancer |
| PBS | phosphate buffered saline |
| PCT | patent cooperation treaty |
| RTK | receptor tyrosine kinase |
| TGI | tumor growth inhibition |
| Tx begins | treatment begins |

Cell Cuture Reagents

| | |
|---|---|
| Tween ® 80 | polyoxyethylene (20) sorbitan monooleate (Uniqema Americas, Inc., Wilmington, DE) |
| Pluronic ® F68 | polyoxyethylene-polyoxypropylene block co-polymer (BASF Corp., Mount Olive, NJ) |

EXAMPLES

In Vitro Cell-Based Combination Studies

Cell lines were purchased from American Type Culture Collection (ATCC), German Collection of Microorganisms and Cell Cultures (DSMZ), and Japanese Collection of Research Bioresources (JCRB). Each line was cultured in its recommended growth medium. Cell line A375sq2 was made in accordance with the procedure set forth in J. Med. Chem. 2009, 52, 6189-6192, footnote 13.

For Examples 1 to 71, cells were seeded into 384-well cell culture plates at initial densities ranging from 300 to 7500 cells per well in a 30 µL volume, depending on the growth rate of the cell line, so that adherent cells would remain at subconfluent densities by the end of the 72-hour treatment period. In order to determine the appropriate concentration range to test in subsequent combination experiments, 10 µL of a 19-point, two-fold serial titration of compound starting at a high final concentration of 20 µM, as well as a 0.25% dimethyl sulfoxide (DMSO) control were added to the cells 16 hours after seeding. CellTiter-Glo® Luminescent Cell Viability Assay (Promega; Madison, Wis.) was used to determine the number of viable cells based on quantitation of the amount of ATP present, an indicator of metabolically active cells. Luminescence was measured with an EnVision® Multilabel Reader (Perkin Elmer; Waltham, Mass.) for each cell line at time zero ($V_0$) before the addition of compounds, as well as after 72 hours of compound treatment ($T_{72}$). Growth inhibition (GI) was calculated according to the following equations, where $V_{72}$ was luminescence of DMSO control at 72 hours and $T_{72}$ was luminescence of the compound-treated sample: if $T_{72} \geq V_0$, then $GI=100\times(1-((T_{72}-V_0)/(V_{72}-V_0)))$; if $T_{72}<V_0$, then $GI=100\times(1-((T_{72}-V_0)/V_0))$. This formula is derived from the growth inhibition calculation used in the National Cancer Institute's NCI-60 high throughput screen. On a scale of 0 to 200 percent growth inhibition, a value of 0 represents uninhibited growth (i.e. DMSO control), 100 typically represents stasis (signal equivalent at time zero reading), and 200 represents complete cell killing. Sigmoidal dose response curves were plotted using a 4-parameter logistic model. For all combinations tested in any given cell line, the starting high concentration and dilution factor of each compound was chosen to well-define the curve maximum, curve minimum, and slope over a range of 9 doses.

Two-way combination experiments were conducted essentially as described above, with the following exceptions. To each well, 5 µL of a 9-point serial titration of the first compound (starting high final concentration and dilution factor determined as previously described) along with DMSO control was added to the cells in 10 identical rows (x-axis) of a 384-well plate. Then, 5 µL of a 9-point serial titration of the second compound (starting high final concentration and dilution factor determined as previously described) along with DMSO control were added to the cells in 10 identical columns (y-axis). The final concentration of DMSO in each well was 0.25%. Duplicate 100-well (10×10) matrices were run on each 384-well plate. Growth inhibition for each well of the matrix was calculated as previously described, and the data were analyzed for synergistic interactions using Chalice™ Analyzer software (Zalicus; Cambridge, Mass.) which generated synergy scores based on the Loewe Additivity model (Lehár, J., et al. (2009). "Synergistic drug combinations tend to improve therapeutically relevant selectivity." Nat Biotech 27(7): 659-666) and Rickles, et al (2012) "Adenosine A2A and Beta-2 Adrenergic Receptor Agonists: Novel Selective and Synergistic Multiple Myeloma Targets Discovered through Systematic Combination Screening" Mol Cancer Therapeutics 11 (7): 1432.

The Loewe ADD (additivity) model quantifies combination effects. Combinations were ranked initially by Additivity Excess Volume, which is defined as ADD Volume=$\Sigma C_X, C_Y (I_{data}-I_{Loewe})$. where $I_{Loewe}(C_X,C_Y)$ is the inhibition that satisfies $(C_X/EC_X)+(C_Y/EC_Y)=1$, and $EC_{X,Y}$ are the effective concentrations at $I_{Loewe}$ for the single agent curves. A "Synergy Score" was also used, where the Synergy Score $S=\log f_X \log f_Y \Sigma I_{data}(I_{data}-I_{Loewe})$, summed over all non-single-agent concentration pairs, and where $\log f_{X,Y}$ is the natural logarithm of the dilution factors used for each single agent. This effectively calculates a volume between the measured and Loewe additive response surfaces, weighted towards high inhibition and corrected for varying dilution factors. An uncertainty $\sigma_S$ was calculated for each synergy score, based on the measured errors for the $I_{data}$ values and standard error propagation.

In the examples shown, the Growth Inhibition (%) matrices contain the consensus growth inhibition values calculated from the luminescence data using the formulas described above; the ADD Model Growth Inhibition (%) matrices contain the predicted growth inhibition values based on the Loewe additivity model, which was derived from the modeled single agent growth inhibition curves; and the ADD Excess Growth Inhibition (%) matrices contain the values of growth inhibition in excess of the additivity model. The additivity model serves as a "null-hypothesis" and assumes no synergistic interaction between the two agents. Any activity observed after subtraction of the ADD model from the Growth Inhibition dose response matrix (=ADD Excess Growth Inhibition) is indicative of synergy.

For Examples 72-89, two-way combination experiments were carried out in a similar manner as described above, but using a high-throughput screening format. Cells were thawed from a liquid nitrogen preserved state. Screening began after the cells were expanded and were dividing at their expected doubling times. Cells were seeded in growth media in either black 1536-well or 384-well tissue culture treated plates at the cell densities as listed in the table below.

| Cell Line | Plate Format | Cell Density |
|---|---|---|
| RT4 | 384 | 500 |
| SJSA-1 | 1536 | 100 |
| KS-1 | 1536 | 100 |
| MCF7 | 384 | 500 |
| RKO | 1536 | 100 |
| SNG-M | 1536 | 100 |
| RPMI-2650 | 1536 | 200 |
| G-401 | 1536 | 100 |
| CML-T1 | 1536 | 100 |
| EOL-1 | 384 | 500 |
| MOLM-13 | 384 | 500 |
| SK-HEP-1 | 1536 | 100 |
| A427 | 1536 | 100 |
| DOHH-2 | 1536 | 100 |
| 22RV1 | 1536 | 100 |
| A375 | 1536 | 100 |
| C32 | 384 | 500 |
| MKN45 | 1536 | 100 |
| NOI-SNJ-1 | 1536 | 100 |
| SW982 | 1536 | 100 |
| HT-29 | 1536 | 100 |
| PC-3 | 1536 | 100 |

Cells were equilibrated in assay plates via centrifugation and placed in incubators attached to the Dosing Modules at 37° C. for 24 hours before treatment. At the time of treatment, a set of untreated assay plates were collected and ATP levels were measured by adding ATPLite 1 step Luminescent Assay reagent (Perkin Elmer; Waltham, Mass.). These Tzero ($T_0$) plates were read using ultrasensitive luminescence on an EnVision® Multilabel Reader (Perkin Elmer; Waltham, Mass.). Treated assay plates were incubated with compound for 72 hours and were assayed for viable cell number at the endpoint. All data points were collected via automated processes; quality controlled; and analyzed using Chalice™ Analyzer software (Zalicus; Cambridge, Mass.) which generated synergy scores based on the Loewe Additivity model (Lehár et al., supra). Assay plates were accepted if they passed the following quality control standards: relative luciferase values were consistent throughout the entire experiment, Z-factor scores were greater than 0.6, and untreated/vehicle controls behaved consistently on the plate. The synergistic interaction of each experimental combination was evaluated for statistical significance. The synergy scores calculated for individual replicates of heterologous combinations (A×B) were compared to the synergy scores of individual replicates of the component self-crosses (A×A and B×B) using two sample Student's t-test with unequal variance. Only those combinations in which the synergy score of A×B was statistically significant (p-value<0.05) when compared to both A×A and B×B were considered synergistic.

Three-way combination experiments were conducted essentially as described above, with the following exceptions. Ten identical 384-well plates each containing duplicate 100-well two-way combinations were set-up as before, except that 3.3 μL of 3× final concentration of each compound were added. Then 3.3 μL of a single fixed concentration of the third compound were added to all of the wells of the matrix on a given plate. Thus the ten plates comprised the 9-point serial titration of the third compound (z-axis; starting high final concentration and dilution factor determined as previously described), along with a DMSO control (i.e. no compound 3 added) plate. Growth inhibition for each well of the matrix was calculated as previously described. Examples of cell lines used in the above-identified experiments are set forth in the table below. The tissue column of the table indicate the type of tissue from which the cells were obtained, and the mutation column indicates certain mutations identified in the particular cell line.

| Cell Line | Tissue | Mutation |
| --- | --- | --- |
| HT-1197 | Bladder | NRAS, PI3K |
| RT4 | Bladder | TSC1 |
| KNS-81-FD | Brain; CNS | EGFR |
| CAL-51 | Breast | PI3K |
| MCF7 | Breast | PI3K |
| MDA-MB-175-VII | Breast | HER2 autocrine loop |
| UACC-812 | Breast | HER2 amplified |
| HCT116 | Colon | KRAS, PI3K |
| LS 174T | Colon | KRAS, PI3K |
| RKO | Colon | BRAF, PI3K |
| SW48 | Colon | EGFR |
| BV-173 | Haematopoietic and lymphoid (CML) | BCR-ABL |
| CML-T1 | Haematopoietic and lymphoid (CML) | BCR-ABL |
| GDM-1 | Haematopoietic and lymphoid (AML) | None identified |
| ML-2 | Haematopoietic and lymphoid (AML) | KRAS |
| MOLM-13 | Haematopoietic and lymphoid (AML) | FLT3 ITD |
| OCI-AML3 | Haematopoietic and lymphoid (AML) | Not known |
| CAL-54 | Kidney | MET amplified |
| SK-HEP-1 | Liver | BRAF |
| A427 | Lung (NSCLC) | KRAS |
| A549 | Lung | KRAS |
| NCI-H1666 | Lung (NSCLC) | BRAF (not V600E) |
| NCI-H460 | Lung (NSCLC) | KRAS, PI3K |
| A2780 | Ovary | PTEN |
| A375sq2 | Skin (Melanoma) | BRAF |
| A375 | Skin (Melanoma) | BRAF |
| C32 | Skin (Melanoma) | BRAF, PTEN |
| G-361 | Skin (Melanoma) | BRAF |
| SH-4 | Skin (Melanoma) | BRAF |
| A204 | Soft tissue (rhabdomyosarcoma) | None identified |
| G-401 | Soft tissue (kidney) | None identified |
| MKN45 | Stomach | MET amplified |

Figure 89:
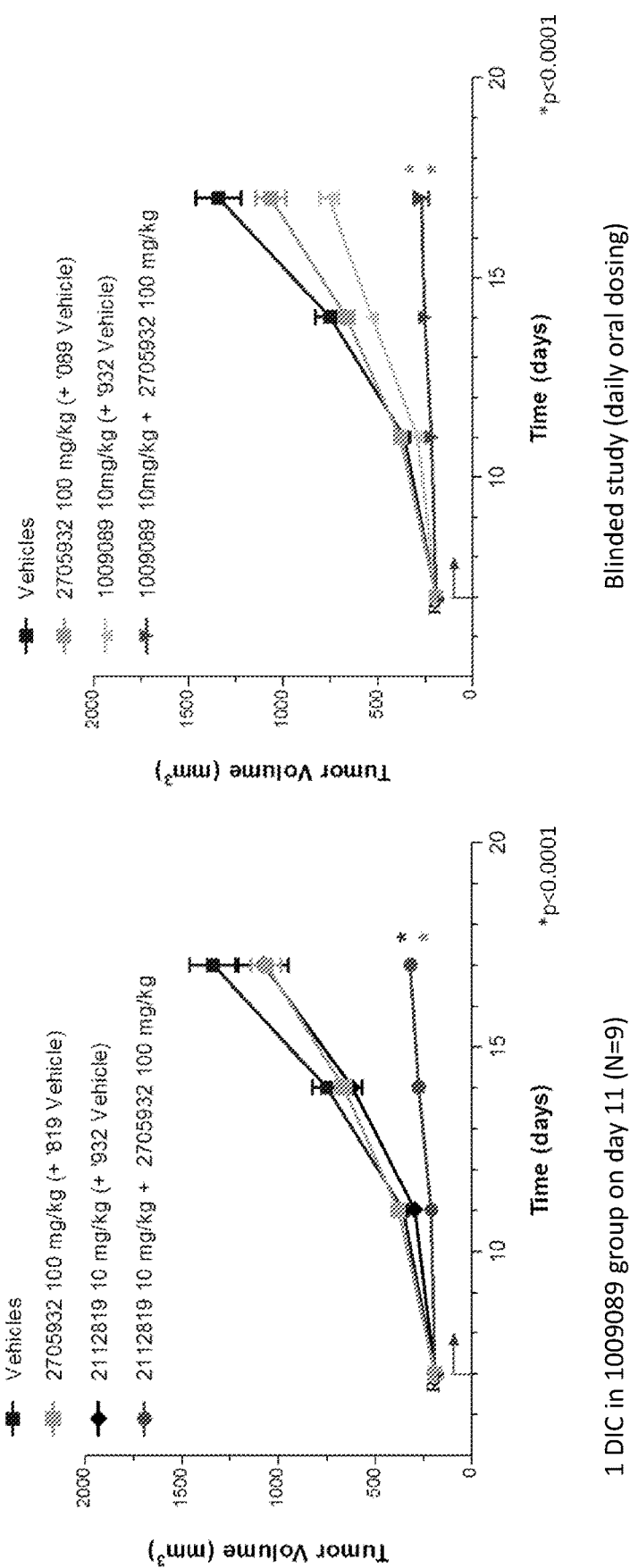
FIG. 89 shows tumor xenograft data for the combination of AMG 232 and BRAF inhibitor AMG 2112819 or MEK inhibitor 1009089 in a RKO tumor.
Figure 90:
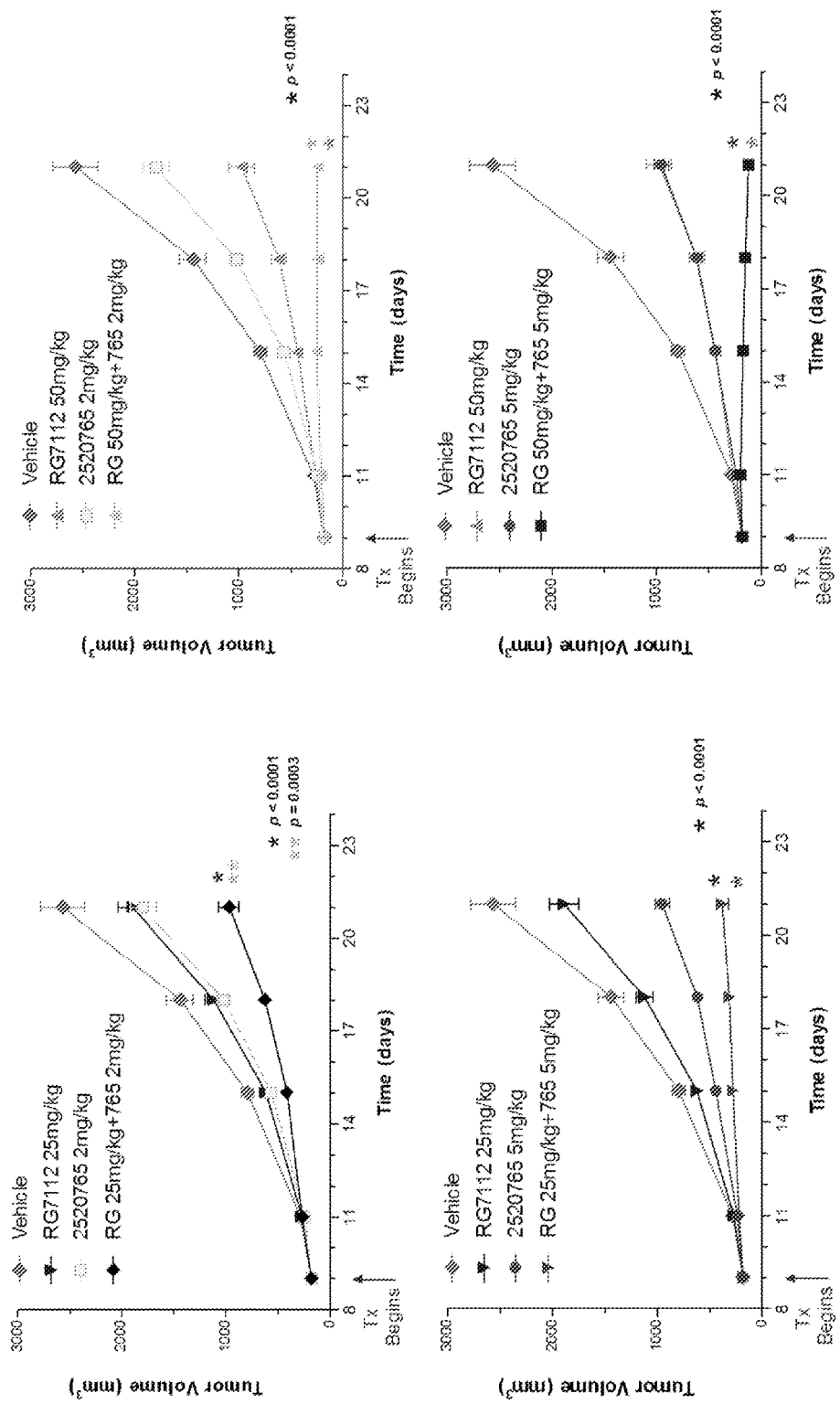
FIG. 90 shows tumor xenograft data for the combination of RG7112 and PI3K inhibitor AMG 2520765 in a U87 tumor.
Figure 91:
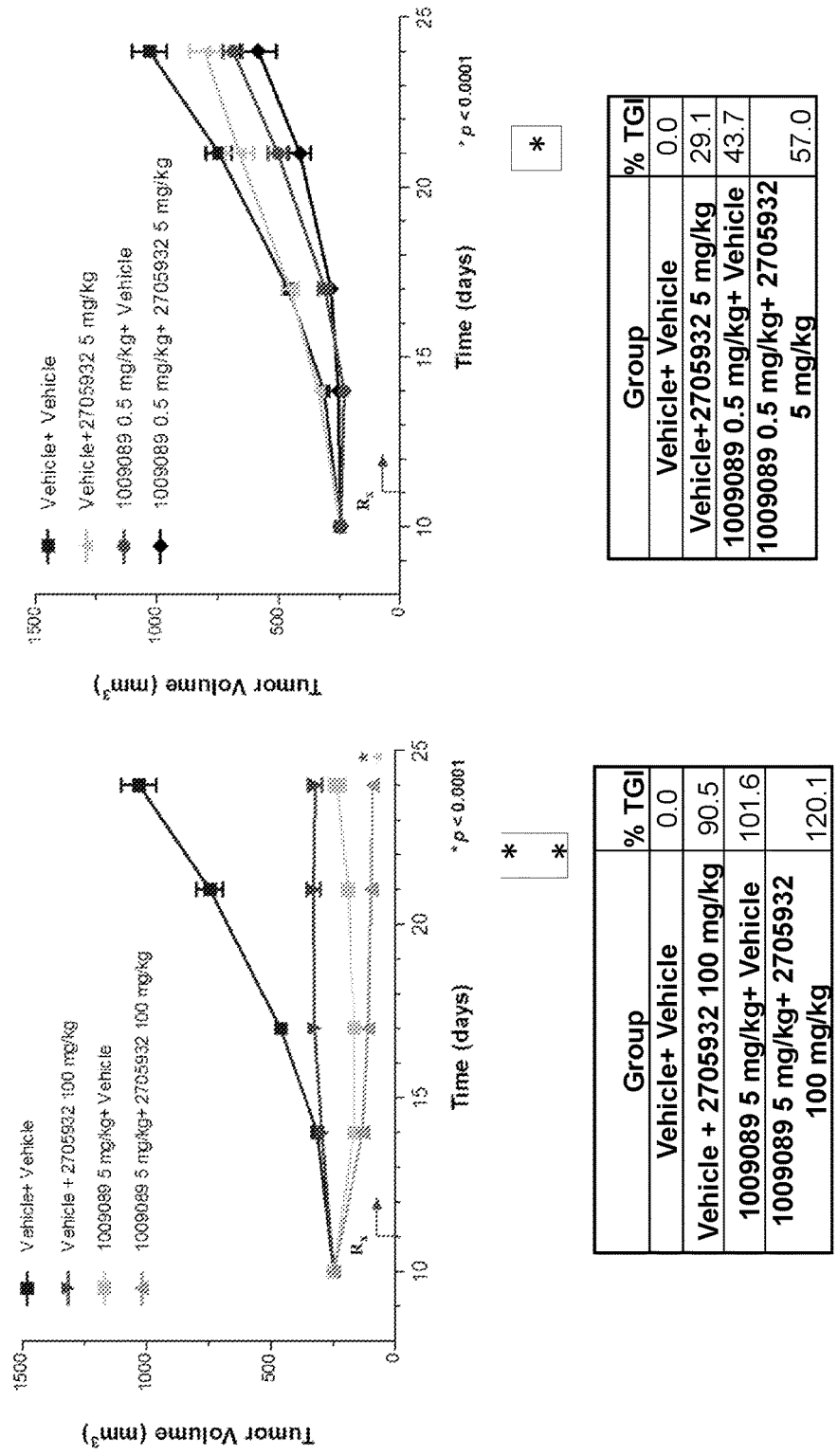
FIG. 91 shows tumor xenograft data for the combination of AMG 232 and MEK inhibitor AMG 1009089 in an A375 tumor.
Figure 92:
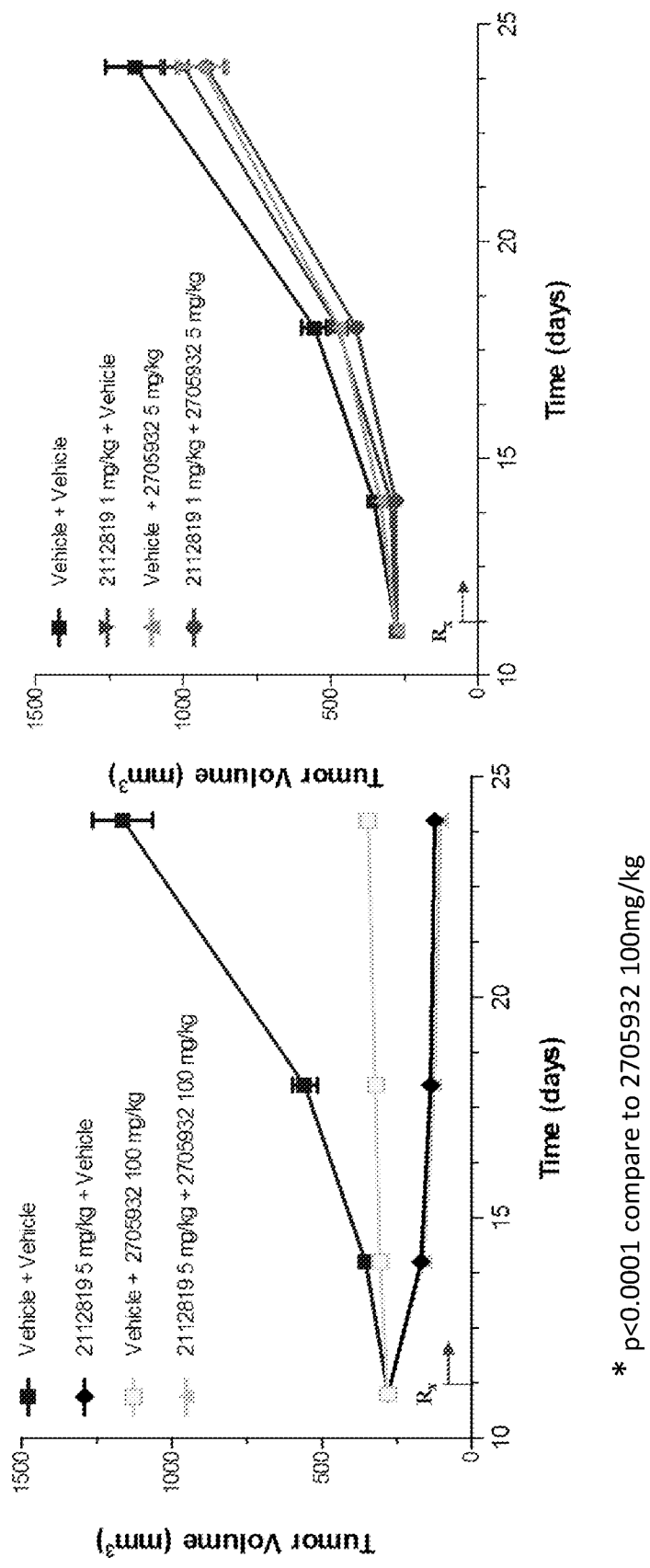
FIG. 92 shows tumor xenograft data for the combination of AMG 232 and BRAF inhibitor AMG 2112819 in an A375sq2 tumor.
Figure 93:
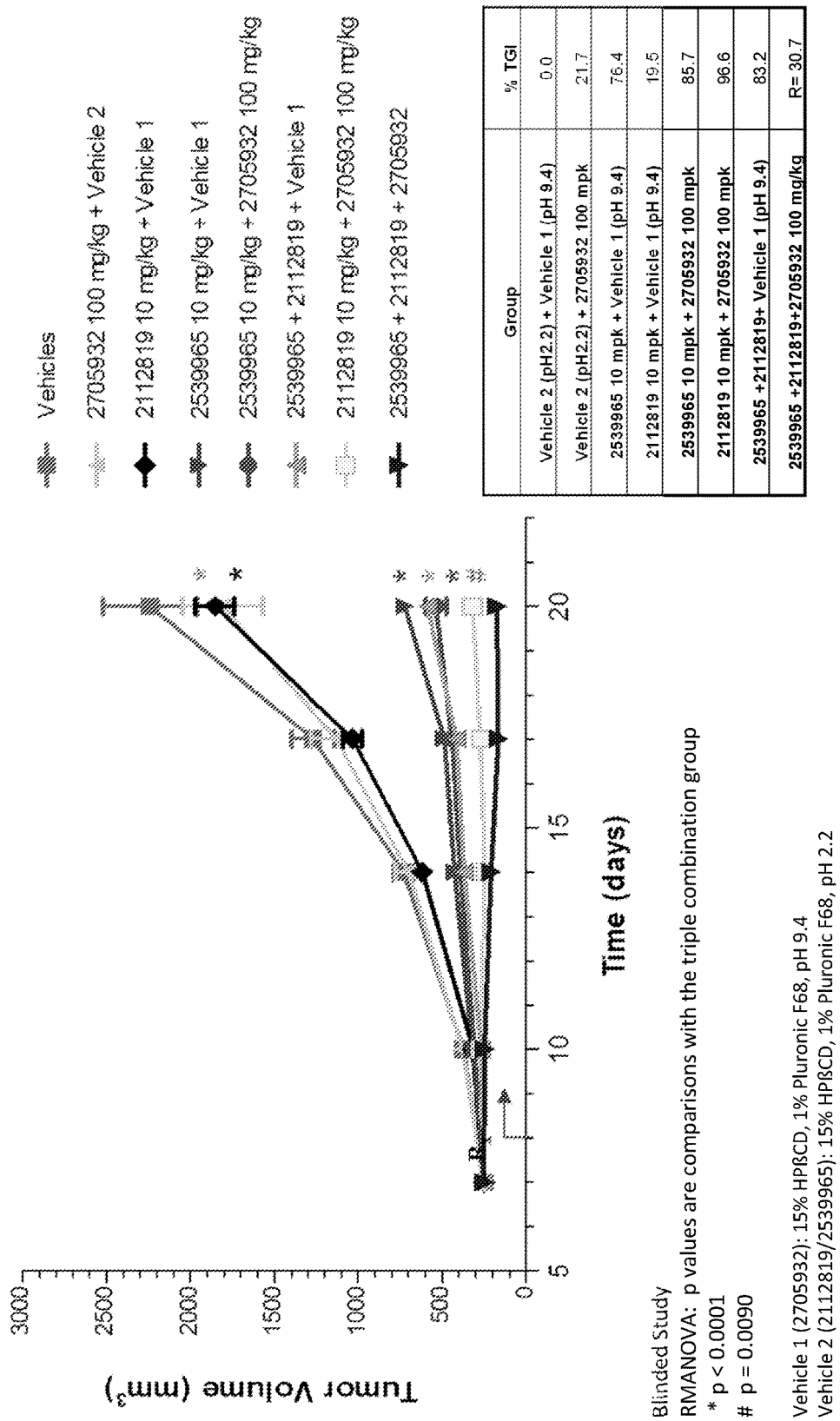
FIG. 93 shows tumor xenograft data for the combination of AMG 232, BRAF inhibitor AMG 2112819 and PI3K inhibitor 2539965 in a RKO tumor.
Figure 94:
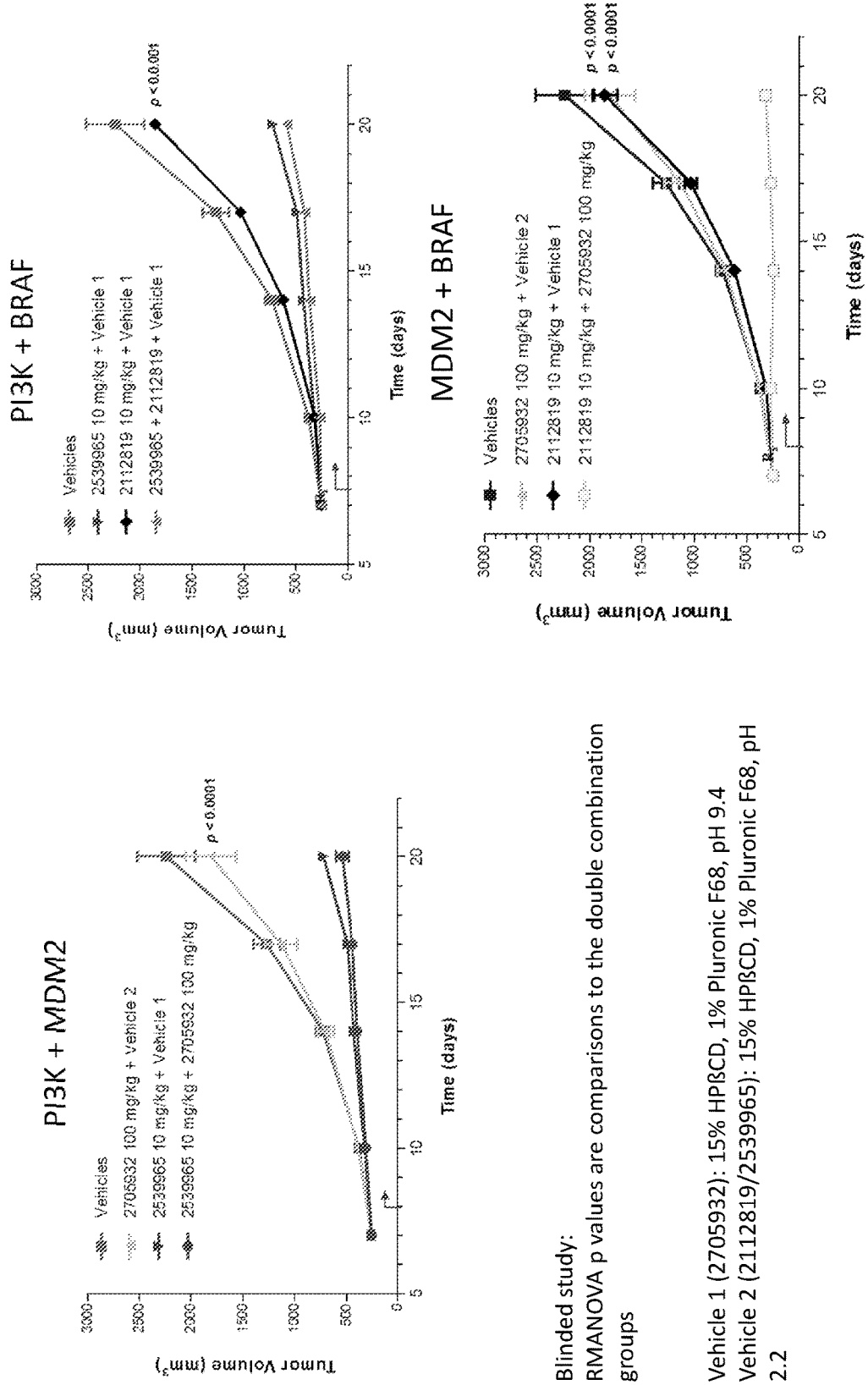
FIG. 94 shows tumor xenograft data for various combinations of AMG 232, BRAF inhibitor AMG 2112819 and PI3k inhibitor AMG2539965 in a RKO tumor.
Figure 95:
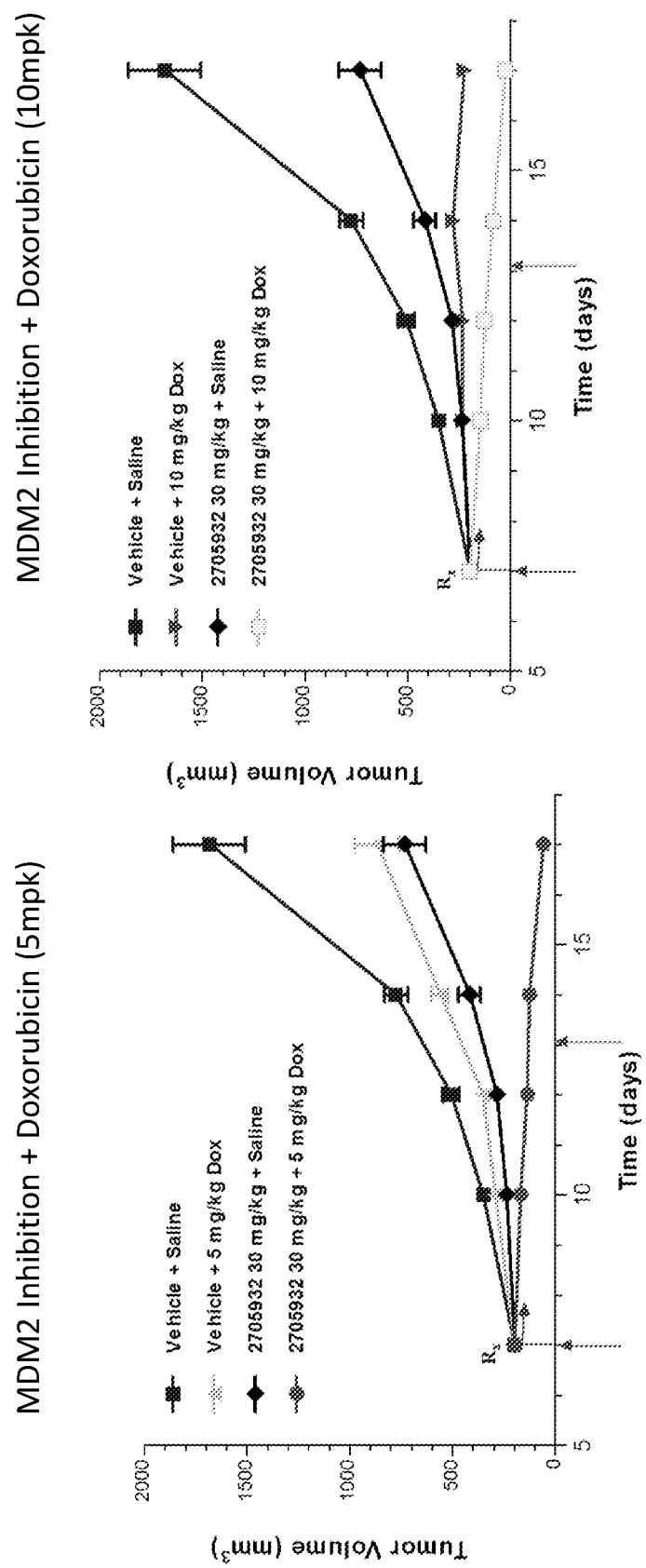
FIG. 95 shows tumor xenograft data for the combination of AMG 232 and doxorubicin in a MOLM13 tumor.
Figure 96:
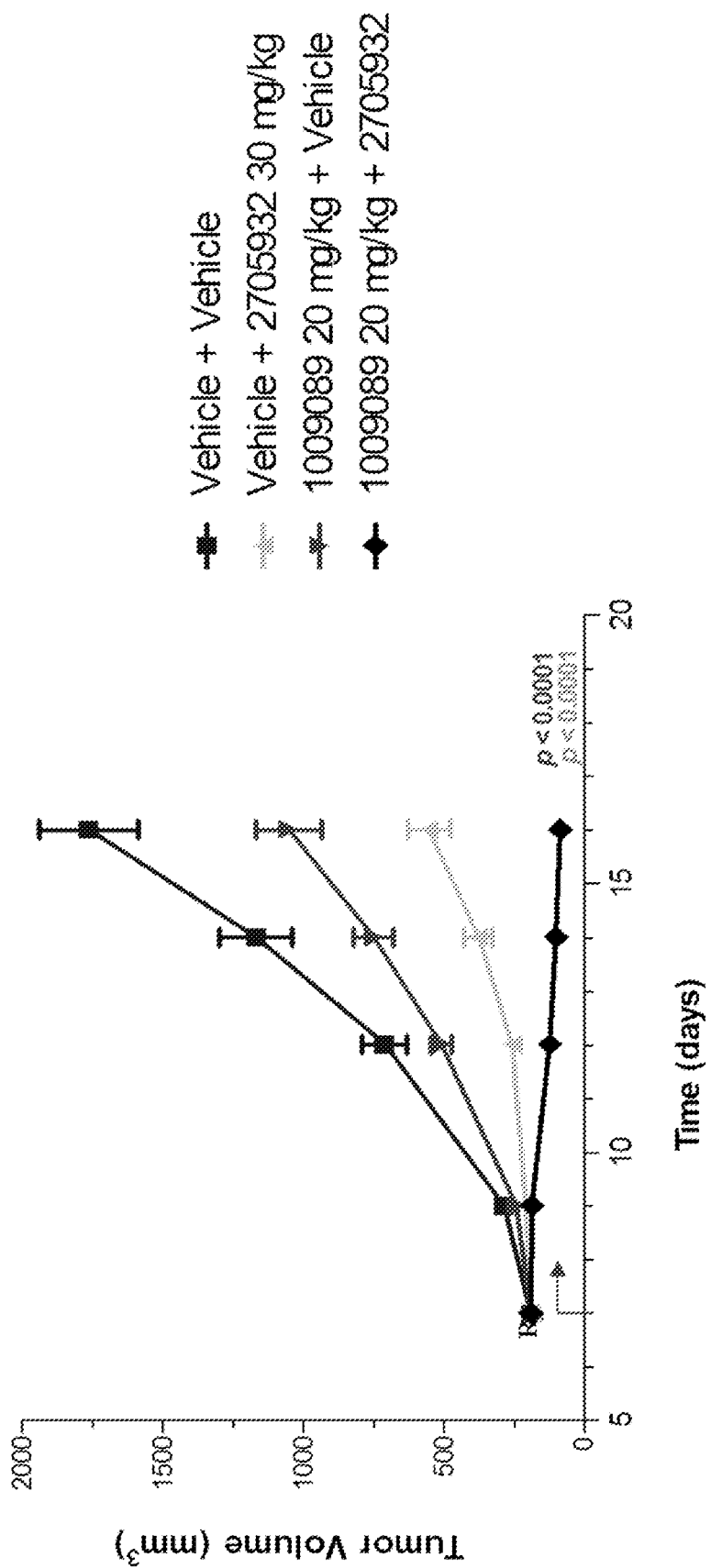
FIG. 96 shows tumor xenograft data for the combination of AMG 232 and MEK inhibitor AMG 1009089 in a MOLM13 tumor.
Figure 97:
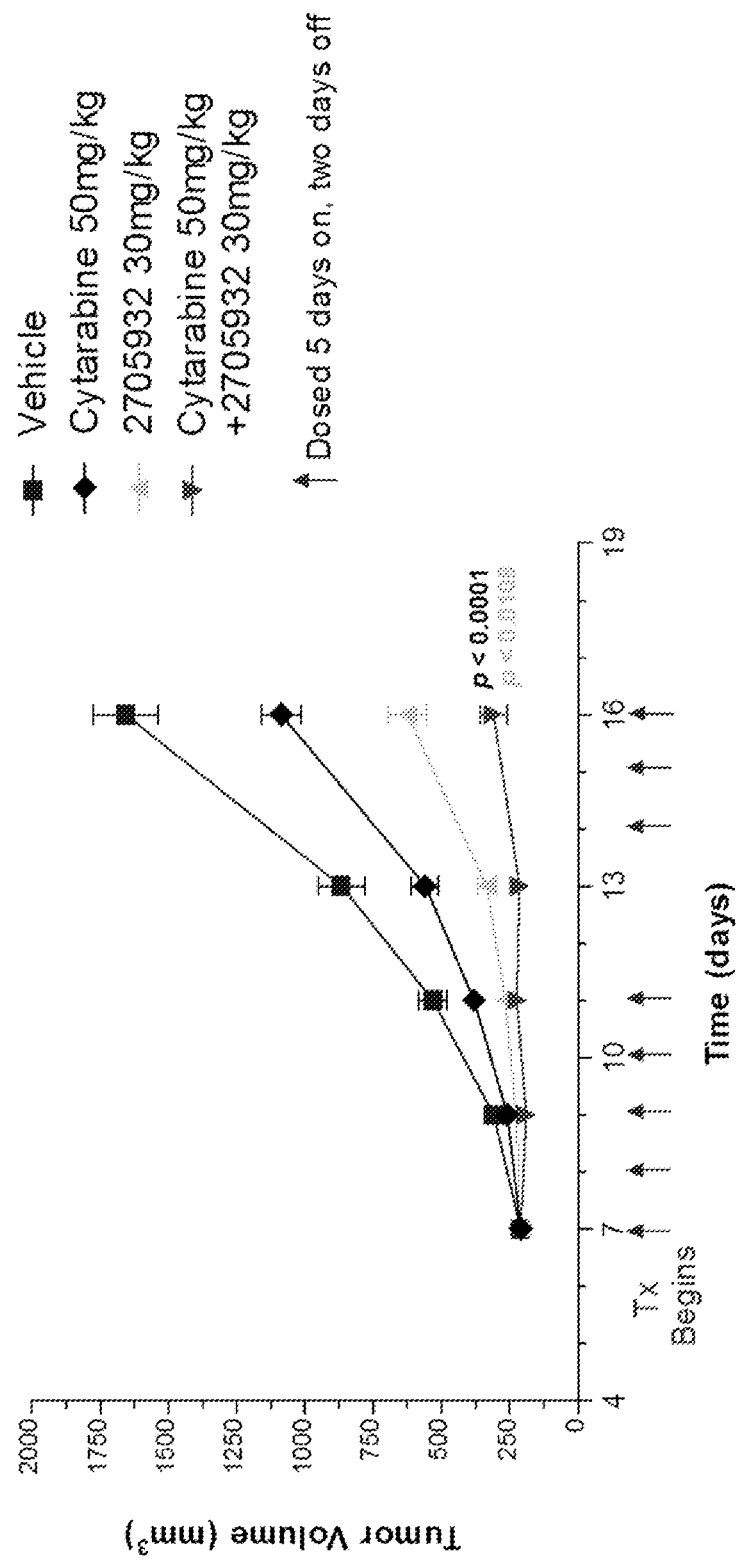
FIG. 97 shows tumor xenograft data for the combination of AMG 232 and cytarabine in a MOLM13 tumor.
Figure 98:
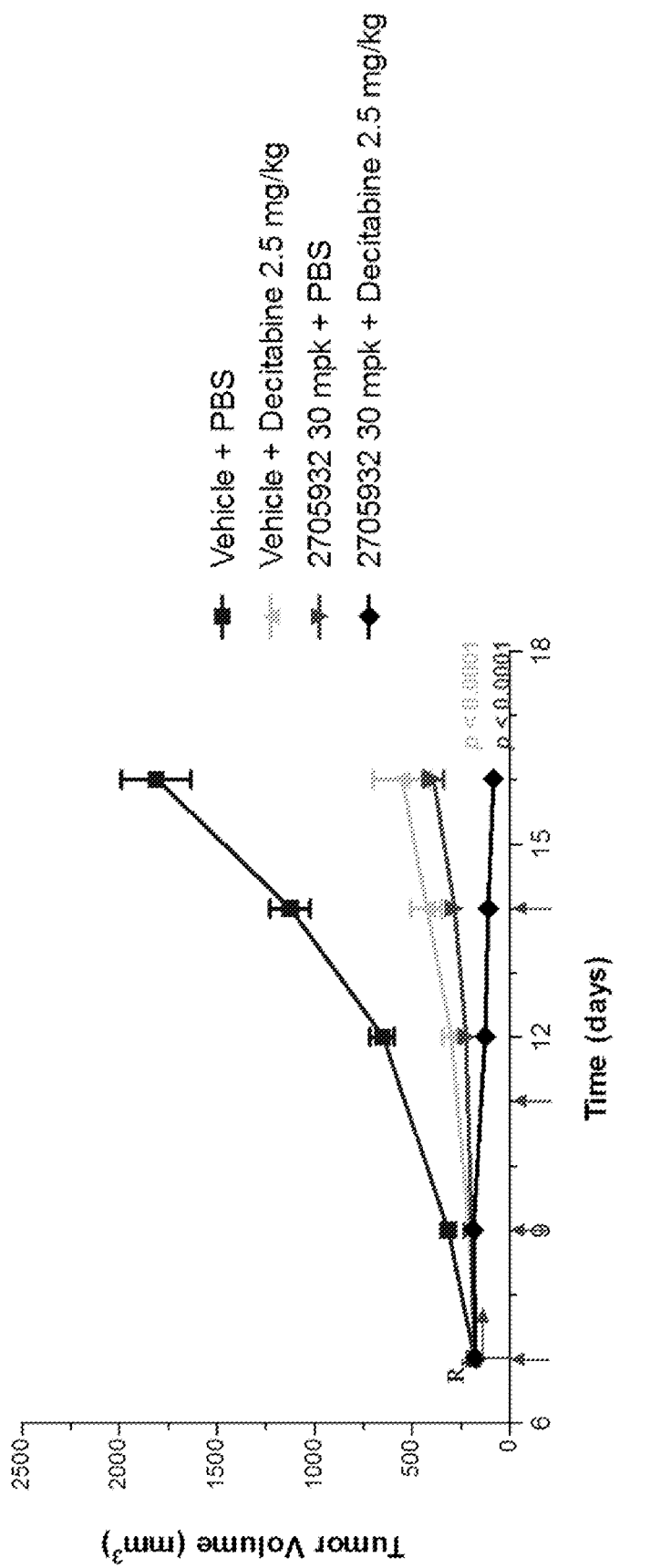
FIG. 98 shows tumor xenograft data for the combination of AMG 232 and decitabine in a MOLM13 tumor.
Figure 99:
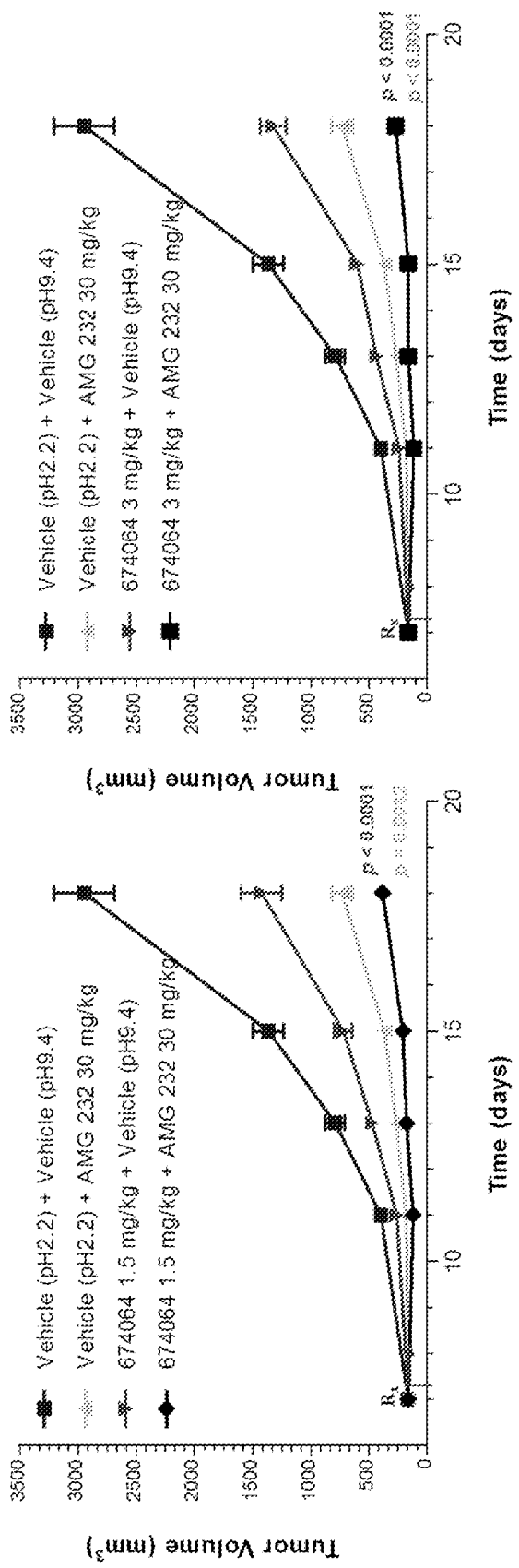
FIG. 99 shows tumor xenograft data for the combination of AMG 232 and Sorafanib in a MOLM13 tumor.

The results of the in vitro cell-based combination studies are shown in FIGS. 1 to 89.

In FIGS. 1 to 66, the Growth Inhibition (%) matrices represent the consensus growth inhibition values from multiple experimental replicates for a given combination calculated according to formulas described above. For example, in FIG. 1, the growth inhibition obtained when 2.5 μM Compound A and 3 μM Compound 1 were combined was 114%. The ADD Model Growth Inhibition (%) matrices represent the predicted growth inhibition values for an additive interaction between two compounds based on the Loewe additivity model and was derived from the experimental growth inhibition activities of each of the agents alone. The ADD Excess Growth Inhibition (%) matrices represent the growth inhibition values in excess of the additivity model. For example, in FIG. 1a, when 2.5 μM Compound A was combined with 3 μM Compound 1, the growth inhibition in excess of the additivity model was 26% (114% experimental growth inhibition−88% model=26%). The shading of the matrices corresponds to the degree of growth inhibition, with darker shading/positive growth inhibition values representing larger effects; negative growth inhibition values were excluded from synergy score calculations. Synergy scores were calculated based on the sum of the excess growth inhibition values for a given combination, with normalization factors for the concentration ranges of the component agents tested and additional weighting given to synergistic interactions that occur at high effect levels (Lehar et al., supra). For example, in FIG. 1a, the synergy score for the combination of Compound A×Compound 1 was 0.532; the synergy score for the self-cross combination of Compound A×Compound A was 0.621; and the synergy score for the self-cross combination of Compound 1×Compound 1 was 0.432.

In FIGS. 67 to 84, the first label on the Y axis indicates the target of the compound tested in combination with the particular MDM2 inhibitor. For example, in FIG. 67, the first target is BRAF (the compound tested is vemurafenib) and the last is MEK (the compound tested is AZD8330). The next section on the Y axis indicates the exact combination. For example, in FIG. 67, AMG 232×Vemurafenib means that the combination tested was AMG 232 and Vemurafenib. On the X axis, at the top of the grid, the cancer cell line that was tested is indicated. Above the cancer cell line, mutational status is indicated For example, in FIG. 67, KRAS and BRAF indicates that the particular cell lines below these designations contain a KRAS or BRAF mutation as indicated (mutation data obtained from the literature or the Sanger (Cosmic) or Broad Institute (Cancer Cell Line Encyclopedia) cancer genomics databases). It should be noted that the cell lines used in these experiments are known to those skilled in the art, and the various mutations associated with those cells lines may be readily determined by one skilled in the art. Also, on FIG. 67, TP53 indicates that the designated cell lines contain a mutation in TP53. As mentioned above, MDM2 inhibitors show activity in cancer having wild type TP53. The shading in each box of the grid indicates the level of synergy identified, with darker indicating higher synergy. The number in the box is the synergy score, and if a number is underlined it indicates that the experiment showed statistical significance.

In Vivo Tumor Xenograft Combination Studies

In vivo tumor xenograft studies were conducted following these general procedures: Tumor cells (Table 1) were cultured, harvested and implanted subcutaneously into the right flank of female athymic nude mice. When tumors reached about 200 mm$^3$, mice were randomized into treatment groups (n=10/group) and treatment was initiated (on days indicated on graphs). Compound names, dosing frequency, and routes of administration are listed in Table 2. Tumor sizes and body weights were measured 2 to 3 times per week. Tumor volume was measured by digital calipers, calculated as L×W×H and expressed in mm$^3$. Statistical significance of observed differences between growth curves was evaluated by repeated measures analysis of covariance (RMANOVA) of the log transformed tumor volume data with Dunnett adjusted multiple comparisons comparing the control group to the treatment groups. For combination studies, RMANOVA was run with the combination group compared one to one with each single agent treatment group.

BD Matrigel™ Basement Membrane Matrix is a solubilized basement membrane preparation extracted from the Engelbrcth-Holm-Swarm (EHS) mouse sarcoma (BD Biosciences, San Jose, Calif.)

All studies were measured in a blinded manner.

TABLE 1

| Cell Line | Tumor Type | Cells/mouse | Source # | Matrigel (cells:matrigel) |
|---|---|---|---|---|
| RKO | Colon | 5 × 10$^6$ | (ATCC) CRL-2577 | 1:1 |
| SJSA-1 | Osteosarcoma | 5 × 10$^6$ | (ATCC) CRL-2098 | 2:1 |
| HCT116 | Colorectal | 2 × 10$^6$ | (ATCC) CCL-247 | 2:1 |
| A375sq2 | Melanoma | 5 × 10$^6$ | See Reference above | 2:1 |
| NCI-H460 | Non-small cell lung | 5 × 10$^6$ | (ATCC) HTB-177 | no |
| U87 | Glioblastoma | 5 × 10$^6$ | (ATCC) HTB-14 | no |
| Molm13 | Acute myelogenous leukemia | 2.5 × 10$^6$ | (DSMZ) AC-554 | 1:1 |

TABLE 2

| Treatment | Route | Frequency |
|---|---|---|
| AMG 232 | PO | QD |
| 1009089 (MEK) | PO | QD |
| cisplatin | IP | 1x/wk |
| CPT-11 | IP | 1x/wk |
| doxorubicin | IV | 1x/wk |
| 2112819 (BRAF) | PO | QD |
| RG7112 (MDM2) | PO | QD |
| 2520765 (PI3K) | PO | QD |
| cytarabine | IP | 5 days on, 2 days off |
| decitabine | IP | 3x/wk |

Definition of abbreviations: PO: oral gavage IP: intraperitoneal IV: intravenous QD: once per day Wk: week In vivo combination studies conducted:
1. AMG 232+MEK (RKO),
2. AMG 232+BRAF (RKO)
3. AMG 232+cisplatin (H460)
4. AMG 232+cisplatin (HCT-116)
5. AMG 232+doxorubicin (SJSA-1)
6. AMG 232+irinotecan (HCT116)
7. AMG 232+MEK (A375sq2)
8. AMG 232+BRAF (A375sq2)
9. AMG 232+BRAF+PI3K (RKO, triple combination)
10. AMG 232+doxorubicin (Molm-13)
11. AMG 232+MEK (Molm-13)
12. AMG 232+cytarabine (Molm-13)
13. AMG 232+decitabine (Molm-13)
14. AMG 232+sorafenib (Molm-13)

The results of the in vivo tumor xenograft combination studies are shown in FIGS. 85-99.

Table A below illustrates specific combinations of an MDM2 inhibitor with one or more additional pharmaceutically active agents for particular cancers types. The data obtained and summarized in the Figures indicates that the combinations set forth in Table A show enhanced anti-cancer activity over what is expected when the individual members of the combination therapy are used alone. It is noted that the magnitude of the therapeutic synergy that is seen can vary depending on the type of cancer treated and agent used.

TABLE A

| MDM2 Inhibitor | Additional Pharmaceutically Active Agent | Cancer Type |
|---|---|---|
| AMG 232 | vemurafenib | melanoma |
| AMG 232 | vemurafenib | colon |
| AMG 232 | vemurafenib | liver |
| AMG 232 | vemurafenib | sarcoma |
| AMG 232 | vemurafenib | AML |
| AMG 232 | vemurafenib | CML |
| AMG 232 | vemurafenib | DLBCL |

TABLE A-continued

| MDM2 Inhibitor | Additional Pharmaceutically Active Agent | Cancer Type |
|---|---|---|
| AMG 232 | vemurafenib | kidney |
| AMG 232 | dabrafenib | melanoma |
| AMG 232 | dabrafenib | colon |
| AMG 232 | dabrafenib | liver |
| AMG 232 | dabrafenib | sarcoma |
| AMG 232 | dabrafenib | glioblastoma |
| AMG 232 | dabrafenib | head and neck |
| AMG 232 | dabrafenib | AML |
| AMG 232 | dabrafenib | CML |
| AMG 232 | dabrafenib | DLBCL |
| AMG 232 | RAF265 | melanoma |
| AMG 232 | RAF265 | colon |
| AMG 232 | RAF265 | liver |
| AMG 232 | RAF265 | sarcoma |
| AMG 232 | RAF265 | NSCLC |
| AMG 232 | RAF265 | stomach |
| AMG 232 | RAF265 | endometrium |
| AMG 232 | RAF265 | glioblastoma |
| AMG 232 | RAF265 | head and neck |
| AMG 232 | RAF265 | bladder |
| AMG 232 | RAF265 | AML |
| AMG 232 | RAF265 | CML |
| AMG 232 | RAF265 | DLBCL |
| AMG 232 | MLN2480 | melanoma |
| AMG 232 | MLN2480 | colon |
| AMG 232 | MLN2480 | liver |
| AMG 232 | MLN2480 | NSCLC |

TABLE A-continued

| MDM2 Inhibitor | Additional Pharmaceutically Active Agent | Cancer Type |
|---|---|---|
| AMG 232 | MLN2480 | endometrium |
| AMG 232 | MLN2480 | bladder |
| AMG 232 | MLN2480 | AML |
| AMG 232 | MLN2480 | CML |
| AMG 232 | MLN2480 | DLBCL |
| AMG 232 | trametinib | melanoma |
| AMG 232 | trametinib | colon |
| AMG 232 | trametinib | liver |
| AMG 232 | trametinib | sarcoma |
| AMG 232 | trametinib | NSCLC |
| AMG 232 | trametinib | stomach |
| AMG 232 | trametinib | prostate |
| AMG 232 | trametinib | kidney |
| AMG 232 | trametinib | glioblastoma |
| AMG 232 | trametinib | breast |
| AMG 232 | trametinib | head and neck |
| AMG 232 | trametinib | bladder |
| AMG 232 | trametinib | AML |
| AMG 232 | trametinib | CML |
| AMG 232 | trametinib | DLBCL |
| AMG 232 | pimasertib | melanoma |
| AMG 232 | pimasertib | colon |
| AMG 232 | pimasertib | liver |
| AMG 232 | pimasertib | NSCLC |
| AMG 232 | pimasertib | stomach |
| AMG 232 | pimasertib | prostate |
| AMG 232 | pimasertib | kidney |
| AMG 232 | pimasertib | glioblastoma |
| AMG 232 | pimasertib | breast |
| AMG 232 | pimasertib | head and neck |
| AMG 232 | pimasertib | AML |
| AMG 232 | pimasertib | CML |
| AMG 232 | pimasertib | DLBCL |
| AMG 232 | pimasertib | bladder |
| AMG 232 | MEK162 | melanoma |
| AMG 232 | MEK162 | colon |
| AMG 232 | MEK162 | liver |
| AMG 232 | MEK162 | NSCLC |
| AMG 232 | MEK162 | stomach |
| AMG 232 | MEK162 | prostate |
| AMG 232 | MEK162 | glioblastoma |
| AMG 232 | MEK162 | bladder |
| AMG 232 | MEK162 | AML |
| AMG 232 | MEK162 | CML |
| AMG 232 | MEK162 | DLBCL |
| AMG 232 | TAK-733 | melanoma |
| AMG 232 | TAK-733 | colon |
| AMG 232 | TAK-733 | liver |
| AMG 232 | TAK-733 | sarcoma |
| AMG 232 | TAK-733 | NSCLC |
| AMG 232 | TAK-733 | stomach |
| AMG 232 | TAK-733 | prostate |
| AMG 232 | TAK-733 | kidney |
| AMG 232 | TAK-733 | glioblastoma |
| AMG 232 | TAK-733 | breast |
| AMG 232 | TAK-733 | head and neck |
| AMG 232 | TAK-733 | bladder |
| AMG 232 | TAK-733 | AML |
| AMG 232 | TAK-733 | CML |
| AMG 232 | TAK-733 | DLBCL |
| AMG 232 | GDC-0973 | melanoma |
| AMG 232 | GDC-0973 | colon |
| AMG 232 | GDC-0973 | liver |
| AMG 232 | GDC-0973 | NSCLC |
| AMG 232 | GDC-0973 | stomach |
| AMG 232 | GDC-0973 | prostate |
| AMG 232 | GDC-0973 | kidney |
| AMG 232 | GDC-0973 | glioblastoma |
| AMG 232 | GDC-0973 | breast |
| AMG 232 | GDC-0973 | bladder |
| AMG 232 | GDC-0973 | head and neck |
| AMG 232 | GDC-0973 | sarcoma |
| AMG 232 | GDC-0973 | AML |
| AMG 232 | GDC-0973 | CML |
| AMG 232 | GDC-0973 | DLBCL |
| AMG 232 | AZD8330 | melanoma |
| AMG 232 | AZD8330 | colon |
| AMG 232 | AZD8330 | liver |
| AMG 232 | AZD8330 | sarcoma |
| AMG 232 | AZD8330 | NSCLC |
| AMG 232 | AZD8330 | stomach |
| AMG 232 | AZD8330 | prostate |
| AMG 232 | AZD8330 | kidney |
| AMG 232 | AZD8330 | glioblastoma |
| AMG 232 | AZD8330 | breast |
| AMG 232 | AZD8330 | head and neck |
| AMG 232 | AZD8330 | bladder |
| AMG 232 | AZD8330 | AML |
| AMG 232 | AZD8330 | CML |
| AMG 232 | AZD8330 | DLBCL |
| AMG 232 | BKM120 | prostate |
| AMG 232 | BKM120 | breast |
| AMG 232 | BKM120 | melanoma |
| AMG 232 | BKM120 | NSCLC |
| AMG 232 | BKM120 | kidney |
| AMG 232 | BKM120 | stomach |
| AMG 232 | BKM120 | head and neck |
| AMG 232 | BKM120 | bladder |
| AMG 232 | BKM120 | sarcoma |
| AMG 232 | BKM120 | AML |
| AMG 232 | BKM120 | CML |
| AMG 232 | GDC-0941 | prostate |
| AMG 232 | GDC-0941 | breast |
| AMG 232 | GDC-0941 | endometrium |
| AMG 232 | GDC-0941 | melanoma |
| AMG 232 | GDC-0941 | NSCLC |
| AMG 232 | GDC-0941 | kidney |
| AMG 232 | GDC-0941 | glioblastoma |
| AMG 232 | GDC-0941 | stomach |
| AMG 232 | GDC-0941 | head and neck |
| AMG 232 | GDC-0941 | bladder |
| AMG 232 | GDC-0941 | sarcoma |
| AMG 232 | GDC-0941 | AML |
| AMG 232 | GDC-0941 | CML |
| AMG 232 | GDC-0941 | DLBCL |
| AMG 232 | BYL719 | prostate |
| AMG 232 | BYL719 | breast |
| AMG 232 | BYL719 | endometrium |
| AMG 232 | BYL719 | melanoma |
| AMG 232 | BYL719 | NSCLC |
| AMG 232 | BYL719 | kidney |
| AMG 232 | BYL719 | glioblastoma |
| AMG 232 | BYL719 | stomach |
| AMG 232 | BYL719 | head and neck |
| AMG 232 | BYL719 | bladder |
| AMG 232 | BYL719 | sarcoma |
| AMG 232 | BYL719 | AML |
| AMG 232 | BYL719 | DLBCL |
| AMG 232 | GSK-2636771 | AML |
| AMG 232 | GSK-2636771 | DLBCL |
| AMG 232 | MK-2206 | prostate |
| AMG 232 | MK-2206 | breast |
| AMG 232 | MK-2206 | melanoma |
| AMG 232 | MK-2206 | endometrium |
| AMG 232 | MK-2206 | head and neck |
| AMG 232 | MK-2206 | sarcoma |
| AMG 232 | MK-2206 | AML |
| AMG 232 | MK-2206 | DLBCL |
| AMG 232 | GDC-0068 | prostate |
| AMG 232 | GDC-0068 | breast |
| AMG 232 | GDC-0068 | endometrium |
| AMG 232 | GDC-0068 | melanoma |
| AMG 232 | GDC-0068 | glioblastoma |
| AMG 232 | GDC-0068 | head and neck |
| AMG 232 | GDC-0068 | sarcoma |
| AMG 232 | GDC-0068 | AML |
| AMG 232 | GDC-0068 | DLBCL |
| AMG 232 | AZD5363 | prostate |
| AMG 232 | AZD5363 | breast |
| AMG 232 | AZD5363 | endometrium |
| AMG 232 | AZD5363 | melanoma |
| AMG 232 | AZD5363 | glioblastoma |
| AMG 232 | AZD5363 | head and neck |
| AMG 232 | AZD5363 | sarcoma |

TABLE A-continued

| MDM2 Inhibitor | Additional Pharmaceutically Active Agent | Cancer Type |
| --- | --- | --- |
| AMG 232 | AZD5363 | AML |
| AMG 232 | AZD5363 | CML |
| AMG 232 | AZD5363 | DLBCL |
| AMG 232 | GDC-0980 | prostate |
| AMG 232 | GDC-0980 | breast |
| AMG 232 | GDC-0980 | melanoma |
| AMG 232 | GDC-0980 | kidney |
| AMG 232 | GDC-0980 | glioblastoma |
| AMG 232 | GDC-0980 | stomach |
| AMG 232 | GDC-0980 | head and neck |
| AMG 232 | GDC-0980 | bladder |
| AMG 232 | GDC-0980 | liver |
| AMG 232 | GDC-0980 | sarcoma |
| AMG 232 | GDC-0980 | AML |
| AMG 232 | GDC-0980 | DLBCL |
| AMG 232 | AZD2014 | prostate |
| AMG 232 | AZD2014 | breast |
| AMG 232 | AZD2014 | endometrium |
| AMG 232 | AZD2014 | melanoma |
| AMG 232 | AZD2014 | NSCLC |
| AMG 232 | AZD2014 | kidney |
| AMG 232 | AZD2014 | glioblastoma |
| AMG 232 | AZD2014 | stomach |
| AMG 232 | AZD2014 | head and neck |
| AMG 232 | AZD2014 | bladder |
| AMG 232 | AZD2014 | liver |
| AMG 232 | AZD2014 | sarcoma |
| AMG 232 | AZD2014 | AML |
| AMG 232 | AZD2014 | DLBCL |
| AMG 232 | MLN0128 | prostate |
| AMG 232 | MLN0128 | breast |
| AMG 232 | MLN0128 | endometrium |
| AMG 232 | MLN0128 | melanoma |
| AMG 232 | MLN0128 | NSCLC |
| AMG 232 | MLN0128 | glioblastoma |
| AMG 232 | MLN0128 | stomach |
| AMG 232 | MLN0128 | head and neck |
| AMG 232 | MLN0128 | bladder |
| AMG 232 | MLN0128 | liver |
| AMG 232 | MLN0128 | sarcoma |
| AMG 232 | MLN0128 | AML |
| AMG 232 | MLN0128 | DLBCL |
| AMG 232 | dasatinib | bladder |
| AMG 232 | dasatinib | colon |
| AMG 232 | dasatinib | endometium |
| AMG 232 | dasatinib | glioblastoma |
| AMG 232 | dasatinib | head and neck |
| AMG 232 | dasatinib | kidney |
| AMG 232 | dasatinib | NSCLC |
| AMG 232 | dasatinib | melanoma |
| AMG 232 | dasatinib | sarcoma |
| AMG 232 | dasatinib | AML |
| AMG 232 | dasatinib | CML |
| AMG 232 | dasatinib | DLBCL |
| AMG 232 | panobinostat | kidney |
| AMG 232 | panobinostat | head and neck |
| AMG 232 | panobinostat | melanoma |
| AMG 232 | panobinostat | sarcoma |
| AMG 232 | panobinostat | stomach |
| AMG 232 | panobinostat | AML |
| AMG 232 | panobinostat | DLBCL |
| AMG 232 | panobinostat | liver |
| AMG 232 | doxorubicin | breast |
| AMG 232 | doxorubicin | AML |
| AMG 232 | etoposide | sarcoma |
| AMG 232 | cytarabine | AML |
| AMG 232 | decitabine | AML |
| AMG 232 | navitoclax | bladder |
| AMG 232 | navitoclax | breast |
| AMG 232 | navitoclax | endometrium |
| AMG 232 | navitoclax | glioblastoma |
| AMG 232 | navitoclax | head and neck |
| AMG 232 | navitoclax | kidney |
| AMG 232 | navitoclax | liver |
| AMG 232 | navitoclax | melanoma |
| AMG 232 | navitoclax | sarcoma |
| AMG 232 | navitoclax | stomach |
| AMG 232 | navitoclax | AML |
| AMG 232 | navitoclax | CML |
| AMG 232 | navitoclax | DLBCL |
| AMG 232 | ABT-199 | glioblastoma |
| AMG 232 | ABT-199 | head and neck |
| AMG 232 | ABT-199 | kidney |
| AMG 232 | ABT-199 | sarcoma |
| AMG 232 | ABT-199 | AML |
| AMG 232 | ABT-199 | CML |
| AMG 232 | ABT-199 | DLBCL |
| AMG 232 | imatinib | CML |
| AMG 232 | ponatinib | CML |
| AMG 232 | bosutinb | CML |
| AMG 232 | nilotinib | CML |
| AMG 232 | quizartinib | AML |
| AMG 232 | midostaurin | AML |
| AMG 232 | cisplatin | Ovarian |
| AMG 232 | cisplatin | Colon |
| AMG 232 | cisplatin | NSCLC |
| AMG 232 | cisplatin | esophageal/stomach |
| AMG 232 | cispaltin | Breast |
| AMG 232 | doxorubicin | Breast |
| AMG 232 | doxorubicin | stomach |
| AMG 232 | doxorubicin | ovarian |
| AMG 232 | doxorubicin | AML |
| AMG 232 | doxorubicin | ALL |
| AMG 232 | doxorubicin | MDS |
| AMG 232 | doxorubicin | NHL |
| AMG 232 | doxorubicin | Hodgkin's lymphoma |
| AMG 232 | decitabine | MDS |
| AMG 232 | sorafenib | kidney |
| AMG 232 | sorafenib | liver |
| AMG 232 | sorafenib | AML |
| AM-7209 | vemurafenib | melanoma |
| AM-7209 | vemurafenib | colon |
| AM-7209 | vemurafenib | liver |
| AM-7209 | vemurafenib | sarcoma |
| AM-7209 | vemurafenib | AML |
| AM-7209 | vemurafenib | CML |
| AM-7209 | vemurafenib | DLBCL |
| AM-7209 | dabrafenib | melanoma |
| AM-7209 | dabrafenib | colon |
| AM-7209 | dabrafenib | liver |
| AM-7209 | dabrafenib | sarcoma |
| AM-7209 | dabrafenib | glioblastoma |
| AM-7209 | dabrafenib | stomach |
| AM-7209 | dabrafenib | head and neck |
| AM-7209 | dabrafenib | AML |
| AM-7209 | dabrafenib | CML |
| AM-7209 | dabrafenib | DLBCL |
| AM-7209 | dabrafenib | prostate |
| AM-7209 | dabrafenib | endometrium |
| AM-7209 | RAF265 | melanoma |
| AM-7209 | RAF265 | colon |
| AM-7209 | RAF265 | liver |
| AM-7209 | RAF265 | sarcoma |
| AM-7209 | RAF265 | NSCLC |
| AM-7209 | RAF265 | stomach |
| AM-7209 | RAF265 | endometrium |
| AM-7209 | RAF265 | kidney |
| AM-7209 | RAF265 | glioblastoma |
| AM-7209 | RAF265 | head and neck |
| AM-7209 | RAF265 | bladder |
| AM-7209 | RAF265 | AML |
| AM-7209 | RAF265 | CML |
| AM-7209 | RAF265 | DLBCL |
| AM-7209 | MLN2480 | melanoma |
| AM-7209 | MLN2480 | colon |
| AM-7209 | MLN2480 | liver |
| AM-7209 | MLN2480 | sarcoma |
| AM-7209 | MLN2480 | NSCLC |
| AM-7209 | MLN2480 | breast |
| AM-7209 | MLN2480 | AML |
| AM-7209 | MLN2480 | CML |
| AM-7209 | MLN2480 | DLBCL |
| AM-7209 | trametinib | melanoma |
| AM-7209 | trametinib | colon |

TABLE A-continued

| MDM2 Inhibitor | Additional Pharmaceutically Active Agent | Cancer Type |
|---|---|---|
| AM-7209 | trametinib | liver |
| AM-7209 | trametinib | sarcoma |
| AM-7209 | trametinib | NSCLC |
| AM-7209 | trametinib | stomach |
| AM-7209 | trametinib | endometrium |
| AM-7209 | trametinib | prostate |
| AM-7209 | trametinib | kidney |
| AM-7209 | trametinib | glioblastoma |
| AM-7209 | trametinib | breast |
| AM-7209 | trametinib | head and neck |
| AM-7209 | trametinib | bladder |
| AM-7209 | trametinib | AML |
| AM-7209 | trametinib | CML |
| AM-7209 | trametinib | DLBCL |
| AM-7209 | pimasertib | melanoma |
| AM-7209 | pimasertib | colon |
| AM-7209 | pimasertib | liver |
| AM-7209 | pimasertib | NSCLC |
| AM-7209 | pimasertib | stomach |
| AM-7209 | pimasertib | endometrium |
| AM-7209 | pimasertib | prostate |
| AM-7209 | pimasertib | kidney |
| AM-7209 | pimasertib | glioblastoma |
| AM-7209 | pimasertib | breast |
| AM-7209 | pimasertib | head and neck |
| AM-7209 | pimasertib | bladder |
| AM-7209 | pimasertib | AML |
| AM-7209 | pimasertib | CML |
| AM-7209 | pimasertib | sarcoma |
| AM-7209 | MEK162 | melanoma |
| AM-7209 | MEK162 | colon |
| AM-7209 | MEK162 | liver |
| AM-7209 | MEK162 | NSCLC |
| AM-7209 | MEK162 | stomach |
| AM-7209 | MEK162 | prostate |
| AM-7209 | MEK162 | kidney |
| AM-7209 | MEK162 | glioblastoma |
| AM-7209 | MEK162 | head and neck |
| AM-7209 | MEK162 | bladder |
| AM-7209 | MEK162 | AML |
| AM-7209 | MEK162 | CML |
| AM-7209 | TAK-733 | melanoma |
| AM-7209 | TAK-733 | colon |
| AM-7209 | TAK-733 | liver |
| AM-7209 | TAK-733 | sarcoma |
| AM-7209 | TAK-733 | NSCLC |
| AM-7209 | TAK-733 | stomach |
| AM-7209 | TAK-733 | endometrium |
| AM-7209 | TAK-733 | prostate |
| AM-7209 | TAK-733 | kidney |
| AM-7209 | TAK 733 | glioblastoma |
| AM-7209 | TAK-733 | breast |
| AM-7209 | TAK-733 | head and neck |
| AM-7209 | TAK-733 | bladder |
| AM-7209 | TAK-733 | AML |
| AM-7209 | TAK-733 | CML |
| AM-7209 | TAK-733 | DLBCL |
| AM-7209 | GDC-0973 | melanoma |
| AM-7209 | GDC-0973 | colon |
| AM-7209 | GDC-0973 | liver |
| AM-7209 | GDC-0973 | sarcoma |
| AM-7209 | GDC-0973 | NSCLC |
| AM-7209 | GDC-0973 | stomach |
| AM-7209 | GDC-0973 | endometrium |
| AM-7209 | GDC-0973 | prostate |
| AM-7209 | GDC-0973 | kidney |
| AM-7209 | GDC-0973 | glioblastoma |
| AM-7209 | GDC-0973 | breast |
| AM-7209 | GDC-0973 | head and neck |
| AM-7209 | GDC-0973 | bladder |
| AM-7209 | GDC-0973 | AML |
| AM-7209 | GDC-0973 | CML |
| AM-7209 | GDC-0973 | DLBCL |
| AM-7209 | AZD8330 | melanoma |
| AM-7209 | AZD8330 | colon |
| AM-7209 | AZD8330 | liver |
| AM-7209 | AZD8330 | sarcoma |
| AM-7209 | AZD8330 | NSCLC |
| AM-7209 | AZD8330 | stomach |
| AM-7209 | AZD8330 | prostate |
| AM-7209 | AZD8330 | kidney |
| AM-7209 | AZD8330 | glioblastoma |
| AM-7209 | AZD8330 | breast |
| AM-7209 | AZD8330 | head and neck |
| AM-7209 | AZD8330 | bladder |
| AM-7209 | AZD8330 | AML |
| AM-7209 | AZD8330 | CML |
| AM-7209 | AZD8330 | DLBCL |
| AM-7209 | BKM120 | prostate |
| AM-7209 | BKM120 | breast |
| AM-7209 | BKM120 | melanoma |
| AM-7209 | BKM120 | NSCLC |
| AM-7209 | BKM120 | kidney |
| AM-7209 | BKM120 | glioblastoma |
| AM-7209 | BKM120 | stomach |
| AM-7209 | BKM120 | head and neck |
| AM-7209 | BKM120 | bladder |
| AM-7209 | BKM120 | sarcoma |
| AM-7209 | BKM120 | AML |
| AM-7209 | BKM120 | CML |
| AM-7209 | GDC-0941 | prostate |
| AM-7209 | GDC-0941 | breast |
| AM-7209 | GDC-0941 | colon |
| AM-7209 | GDC-0941 | endometrium |
| AM-7209 | GDC-0941 | melanoma |
| AM-7209 | GDC-0941 | NSCLC |
| AM-7209 | GDC-0941 | kidney |
| AM-7209 | GDC-0941 | glioblastoma |
| AM-7209 | GDC-0941 | stomach |
| AM-7209 | GDC-0941 | head and neck |
| AM-7209 | GDC-0941 | bladder |
| AM-7209 | GDC-0941 | sarcoma |
| AM-7209 | GDC-0941 | AML |
| AM-7209 | GDC-0941 | DLBCL |
| AM-7209 | GDC-0941 | liver |
| AM-7209 | BYL719 | prostate |
| AM-7209 | BYL719 | breast |
| AM-7209 | BYL719 | colon |
| AM-7209 | BYL719 | melanoma |
| AM-7209 | BYL719 | NSCLC |
| AM-7209 | BYL719 | kidney |
| AM-7209 | BYL719 | glioblastoma |
| AM-7209 | BYL719 | stomach |
| AM-7209 | BYL719 | head and neck |
| AM-7209 | BYL719 | bladder |
| AM-7209 | BYL719 | liver |
| AM-7209 | BYL719 | sarcoma |
| AM-7209 | BYL719 | AML |
| AM-7209 | BYL719 | DLBCL |
| AM-7209 | GSK-2636771 | breast |
| AM-7209 | GSK-2636771 | NSCLC |
| AM-7209 | GSK-2636771 | liver |
| AM-7209 | GSK-2636771 | sarcoma |
| AM-7209 | GSK-2636771 | AML |
| AM-7209 | GSK-2636771 | DLBCL |
| AM-7209 | MK-2206 | prostate |
| AM-7209 | MK-2206 | breast |
| AM-7209 | MK-2206 | colon |
| AM-7209 | MK-2206 | endometrium |
| AM-7209 | MK-2206 | melanoma |
| AM-7209 | MK-2206 | NSCLC |
| AM-7209 | MK-2206 | glioblastoma |
| AM-7209 | MK-2206 | stomach |
| AM-7209 | MK-2206 | head and neck |
| AM-7209 | MK-2206 | sarcoma |
| AM-7209 | MK-2206 | liver |
| AM-7209 | MK-2206 | AML |
| AM-7209 | MK-2206 | CML |
| AM-7209 | MK-2206 | DLBCL |
| AM-7209 | GDC-0068 | prostate |
| AM-7209 | GDC-0068 | breast |
| AM-7209 | GDC-0068 | colon |
| AM-7209 | GDC-0068 | endometrium |
| AM-7209 | GDC-0068 | melanoma |

TABLE A-continued

| MDM2 Inhibitor | Additional Pharmaceutically Active Agent | Cancer Type |
|---|---|---|
| AM-7209 | GDC-0068 | NSCLC |
| AM-7209 | GDC-0068 | glioblastoma |
| AM-7209 | GDC-0068 | stomach |
| AM-7209 | GDC-0068 | head and neck |
| AM-7209 | GDC-0068 | liver |
| AM-7209 | GDC-0068 | sarcoma |
| AM-7209 | GDC-0068 | AML |
| AM-7209 | GDC-0068 | DLBCL |
| AM-7209 | AZD5363 | prostate |
| AM-7209 | AZD5363 | breast |
| AM-7209 | AZD5363 | colon |
| AM-7209 | AZD5363 | endometrium |
| AM-7209 | AZD5363 | NSCLC |
| AM-7209 | AZD5363 | glioblastoma |
| AM-7209 | AZD5363 | stomach |
| AM-7209 | AZD5363 | head and neck |
| AM-7209 | AZD5363 | liver |
| AM-7209 | AZD5363 | sarcoma |
| AM-7209 | AZD5363 | AML |
| AM-7209 | AZD5363 | CML |
| AM-7209 | AZD5363 | DLBCL |
| AM-7209 | GDC0980 | prostate |
| AM-7209 | GDC0980 | breast |
| AM-7209 | GDC0980 | colon |
| AM-7209 | GDC0980 | endometrium |
| AM-7209 | GDC0980 | melanoma |
| AM-7209 | GDC0980 | NSCLC |
| AM-7209 | GDC0980 | kidney |
| AM-7209 | GDC0980 | glioblastoma |
| AM-7209 | GDC0980 | stomach |
| AM-7209 | GDC0980 | head and neck |
| AM-7209 | GDC0980 | bladder |
| AM-7209 | GDC0980 | sarcoma |
| AM-7209 | GDC0980 | AML |
| AM-7209 | GDC0980 | DLBCL |
| AM-7209 | AZD2014 | prostate |
| AM-7209 | AZD2014 | breast |
| AM-7209 | AZD2014 | colon |
| AM-7209 | AZD2014 | melanoma |
| AM-7209 | AZD2014 | NSCLC |
| AM-7209 | AZD2014 | kidney |
| AM-7209 | AZD2014 | stomach |
| AM-7209 | AZD2014 | head and neck |
| AM-7209 | AZD2014 | bladder |
| AM-7209 | AZD2014 | liver |
| AM-7209 | AZD2014 | sarcoma |
| AM-7209 | AZD2014 | AML |
| AM-7209 | AZD2014 | DLBCL |
| AM-7209 | MLN0128 | prostate |
| AM-7209 | MLN0128 | breast |
| AM-7209 | MLN0128 | colon |
| AM-7209 | MLN0128 | endometrium |
| AM-7209 | MLN0128 | melanoma |
| AM-7209 | MLN0128 | NSCLC |
| AM-7209 | MLN0128 | glioblastoma |
| AM-7209 | MLN0128 | stomach |
| AM-7209 | MLN0128 | head and neck |
| AM-7209 | MLN0128 | bladder |
| AM-7209 | MLN0128 | liver |
| AM-7209 | MLN0128 | sarcoma |
| AM-7209 | MLN0128 | AML |
| AM-7209 | MLN0128 | DLBCL |
| AM-7209 | navitoclax | bladder |
| AM-7209 | navitoclax | breast |
| AM-7209 | navitoclax | colon |
| AM-7209 | navitoclax | endometrium |
| AM-7209 | navitoclax | glioblastoma |
| AM-7209 | navitoclax | head and neck |
| AM-7209 | navitoclax | kidney |
| AM-7209 | navitoclax | liver |
| AM-7209 | navitoclax | NSCLC |
| AM-7209 | navitoclax | melanoma |
| AM-7209 | navitoclax | sarcoma |
| AM-7209 | navitoclax | stomach |
| AM-7209 | navitoclax | AML |
| AM-7209 | navitoclax | CML |
| AM-7209 | navitoclax | DLBCL |
| AM-7209 | ABT-199 | glioblastoma |
| AM-7209 | ABT-199 | head and neck |
| AM-7209 | ABT-199 | liver |
| AM-7209 | ABT-199 | sarcoma |
| AM-7209 | ABT-199 | AML |
| AM-7209 | ABT-199 | CML |
| AM-7209 | ABT-199 | DLBCL |
| AM-7209 | doxorubicin | AML |
| AM-7209 | etoposide | sarcoma |
| AM-7209 | etoposide | stomach |
| AM-7209 | Irinotecan | colon |
| AM-7209 | cytarabine | AML |
| AM-7209 | decitabine | AML |
| AM-7209 | dasatinib | bladder |
| AM-7209 | dasatinib | colon |
| AM-7209 | dasatinib | endometrium |
| AM-7209 | dasatinib | glioblastoma |
| AM-7209 | dasatinib | head and neck |
| AM-7209 | dasatinib | kidney |
| AM-7209 | dasatinib | liver |
| AM-7209 | dasatinib | NSCLC |
| AM-7209 | dasatinib | melanoma |
| AM-7209 | dasatinib | prostate |
| AM-7209 | dasatinib | sarcoma |
| AM-7209 | dasatinib | AML |
| AM-7209 | dasatinib | CML |
| AM-7209 | dasatinib | DLBCL |
| AM-7209 | panobinostat | endometrium |
| AM-7209 | panobinostat | head and neck |
| AM-7209 | panobinostat | kidney |
| AM-7209 | panobinostat | liver |
| AM-7209 | panobinostat | melanoma |
| AM-7209 | panobinostat | sarcoma |
| AM-7209 | panobinostat | stomach |
| AM-7209 | panobinostat | AML |
| AM-7209 | panobinostat | CML |
| AM-7209 | panobinostat | DLBCL |
| AM-7209 | ponatinib | CML |
| AM-7209 | imatinib | CML |
| AM-7209 | bosutinib | CML |
| AM-7209 | nilotinib | CML |
| AM-7209 | quizartinib | AML |
| AM-7209 | midostaurin | AML |
| AM-7209 | cisplatin | Ovarian |
| AM-7209 | cisplatin | Colon |
| AM-7209 | cisplatin | NSCLC |
| AM-7209 | cisplatin | esophageal/stomach |
| AM-7209 | cispaltin | Breast |
| AM-7209 | doxorubicin | Breast |
| AM-7209 | doxorubicin | stomach |
| AM-7209 | doxorubicin | ovarian |
| AM-7209 | doxorubicin | AML |
| AM-7209 | doxorubicin | ALL |
| AM-7209 | doxorubicin | MDS |
| AM-7209 | doxorubicin | NHL |
| AM-7209 | doxorubicin | Hodgkin's lymphoma |
| AM-7209 | decitabine | MDS |
| AM-7209 | sorafenib | kidney |
| AM-7209 | sorafenib | liver |
| AM-7209 | sorafenib | AML |

What is claimed is:

1. A method of treating acute myelogenous leukemia (AML), the method comprising administering to a patient in need thereof a therapeutically effective amount of 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid and decitabine.

2. The method of claim 1, wherein the compound 2-((3R, 5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered orally.

3. The method of claim 1, wherein the compound 2-((3R, 5R,6S)-5-(3-chlorophenyl)-6-(4-chlorophenyl)-1-((S)-1-

(isopropylsulfonyl)-3-methylbutan-2-yl)-3-methyl-2-oxopiperidin-3-yl)acetic acid is in a solid dosage form.

4. The method of claim 3, wherein the solid dosage form is a capsule.

5. The method of claim 3, wherein the solid dosage form is a tablet.

6. The method of claim 1, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered in a dosage in the range of about 0.01 to about 100 mg/kg body weight.

7. The method of claim 1, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered before decitabine.

8. The method of claim 1, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered after decitabine.

9. The method of claim 1, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered simultaneously with decitabine.

10. The method of claim 1, wherein the acute myelogenous leukemia has a FLT3-ITD mutation.

11. A method of treating acute myelogenous leukemia (AML), the method comprising administering to a patient in need thereof a therapeutically effective amount of
2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid and cytarabine.

12. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered orally.

13. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is in a solid dosage form.

14. The method of claim 13, wherein the solid dosage form is a capsule.

15. The method of claim 13, wherein the solid dosage form is a tablet.

16. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered in a dosage in the range of about 0.01 to about 100 mg/kg body weight.

17. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered before cytarabine.

18. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered after cytarabine.

19. The method of claim 11, wherein the compound 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid is administered simultaneously with cytarabine.

20. The method of claim 11, wherein the acute myelogenous leukemia has a FLT3-ITD mutation.

* * * * *